(12) United States Patent
Elenitoba-Johnson et al.

(10) Patent No.: US 10,590,488 B2
(45) Date of Patent: Mar. 17, 2020

(54) RECURRENT GENE FUSIONS IN CUTANEOUS CD30-POSITIVE LYMPHOPROLIFERATIVE DISORDERS

(71) Applicant: The Regents of the University of Michigan, Ann Arbor, MI (US)

(72) Inventors: Kojo Elenitoba-Johnson, Ann Arbor, MI (US); Mark J. Kiel, Ann Arbor, MI (US); Delphine Rolland, Ann Arbor, MI (US); Bryan L. Betz, Ann Arbor, MI (US); Nathanael G. Bailey, Ann Arbor, MI (US); Thirunavukkarasu Velusamy, Ann Arbor, MI (US); Megan Lim, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/547,325

(22) PCT Filed: Jan. 29, 2016

(86) PCT No.: PCT/US2016/015714
§ 371 (c)(1),
(2) Date: Jul. 28, 2017

(87) PCT Pub. No.: WO2016/123517
PCT Pub. Date: Aug. 4, 2016

(65) Prior Publication Data
US 2018/0010196 A1 Jan. 11, 2018

Related U.S. Application Data

(60) Provisional application No. 62/110,034, filed on Jan. 30, 2015.

(51) Int. Cl.
*C07H 21/04* (2006.01)
*C12Q 1/68* (2018.01)
(Continued)

(52) U.S. Cl.
CPC .......... *C12Q 1/6886* (2013.01); *C12Q 1/686* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| 2002/0090705 | A1 | 7/2002 | Meyers |
| 2004/0203011 | A1 | 10/2004 | Morris et al. |
| 2015/0017637 | A1 | 1/2015 | Chinnaiyan et al. |

OTHER PUBLICATIONS

Crescenzo et al. (Cancer Cell, vol. 27, pp. 516-532, Apr. 13, 2015) (Year: 2015).*

(Continued)

*Primary Examiner* — Jeanine A Goldberg
(74) *Attorney, Agent, or Firm* — Casmir Jones, SC; Robert A. Goetz

(57) ABSTRACT

Provided herein are kits, compositions and methods for cancer diagnosis, research and therapy, including but not limited to, cancer markers. In particular, the present invention relates to recurrent gene fusions (e.g., recurrent translocations involving TYK2) as diagnostic markers and clinical targets for cutaneous CD30-positive lymphoproliferative disorders (e.g., lymphomatoid papulosis; primary cutaneous anaplastic large cell lymphoma).

1 Claim, 52 Drawing Sheets

Specification includes a Sequence Listing.

(51) Int. Cl.
*C12Q 1/6886* (2018.01)
*C12Q 1/686* (2018.01)

(56) References Cited

OTHER PUBLICATIONS

Tron et al. (Leukemia &Lymphoma, vol. 57, No. 12, pp. 2927-2929, 2016) (Year: 2016).*
Leitner et al. (Cytokine, vol. 89, pp. 209-218, 2017) (Year: 2017).*
Velusamy et al. (Blood, vol. 124, No. 25, pp. 3768-3771, 2014). (Year: 2014).*
Atlas of Genetics and Cytogenetics in Oncology and Haematology, TKY2, 2018.*
Bekkenk MW, et al., "Primary and secondary cutaneioius CD30+. . . " Blood 2000;95:3653-61.
Chen YW, et al., "Multiple BCL6 translocation partners in individual cases of gastric lymphoma" Blood 2003;102:1931-2.
Chiarle R, et al., The anaplastic lymphoma kinase in the pathogenesis of cancer, Nature reviews Cancer 2008;8:11-23.
Greuber EK, et al., "Role of ABL family kinases in cancer: from leukemia to solid tumours" Nature reviews Cancer 2013;13:559-71.
Harper DP, et al., "Chromosomal Rearrangements Leading to MLL Gene Fusions: Clinical and Biological Aspects" Cancer research 2008;68:10024-7.
International Search Report, International Patent Application No. PCT/US2016/015714, dated Jul. 15, 2016.
Iyer MK, "ChimeraScan: a tool for identifying chimeric transcription in sequencing data." Bioinformatics 2011;27:2903-4.
Mitelman F, et al., "The impact of translocations and gene fusions on cancer causation" Nature reviews Cancer 2007;7:233-45.
Rowley JD, "Chromosome translocations: dangerous liaisons revisited" Nature reviews Cancer 2001;1:245-50.
Swerdlow SH, et al., "The 2016 revision of the World Health Organization classification of lymphoid neoplasms" WHO Classification of Tumours of Haematopoietic and Lymphoid Tissues. Lyon: IARC; 2008; pp. 2375-2390.
Velusamy, T. et al. "A Novel Recurrent NPM1-TYK2 Gene Fusion in Cutaneous CD30-positive Lymphopoliferative Disorders" Blood, Oct. 27, 2014, vol. 24, No. 25; pp. 3768-3771.

* cited by examiner

FIG. 1

FISH Results and Clinical Data for Cutaneous CD30-Positive Lymphoproliferative Disorders

| Case | Diagnosis | FISH Results | | | | Clinical Data | | | | |
|---|---|---|---|---|---|---|---|---|---|---|
| | | TYK2 Break-Apart | Percent Positive | NPM1-TYK2 Fusion | Percent Positive | Age (years) | Sex | Site(s) | Treatment Received | Last Known Status |
| 1 | PC-ALCL | Negative | 0% | N/P | 0% | 47 | Male | Lower extremity, regional lymph node | Radiation, cyclophosphamide, adriamycin, vincristine, prednisone | Remission |
| 2 | PC-ALCL | Negative | 0% | N/P | 0% | 28 | Female | Lower extremity | Radiation, cyclophosphamide, adriamycin, vincristine, prednisone | Remission |
| 3 | LyP | Negative | 0% | N/P | 0% | 65 | Female | Trunk, upper and lower extremities | Radiation, topical steroids | Persistent disease |
| 4 | LyP | Negative | 0% | N/P | 0% | 63 | Male | Upper extremity | Methotrexate | Persistent disease |
| 5 | LyP | Negative | 0% | N/P | 0% | 12 | Female | Upper and lower extremities | N/A | Persistent disease |
| 6 | LyP | Negative | 0% | N/P | 0% | 50 | Female | Trunk, upper and lower extremities, vulva | Methotrexate, topical steroids, phototherapy | Persistent disease |
| 7 | LyP | Negative | 0% | N/P | 0% | 59 | Male | Trunk, upper and lower extremities | Radiation, methotrexate, bexarotene | Deceased, renal failure |
| 8 | LyP | Negative | 0% | N/P | 0% | 37 | Female | Face, neck, upper and lower extremities | Topical steroids | Persistent disease |
| 9 | LyP | Negative | 0% | N/P | 0% | 55 | Male | Trunk, upper and lower extremities, scalp | Topical steroids | Persistent disease |
| 10 | LyP | Positive | 75% | Negative | 0% | 40 | Male | Trunk, upper and lower extremities | Radiation, methotrexate, topical steroids | Persistent disease |
| 11 | LyP | Negative | 0% | N/P | 0% | 56 | Male | Upper extremity | Radiation, methotrexate, topical steroids | Persistent disease |
| 12 | PC-ALCL | Negative | 0% | N/P | 0% | 55 | Male | Trunk, upper and lower extremities | Radiation, topical steroids | Persistent disease |
| 13 | PC-ALCL | Negative | 0% | N/P | 0% | 56 | Female | Trunk, upper and lower extremities | Radiation, topical steroids | Persistent disease |
| 14 | LyP | Positive | 85% | Positive | 85% | 71 | Male | Trunk, upper and lower extremities | Radiation, methotrexate, phototherapy | Persistent disease |

FIG. 1 (Cont.)

| Case | Diagnosis | FISH Results | | | | Clinical Data | | | | |
|---|---|---|---|---|---|---|---|---|---|---|
| | | TYK2 Break-Apart | Percent Positive | NPM1-TYK2 Fusion | Percent Positive | Age (years) | Sex | Site(s) | Treatment Received | Last Known Status |
| 15 | LyP | Negative | 0% | N/P | 0% | 62 | Male | Lower extremity | Radiation, topical steroids | Persistent disease |
| 16 | LyP | Negative | 0% | N/P | 0% | 46 | Female | Upper and lower extremities, buttocks | Methotrexate | Persistent disease |
| 17 | PC-ALCL | Negative | 0% | N/P | 0% | 74 | Male | Upper back | Radiation | Remission |
| 18 | PC-ALCL | Negative | 0% | N/P | 0% | 80 | Male | Upper extremity, regional lymph node | Radiation, cyclophosphamide, adriamycin, vincristine, prednisone, etoposide, carboplatin, palatrexate | Persistent disease |
| 19 | LyP | Positive | 30% | Negative | 0% | 49 | Female | Trunk, upper and lower extremities | Methotrexate | Persistent disease |
| 20 | LyP | Negative | 0% | N/P | 0% | 81 | Female | Upper and lower extremities, buttocks | Topical steroids, phototherapy | Persistent disease |
| 21 | LyP | Negative | 0% | N/P | 0% | 45 | Male | Lower extremities, buttocks, axilla | Topical steroids, phototherapy | Persistent disease |
| 22 | PC-ALCL | Negative | 0% | N/P | 0% | 56 | Female | N/A | N/A | N/A |
| 23 | PC-ALCL | Negative | 0% | N/P | 0% | 87 | Female | N/A | N/A | N/A |
| 24 | PC-ALCL | Positive | 20% | Negative | 0% | 53 | Female | N/A | N/A | N/A |
| 25 | PC-ALCL | Negative | 0% | N/P | 0% | 25 | Female | N/A | N/A | N/A |
| 26 | PC-ALCL | Negative | 0% | N/P | 0% | 56 | Male | N/A | N/A | N/A |
| 27 | PC-ALCL | Negative | 0% | N/P | 0% | 78 | Female | N/A | N/A | N/A |
| 28 | PC-ALCL | Positive | 80% | Negative | 0% | 31 | Male | Thigh | Radiation, methotrexate | N/A |
| 29 | PC-ALCL | Negative | 0% | N/P | 0% | 43 | Male | N/A | N/A | N/A |
| 30 | PC-ALCL | Positive | 90% | Positive | 90% | N/A | N/A | N/A | N/A | N/A |

FIG. 1 (Cont.)

| Case | Diagnosis | FISH Results | | | Clinical Data | | | | | |
|---|---|---|---|---|---|---|---|---|---|---|
| | | TYK2 Break-Apart | Percent Positive | NPM1-TYK2 Fusion | Percent Positive | Age (years) | Sex | Site(s) | Treatment Received | Last Known Status |
| 1 | PC-ALCL | Negative | 0% | Negative | 0% | N/A | N/A | N/A | N/A | N/A |
| 32 | PC-ALCL | Positive | 90% | Negative | 0% | N/A | N/A | N/A | N/A | N/A |
| 33 | PC-ALCL | Negative | 0% | Negative | 0% | N/A | N/A | N/A | N/A | N/A |
| 34 | PC-ALCL | Negative | 0% | Negative | 0% | N/A | N/A | N/A | N/A | N/A |
| 35 | PC-ALCL | Negative | 0% | Negative | 0% | N/A | N/A | N/A | N/A | N/A |
| 36 | PC-ALCL | Negative | 0% | Negative | 0% | N/A | N/A | N/A | N/A | N/A |
| 37 | PC-ALCL | Negative | 0% | Negative | 0% | N/A | N/A | N/A | N/A | N/A |
| 38 | PC-ALCL | Negative | 0% | Negative | 0% | N/A | N/A | N/A | N/A | N/A |
| 39 | PC-ALCL | Negative | 0% | Negative | 0% | N/A | N/A | N/A | N/A | N/A |
| 40 | PC-ALCL | Negative | 0% | Negative | 0% | N/A | N/A | N/A | N/A | N/A |
| 41 | PC-ALCL | Negative | 0% | Negative | 0% | N/A | N/A | N/A | N/A | N/A |
| 42 | PC-ALCL | Negative | 0% | Negative | 0% | N/A | N/A | N/A | N/A | N/A |
| 43 | PC-ALCL | Negative | 0% | Negative | 0% | N/A | N/A | N/A | N/A | N/A |
| 44 | PC-ALCL | Negative | 0% | Negative | 0% | N/A | N/A | N/A | N/A | N/A |
| 45 | PC-ALCL | Negative | 0% | Negative | 0% | N/A | N/A | N/A | N/A | N/A |
| 46 | LyP | Negative | 0% | Negative | 0% | 58 | Male | Upper back | Topical steroids | Remission |
| 47 | LyP | Negative | 0% | Negative | 0% | 49 | Female | Lower extremities, scalp | Methotrexate, topical steroids | Persistent disease |

FISH, fluorescence in-situ hybridization; PC-ALCL, Primary cutaneous anaplastic large cell lymphoma; LyP, Lymphomatoid Papulosis; N/P, not performed; N/A, information not available

Summary of RNAseq data for MyLa

| Chr | Start | End | Strand | Gene | Chr | Start | End | Strand | Gene | Type | Total Reads | Breakpoint Spanning Reads |
|---|---|---|---|---|---|---|---|---|---|---|---|---|
| chr5 | 170,814,707 | 170,832,406 | + | NPM1 | chr19 | 10,461,203 | 10,468,813 | - | TYK2 | Interchromosomal | 803 | 765 |
| chr6 | 29,910,246 | 29,911,319 | + | HLA-A | chr6 | 31,323,093 | 31,324,114 | - | HLA-B | Intrachromosomal_Converging | 84 | 0 |
| chr1 | 35,652,501 | 35,658,742 | - | SFPQ | chr1 | 35,641,980 | 35,642,999 | . | A1BG1BB9 | Read_Through | 36 | 1 |
| chr13 | 41,885,340 | 41,885,717 | + | NAA16 | chr16 | 70,404,125 | 70,407,280 | + | ERO1A, ERO1B | Interchromosomal | 36 | 33 |
| chr12 | 4,829,751 | 4,874,711 | - | GALNT8 | chr12 | 4,959,303 | 4,963,277 | + | KCN6 | Read_Through | 19 | 12 |
| chr10 | 17,220,257 | 17,278,591 | + | VIM | chr1 | 115,520,177 | 115,537,989 | + | SYCP1 | Interchromosomal | 24 | 0 |
| chr1 | 27,022,521 | 27,100,207 | + | ARID1A | chr1 | 27,117,249 | 27,124,893 | + | PIGV | Read_Through | 15 | 14 |
| chr5 | 70,196,800 | 70,196,975 | + | SERF1 | chr5 | 69,822,333 | 69,328,524 | + | SERF1B | Intrachromosomal_Complex | 14 | 14 |
| chr5 | 69,321,472 | 69,321,557 | + | SERF1 | chr5 | 68,322,233 | 69,328,524 | + | SERF1B | Overlapping_Complex | 14 | 14 |
| chr5 | 70,196,800 | 70,196,975 | + | SERF1 | chr5 | 70,197,651 | 70,203,843 | + | SERF1B | Intrachromosomal_Complex | 14 | 14 |
| chr5 | 69,321,472 | 69,321,557 | + | SERF1 | chr5 | 70,197,651 | 70,203,843 | + | SERF1B | Intrachromosomal | 14 | 14 |
| chr14 | 24,761,389 | 24,768,665 | - | DHRS1 | chr14 | 24,734,743 | 24,740,741 | + | RAB8GTA | Read_Through | 16 | 0 |
| chr19 | 17,940,916 | 17,958,840 | - | JAK3 | chr19 | 17,927,321 | 17,927,867 | + | IXBL3 | Read_Through | 10 | 8 |
| chr2 | 88,381,642 | 88,093,286 | + | RGPD2, RGPD1 | chr2 | 109,111,746 | 109,125,853 | + | GCC2 | Intrachromosomal_Diverging | 14 | 7 |
| chr2 | 108,453,906 | 108,489,353 | + | RGPD4 | chr2 | 109,111,746 | 109,125,853 | + | GCC2 | Intrachromosomal | 14 | 7 |
| chr2 | 87,208,275 | 87,214,901 | + | RGPD2, RGPD1 | chr2 | 109,111,746 | 109,125,853 | + | GCC2 | Intrachromosomal | 14 | 7 |
| chr6 | 29,691,116 | 29,691,703 | + | HLA-F | chr6 | 31,321,648 | 31,324,449 | - | HLA-B | Intrachromosomal_Converging | 11 | 0 |
| chr2 | 133,015,101 | 133,015,341 | + | ANKRD30BL | chr6 | 46,188,466 | 46,459,059 | + | RCAN2 | Interchromosomal | 10 | 0 |
| chr7 | 64,541,128 | 64,541,537 | - | BC044608 | chr7 | 56,078,743 | 56,088,923 | - | PSPH | Intrachromosomal | 9 | 0 |
| chr14 | 22,205,020 | 22,205,293 | + | TCRA,TCR | chr14 | 22,975,893 | 23,019,607 | + | TCRA,TRA@,TRAC | Intrachromosomal | 8 | 0 |
| chr11 | 61,560,108 | 61,560,499 | + | FEN1 | chr11 | 61,605,249 | 61,634,834 | - | FADS2 | Read_Through | 8 | 8 |
| chr19 | 10,713,120 | 10,713,236 | + | SLC44A2 | chr19 | 17,448,816 | 17,453,539 | + | GTPBP3 | Intrachromosomal_Converging | 6 | 6 |
| chr19 | 5,785,393 | 5,791,246 | + | DUS31 | chr19 | 5,782,970 | 5,784,449 | + | PAK32 | Read_Through | 5 | 5 |
| chr6 | 31,323,343 | 31,324,449 | - | HLA-B | chr6 | 29,911,044 | 29,913,660 | + | HLA-A | Intrachromosomal_Converging | 9 | 0 |
| chr8 | 67,834,848 | 67,837,778 | - | SNHG6 | chr8 | 67,834,708 | 67,834,783 | + | SMCRD87 | Overlapping_Complex | 6 | 0 |
| chr2 | 130,620,478 | 130,759,728 | - | FLJ43663 | chr7 | 130,557,250 | 130,569,154 | + | LOC646329 | Read_Through | 8 | 7 |
| chr12 | 57,127,930 | 57,146,145 | - | PRIM1 | chr12 | 57,106,210 | 57,108,470 | + | NACA | Read_Through | 7 | 0 |
| chr2 | 2,752,261 | 2,755,510 | + | C5orf38 | chr2 | 99,614,625 | 99,757,881 | + | TSGA10 | Interchromosomal | 12 | 0 |
| chr6 | 34,204,576 | 34,208,591 | + | HMGA1 | chr5 | 180,374,511 | 180,377,905 | + | BTNL3 | Interchromosomal | 5 | 0 |
| chr5 | 180,335,076 | 180,374,754 | - | BTNL8 | chr6 | 34,212,637 | 34,214,207 | + | HMGA1 | Interchromosomal | 5 | 0 |
| chr19 | 1,269,266 | 1,274,438 | + | CREBP | chr19 | 1,277,161 | 1,279,242 | + | C19orf24 | Read_Through | 4 | 4 |
| chr5 | 156,693,090 | 156,714,116 | + | CYFIP2 | chr15 | 22,938,128 | 22,993,154 | + | CYFIP1 | Interchromosomal | 6 | 3 |
| chr19 | 17,516,551 | 17,517,104 | + | AK311380, AK055623 | chr19 | 17,531,121 | 17,532,021 | + | FAM125A | Read_Through | 4 | 3 |

| | | | | | | | | |
|---|---|---|---|---|---|---|---|---|
| chr16 | 70,022,243 | 70,076,905 | PDXDC2P | | chr16 | 30,234,349 | 30,246,899 | LOC613037 | Intrachromosomal | 4 | 0 |
| chr6 | 136,589,299 | 136,610,983 | BCLAF1 | - | chr1 | 36,767,153 | 36,770,956 | THRAP3 | Interchromosomal | 4 | 0 |
| chr16 | 70,020,283 | 70,076,905 | PDXDC2P | | | | | LOC100132247 | | 4 | 0 |
| | | | | | chr16 | 21,415,197 | 22,426,405 | NPIPL3 | Intrachromosomal | 4 | 0 |
| | | | | | | | | LOC100271836 | | 4 | 0 |
| chr7 | 100,071,896 | 100,075,901 | TSC22D4 | | chr7 | 100,054,237 | 100,061,893 | C7orf61 | Read_Through | 4 | 0 |
| chr17 | 57,842,885 | 57,876,211 | DHX40 | + | chr17 | 58,029,722 | 58,040,644 | RNFT1 | Intrachromosomal_Converging | 4 | 0 |
| chr2 | 223,289,321 | 223,269,559 | SGPP2 | + | chr9 | 137,218,315 | 137,332,430 | RXRA | Interchromosomal | 4 | 0 |
| chr17 | 147,931,733 | 147,931,992 | FLJ35739 | + | chr1 | 145,004,780 | 145,005,286 | BC065231 | Interchromosomal_Converging | 4 | 0 |
| chr2 | 219,524,378 | 219,526,575 | BCS1L | + | chr12 | 9,013,730 | 9,029,375 | A2ML1 | Interchromosomal | 3 | 0 |
| chr7 | 96,238,999 | 96,339,202 | SHFM1 | + | chr7 | 96,250,968 | 96,275,247 | LOC100506636 | Read_Through | 3 | 0 |
| chr1 | 241,803,183 | 241,803,700 | OPN3 | - | chr1 | 241,792,166 | 241,799,231 | CHML | Overlapping_Complex | 3 | 0 |
| chr1 | 145,578,452 | 145,575,699 | BC110832, LOC728855 | + | chr1 | 145,004,780 | 145,005,286 | BC065231 | Intrachromosomal_Complex | 3 | 0 |
| chr8 | 92,082,423 | 52,096,341 | OTC268 | - | chr8 | 92,114,846 | 92,231,463 | LRRC59 | Read_Through | 3 | 0 |
| chr2 | 133,249,448 | 133,249,658 | MZT2A | + | chr24 | 103,398,715 | 103,440,435 | CCDC242B3 | Intrachromosomal | 3 | 0 |
| chr15 | 74,244,204 | 74,249,419 | BC043527 | - | chr3 | 190,956,535 | 190,957,909 | OSTN | Interchromosomal | 3 | 0 |
| chr2 | 48,667,907 | 48,738,606 | PPP1R21 | + | chr2 | 48,752,063 | 49,003,655 | STOM1 GTF2A1 | Read_Through | 3 | 0 |
| chr1 | 144,340,525 | 144,340,772 | LOC728855 | - | chr1 | 145,004,780 | 145,005,286 | BC065231 | Intrachromosomal_Diverging | 3 | 0 |
| chr1 | 145,744,200 | 145,744,385 | LOC, LOC285783 | + | chr1 | 145,004,780 | 145,005,286 | BC065231 | Intrachromosomal_Diverging | 3 | 0 |
| chr11 | 62,344,126 | 62,359,108 | TUT1 | - | chr11 | 52,327,072 | 63,342,400 | EEF1G | Read_Through | 3 | 0 |
| chr11 | 133,826,565 | 133,825,879 | IGSF9B | | chr24 | 35,545,710 | 35,552,588 | FAM177A1 | Interchromosomal | 3 | 0 |
| chr17 | 35,955,518 | 36,956,157 | PIP4K2B | + | chr19 | 47,567,446 | 47,615,845 | ZC3H4 | Interchromosomal | 3 | 0 |
| | 39,538,962 | 39,539,049 | MYCBP, RPL5C | - | | 39,341,478 | 39,377,105 | RHBDL2 | Intrachromosomal_Complex | 3 | 0 |
| chr8 | 144,661,865 | 144,672,250 | EEF1D | - | chr8 | 144,656,954 | 144,659,908 | NAPRT1 | Read_Through | 3 | 0 |
| chr22 | 132,589,111 | 132,594,378 | EP400NL | + | chr12 | 132,604,964 | 132,613,428 | EP400NL | Read_Through | 3 | 0 |
| chr12 | 132,589,111 | 132,594,375 | EP400NL | + | chr12 | 132,472,249 | 132,475,258 | EP400 | Intrachromosomal_Complex | 3 | 0 |
| chr4 | 153,409,656 | 153,321,021 | POLYPP4 | - | chr4 | 153,470,337 | 153,509,199 | POLYPP3 | Read_Through | 3 | 0 |
| chr9 | 111,754,668 | 111,754,848 | 5_85_rRNA | - | chr1 | 22,140,890 | 22,151,713 | IDI_RAD2 | Interchromosomal | 3 | 0 |
| chr11 | 144,520,773 | 144,521,008 | LOC728875 | - | chr1 | 145,004,780 | 145,005,286 | BC065231 | Intrachromosomal_Diverging | 3 | 0 |
| chr9 | 38,543,235 | 38,577,260 | ANKRD18A | - | chr17 | 34,433,060 | 34,499,322 | TBC1D38 | Interchromosomal | 2 | 0 |
| chr9 | 49,866,045 | 49,867,208 | TUBA1K | - | chr3 | 45,285,953 | 45,267,813 | TMEM158 | Interchromosomal | 2 | 0 |
| chr12 | 38,543,235 | 38,577,260 | ANKRD18A | + | chr17 | 60,345,505 | 60,348,386 | TBC1D3P2 | Interchromosomal | 2 | 0 |
| chr9 | 36,955,518 | 36,956,157 | PIP4K2B | | chr4 | 6,526,151 | 6,557,483 | PLEKHG6 | Interchromosomal | 2 | 0 |
| chr1 | 140,083,053 | 140,084,821 | SSNA1 | + | chr1 | 62,146,718 | 62,159,455 | TM2D1 | Interchromosomal | 2 | 0 |
| chr9 | 36,258,113 | 36,358,495 | GNE | + | chr1 | 54,882,194 | 54,872,091 | SSBP3 | Interchromosomal | 2 | 0 |
| chr10 | 42,291,846 | 49,338,995 | AK309921 | - | chr7 | 42,948,871 | 42,957,057 | C7orf25 | Interchromosomal | 2 | 0 |
| chr11 | 117,249,558 | 117,886,716 | SDT2 | + | chr11 | 117,073,717 | 117,075,507 | PAFAH | Read_Through | 2 | 0 |
| chr3 | 52,321,835 | 52,325,126 | GLYCTK | - | chr3 | 52,350,334 | 52,434,512 | DNAH1 | Read_Through | 2 | 0 |
| chr16 | 17,564,280 | 17,564,737 | XYLT1 | - | chr13 | 49,671,173 | 48,715,097 | TRPM4 | Interchromosomal | 2 | 0 |
| chr9 | 38,543,235 | 38,577,260 | ANKRD18A | - | chr17 | 36,337,527 | 36,343,994 | TBC1D3 TBC1D3F | Interchromosomal | 2 | 0 |
| chr4 | 25,943,988 | 25,944,827 | MAN1I3 | + | chr8 | 25,749,048 | 25,864,639 | BC113 | Interchromosomal | 2 | 0 |
| chr19 | 35,266,416 | 36,266,565 | ARHGAP33 | + | chr3 | 63,898,262 | 63,982,294 | ATXN7 | Interchromosomal | 2 | 0 |

FIG. 3 (Cont.)

| | | | | | | | | | |
|---|---|---|---|---|---|---|---|---|---|
| chr8 | 145,533,246 | 145,533,556 | DGAT1 | | chr16 | 29,848,042 | 29,849,359 | + | MVP | Interchromosomal | | 2 | 0 |
| chr9 | 38,543,235 | 38,577,260 | ANKRD18A | - | chr17 | 34,581,084 | 34,587,366 | - | TBC1D3H, TBC1D3C, TBC1D3G | Interchromosomal | | 2 | 0 |
| chr16 | 72,186,531 | 72,305,063 | PKNOX1 | | chr5 | 52,295,095 | 52,365,010 | | TMEM189, TMEM189-UBE2V1 | Interchromosomal | | 2 | 0 |
| chr2 | 97,760,457 | 97,760,581 | FAHD2B | - | chr20 | 48,697,660 | 48,770,334 | - | TMEM189, TMEM189-UBE2V1 | Interchromosomal | | 2 | 0 |
| chr2 | 133,015,301 | 133,015,541 | ANKRD30BL | | chr2 | 180,306,710 | 180,726,231 | | ZNF385B | Intrachromosomal_Complex | | 2 | 0 |
| chr9 | 38,543,235 | 38,577,260 | ANKRD18A | - | chr17 | 36,288,630 | 36,295,097 | + | TBC1D3, TBC1D3F | Interchromosomal | | 2 | 0 |
| chr19 | 54,894,137 | 54,897,584 | TSEN34 | + | chr19 | 54,705,009 | 54,711,514 | + | RPS9 | Read_Through | | 2 | 0 |
| chr19 | 10,982,252 | 11,018,820 | CARM1 | + | chr5 | 130,397,777 | 130,435,442 | - | PIK3R4 | Interchromosomal | | 2 | 0 |
| chr1 | 155,290,639 | 155,292,920 | PKLR | + | chr12 | 102,091,416 | 102,117,845 | + | CHPT1 | Interchromosomal | | 2 | 0 |
| chr9 | 123,455,203 | 123,476,764 | MEGF9 | - | chr9 | 123,518,253 | 123,555,668 | - | FBXW2 | Adjacent_Complex | | 2 | 0 |
| chr10 | 51,606,983 | 51,623,535 | TMEM123 | - | chr10 | 51,234,687 | 51,247,973 | + | SGSM3 | Intrachromosomal | | 2 | 0 |
| chr22 | 40,742,503 | 40,761,059 | ACA1 | + | chr22 | 40,766,594 | 40,806,292 | + | SGSM3 | Read_Through | | 2 | 0 |
| chr17 | 123,671,258 | 124,028,580 | FLJ33817 | | chr17 | 70,642,084 | 70,845,942 | | SLC39A11 | Intrachromosomal | | 2 | 0 |
| chr6 | 7,910,746 | 7,911,046 | TXNDC5 | - | chr12 | 17,271,291 | 17,279,591 | + | VM1 | Interchromosomal | | 2 | 0 |
| chr9 | 100,818,908 | 100,819,221 | NANS | + | chr1 | 38,463,441 | 38,471,186 | - | FH13 | Interchromosomal | | 2 | 0 |
| chr10 | 11,653,441 | 11,653,678 | USP6NL | - | chr7 | 26,438,338 | 26,538,593 | - | LOC441204 | Interchromosomal | | 2 | 0 |
| chr10 | 144,607,486 | 144,607,706 | UTRN | - | chr3 | 50,650,278 | 50,686,727 | + | MAPKAPK3 | Interchromosomal | | 2 | 0 |
| chr16 | 30,064,410 | 30,078,686 | ALDOA | + | chrM | 10,059 | 10,404 | + | AD_1 | Interchromosomal | | 2 | 0 |
| chr17 | 72,920,308 | 72,921,034 | OTOP2 | + | chr20 | 25,167,654 | 36,189,968 | + | LOC284801 | Interchromosomal | | 2 | 0 |
| chr7 | 56,088,765 | 56,119,267 | PSPH | - | chr7 | 55,840,871 | 55,841,375 | + | CCT6 | Intrachromosomal_Converging | | 2 | 0 |
| chr7 | 222,883,905 | 222,904,857 | BROX | | chr1 | 222,906,202 | 222,908,532 | + | AK025140 | Read_Through | | 2 | 0 |
| chr7 | 45,796,572 | 45,808,616 | SEPT7P2 | | chr7 | 56,078,743 | 56,079,561 | - | PSPH | Intrachromosomal_Complex | | 2 | 0 |
| chr10 | 51,371,394 | 51,387,782 | TMEM23A, TMEM23 | + | chr10 | 51,224,687 | 51,247,973 | + | AGAP6 | Intrachromosomal_Diverging | | 2 | 0 |
| chr9 | 2,621,792 | 2,654,484 | VLDLR | + | chr2 | 112,973,438 | 112,996,104 | - | ZC3H8 | Interchromosomal | | 2 | 0 |
| chr10 | 46,584,431 | 46,620,057 | PTPN20A | + | chr2 | 42,948,871 | 42,957,057 | - | C2orf23 | Interchromosomal | | 2 | 0 |
| chr2 | 96,675,298 | 96,676,479 | LOC729234 | + | chr20 | 48,697,660 | 48,770,334 | - | TMEM189, TMEM189-UBE2V1 | Interchromosomal | | 2 | 0 |
| chr5 | 180,255,695 | 180,258,595 | AK026301 | | chr8 | 38,845,454 | 38,846,180 | + | HTRA4 | Interchromosomal | | 2 | 0 |
| chr19 | 46,320,055 | 46,356,547 | SYMPK | - | chr12 | 122,267,971 | 122,370,561 | + | SETD1B | Interchromosomal | | 2 | 0 |
| chr20 | 30,418,734 | 30,418,984 | ZNF771 | + | chr20 | 33,705,827 | 33,823,993 | - | EDEM2 | Interchromosomal | | 2 | 0 |
| chr16 | 1,607,935 | 1,636,279 | IFT140 | - | chr16 | 1,603,555 | 1,604,130 | - | BC114455 | Overlapping_Complex | | 2 | 0 |

FIG. 10
pSTAT5
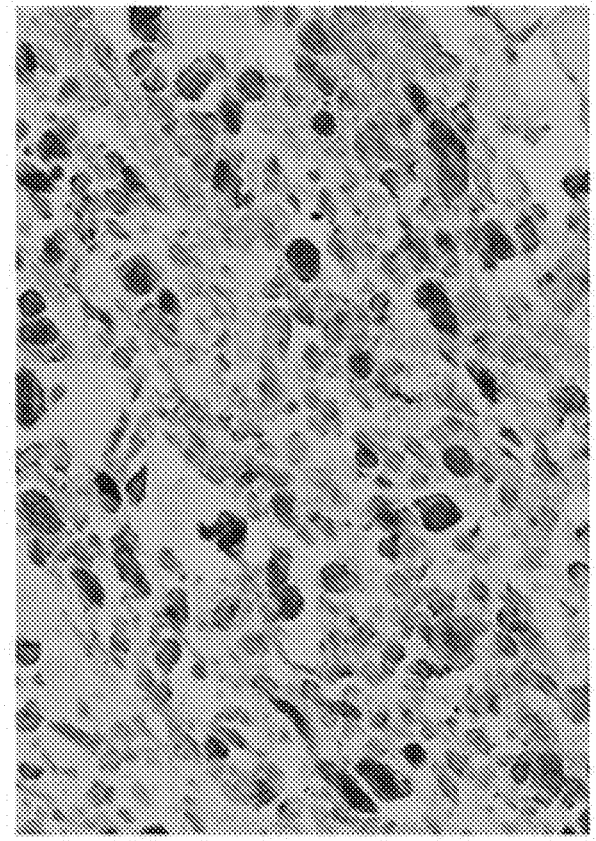
CD30+LPD
*NPM1-TYK2* +
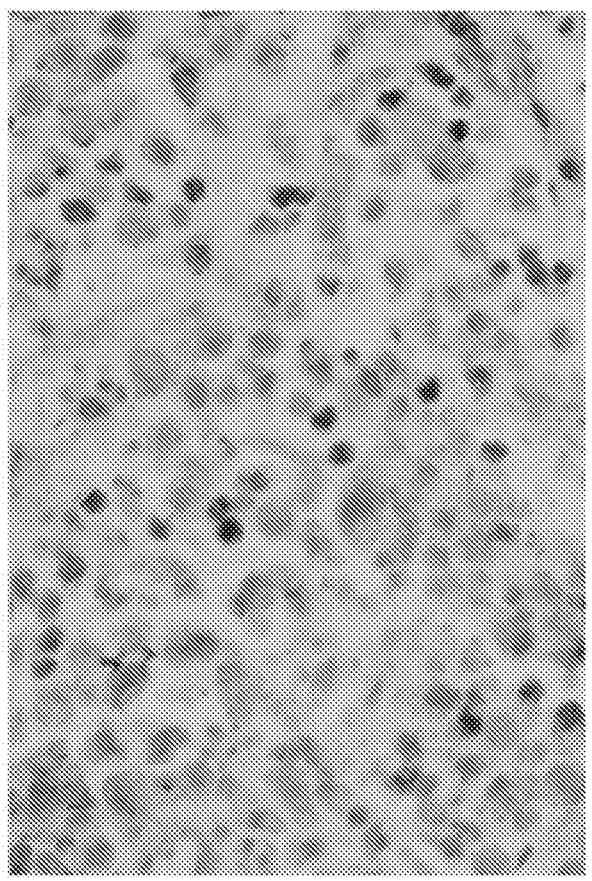
CD30+LPD
*NPM1-TYK2* -

FIG. 11A

TYK2 cDNA 4262 bp

```
AAGCAGTAGCTACCCGCGGGAGCGGGGAGGGGTCCGGGTTCGAGCTTGTGTTCCCCCGGAAGGGTGAGTC
TGGACGCGGGCGCGGAAGGAGCGCGGCCGGAGGTCCTCAGGAAGAAGCCGCGGGGACTGGCTGCGCTTGA
CAGGCTGCACTTGGATGGGAGCACCTGGTGCCTCGGGACTGCTCCGATGCCCGGGTCTGTGCTGAATGTG
TAATATGCGGAACTATATTGAAACATTACAACCATCTTTTGATGGCAACACCCTGAGGACCTCCCTTTTC
CAGATGGGGAAACTGAGGCCCAGAATTGCTAAGTGGCTTGCTTGAGTTGACACAGGGAGCTCCAGGACTC
ACCCTCAGCTGAGCCACCTGCCGGGAGCATGCCTCTGCGCCACTGGGGATGGCCAGGGGCAGTAAGCCC
GTTGGGGATGGAGCCCAGCCCATGGCTGCCATGGGAGGCCTGAAGGTGCTTCTGCACTGGGCTGGTCCAG
GCGGCGGGGAGCCCTGGGTCACTTTCAGTGAGTCATCGCTGACAGCTGAGGAAGTCTGCATCCACATTGC
ACATAAAGTTGGTATCACTCCTCCTTGCTTCAATCTCTTTGCCCTCTTCGATGCTCAGGCCCAAGTCTGG
TTGCCCCCAAACCACATCCTAGAGATCCCCAGAGATGCAAGCCTGATGCTATATTTCCGCATAAGGTTTT
ATTTCCGGAACTGGCATGGCATGAATCCTCGGGAACCGGCTGTGTACCGTTGTGGCCCCCAGGAACCGA
GGCATCCTCAGATCAGACAGCACAGGGGATGCAACTCCTGGACCCAGCCTCATTTGAGTACCTCTTTGAG
CAGGGCAAGCATGAGTTTGTGAATGACGTGGCATCACTGTGGGAGCTGTCGACCGAGGAGGAGATCCACC
ACTTTAAGAATGAGAGCCTGGGCATGGCCTTTCTGCACCTCTGTCACCTCGCTCTCCGCCATGGCATCCC
CCTGGAGGAGGTGGCCAAGAAGACCAGCTTCAAGGACTGCATCCCGCGCTCCTTCCGCCGGCATATCCGG
CAGCACAGCGCCCTGACCCGGCTGCGCCTTCGGAACGTCTTCCGCAGGTTCCTGCGGGACTTCCAGCCGG
GCCGACTCTCCCAGCAGATGGTCATGGTCAAATACCTAGCCACACTCGAGCGGCTGGCACCCCGCTTCGG
CACAGAGCGTGTGCCCGTGTGCCACCTGAGGCTGCTGGCCCAGGCCGAGGGGAGCCCTGCTACATCCGG
GACAGTGGGGTGGCCCCTACAGACCCTGGCCCTGAGTCTGCTGCTGGGCCCCAACCCACGAGGTGCTGG
TGACAGGCACTGGTGGCATCCAGTGGTGGCCAGTAGAGGAGGAGGTGAACAAGGAGGAGGGTTCTAGTGG
CAGCAGTGGCAGGAACCCCCAAGCCAGCCTGTTTGGGAAGAAGGCCAAGGCTCACAAGGCAGTCGGCCAG
CCGGCAGACAGGCCGCGGGAGCCACTGTGGGCCTACTTCTGTGACTTCCGGGACATCACCCACGTGGTGC
TGAAAGAGCACTGTGTCAGCATCCACCGGCAGGACAACAAGTGCCTGGAGCTGAGCTTGCCTTCCCGGGC
TGCGGCGCTGTCCTTCGTGTCGCTGGTGGACGGCTATTTCCGCCTGACGGCCGACTCCAGCCACTACCTG
TGCCACGAGGTGGCTCCCCACGGCTGGTGATGAGCATCCGGGATGGGATCCACGGACCCCTGCTGGAGC
CATTTGTGCAGGCCAAGCTGCGGCCCGAGGACGGCCTGTACCTCATTCACTGGAGCACCAGCCACCCCTA
CCGCCTGATCCTCACAGTGGCCCAGCGTAGCCAGGCACCAGACGGCATGCAGAGCTTGCGGCTCCGAAAG
TTCCCCATTGAGCAGCAGGACGGGGCCTTCGTGCTGGAGGGCTGGGGCCGGTCCTTCCCCAGCGTTCGGG
AACTTGGGGCTGCCTTGCAGGGCTGCTTGCTGAGGGCCGGGGATGACTGCTTCTCTCTGCGTCGCTGTTG
CCTGCCCCAACCAGGAGAAACCTCCAATCTCATCATCATGCGGGGGGCTCGGGCCAGCCCCAGGACACTC
AACCTCAGCCAGCTCAGCTTCCACCGGGTTGACCAGAAGGAGATCACCCAGCTGTCCCACTTGGGCCAGG
GCACAAGGACCAACGTGTATGAGGGCCGCCTGCGAGTGGAGGGCAGCGGGGACCCTGAGGAGGGCAAGAT
GGATGACGAGGACCCCCTCGTGCCTGGCAGGGACCGTGGGCAGGAGCTACGAGTGGTGCTCAAAGTGCTG
GACCCTAGTCACCATGACATCGCCCTGGCCTTCTACGAGACAGCCAGCCTCATGAGCCAGGTCTCCCACA
CGCACCTGGCCTTCGTGCATGGCGTCTGTGTGCGCGGCCCTGAAAATATCATGGTGACAGAGTACGTGGA
GCACGGACCCCTGGATGTGTGGCTGCGGAGGGAGCGGGGCCATGTGCCCATGGCTTGGAAGATGGTGGTG
GCCCAGCAGCTGGCCAGCGCCCTCAGCTACCTGGAGAACAAGAACCTGGTTCATGGTAATGTGTGTGGCC
GGAACATCCTGCTGGCCCGGCTGGGGTTGGCAGAGGGCACCAGCCCCTTCATCAAGCTGAGTGATCCTGG
CGTGGGCCTGGGCGCCCTCTCCAGGGAGGAGCGGGTGGAGAGGATCCCCTGGCTGGCCCCGAATGCCTA
CCAGGTGGGGCCAACAGCCTAAGCACCGCCATGGACAAGTGGGGGTTTGGCGCCACCCTCCTGGAGATCT
GCTTTGACGGAGAGGCCCCTCTGCAGAGCCGCAGTCCCTCCGAGAAGGAGCATTTCTACCAGAGGCAGCA
```

FIG. 11A (Cont.)

```
CCGGCTGCCCGAGCCCTCCTGCCCACAGCTGGCCACACTCACCAGCCAGTGTCTGACCTATGAGCCAACC
CAGAGGCCATCATTCCGCACCATCCTGCGTGACCTCACCCGGCTGCAGCCCCACAATCTTGCTGACGTCT
TGACTGTGAACCCGGACTCACCGGCGTCGGACCCTACGGTTTTCCACAAGCGCTATTTGAAAAAGATCCG
AGATCTGGGCGAGGGTCACTTCGGCAAGGTCAGCTTGTACTGCTACGATCCGACCAACGACGGCACTGGC
GAGATGGTGGCGGTGAAAGCCCTCAAGGCAGACTGCGGCCCCAGCACCGCTCGGGCTGGAAGCAGGAGA
TTGACATTCTGCGCACGCTCTACCACGAGCACATCATCAAGTACAAGGGCTGCTGCGAGGACCAAGGCGA
GAAGTCGCTGCAGCTGGTCATGGAGTACGTGCCCTGGGCAGCCTCCGAGACTACCTGCCCCGGCACAGC
ATCGGGCTGGCCCAGCTGCTGCTCTTCGCCCAGCAGATCTGCGAGGGCATGGCCTATCTGCACGCGCAGC
ACTACATCCACCGAGACCTAGCCGCGCGCAACGTGCTGCTGGACAACGACAGGCTGGTCAAGATCGGGGA
CTTTGGCCTAGCCAAGGCCGTGCCCGAAGGCCACGAGTACTACCGCGTGCGCGAGGATGGGGACAGCCCC
GTGTTCTGGTATGCCCCAGAGTGCCTGAAGGAGTATAAGTTCTACTATGCGTCAGATGTCTGGTCCTTCG
GGGTGACCCTGTATGAGCTGCTGACGCACTGTGACTCCAGCCAGAGCCCCCCCACGAAATTCCTTGAGCT
CATAGGCATTGCTCAGGGTCAGATGACAGTTCTGAGACTCACTGAGTTGCTGGAACGAGGGGAGAGGCTG
CCACGGCCCGACAAATGTCCCTGTGAGGTCTATCATCTCATGAAGAACTGCTGGGAGACAGAGGCGTCCT
TTCGCCCAACCTTCGAGAACCTCATACCCATTCTGAAGACAGTCCATGAGAAGTACCAAGGCCAGGCCCC
TTCAGTGTTCAGCGTGTGCTGAGGCACAATGGCAGCCCTGCCTGGGAGGACTGGACCAGGCAGTGGCTGC
AGAGGGAGCCTCCTGCTCCCTGCTCCAGGATGAAACCAAGAGGGGGATGTCAGCCTCACCCACACCGTGT
GCCTTACTCCTGTCTAGAGACCCCACCTCTGTGAACTTATTTTTCTTTCTTGGCCGTGAGCCTAACCATG
ATCTTGAGGGACCCAACATTTGTAGGGGCACTAATCCAGCCCTTAAATCCCCCAGCTTCCAAACTTGAGG
CCCACCATCTCCACCATCTGGTAATAAACTCATGTTTTCTCTGCTGGAAAAAAAAAAAAAAA (SEQ ID
NO: 90)
```

FIG. 11B

TYK2 ORF 3564 bp

ATGCCTCTGCGCCACTGGGGGATGGCCAGGGGCAGTAAGCCCGTTGGGGATGGAGCCCAGCCCATGGCTG
CCATGGGAGGCCTGAAGGTGCTTCTGCACTGGGCTGGTCCAGGCGGCGGGGAGCCCTGGGTCACTTTCAG
TGAGTCATCGCTGACAGCTGAGGAAGTCTGCATCCACATTGCACATAAAGTTGGTATCACTCCTCCTTGC
TTCAATCTCTTTGCCCTCTTCGATGCTCAGGCCCAAGTCTGGTTGCCCCCAAACCACATCCTAGAGATCC
CCAGAGATGCAAGCCTGATGCTATATTTCCGCATAAGGTTTTATTTCCGGAACTGGCATGGCATGAATCC
TCGGGAACCGGCTGTGTACCGTTGTGGGCCCCAGGAACCGAGGCATCCTCAGATCAGACAGCACAGGGG
ATGCAACTCCTGGACCCAGCCTCATTTGAGTACCTCTTTGAGCAGGGCAAGCATGAGTTTGTGAATGACG
TGGCATCACTGTGGGAGCTGTCGACCGAGGAGGAGATCCACCACTTTAAGAATGAGAGCCTGGGCATGGC
CTTTCTGCACCTCTGTCACCTCGCTCTCCGCCATGGCATCCCCCTGGAGGAGGTGGCCAAGAAGACCAGC
TTCAAGGACTGCATCCCGCGCTCCTTCCGCCGGCATATCCGGCAGCACAGCGCCCTGACCCGGCTGCGCC
TTCGGAACGTCTTCCGCAGGTTCCTGCGGGACTTCCAGCCGGGCCGACTCTCCCAGCAGATGGTCATGGT
CAAATACCTAGCCACACTCGAGCGGCTGGCACCCCGCTTCGGCACAGAGCGTGTGCCCGTGTGCCACCTG
AGGCTGCTGGCCCAGGCCGAGGGGGAGCCCTGCTACATCCGGGACAGTGGGGTGGCCCCTACAGACCCTG
GCCCTGAGTCTGCTGCTGGGCCCCCAACCCACGAGGTGCTGGTGACAGGCACTGGTGGCATCCAGTGGTG
GCCAGTAGAGGAGGAGGTGAACAAGGAGGAGGGTTCTAGTGGCAGCAGTGGCAGGAACCCCCAAGCCAGC
CTGTTTGGGAAGAAGGCCAAGGCTCACAAGGCAGTCGGCCAGCCGGCAGACAGGCCGCGGGAGCCACTGT
GGGCCTACTTCTGTGACTTCCGGGACATCACCCACGTGGTGCTGAAAGAGCACTGTGTCAGCATCCACCG
GCAGGACAACAAGTGCCTGGAGCTGAGCTTGCCTTCCCGGGCTGCGGCGCTGTCCTTCGTGTCGCTGGTG
GACGGCTATTTCCGCCTGACGGCCGACTCCAGCCACTACCTGTGCCACGAGGTGGCTCCCCCACGGCTGG
TGATGAGCATCCGGGATGGGATCCACGGACCCCTGCTGGAGCCATTTGTGCAGGCCAAGCTGCGGCCCGA
GGACGGCCTGTACCTCATTCACTGGAGCACCAGCCACCCCTACCGCCTGATCCTCACAGTGGCCCAGCGT
AGCCAGGCACCAGACGGCATGCAGAGCTTGCGGCTCCGAAAGTTCCCCATTGAGCAGCAGGACGGGGCCT
TCGTGCTGGAGGGCTGGGGCCGGTCCTTCCCCAGCGTTCGGGAACTTGGGGCTGCCTTGCAGGGCTGCTT
GCTGAGGGCCGGGGATGACTGCTTCTCTCTGCGTCGCTGTTGCCTGCCCCAACCAGGAGAAACCTCCAAT
CTCATCATCATGCGGGGGGCTCGGGCCAGCCCCAGGACACTCAACCTCAGCCAGCTCAGCTTCCACCGGG
TTGACCAGAAGGAGATCACCCAGCTGTCCCACTTGGGCCAGGGCACAAGGACCAACGTGTATGAGGGCCG
CCTGCGAGTGGAGGGCAGCGGGGACCCTGAGGAGGGCAAGATGGATGACGAGGACCCCCTCGTGCCTGGC
AGGGACCGTGGGCAGGAGCTACGAGTGGTGCTCAAAGTGCTGGACCCTAGTCACCATGACATCGCCCTGG
CCTTCTACGAGACAGCCAGCCTCATGAGCCAGGTCTCCCACACGCACCTGGCCTTCGTGCATGGCGTCTG
TGTGCGCGGCCCTGAAAATATCATGGTGACAGAGTACGTGGAGCACGGACCCCTGGATGTGTGGCTGCGG
AGGGAGCGGGGCCATGTGCCCATGGCTTGGAAGATGGTGGTGGCCCAGCAGCTGGCCAGCGCCCTCAGCT
ACCTGGAGAACAAGAACCTGGTTCATGGTAATGTGTGTGGCCGGAACATCCTGCTGGCCCGGCTGGGGTT
GGCAGAGGGCACCAGCCCCTTCATCAAGCTGAGTGATCCTGGCGTGGGCCTGGGCGCCCTCTCCAGGGAG
GAGCGGGTGGAGAGGATCCCCTGGCTGGCCCCGAATGCCTACCAGGTGGGGCCAACAGCCTAAGCACCG
CCATGGACAAGTGGGGGTTTGGCGCCACCCTCCTGGAGATCTGCTTTGACGGAGAGGCCCCTCTGCAGAG
CCGCAGTCCCTCCGAGAAGGAGCATTTCTACCAGAGGCAGCACCGGCTGCCCGAGCCCTCCTGCCCACAG
CTGGCCACACTCACCAGCCAGTGTCTGACCTATGAGCCAACCCAGAGGCCATCATTCCGCACCATCCTGC
GTGACCTCACCCGGCTGCAGCCCCACAATCTTGCTGACGTCTTGACTGTGAACCCGGACTCACCGGCGTC
GGACCCTACGGTTTTCCACAAGCGCTATTTGAAAAAGATCCGAGATCTGGGCGAGGGTCACTTCGGCAAG
GTCAGCTTGTACTGCTACGATCCGACCAACGACGGCACTGGCGAGATGGTGGCGGTGAAAGCCCTCAAGG
CAGACTGCGGCCCCCAGCACCGCTCGGGCTGGAAGCAGGAGATTGACATTCTGCGCACGCTCTACCACGA

FIG. 11B (Cont.)

```
GCACATCATCAAGTACAAGGGCTGCTGCGAGGACCAAGGCGAGAAGTCGCTGCAGCTGGTCATGGAGTAC
GTGCCCCTGGGCAGCCTCCGAGACTACCTGCCCCGGCACAGCATCGGGCTGGCCCAGCTGCTGCTCTTCG
CCCAGCAGATCTGCGAGGGCATGGCCTATCTGCACGCGCAGCACTACATCCACCGAGACCTAGCCGCGCG
CAACGTGCTGCTGGACAACGACAGGCTGGTCAAGATCGGGGACTTTGGCCTAGCCAAGGCCGTGCCCGAA
GGCCACGAGTACTACCGCGTGCGCGAGGATGGGGACAGCCCCGTGTTCTGGTATGCCCCAGAGTGCCTGA
AGGAGTATAAGTTCTACTATGCGTCAGATGTCTGGTCCTTCGGGGTGACCCTGTATGAGCTGCTGACGCA
CTGTGACTCCAGCCAGAGCCCCCCCACGAAATTCCTTGAGCTCATAGGCATTGCTCAGGGTCAGATGACA
GTTCTGAGACTCACTGAGTTGCTGGAACGAGGGGAGAGGCTGCCACGGCCCGACAAATGTCCCTGTGAGG
TCTATCATCTCATGAAGAACTGCTGGGAGACAGAGGCGTCCTTTCGCCCAACCTTCGAGAACCTCATACC
CATTCTGAAGACAGTCCATGAGAAGTACCAAGGCCAGGCCCCTTCAGTGTTCAGCGTGTGCTGA (SEQ
ID NO: 91)
```

FIG. 11C

```
TYK2 protein (~134 kD)

MPLRHWGMARGSKPVGDGAQPMAAMGGLKVLLHWAGPGGGEPWVTFSESSLTAEEVCIHIAHKVGITPPC
FNLFALFDAQAQVWLPPNHILEIPRDASLMLYFRIRFYFRNWHGMNPREPAVYRCGPPGTEASSDQTAQG
MQLLDPASFEYLFEQGKHEFVNDVASLWELSTEEEIHHFKNESLGMAFLHLCHLALRHGIPLEEVAKKTS
FKDCIPRSFRRHIRQHSALTRLRLRNVFRRFLRDFQPGRLSQQMVMVKYLATLERLAPRFGTERVPVCHL
RLLAQAEGEPCYIRDSGVAPTDPGPESAAGPPTHEVLVTGTGGIQWWPVEEEVNKEEGSSGSSGRNPQAS
LFGKKAKAHKAVGQPADRPREPLWAYFCDFRDITHVVLKEHCVSIHRQDNKCLELSLPSRAAALSFVSLV
DGYFRLTADSSHYLCHEVAPPRLVMSIRDGIHGPLLEPFVQAKLRPEDGLYLIHWSTSHPYRLILTVAQR
SQAPDGMQSLRLRKFPIEQQDGAFVLEGWGRSFPSVRELGAALQGCLLRAGDDCFSLRRCCLPQPGETSN
LIIMRGARASPRTLNLSQLSFHRVDQKEITQLSHLGQGTRTNVYEGRLRVEGSGDPEEGKMDDEDPLVPG
RDRGQELRVVLKVLDPSHHDIALAFYETASLMSQVSHTHLAFVHGVCVRGPENIMVTEYVEHGPLDVWLR
RERGHVPMAWKMVVAQQLASALSYLENKNLVHGNVCGRNILLARLGLAEGTSPFIKLSDPGVGLGALSRE
ERVERIPWLAPECLPGGANSLSTAMDKWGFGATLLEICFDGEAPLQSRSPSEKEHFYQRQHRLPEPSCPQ
LATLTSQCLTYEPTQRPSFRTILRDLTRLQPHNLADVLTVNPDSPASDPTVFHKRYLKKIRDLGEGHFGK
VSLYCYDPTNDGTGEMVAVKALKADCGPQHRSGWKQEIDILRTLYHEHIIKYKGCCEDQGEKSLQLVMEY
VPLGSLRDYLPRHSIGLAQLLLFAQQICEGMAYLHAQHYIHRDLAARNVLLDNDRLVKIGDFGLAKAVPE
GHEYYRVREDGDSPVFWYAPECLKEYKFYYASDVWSFGVTLYELLTHCDSSQSPPTKFLELIGIAQGQMT
VLRLTELLERGERLPRPDKCPCEVYHLMKNCWETEASFRPTFENLIPILKTVHEKYQGQAPSVFSVC&
(SEQ ID NO: 92)
```

FIG. 11D

TYK2

AAGCAGTAGCTACCCGCGGGAGCGGGGAGGGGTCCGGGTTCGAGCTTGTGTTCCCCCGGAAGGGTGAGTCTGGACGC
GGGCGCGGAAGGAGCGCGGCCGGAGGTCCTCAGGAAGAAGCCGCGGGGACTGGCTGCGCTTGACAGGCTGCACTTGG
ATGGGAGCACCTGGTGCCTCGGGACTGCTCCGATGCCCGgtgggtgcacatcccagttcccgccgttgccggccggg
tttagaggtttttgggggggaggacatggggcgtgcagccttcccagttgcaaacttcactccgaccctgtcttcaaa
gctgggtctgggtccagtggggacgagaaaggaggaaggaggaagtaggctccgcgaaagccccatccccgggatct
catctataacatgaataggtattaatggcaaaggctaattaagcgcttactgtataccaggcactttctctgcctcc
tcgcgttaaatcctcccagcagccttttgaggtagacactgttacatgcccatttttccagatgaggaaaccagcaa
catgggtggaagtgacagcccctccacttccatactggcgcctcaggaggctcaggccctggattgggggggatgg    Ex 1
agctggacataaactctcctaggcttggggagtcaacagggactgaggtcactcatggggggtaaatgtgggagag
gagaattgtggcctgaaagaggccatcaccacgatgaaactaataacaattatgttattcttgttttggtcatattt
gttcttttgtgtgtgcctgaatcagGGTCTGTGCTGAATGTGTAATATGCGGAACTATATTGAAACATTACAACCA
TCTTTTGATGGCAACACCCTGAGGACCTCCCTTTTCCAGATGGGGAAACTGAGGCCCAGAATTGCTAAGTGGCTTGC
TTGAGTTGACACAGGGAGCTCCAGGACTCACCCTCAGgtatgtttgaccacatctgcctgtctggttattttgggga
ggtgtgttaagagcagatttttattttactttttatttatttatttatttatttatttatttattttattgtattta
gtagagatggggtttcaccatgttggtcaagatggtctcaatctccagacctcgtgatctgtccgccttggcctcc
aaagtgctgggattacagtcatgagccaccgcgcctggcccttttatatattttattacttattatttatttat
ttatttatatttttagagtcagggtctcactctgtcacccaggctggaatgcagtggtgcgatcactgctcactgca   Ex 2
gcctccaactcctgggctcaggagatcctcccacttcagcctcccgagtagcttggagtacagatgtgcaccccac
gcctggctaaatttttaaaaatttcttgtagaggccgggcacagtggctcacgcctgtaatcccagcactttgggagg
ccgaggcggtggatcacctgaggtcagaggttcaagaccagcctggccaacatggcaaaaccctgtctctactaaa
aatacaaaaattagccgggtgtggtggcaggcgccagctactcaggaggctgaggcaggagaatcacttaaacccag
gaggcagaggttgtggtgagcaagattgtaccattgcactccagcctgggcaacaagagtgaaactctgtctcaaaa
ataagataagataagataagataagataagataagataagatataaaataaaacgtcttgtagaaacagggt
cttgctatatggcctaggctggtctcgagctcctgggctcaagcaatcctcttgcctcaacatcccaaagtcctggg
attagaggcgtgagccactgtacctgggcagagcagatttttatatctgtgtcaatttgtggaaagagaggagggtt
cagtgttattgttgatgagagatctaggtggggatgcataccccaaccctgtccaataaatgtggaaaacgagactc
agagagggaatcgggtctctaatgtcatgccaagatgggagcccagaatcttcccctcaggccttagctggggtggg
tggaaggttgaagagctaacaggggtctctgggctgagacttgggagctgacagattgtcccctttccagCTGAGCC
ACCTGCCGGGAGCATGCCTCTGCGCCACTGGGGGATGGCCAGGGGCAGTAAGCCCGTTGGGGATGGAGCCCAGCCCA
TGGCTGCCATGGGAGGCCTGAAGGTGCTTCTGCACTGGGCTGGTCCAGGCGGCGGGGAGCCCTGGGTCACTTTCAGT
GAGTCATCGCTGACAGCTGAGGAAGTCTGCATCCACATTGCACATAAAGTTGgtgagtctggggcgttggcaccatg    Ex 3
gggactggggtgggtgtgcaagcagcagctggccccatccatccgtctatccacccacccaccatccacccaccc
atccacccactcatccatccatccatccatccacccatccacccacccatccacccatccaaccacccatccatcca
cccacccacccatccatccacccatgcatccatccatcctcccatccacccatccacccacccattcacccacccat
tcacccatccacccaccctttcacccatccacccatccacccattcatccacccacccacccacccatccatccacc
cacgcatccatccacccaccccaccatccatccacccacgcatccatccatacatccacccacccactcatcc
atccacccacctatccacctatccatccacctactcacccaccatccaccacctatccacccacccacccatcca
cccatccatccacccaccattcatccatctatccatccatccacccatcgatccatccatccatccacccatccatcc
atccacccatccatccacccaccatccatccatccatcatccatccatccatcatccatccatccatccaccca
cccacccatccatccacccacccacccatccatccatccatccatccaccccaccactcacccactcacccacctat
ccatgcatccatccacccacccatccatcctccacccatttcatccatctatccatccatccatccatccatc
catccatccatccatccacccacccaccctattcatccatctatccatccatccatccatccatccatccatccatcc
atccatccatccacccgttcatctggtgaacatttttgtaagcatctactgtgtggcagctgcaaatcactgcc
tttgtagagctgaaatttttagtagggaggacagcaagaaatataataaatcagaaaacttggccaggtgcagtagct
gacacttgtaatcccagtacttgaggaggcccaggcaggaggattgcttgaggccagtagttggagaccagcctggg

FIG. 11D (Cont.)

```
caacatagggagaccttgtctcaacaaaataattttttagaaattagccaggcatggtggtacatgcctgtagtccca
gcaacttgagagcctgaggcaagaggatcgcttgagcccaggagttcaagcctgcaatgaggtatggtttcgtcact
gcactccagcctgggtgacagagtgagacccagtgtcattaaaaaaagaaagtcaggccgggcgcggtggctcatgc
ctgtaatcccagcactttgggaggctgaggctggtggatcacttgaggtcagaagtttgagagcagcctggccaaca
tggcaaaactccagctctactaaaaatacaaaaactagccgggcgtggggtgcgcacctgtaattccagctactcag
gaggctgaggcaggagaatagcttgaacctgggacatggaggttgcagtgagccgagatcacagcactgcactccag
gctgggtgacagagctagactccgtttcaaaaataaaaaaaggccaggtgcggtggctcatgcctgtaatcccaaca
ctttcagaggctgaggcgggcagatcacctgagatcaggagttcaagaccagcctggccaatgtagtgaaaccgcat
ctctactaaaaatacaaaatgtagccaggcatggtggcaggtgcctgcaatcccagctactcagaaggctgaggcag
gagaatagcttgaacctgggacatggaggttgcagtgagccgagatcacagcactgcactccaggctgggtgacaga
gctagactccgtttcaaaaataaaaaaaggccaggtgcggtggctcatgcctgtaatcccaacactttcagaggctg
aggcgggcagatcacctgagatcaggagttcaagaccagcctggccaatgtagtgaaaccgcatctctactaaaaat
acaaaatgtagccaggcatggtggcaggtgcctgcaatcctagctactcaggaggctgaggcaggagaattgcttga
acttggggaggtggaggctgcagtgagctgagatcgtgccattgtactccagcctgggcaacaagagcgaaactccat
ctcaaagaaaaaaaaaaaaaaaaagaaagaaaggctttccctcctcctgcacaggaaattgcacttccaaatatat
ctactacagtctttcttttttttcttttttttgagatggagtctcgctctgtcccaggctgaagtgcaatggcgcaat
ctcagctaactgcaacctccgcctcccgggttcaagcgattctccggcctcagcctcccgagtagctgggactacag
gtgtgtgccaccatgcccggctagatttttttttttttttgtattttttagtagaggtggggtttcaccgtgttagc
caggatggtcttgatctcctgacctcgtgatctgcccgcctcggccctccaaagtgctgggattacaggtgtgagcc
accatgcccggcccaattttcttttttttaatgacatagggtctcactctgtcacccaggctggagtgcagtggtgtg
acctcagctcactgcaacctccatgtcccaggttcaagccattcctgcctcagccgcctgagtagctggaattac
aggtgcacaccccacgcccggctagtttttatattttagtagagctggagttttgccatgttggccaggctggtct
cgaacttctgacctcaagtgatccacctgcctcagcctcccaaagtgctgggattacaggcgtgagccaccatgccc
aaccaaggaaaggcctttctaaggcggctttggttacatataccttcctccagaaactcctcttacctccccattc
ccagctttccatgactggatgggggcattgtaatcaattttttataacacttcctacttcccattgatggctgagtc
ttttttttttttttctttcgtagagacagtctctctcttgcccaggctgaaatgcagtggtgcaatcatgacgcattg
cagcctctaactgccaggctcaagtgattttcctgcctcagtctcccaaatagctggggctacaggcacatgtcac
cacacccggataattttttgtatttttgcatgttgcctcatgctggtctcaaactcctgggctcaagccatccaccc
gccttggcttcccaaagtgttgggaggcatgagccatcgcgcctggccatgactgatttttttttttttttgaaac
gaagtctcgctcagtcctcaaagctggagtgcaatggcacaatcttggctcactgcaacctccgcctcccgggttct
agcgatcctcctgcctcagcctcctgagtagctgggattacaggcgcctgccaccacgcccagctaattttgtatt
tttagtagagacggggtttcaccatgttggtcaggctggtcttgaacatgcatgctgttccccctgcctcggcctct
caaagtgctgggatgacaggtgtgagccaccgtgcccggctttttttttttttttttttttgagacggagtctcgc
tctgtcacccaggctggagtgcagtggtgtgatctcggctcactgcaacctccgcctcccgggttcaagtgattctc
ctgcctcagcctcctgagtagctgggattacaggcgcccaccaccacacctggctaattttgtattttcagtagag
acggggtttcaccatgttggccaggctggtctcgaactcctgacctcaagtgatccacctgcctcagactcccaaa
gtgttgggattacaagtgtgcaccctcgagcctggccatggctgattctttgttttgttttgttgtgttgtttgaga
cagagtctcgctctgtcgcccaggctggagtgcagtggcgcgatctcagctcactgcaagctccgccttccgggttc
acgccattctcctgcctcagcctcccgaggagctgggactataggcacccaccaccacgcctggctaatttttgta
ttttagtagagacagggtttcactgtgctagccaggatggtctcgatctcctgacctcgtgatccgcccacctcag
cctcccaaagtgctgggattacaggtgtgagccactgtgcccgccccatgactgattattaaaggattcagacagg
tgtgcgggtgatgtgaaacacgctcagcagagggaacagcatgcatggaggcccggagagcttgatctgtttgagga
agcgaaagaccttcagggtgactggggtatcaattttgagagtttggaagggaagtaacaattgaaattggggcat
agcaggcaaaagccaggtgggggtactcagaatcaagggtcaaggggttgggcattctcgggagcaatggggagc
catggaaggtttaagccagagagtgaagcagtctgactagttcttttattttattttttattttttgactggttctt
taagaagttgtctcaagccaggcacagtgggtcacgcctgtaatcccagcactttgggaggctgaggcgggcagatc
acttgaggttaggagtttgagaccagcatggccaacatggtgaaacccgtctctactaaaaatataaaaattagct
gggcgtggtgacgcacatcccagctacttgggaggctgaggcaggagaatcacttaaacctgggaggcggagttgca
gtgagccgagatcgcaccactgcactccagcctgggtgacagagactcggtctcaaaaaacaaaaatatgaaacatt
```

FIG. 11D (Cont.)

ggccaggtgccgtagctcacacttgtaatccttgcgcttagggaggccaaggcgggtggatcacttgaggtcaggag
ttggagaccagtctggtcaacatgatgaaaccccatctctactgaaaatacaaaaaattagccgggcgtggtggcgg
gcgcctgtaatcccagctactcaggaggctgaggcaggagaatcgcttgaacccaggggtggaggttacagtgagc
cgagatcacgccactgcactccagcctgggcaacaagagcaaaaactctatccaaaaaaaaaaaaaatacaaaaaat
tagctgggcatggtggcacatgcctgtagtcccagctactcaggaggctgagacaggagaatgacttgaacctgaaa
ggcagaagttgcggtgaaccaagattgcaacattgcactccagtctgggtgactccatctaaaaaaaatatatattg
tttcacagggaggtatcctcccttcacagaggggcagtataattccatggtgtgactttggagagtgatttgataac
acagtcaaagctggatgcagtggctcacgcctgcaatcccagcagttttggaggctaagcgtggaggatcacttgag
cccaggagttcaagatcagcctgggcaacatcgcgaaacccgtctctactaaaaatacaaaaaattagccaggtgt
gctgtgtgctggtgtgcacctgtagtcccagctactcaggaggctgaggtgggaggatcacttgagcccgggaggtt
gaagctacagtgatcatgccactgcccttcagcctaggtgacagagcaagatgctgtctcaaaaaaaaaaaaaaaaa
aaaaaatatatatatatatatatatatatatagctgtgtgtggtggcgtgttcctgtatttcccagctactcaggag
actgaggcaggaggactgcttgagccagggaggtcatggctgcactgagccatgattgcaccactgtattccagcct
atatgtcagagcaagatcctgcttcaaaaaaaaaaaaaaacccaggccgggcgccgtggctcacgcctgtaatccca
gcactttgggaggctgaggtgggcgaatcatgaggtcaggagattgcgaccgtcctggctaacacggtgaaacccccg
tctctactaaaaaatacaaaaaattagctgggcatggtggcgggcgcctgtagtcccagctactcgggaggctga
ggcaggagaatggcgtgaacccaggaggcagagcttgcagtgagcggagattgagccaccacactccagcctgggcg
acagatcgagactccgtctcaaaaaaaaaaacaaaaactcagaaacatcttccctgaggccatatagttccactcct
ggacagtgacagtcactctataaacagtcagctcatgtgctcccagggacacttatgagaatgtttagagccgcctt
gtttatcatatggaaaggggagaccattgcaaagtccctcaataagagactgcctaagtaaattgcaatctggttg
aatactggactactgcgcagccgggagaaggaatttaaccagaattactcatgtcattctgcatgaagctttataac
ctctcgtagcctgaaaaagcacattgcagagggacgtctgcagtataataccacacatttacagttcataacttttt
ttttttttgagacagagtttcgctcctgttgcccaggttggagtgcaatagcacgatctcagctcaccgcaacctcca
cctcccaggttcaattctcctgcctcagcctcccgagtagctgggattacaggcatgcgccaccacgcccagctaat
tttgtattttagtagagacggggtttctccattttggtcaggctggtctcgaactcccgacctcaggtgatccgcc
tccctcagcctcccaaagtgctgggattacaggcgtgagccactgtgcccagccacagttcataacatttaaggcta
gattgtagaggatatgaaaattataaacactacttcagggcagagcacactggcttatgcctgtaatcccagcactt
tggaggctgagtagctcagcctcccagctactcaggaggctgaggtgggaggatcacttgagcctaggagtttgaga
ccagcctggacaacatggtgagacccctctctacaaaaactacaaaaatcagctgggcatggtggcgtgcgcctgt
agtcccagctccttgggaggctgaggcaggaggattgctttagcccagtaagtcgagggtgcagtgagccatgatca
caccactgcactccagccacacctggctaatttattttattttttagtttttttagagatgagggtctcactatgtt
gcttaggctggtcttgaactcctaggttcaagtgattctcccgccttagcctcccaaagtgctgggattacagatgt
gagccaccatacccagctttagataaaattatttatttcattttattattatttttttagacagagcctcactcttt
cacccaggctggagcgcagtggcgtgatctcggctcactgcaacctctgcctccaggttcaagcaattctcttgcct
cagcctgctgagtagctgcgattacaggtgctcaccccacacccagctaattttttgtattttttagtagagacgagg
ttttgctctggtggccaggctggtctcaaactcctgccctcaagtgcttcacctgcctcagcttccgaaagtgctgg
gactataggcatgggccactgcacccagccagataccatttttttttttttttttgagacagtcttgctgtgtcgcc
aggctggagtgcagtggcacaatctcggctcactgcaccctccacctcccggttcaagcgattgtcctgcgtcaac
ctccggagtagctgggactaaaggtgcaccccaccatggccagccaattttttttttttcagatctcactctgccgcc
caggctggagctcagtggcacgatcttggctcactgcaacctccgcctcccgggttcaagcagtcctcctgcctcag
cctcccaagtagctggaattacaggcacatgccaccaggtccagctatttttttttttaatagagatgggatttcac
catgctggccacgctggtctcgaactcctgacctcaagtgatccacctgcctcagactcccaaagtgttgggattac
aagtgtgcaccctcgagcctggccatggctgattctttgttttgttttgttgttgttgagacagagtctcgctc
tgtcgcccaggctggagtgcagtggcgcaatctcggctcactgcaagttccacctcctgaattcacaccattctctt
gcctcagcctcccaagtagctgggactacaggcatccgccaccatgcctggctaattttttgtattttttagtagag
acggggtttcaccatgttagccaagatggtcttgatctcctgacctcgtggtctgcccacctcagcctcccaaagtg
ctgggattataggcgtgagccactgcgcccggccgacaggtacaattttttaaatgacatcagtagaagaaagatacc
ctgggtagctggtgtgggaaattacagcaagtctggagactggattgggggttgaggtttgcatttgaaggtggtgga
tggagccccaggacatggagggtgcaggaagagcaggtcttggtgaccgatctgtttggagcaggtggggagaggtt

FIG. 11D (Cont.)

```
gaagataaggaccaagttcctggtttgaagaactgggcagaagccacacacctggctcatagccataatcccatca
actccagagattgaggtgggaggatcgcttgagccctggaggttgaggctgcagtgagctaggattgcaccactgca
ctgcaacctgggtggcaaagaaagaccctgaccettaaaaaaaaaggggcagaggaagggaaggttggagtttgcca
accacagataagatatgttgtttggaacaagccatatctaagggggggcctgtgatgtccagggggagacagccagg
aggtgactggatgtttctttggggctggagttcagggagacgccagacaattgcagcagtttgtagagttatgtggg
tcaggctaggattagttttgctgcaggaataagcaatcccccaaatcttaatcaaggtttacctaaaatcggccga
gcacagtggctcatgcctgtaatctcagcactttgggggggccaaggtgggcagatcacctgaggtcaggagtttgag
accagcctggccaacatggcgaaaccctgtctcttctaaaaatacaaaaactagccggggttggtggcgcacacctg
taatcccagcaactcaggaggctgagacaggagaatcacttgaacccaggaggcggaagttgcagcgagccaagatc
gtgtcactgctctccagcctgggcaacagcaagactccatctcaaaaaaaaaaaaaagttttttacttaaaatcaagt
acaggttggatggttcacctctgtcttacagcttcaccatctgtcacaagaagccttcatcatacctcgggtggtga
aggtggcaagagaatttattccaggcttggaaatgtaccagcccttttggccagaaaccagcagtgcaattggctc
catcctagctgcaagggaggctgggaaatgtagtcctcctgtgaggccacagcatgggcaacatacgcactgtcctc
tgcccaggggcaacgtgagactgaagctgcaggtgggggagggggcctcagaggggagtgtgaaggcagacattgggt
ctgggggggtctttgggggctgacggtagcaaatgacgtgactcctgacctcgtttctcacctgatccagGTATCACTC
CTCCTTGCTTCAATCTCTTTGCCCTCTTCGATGCTCAGGCCCAAGTCTGGTTGCCCCCAAACCACATCCTAGAGATC
CCCAGAGATGCAAGCCTGATGCTATATTTCCGCATAAGgtgggtggagaccttttgcaaagctcgtccctcctgtgc
tgaagctggtctgactctgtgctaagcccagctgcgtccctccttcctgcagGTTTTATTTCCGGAACTGGCATGG
CATGAATCCTCGGGAACCGGCTGTGTACCGTTGTGGGCCCCCAGGAACCGAGGCATCCTCAGATCAGACAGCACAGG
GGATGCAACTCCTGGACCCAGCCTCATTTGAGTACCTCTTTGAGCAGtatgagcagggctggggtggcaagactat
ttgtgggagacttaggggcagttgaggagccccatttccctccctgattcaatatagctaataggtttcaactcat
gctatctgggatctttttttttttttgagacggagtcttgctctgtcgcccaggctgaagtgcagtgatgtgatc
tcggctcactgcaagctccgcctcccaggttccgtcattttcctgcctcagcctcccaagtagctgggactacagg
cgccgccaccatgcccagctaattttttttgtattttttagtggagacggggtttcacagtgttagctaggatggtctc
catctcctgacctcgtgatctgcccgcctcggcctcccaaagtgctgggattacaggcgtgagccaccgctcccagc
cgatctttttttttttgaaatggagtcttgctctgtggcccaggctggagtgcagtggcgtgatctcagctcactgca
acttccacctcccaggttgaagcgattcttccacctcagcctcccaagtaactgagattacagaagcccgccaccac
cccaggctaatttttctatttttagtaaagacggggtttcaccatgttggccaggctggtctcaaactcctgacctc
aagtgattcacctgcctcagcctcctaaattgtgggattataggtgtgagccaccatgcccagccaagagttcaggt
tgaaggggatagagtgctgtgattgattagtaatgtctgccacaggcacaagattgacaagaggagggtgtatgct
gtgtatttggccttttccagtaaatggtggtctctccctcctcaaggtggtaagacgcaggaaattagagttctctg
gctagagtaagcttgtccaacccctggcctgcggactgcatgctgcccaggacagctttgaatgaagcccaacacaa
attcataaactatcttaaaatattctgagatttgctgtgattttttttttttttgagacagagttttcattcttgt
tgctcaggctggagtgcaatgtcatgatctcagctcactgcaacctctgcctcccaggttcaagtgattctcctgcc
tcagcctcccagtagctggattacagacatgcgccaccacacctggctaatttttgtattttttagtataggcgagt
tttctccatgttggtcaggctggtctcaaactcctgacctcaggtgaccccgccgccttggcctcccaaagtgctgg
gattataggcgtgagccaccatgccccggcttgcgatattctttttttttttttttttagctcatcagctatcatt
agtgttagtgtattttatgtagggcccaagacacttcttccagtgtggtccaggtagccagaagattggatacctc
tgggctagagaggaacgcattctcacacctccctttctgctcaatttcctgttcccagGGCAAGCATGAGTTTGTGA
ATGACGTGGCATCACTGTGGGAGCTGTCGACCGAGGAGGAGATCCACCACTTTAAGAATGAGAGCCTGGGCATGGCC
TTTCTGCACCTCTGTCACCTCGCTCTCCGCCATGGCATCCCCTGGAGGAGGTGGCCAAGAAGACCAGgtgtctggg
aatgggtggggacgctgtgtaggcagggggaaatgtcctgagcatctgggagccagggtagactttgcatattgcc
gtgcctctactttttttttttttctgagccggagtctctctctgtcacctaggctggagtacagtggcgcaatcttgg
ctcactgcaacctctgcgtcccaggttcaagagattctccttcctcagcctcctgagtagctgggattacaggtgcc
caccatcaagcccagctaatttttgtatttttagtagagacagactgagtttcatcatgttggccaggctggtctcg
aactcctgacctcaagcgatcctccgcccttggcttcccaagtagctgagactacaggctcaagtcaccacacctgg
ctagtgtgcctgttttccagatgaggcagctgaggctcaaagaggttaagccacttgccctgtgtcacccagctggg
cctgcaaccccaggtccctgaccagccctcactgtgttttcccccagCTTCAAGGACTGCATCCCGCGCTCCTTCCG
CCGGCATATCCGGCAGCACAGCGCCCTGACCCGGCTGCGGCTTCGGAACGTCTTCCGCAGGTTCCTGCGGGACTTCC
```

```
ggccctgggagatcagctgctaactttcaccatggcggtattctgtgccacatgatcccgcagCTGTCCCACTTGGG
CCAGGGCACAAGGACCAACGTGTATGAGGGCCGCCTGCGAGTGGAGGGCAGCGGGGACCCTGAGGAGGGCAAGATGG
ATGACGAGGACCCCCTCGTGCCTGGCAGGGACCGTGGGCAGGAGCTACGAGTGGTGCTCAAAGTGCTGGACCCTAGT
CACCATGACATCGCCCTGgtgagtgggcagggccaggcctggggtgtgtctgtggaggaggtggccggaggaggtg
ggatgggagggtgtgtctgtggaggaggtgggatgggaggggtgtgtccgtggaggaggtgggatgggagggtcg      Ex 15
gctttgcagccacctgacctgcccgtccccacagGCCTTCTACGAGACAGCCAGCCTCATGAGCCAGGTCTCCCAC
ACGCACCTGGCCTTCGTGCATGGCGTCTGTGTGCGCGGCCCTGAAAgtgagtgggtcccgccataccatcccccctt
tggcaggccaccctgacttataccoactccctgatctgtacccaaccctcgacctacacccaacctatgcctat
ttctcaactctcacctgtactctgatcccgggctacaccttgaccttcaacctagaccccaaccctaacgatattc
cagcccataacttacatcccaacacgtcgaccctcacctgcctcagtctcaaccccacctgattcccaactaca
tccccacttccatcaacctcccaaacaacctctacagtccagccccatctgctcctggcccatcagcactatggc
ctcaggcagactccagtgctgatgtgtgctgattctctaggcctcagccctgcacatccaacctgcctaaccc
acctcttcctttcctctgcaggtagctcaaaactccttgtataggctaggtgtggtggctcacacctatcccagcac
tttgggaggcagaggtgggaggatcgcttaaacccaggagttcaagaccagcctgggtaacatgtccagacccta    Exonic
tttacaaaaatttaaaaatcagggccaggcatggtgacctatgcctgtagtcctagctacttgtgaggctggaatg   junction
gaaggatcacttgagcccaggagttcaaggctgcagtgagccatgattgtaccactgcactccagcctgggcgacag  for
ggcgagactctgtctcaaaaaatataataaataaataaaaaataaagcccttgtacagaacaaccctagaccccaccc NPM/TYK2
atccctcaacccctgtgtgtgtgtgtgtgcatctcccccactttccctggaccctggccgacacctgaccc
acatccctctgactactctggtacccaaacatctcctacacccaacctcaagccctagcctctgcttatccatgc
ccatccccccatccctagttgcttactttgtaggctcacctttatctctttttttgtgagactagggtctccctct
gttgcccggctgcaatgcagtggtgccatcatggctcactgaagcctcgacctcccgggctcaagcgatccttccg
cctcagcctcttgagcacctgggatgacaggcgtgtgctatcacacccggctgattttaaaaattttttgtagaga
tggggtctcactatgttgcttaggctgatctcaaactcctgggctcaagggatcttcctgcctcagcctcccaaagt
gacaggattgcaggcatgagccactgtacctgccacctttatctcttttttttttaattttttgagacggagtc
tcactgtgtcacccaggctgaatacagtggcgtgatctcggctcactgcaacctccgcctcccggttcaagcaat       Ex 13
tctcctgcctcagcctcccgaatagctgggattacaggcatgtgccaccatgccagctaattttttttttttctt
cttttgagatggagtcttgctctatcgcccaggctggagtgcaatgacgtgatctcggctcactgcaagctccgtc
tcccaccattcttctgcctcagcctcccaagtagctgggactaccggcgcccaccatgcctgcctaatttttttt     Ex 14
gtctttttagtagagatgggtttcactgtaattttttttgtattttagtagagttggggtttcaccatattgacca
ggctggtctcgaactcctgaacttgtgatccgcccgcctcagcctcccaaagtgctgggattacaggcgtgagccac
cgcgcccggctgtattttttttttagtagtgatggagtttcatcatgttgggcaggctgcccttgaactcctgacc
tcaggtgatccacctgcctcagcctcccaaagtgctgggattacaggcgtgagccactacgccagcccacctttct
ctcttgaacttcaacttcttccgtgccccatcccacttggaccccaatgccctcatccaccgctgcctctgctgcat
tccgcatttcttctctcccaaactcactttcaacccagaccaaactccacccacctctgccctgacacctcccc
agccacatgccaagtccctccctggcgtctccccaattcccgccatccagagggcagaagcaggcaggttgcccc
agagcagctgtgtcttacagATATCATGGTGACAGAGTACGTGGAGCACGGACCCCTGGATGTGTGGCTGCGGAGG
GAGCGGGGCCATGTGCCCATGGCTTGGAAGATGGTGGTGGCCCAGCAGCTGGCCAGCGCCCTCAGCTACCTGgtgtg
tggcctgtgtgtggggcctgggtcggtcaggagggccaggagcccaggagttcgagaccagcctgggcaacagggc
gagaccccatcttttgtttgttttgttttaggtggagtttcgccctgtcaccaggctggagtgcaatggcatga
tctcggctcactgcaaccttcgcctccgggttcaaatgattctcccgcctcagcctcccaagtagctgggattata
ggctcctgccatcacgcccagctaattttttgtatttttagtagagatgggtttcaccatgttggtcaggctggtct
cgaacttctgacctcgtgatccatccgcctcagcctcccaaagtgctgggattccaggcgtgagccaccacgcccag
ctgcccatctttaaaaataaacaaatagccaggtgtggtggctcatacctgtaatcccagcagtttgggaggcc
aaggcgggtggatcacctgaggtcaggagtttgagaccagcctggccagtatggcaaaaccttgcctctactaaaaa
tacaaaaaaattagccaatgtggtaacttgcacctgtaggccgaggtactcaggaagttgaggtgggaggatcacc
tgagctcaggaatttgaggccgtagtaagctatgatcacaccactgcaccccagcctgggcagcagcatagctagac
cccatctccaccaaaaatttaagaatcagctaggctgtggtgatgtgcacctgtaattctcgctacttggaaggctt
gagcccaggagtttgaagctgcagtgagctatgttcgtgccactatactccaacctgagagacagagtgagacctg
tcttaaaaaaaaaaaaaaaaaaaaacaagaaaaaaataaccccccaaaaaacaaaacagaaagaaacccagtga
```

```
cgggaaggagtttggggggttgaggataaattcctacctaaggtgattctcaggagatgtgggtgggaccctctgctt
tgagggaggcctaggtgccaaggagtcttaatagagcggagtaggcgggcctggggtattccgaaaggatctgcct
ggaggagtggcccgggaaatcgggggttggggagtggtgcagggattggggaggtggagctgaccctcgtgcgctcc
cgaccagGGTCACTTCGGCAAGGTCAGCTTGTACTGCTACGATCCGACCAACGACGGCACTGGCGAGATGGTGGCGG
TGAAAGCCCTCAAGGCAGACTGCGGCCCCCAGCACCGCTCGGGCTGGAAGCAGGAGATTGACATTCTGCGCACGCTC
TACCACGAGCACATCATCAAGTACAAGGGCTGCTGCGAGGACCAAGgtgggcggaccccggcgagtcctagagactt
gaggggggcgtggttagagcgtgggtgtggccttgtgggcggggccagtctggcctagccaattagagactctcaacc
ccaggctgcagtacgcggttcttggcatctgggtgagcgtggctgggctgcctccttcccatctgggggtgctacc
tgctggggccaggatggacgggagccaccagcagctccctcaagtgagaatgggggttctggatgggtccatcccacc
tgagaactgggtctagtgtgcgcgggtcttggccttccctcccgaccttggagggggctctgctgggctcaaggtagg
cggtccccggcccgccctctatcgtccccacgggccgcccctctccgcggcagGCGAGAAGTCGCTGCAGCTGG
TCATGGAGTACGTGCCCCTGGGCAGCCTCCGAGACTACCTGCCCCGGCACAGCATCGGGCTGGCCCAGCTGCTGCTC
TTCGCCCAGCAGATCTGCGAGgttggtcggccccgcccctgcttctggagcttgccccttcctcttcagcttgggct
ggcctgagcgatccggtgcagtctgctctcacgctccgcccctgctcgtttgcccaggctgtcttgtccttgcactg
acctccgaactgtttggcttgcttggccacaccccctcctcccaagggaccacgcacagcggctcggcccctccca
actcgccctcctgcccagctttgctcgtctagccccgtccctgctttctggctcagcctcctttgcttggtgccac
gtgccatccggccctctccagcggccgggtagccaccggcctgacctgactgtccccagccctcctggctgctcag
gtcctgccgccgccccggccgaacccgccccactgaaactcacgagccctgccccgtcccagGGCATGGCCTAT
CTGCACGCGCAGCACTACATCCACCGAGACCTAGCCGCGCGCAACGTGCTGCTGGACAACGACAGGCTGGTCAAGAT
CGGGGACTTTGGCCTAGCCAAGGCCGTGCCCGAAGGCCACGAGTACTACCGCGTGCGCGAGGATGGGGACAGCCCCG
TGTTCTGgtgaccaggcggggtgcagtctgagggggtgctgggggtcacttggaacaggcagggtggagtagacggat
gctgggtatcatgataggcatgatcccagtgaagcgcggcggggcctagcggtgcggggtggggcctatggaggc
aaggggcggtgtatagagtgcggcttggcctggtgggcggggttaacccggcctagccaatgagcggcctagccaat
gagcatatcaccccgctcaggctgcgctcttaaggggtgggtcccaactgagcccagagggtccttcagtctcaggtg
agggcttcagcctggtctgatccccaagccctcagtgcagccccgtggcctgagtgccccctccccctagGTAT
GCCCCAGAGTGCCTGAAGGAGTATAAGTTCTACTATGCGTCAGATGTCTGGTCCTTCGGGGTGACCCTGTATGAGCT
GCTGACGCACTGTGACTCCAGCCAGAGCCCCCCCACGgtgagagccaggcccgcagcccaccgggagtttgctaga
gcaattagaaaggcataggctgggccaggcgcggtggctcaagcctgtaatcccagcactttgggaggccgaggcgg
gcggatcacgaggtcaggagatcgagaccaacctggctaacacggtgaaaccccgtctctactaaaaatacaaaaaaa
attagccaggcgtggtggcgggcgcctgtagtcccagctactcaggagactgaggcaggagaatggcatgaacccgg
gaggcggagcttgcagtgagccgagatctcccgactgcactccagctgggtgacagagcgagactccgtctaagaca
ggacaggacggagagagagagaaagaaaagaaaggaaagaaagggcataggccgggcgcggtggctgacacctgtaat
cgcagcactttgggaggccgaggcgggcagatcacgaggtcaggagatcgagaccagcctggccaacatggtgaaac
cccgtctctactaaaaatacaaaaattagccgggcgtggtggcaggtgcctgtaatcccagctactcaggcggctga
ggcagggagaattgcttgaacccggtaggcgaaggttgcagtgagccgagatcatgccactgcactccagcctgggt
gaaagagcgagagactgtctcaaaaaaaaaattctggacggtaagaacaatctgctgtgaggcttaataataacggc
aaacacctgactcacgcttactctatgaatattagtttaacgttcacagtaatccaggtggcagatgttattaccc
tatttttacggatgagaaaacaggcccagagaagtgaactcaaattcaaagtcacacagctgagaagtgtaagaggtg
ggattggaacccatgcagtcgatttcatgaagttgcagagtgattttcttttcttttttgagatggagtttcacact
tgtatcccaggctggagtgcaatggcacaatctcggctcactgcaacctccgcctcccaggttcagacgatcctcct
gcctcagcctcccaagtagctgggattacgggcgcctgccattatgcccagctaattttttgtattttttagtagagat
ggggtttcaccatgttggccaggctggtctcgaactcctgacctcaggtgatccaccacctcagccttccaaagtg
ctgggattacaggcatgagccacgctgcctgcctttcattgcctcttgaaaagagcttgtcttgtttatactgtagA
AATTCCTTGAGCTCATAGGCATTGCTCAGGGTCAGATGACAGTTCTGAGACTCACTGAGTTGCTGGAACGAGGGGAG
AGGCTGCCACGGCCCGACAAATGTCCCTGTGAGgtgagacttcctttgtctttccctgaccccactatcctgctgtg
gagagggcagccccccaccagccctggttttttccttctagGTCTATCATCTCATGAAGAACTGCTGGGAGACAGAGGC
GTCCTTTCGCCCAACCTTCGAGACCTTCATACCCATTCTGAAGACAGTCCATGAGAAGTACCAAGGCCAGGCCCCTT
CAGTGTTCAGCGTGTGCTGAGGCACAATGGCAGCCCTGCCTGGGAGGACTGGACCAGGCAGTGGCTGCAGAGGGAGC
CTCCTGCTCCCTGCTCCAGGATGAAACCAAGAGGGGGATGTCAGCCTCACCCACACCGTGTGCCTTACTCCTGTCTA
```

GAGACCCCACCTCTGTGAACTTATTTTTCTTTCTTGGCCGTGAGCCTAACCATGATCTTGAGGGACCCAACATTTGT
AGGGGCACTAATCCAGCCCTTAAATCCCCCAGCTTCCAAACTTGAGGCCCACCATCTCCACCATCTGGTAATAAACT
CATGTTTTCTCTGCTGGA (SEQ ID NO: 93)

FIG. 11E

Intron involved in TYK2 translocation

```
gtgtgtggcctgtgtgtggggcctgggtcggtcagggagggccaggagcccaggagttcgagaccagcctgggcaac
agggcgagaccccatctttttgtttgttttgttttaggtggagtttcgccctgtcacccaggctggagtgcaatgg
catgatctcggctcactgcaaccttcgcctcccgggttcaaatgattctcccgcctcagcctcccaagtagctggga
ttataggctcctgccatcacgcccagctaattttgtattttagtagagatggggtttcaccatgttggtcagget
ggtctcgaacttctgacctcgtgatccatccgcctcagcctcccaaagtgctgggattccaggcgtgagccaccacg
cccagctggccccatcttttaaaaataaacaaatagccaggtgtggtggctcatacctgtaatcccagcagtttggg
aggccaaggcgggtggatcacctgaggtcaggagtttgagaccagcctggccagtatggcaaaaccttgcctctact
aaaaatacaaaaaaaattagccaatgtggtaacttgcacctgtaggccgaggtactcaggaagttgaggtgggagga
tcacctgagctcaggaatttgaggccgtagtaagctatgatcacaccactgcacccagcctgggcagcagcatagc
tagacccatctccaccaaaaatttaagaatcagctaggctgtggtgatgtgcacctgtaattctcgctacttggaa
ggcttgagcccaggagtttgaagctgcagtgagctatgttcgtgccactatactccaacctgagagacagagtgaga
ccctgtcttaaaaaaaaaaaaaaaaaaaaaaaacaagaaaaaaataaccccccaaaaaacaaaacagaaagaaaccc
agtgatagtcacagttgtccttttcacattggctgtccctatggggaccaggtttggggttggcgtctgtgcctctc
ctgagtggccacaccccctctcctgcccacctcag (SEQ ID NO: 94)
```

FIG. 12A

NPM 1 cDNA  1449 bp

AGAAAGGAGTGGGGTTGAAAAGCGCTTGCGCAGGACGGCTACGGTACGGGGGTGGGAGGGCTTCGGAGCA
CGCGCGCGGAGGCGGGACTTGGGAAGCGCTCGCGAGATCTTCAGGGTCTATATATAAGCGCGGGGAGCCT
GCGTCCTTTCCCTGGTGTGATTCCGTCCTGCGCGGTTGTTCTCTGGAGCAGCGTTCTTTTATCTCCGTCC
GCCTTCTCTCCTACCTAAGTGCGTGCCGCCACCCGATGGAAGATTCGATGGACATGGACATGAGCCCCCT
GAGGCCCCAGAACTATCTTTTCGGTTGTGAACTAAAGGCCGACAAAGATTATCACTTTAAGGTGGATAAT
GATGAAAATGAGCACCAGTTATCTTTAAGAACGGTCAGTTTAGGGGCTGGTGCAAAGGATGAGTTGCACA
TTGTTGAAGCAGAGGCAATGAATTACGAAGGCAGTCCAATTAAAGTAACACTGGCAACTTTGAAAATGTC
TGTACAGCCAACGGTTTCCCTTGGGGGCTTTGAAATAACACCACCAGTGGTCTTAAGGTTGAAGTGTGGT
TCAGGGCCAGTGCATATTAGTGGACAGCACTTAGTAGCTGTGGAGGAAGATGCAGAGTCAGAAGATGAAG
AGGAGGAGGATGTGAAACTCTTAAGTATATCTGGAAAGCGGTCTGCCCCTGGAGGTGGTAGCAAGGTTCC
ACAGAAAAAAGTAAAACTTGCTGCTGATGAAGATGATGACGATGATGATGAAGAGGATGATGATGAAGAT
GATGATGATGATGATTTGATGATGAGGAAGCTGAAGAAAAGCGCCAGTGAAGAAATCTATACGAGATA
CTCCAGCCAAAAATGCACAAAAGTCAAATCAGAATGGAAAAGACTCAAAACCATCATCAACACCAAGATC
AAAAGGACAAGAATCCTTCAAGAAACAGGAAAAAACTCCTAAAACACCAAAAGGACCTAGTTCTGTAGAA
GACATTAAAGCAAAAATGCAAGCAAGTATAGAAAAAGGTGGTTCTCTTCCCAAAGTGGAAGCCAAATTCA
TCAATTATGTGAAGAATTGCTTCCGGATGACTGACCAAGAGGCTATTCAAGATCTCTGGCAGTGGAGGAA
GTCTCTTTAAGAAAATAGTTTAAACAATTTGTTAAAAAATTTTCCGTCTTATTTCATTTCTGTAACAGTT
GATATCTGGCTGTCCTTTTTATAATGCAGAGTGAGAACTTTCCCTACCGTGTTTGATAAATGTTGTCCAG
GTTCTATTGCCAAGAATGTGTTGTCCAAAATGCCTGTTTAGTTTTTAAAGATGGAACTCCACCCTTTGCT
TGGTTTTAAGTATGTATGGAATGTTATGATAGGACATAGTAGTAGCGGTGGTCAGACATGGAAATGGTGG
GGAGACAAAAATATACATGTGAAATAAAACTCAGTATTTTAATAAAGTA (SEQ ID NO: 95)

FIG. 12B

```
NPM1 ORF 885 bp

ATGGAAGATTCGATGGACATGGACATGAGCCCCCTGAGGCCCCAGAACTATCTTTTCGGTTGTGAACTAA
AGGCCGACAAAGATTATCACTTTAAGGTGGATAATGATGAAAATGAGCACCAGTTATCTTTAAGAACGGT
CAGTTTAGGGGCTGGTGCAAAGGATGAGTTGCACATTGTTGAAGCAGAGGCAATGAATTACGAAGGCAGT
CCAATTAAAGTAACACTGGCAACTTTGAAAATGTCTGTACAGCCAACGGTTTCCCTTGGGGGCTTTGAAA
TAACACCACCAGTGGTCTTAAGGTTGAAGTGTGGTTCAGGGCCAGTGCATATTAGTGGACAGCACTTAGT
AGCTGTGGAGGAAGATGCAGAGTCAGAAGATGAAGAGGAGGAGGATGTGAAACTCTTAAGTATATCTGGA
AAGCGGTCTGCCCCTGGAGGTGGTAGCAAGGTTCCACAGAAAAAAGTAAAACTTGCTGCTGATGAAGATG
ATGACGATGATGATGAAGAGGATGATGATGAAGATGATGATGATGATTTTGATGATGAGGAAGCTGA
AGAAAAAGCGCCAGTGAAGAAATCTATACGAGATACTCCAGCCAAAAATGCACAAAAGTCAAATCAGAAT
GGAAAAGACTCAAAACCATCATCAACACCAAGATCAAAAGGACAAGAATCCTTCAAGAAACAGGAAAAA
CTCCTAAAACACCAAAAGGACCTAGTTCTGTAGAAGACATTAAAGCAAAAATGCAAGCAAGTATAGAAAA
AGGTGGTTCTCTTCCCAAAGTGGAAGCCAAATTCATCAATTATGTGAAGAATTGCTTCCGGATGACTGAC
CAAGAGGCTATTCAAGATCTCTGGCAGTGGAGGAAGTCTCTTTAA (SEQ ID NO: 96)
```

FIG. 12C

NPM protein (~35kD)

MEDSMDMDMSPLRPQNYLFGCELKADKDYHFKVDNDENEHQLSLRTVSLGAGAKDELHIVEAEAMNYEGS
PIKVTLATLKMSVQPTVSLGGFEITPPVVLRLKCGSGPVHISGQHLVAVEEDAESEDEEEEDVKLLSISG
KRSAPGGGSKVPQKKVKLAADEDDDDDEEDDDEDDDDDFDDEEAEEKAPVKKSIRDTPAKNAQKSNQN
GKDSKPSSTPRSKGQESFKKQEKTPKTPKGPSSVEDIKAKMQASIEKGGSLPKVEAKFINYVKNCFRMTD
QEAIQDLWQWRKSL (SEQ ID NO: 97)

FIG. 12D

Homo sapiens nucleophosmin (nucleolar phosphoprotein B23, numatrin) (NPM1), transcript variant 1, mRNA
NCBI Reference Sequence: NM_002520.6

AGAAAGGAGTGGGGTTGAAAAGCGCTTGCGCAGGACGGCTACGGTACGGGGGTGGGAGG
GCTTCGGAGCACGCGCGCGGAGGCGGGACTTGGGAAGCGCTCGCGAGATCTTCAGGGTC
TATATATAAGCGCGGGGAGCCTGCGTCCTTTCCCTGGTGTGATTCCGTCCTGCGCGGTT    Ex 1
GTTCTCTGGAGCAGCGTTCTTTTATCTCCGTCCGCCTTCTCTCCTACCTAAGTGCGTGC
CGCCACCCGATGAAGATTCGATGGACATGGACATGAGCCCCCTGAGGCCCCAGAACTA
TCTTTTCGgtaactgctggggggagctggagcgaggccgagcggggcctggtggcggtg
agggtgggggtgagggcgggaatccggctgcaaccgggtctggtggagaccgccagac
cgacggggaggcctgagcgggtgggaagagctgcctgagccctggacctggagggattgg
agccgcggggggagccggtggcgtgaaggggaggagacgagcggcctgaagcgtctgg
ggcgtgagcggtccgaggcccggggcctgaggtaaagtggaaccggccgcctggaagtt
cggcctttgccggggatacgtggcggagctccaggcgtggtttatttctaacggcggt
ggttcataggcttctgatgccaggccccgggttggtggtcctggaggctgggttcaccg
ggaagcatgggcctgcttgttggagcgggtagatgcacagcctggcgttattctggcct
cagagcctggagctgccggacgtagacttacctcgcgtgcttcggccagttactggggg
tggggaggcgcggcgcggcgtgaggaggccgcaaccgctgggagcacgtggttgccacg
tggttgggggagggagggggtgtgggcgctacatccgggactcaccggcgtgttgcca
ctcgtgagccagggatgctgtggctctgttgaagtgggaaatgttaagaggctggtagc
actagggttctggaggtctttgttcagtgcttacagcatgtactgtgatgcagctctc
atttttttgagcccctttctgtctcactgcggtaggtggagctagccccactttgcag
atgaggatactggtgcccagagataaactcacttaacgaaggttgtacttagtaaaggc
aataagagactaaatctaaaccaagacgcttgactccgtagctgctgcttcgtgaatat
taatgaggcttcgttttaggggacgtcctcgcatgccgccatttgtgcggcattgacc
aaactgcttttctaaatacaagaaacacgtagagtgttcggtttgagtcagatcaagac
ctaagactattcgcagaatttttgggagcaccacccccctcgacttgcggtagtcctgcc
ccaaaaaggagagtcccacttgggttttgatctcagtaggattaattgcagaagccta
atctttgtactattcagactttgaagtaaatgcaaatcctaccgtgaattttatcttgt
tcattatccgtgctgagatttgttaattaaacgtctgttcacatttaagcatgtatatg
tattggtaacggttagatgatagttaaatggaatcatttaaaattttattctgacagt
gttttgaagaatttgcccattcatggagtgagagtagacatatgtattcaaaacatta
aggctttaattcctagttattttggatagctgagaattctggtaaatttatatcagtac
ttttgataactatcggaaagaaccctccttgtcttaaacataatttctgaatatagtt
tgaggcgtatgtcacttctgttgctttaaagagtggagtgttgatccctgtagcaaac
ttcggttcttttactttgtcattttctttgtaatagtaagctattcatgtttgtaa
ccgttctcatttcgaaattgccatttgggaatttaggtaggtaaatcagctgttttaaa
tagtgggaaacttaacattggacattacatttggtttcagataattgcttcaggttgag
atttactaaaccattgagcttgtttatgcagaataacagtacctatcagcgtagttaga
gatgaaatatggtatgatgagagaatggaattatagtcttttatgggtgtctgtagagg
tttctgttcaagaaatctaggaattgatcattctgctttgccctctggtagctaaaata

FIG. 12D (Cont.)

gtgaaaaactagttcaaaagttagacctgacctttttggttacccacacttaagtttca
gtgttattttctccttgttagagttgcttttttcttcatttacagGTTGTAACTAAA
GGCCGACAAAGATTATCACTTTAAGGTGGATAATGATGAAAATGAGCACCAGTTATCTT
TAAGAACGgtacttaaactttcaaaataaactacttaaccctacttgatttcagccttt  *Ex 2*
tagtttctattcatgtggcttgagacttttttcctttgctgactgcttataaaatact
atttcttcacctgggtattgtgtgtacctcactgtctgtacatctttgaagaacttgg
catctataccactcatttggtaaccatgtaaattccagtcacactgttcaacttgcctt
attttcttcagttgaattacaaagcccttgtaaaggcatcgataatctttcatgtcta
ccagagactagccttctgctcaacttagaagttgctcaataaatatgttaggtggtcta
tattgtgtgtatgcatatttatgcatttcttaaattttctgaatatgagaaactgattt
gccaagatcacaaacctgaggacaacattgcacaaattgttttccagggtaatagtg
agaggtttatacttgtttttaaaaaatcacagtcatgtgcctcattgcaactgctgg
gtcaacagatggatcgcatatacaatggtggtcccataagattattatacttattttt
aatatacctttcctgtttttttttttctttggaggcagtctcgctctgtcacccaggct
ggagtgcagtggtgtaatctcggctcactgcaacctctgatttccgagttcaagtaatt
ccctgcctcaccctcccgagtagctgggattacaggcatgtgccaccacacctggctaa
ttttgtgttttagtagagacgaggttgttaccatgttgtccaggctggtctcaaact
cctgacctcatgatctgcccgcctcagcctccctaagtgttgggattacaggcatgagc
caccaagcccggcccttcctatgcttagatgcacaaatactgtgtttcggttgcttac
agtattcagtacagtaacactgtacaggtttgtagcctaggtgtgtgtagtaggctata
ccatctaggtttgtataagcacattcttatgattgtacaaagatgaaattgtctaacaa
cacatttctcagaacctagccctgtggttaagtgacgcatggctgcatataacatttag
tgggggggtgtaaaataggtggaactcaaaagttgaagtagtatttttttttgttcac
agGTCAGTTTAGGGGCTGGTGCAAAGGATGAGTTGCACATTGTTGAAGCAGAGGCAATG
AATTACGAAGGCAGTCCAATTAAAGTAACACTGGCAACTTTGAAAATGTCTGTACAGCC  *Ex 3*
AACGgtaagggcacttacatactttggatgttgtgtcaaggtttaattctgttttaagg
taggtttggtgtcatttagttgtgccaaggagatagaaagtggttctttatcttctgtc
actggagttcgatggtcaactcttgaacatggggcttctgctgctacttttatcagag
gtggaaaaacaggttcactggtttgttgatttggcttatgtgtttgcctgtaatgttta
ttgttcatttttcttcacatgtttagtgatgaaaaatttctcccttctagGTTTCCCTTG
GGGGCTTTGAAATAACACCACCAGTGGTCTTAAGGTTGAAGTGTGGTTCAGGGCCAGTG
CATATTAGTGGACAGCACTTAGTAGgtatgttattttatatattatactacttagttt  *Ex 4*
gtcctctttagtgcagttgcttggttcccagtttggacttaaagcatgggtatagtact
actgtcttttttaataggttccaatgtgagtctagaaattggagaggacaaataaattt
tggggcggggggagaggaaatcttgctgtcacccaggctagagtacagtggcacgatc
ttggctcactggaacctctcgggattcaagcgatcctcctgtctcagcctcccagta
gctggggccacagacgtgcaccaccaagtccagttgcgtttcatagttatagtagagaa
ggggtttcgtgatgttggccaggccgatcttgaactcctggccttaacgtgatctgcac
gccctggcctctcaaagtgctagtattacacgtgtcagccactgtgcctggcctaaaaa
ttatttttaataaagacagtctcattataacggctggagtgcagtgatgtgatcatag
cttgctatatcctcgaactgctactgggttcacctcagcctctggaatagctagaacta
caggcacactccacgcctggctaattttttttgtatatgtgcagatggggtctcagtat
gttgcccagattggactcttggcctcaagtggtccgccttggcctccccaaagtgagat
tacaggcatgagccaccctccccaggcttcttgcatttaaaacctggcagtgaacatta

FIG. 12D (Cont.)

```
ggcctcaaaatactttttgttaaaaagttccttttcccatgtgctctttttttttttt
tttaaatagaatagaagtctcagtttttagagtatttactatcagtgttctttttttt
ctgacttcttgctgcttgagttttataatgtctaataaattgtattttagCTGTGGAG
GAAGATGCAGAGTCAGAAGATGAAGAGGAGGAGGATGTGAAACTCTTAAGTATATCTG      Ex 5
GAAAGCGGTCTGCCCCTGGAGGTGGTAGCAAGGTTCCACAGgtagagatggcaatttt
attataggttttgtattatagcttttagtttggtgatagaacagctcttgttcatgagt
acgtatcttttctttttaaaagAAAAAAGTAAAACTTGCTGCTGATGAAGATGATGACG
ATGATGATGAAGAGGATGATGATGAAGAgtaagtatgattttagaaacttgatatact    Ex 6
tccggaatcttgacaaaaaaggaatttgacatagttatatgcatgagggttttataa
aagtcatttacaaaagccatcctatgtaatagtttataataaagggcaggtggtcat
ctgttgtcagtttaagttaaatgagctgagttgaaaggatattgggtctgtgagccttt
acaatgctgtgacttgtgactcttcagaagggtagactatagtgtttgtgaagtttgat
tatgtccctttgttctgaagatttagtggatgtgttatacccatcaagcctggtatgtt
ttatggtgagcagttaatgagattgggttgaaagaaaatatgattaaatagctctatat
tcattttacaagttgttactcaaggtttgttattccctaaaaggatttttgtcttatggt
tttatgtagatatttattgacaaaaataagattctaaaagggatattaagatttttcttg
ggatttaaaatatggttggaaacaatatttgatgactttatattaaactagatcaaact
attgttacaaacagttaatacgcacactggtataaagtactgtttataattggtcttat
gtgtgccagtaccagtaatgcattgaatactttgatttggctctcagctttgtccttca
gttctgaggttggtccatatgcatttattgaaaacaaatataagaacatgcactttaaa
agagaacctgcatgaaagatcaaattgggagtttaggttttaagctggtggttcttcaa
aatctttgagcatgacgatgaaggcagaaaacaggaaaaaggccgaaagagccgaaagc
ttaaaaattcaaagtatgaccaggcgcagtggttcacacccgtaatcctaacacccagc
caagatgagaggatctcttgaggccagcccggtcaaaatagcaagacccaatctcaaaa
gaaaaataaaaattcaaagtacttgcatgtcaaacttataaatgaacgcaaacttaaag
gtagtatttgactgttgctgtttttgttttctttttttttttttttttttttgagatgg
agtctccagttgctcaggctggagtgcggtggcgccatctcggctcaccacaacctctg
cctcctgggttcaagcgattgtcctgcctcagcctcccgggtagctgggactgcaggct
cggggcaccatgccctgctaattttgtatttagtagagacagggtttcagtatgttgg
tccggctggtcttgaactcctaacctcgtgatctacctgcctcggtctcccaaagtgct
gggattgcagatgtgaaccactgcgcccagccaaatttttgtattttaatagacatgg
ggtttcaccacgttggctaggctattctcaaactcctaacctcgggcgatctggtcacc
tcatcctcccaaagtgctgggattacaggcatgagccaccgtgcccggccactttttt
cttgagatggtgttttaccatgctactcagactggacttgaatctctgggcacaagcta
tcctcccctctcagactatgaagcaggtggggttacaggagcataaccaagcccagctt
gtttggttatcacttttaagaatatttctcgttagtaagaattgaaatacattccaaga
gaagaatgggaaacaggctaaaaacacaaattagaaatagggatggtatggttcggatt
ggtttagtctgattttgagttacctttgtacaagtttataaaataagtgtttaatagca
ttcaccgaggctcggggacaagcaatcccttccagaaaggctttggagtaggacctgat
tgtagtattgaccctgttggggctttggaagatttccttttttaaaaattgatataatt
aggccaggcatggtggctcacgcctgtaatcccagcactttgggaggctgaggtgggtg
gatcacttgaggtcaggagttcaagaccagcctggccaacatggtgaaaccccgtatct
actaaaaatacaaaaattagctgggtatcgtggtgcctgcctattggtcccagttactt
aggaggttgagtcaggagaattgcttgaacctgggaggtggaggttgcagcaagccaag
```

FIG. 12D (Cont.)

```
aatgcgccaccgtgttccatcctgggcaacagagggagactcccatctcagaaaaatgg
gtataaattcatgatgtaaccacaatgtaattttgtttgtctttaagttgggcattgat
aggaatgaaaagtgtagatatcaaggtccaaatcagtacctggtttttttttgtgggatt
ttttttttttcggcaagtctcgctcttgtgcccaggctggtgtgcaatggtatgatct
ctgctcgctgcaacctctgccttccaggttcaagtgattctcctgcctcggcctccaga
gtagcttggattacaggcacttgccaccacgcctggctaagttttgtattttagtaga
gacggggtttcaccatgttggccaagctggtctcgaactccaaagtgctgggattacag
gcgtgagccaccatgcaccgccgcaagttttcatataagttgaagaaagtgtactaagg
tctgcatagtagtaaggatgccttgagggaaacaaatattaatagaaacttcagtggt
gagatggcaagggcccagcatagatagatggcaatgaaaatgcaaagaggtgcatgaag
gttcgttatagttacttagaaatctaacctttgaacacagatcaaaggggaatttggt
tccttttgaggatggaatgggtatatggtgtgggctcagatgactcttgatttaagca
agaaaggctatgtaatgtgcatagtgctgatgtatactatacatagatgtatgtaatac
gttgatagtatgtggcccttaaatgtctttttaattttggggaatttcttaagtaaa
gctgaattttttttttttttttggagacagtctctgttgccccggctgaagtgcattg
ttggctaggctggagtgcagtggtgcaatcatggctcactgtaacttctgcctcccggg
ttcaagtgattctcctgcctcagcctcccaagtagctgggattacaggcatgtgccagc
atgccaggctaattttttgtattttaatagagatggggtttcgccatgttggtcaggc
tagtcttgaactcctgacctcaggtgatctgcccaccccagcctcccagagtgctgaga
ttacaggtgtgagccaccacaccctgccagtaaagctgttttgatagtagttttgatag
ctattttgatagtagtttaatagacttgttttaacaaataagaaaaaatgtttaaaaaa
agcattctcatcttgtttctagcacaggggaggcacctgcagggattgggttctaatgc
cagaaacttgtactgacaaaatcactgttaaaaagccacttgaagggctatttgtgaca
gcttttaagttatgatacttttctaaatacagcaaatatttcttcggtattggaaag
ataggtgtttcttacatgaagttgctgtattgggatttagagaccagtacgttcagttg
ttgaattaaacgtgaacccttggtatttgctaatagagacttctgcctgacttgccct
ccagtgactcgatttgattactcccctccattgtttacctattaacagttcacacctgt
aatcccagcactttgggtggtcgatgcgggcagatcacctgaggtcaggagttgaagac
cagcctggccaatatggtgaaaccccgtctctgctaacatacagctgggtgtgatggtg
ggcgcttgcaatcccagctgctggggaggctgaggcaggagaattgcttgaacccggga
ggcggaggttgcagtgagccgagatcgcaccattgcattccagattgggcaacaagagt
aaaactcaaaaaaaatagtgtgcagttcagtggttttagtatgcatagttgtgtagcc
atcaccataatcaatttagaacatttcatccctcaatgagaaatcgtactctatagg
tattaccctcatgctcttcagctctagtcaaccacgaatgaactttgtctataggttt
cctgtccctcatattttgcacgaatggacttctgtgactgttttcttagcacagtgttt
tcaagtttcatccatgttatagcattatcagtactccatttatttatatggttgaatac
attgtatgggtatgtttggttattcatcagttggtgagcatttgagttgcttctacttg
ttgactgctatgaacgcttgtagacatgtcatttacttggatgtacacctaaagcaga
gtggctcacccattgtattcccactagcagtgtatgggcttctgatttcactccaacc
tactgatttcactacaccctcacttgccattatctgactctaatcctggtggtatgaag
tgctgattgtgggtttgattgcgtctccctgtggactaataatgagcatcttttcatgt
attcattggccatatctttggagaaatgttttgcccacttaaatccatttacttct
ctttgtctttactaagttgtaagaattcttttttcttttttcttttttgatatgatttt
gtatttttagtagagaagggttttgccatgttggccaggctgttcttaaactcctgtc
```

FIG. 12D (Cont.)

```
ttcagtgatccacctccctctgcctcccaaactgctgagattacagctgtgagccactg
tgcctggcaagaattcttttttttttttttttgacaagtctctgttgcccaggcttgag
tgcagtgatgtgatcttggctcactgcaacctcctcctccttgttcaagcaattcttc
tgcctctcccaagtagttgggattacaggcaccccccaccacgcccggctaatttc
tgtatttaaatagagaccgggtttcgccatgttggccaggctggtcttgaactcctga
ggtcaggcccgcctcggcctcccacaagtgctgggattacaggcgtgagccactgcact
gggcccaagaattctttatgtattctgcaaacaagtcccttatcagacacaagatttac
agattatcttccaccattcgtgaattgttacttaactttcatgatggtggcctttgaa
caagttttaattttatgacgtccgatttcttttgttgcttgtgcctttggtgtcaat
cctaagaaatcattgctaaattcaaagttgtgaaatttgccccttaattctgagttt
tgtcctttatatttagggctttgttccatttgagtaaacttatgtgtatggtgtgaat
ggaggggtctaaatatagactttggatgtagattagcagttgcccaacatgatttgtt
caaaaactattttttccccattgaatgatcttggcaacctttaaaagagtcacttatgg
ctgggtgtggtggctcacacctgtaatcccggcactttgagaggctgaggcaggcggat
catgaccaggagattgagactatcctggccaatttggtgaaaccctgtctctactaaaa
atacaaattttagctgggcatggtagcgtgtgcctgtagtcccagctactcaggaggct
gaggctggagaattcgcttgaacctgggaggcagaggttgcagtgatctgagattgcac
cactgcactccagcctggcgacagagcgagactccgcctcaaaaacaaaaaatcact
gtttctggactgttctgttgatgtgtctatccttaacatgtaagaacagtacaacactg
ttcctctgtggtttttatttatttatttttttgaaatgagtctcactgtcacccaggct
gtagcacagtggcgtgatcttggctcactgcaacctccgcctcctggttcctcctgctt
cagcttcctgagtagctgggattacaggcgcccgccaccatgcccggctaattttgta
ttttagtagagactggggtttcaccattagccaggctggtctcaaactcctgacctcag
gtgatctgcccgtctcggcctcctaaaaagtgccgggattacaagcgtgagccacggtg
ccttggcccctttgtaggtcttatagctgatttttgaaatcaagtgtgagttttctag
ctttcttcctttccagattgcatttggcctctttgggtcccttaagtgtctttttgtt
tttgtttttgagatagggtcttgctctgtcacccaggctggagtgcagtggcagaatt
acacagttacagttcactgtctcaagcagatcctcctgccttagcttttcaaatagcta
ggactacaggcgcacaccaccacgcctgctaattaaaaatttttttgtagagagggtt
ctcattatgttgcctaggctggtcttgaactaaaacgatcctcccacctcagcctcccca
aagtgttaggattataggtgtgagacactgtgccagttcttgggtttgtttataaattt
taggatctgtttctacagagaaaccagcttggggagtcttctaacgattgtatttaacc
tgtatattcggggagtgtttccatcttggcaatatctgaacatggaatgtttctattta
ggtctttaattttttttttaacacaaattcactctgagtgtacagttaatagaacta
tacattacttaaatatacatacattatacagtggtatagtgtgtatttatgcaaaacta
ctcattgagcaacttcatttcccagccctagcgatcacaattataccttctatttctt
tgagtttgactacttttagatacttaatgaatagaatcatacagtgtttgttcttttgt
ggctggcttatttcactttgttcaaggttcagtcatgtagcatgcaagaggattttcat
tgtgtgtacatatcattttcatttagtcatttaacacttgggttgctttcacctcttg
gctgttgtgaacaatgcttcgataaacatgggtgcacaataatcacttcaaggtcctg
ctttcaattcttgtgtctactcccaaattttgaaagtgcttaatgtcttgacatttcat
ttgtagTGATGATGATGATGATTTTGATGATGAGGAAGCTGAAGAAAAGCGCCAGTGA
AGAAAgtgagtagatacaatgctacaaggttgttaaactaacaatagaaatggtgattt
tttagtgctatttgcttgttttgtagttaagggaagctggtgtgggagatcatctcata
```

```
ctgaaaattagtcctgaggaggattacagaaaacttaagagtgggaatggtctgtttt
ctttatccatgtggccctccacccagttgttagtcttgtgtaaccttttgtccaagtg
gttgctgcttttccttccttttttttttttttgagacggagtctcaatgtcacccg
ggctggagtacagtggcgcgatctcagctcactgcaacttctgcctcccgggttgaagc
gattctcctgcctcagcctcctgagtagctggaattacagactcatgccaccaccca
gctaattttgcattttagtagaccaccatgtcggccaggctggtctcgaactcctga
cctcgtgatccacctgcctcggcctcccaaagtcctgggattacaggcatgagccacca
cgccaagcctgtggttgctgcttgtcttacatggcttggacagctttgtttgcactgtt
gttggggtcagggacagtgattaagataaatttctaattgcagTCTATACGAGATACTC
CAGCCAAAAATGCACAAAAGTCAAATCAGAATGGAAAAGACTCAAAACCATCATCAACA   [Ex 8]
CCAAGATCAAAAgtaagtggctacatttacacgtgggtctcattgatctagttgggaa
aaagattctactgtggaagaatctagtgtgtctgaaatttgataggcctttatagaacc
cctgtaattgctgtttaaaagttaaaatcagcttgctgcagccaggctcagtggctcac
tcctgtaatcccagcactttgggaggaggccaaggtgggtgggatcacctgaggtcag
gagtttgagactagcccggccaacatcgtgaaaccctgtctttactaaaaacacaaaaa
ttagccaggcatggtggtatgtgcctgtaattccacctactcaggaggtggagacagga
gaattgcttgaacctgggaggtggagtgcagtgagattgcaccactgcactccagcttg
ggcaaaagagcgagactccgcctccaaaaaaaaaatcagcttgttgtgtgttgtaggt
acacacacacacaaacatactaaatgtaaggtggtggggcggggggagccaatagac
tttttgaaagagatggaccctcactttgtcactcagtctgggttagagttgcgtgatc
tcggcttactgcaaccttcacttcccgggttcaagcgattctcctgcctcagcttccca
agtagctgggactacatgcgcgtgccaccaggcccagcgtattttgtattttgagta
gagatgggggtttcactctatatgttggccaggctggtctcaaaccctgactgcaggtg
atccgccctcctgggcctctcaaagtgtgtgagccaccacgcctggcctgaatttttg
tgattgtgaagtcaatagttgtttcctgtaaggaatctttgttgaaaggtatgtctgca
tagagtagaagttctcaaccttggctgcatgttagcttgaagtagaacatttgggccta
gacagggtgtattgatctcattcctgaccctacccacttccctgcagaaaatgaattt
aaaggaaaaaagtttaaaggaaccccagtacttgtgctctacttatggagattgtcat
aaaaatggtctgggtgggcgccaggcatcagactacagtgacttcttgctttattct
tagggattttctgatttccttttttttttttttaacctgatgaaatagtttatttac
aattaaacgaataaatttcatattctacaacacatataatctattgactaaatgtaac
taatgatgaacctccatacaaacaaccccactaaaaagtgggcaaaggacataaacaga
cactttcaaaagacatacaagtggccaaaagcatatgaaaaacagctcaatatcact
gattagagaaatgcaaatcgaaaccacaatgagataccatctcacaccagtcagaatag
ctattattaaaaactcaaaaaacaacagctgctggcaaggttgcagaaaaagggaatg
cttacacactcttggtgggagtgtaaattagttcaaccattgtggaaagcagagtggcg
attcctcaaagagctaaaaacagaactaccatttgacccagcaatcccattacattccc
aaaggaatataaatcattctaccataagatacatgcacacaaatattcactgcagcac
tattcacaatagcaaagacatggaatcaacctaatacctgatatggtctggctttgtgt
ccccacccacatctcatctcaaattgtaatccccacgtgttggaagaggggcctggtgg
gaggtaattggatcatggggtagatttccctcttgctgttctgttgatagtgaattctc
atgagatctggttgtttgaaagtgtgtagcacctcccctttgtgtctctctcttctg
ctgccatgtaagatgtgccttgcttcccctttgccttctgccatgattgtaaatttcct
gtggcctcctagccatgcttcctatacagcctacagcactgtaagtcaattaaacctct
```

FIG. 12D (Cont.)

```
tttcttcataaattacccaatctcaggtagttctttttttttttttcattttatttat
ttatttatttattttttattttttattttttttttaatttattttttttattgataattct
tgggtgtttctcacagaggggatttggcaggtcatgggacaatagtggagggaaggt
cagcagataaacaagtgaacaaagtctctggttttcctaggcagaggaccctgcggcc
ttccgcagtgtttgtgtacctgattacttgagattagggattggtgatgactcttaacg
agcatgctgccttcaagcatctgtttaacaaagcacatcttgcaccgccttaatccat
ttaacCctgagtggacacagcacatgtttcagagagcacagggttgggggtaaggtcac
agatcaacaggatcccaaggcagaggaattttttcttagtgcagaacaaaatgaaaagtc
tcccatgtctacttctttctacacagacacggcaaccatccgatttctcaatcttttcc
ccacctttcctgcctttctattccacaaagctgccatcgtcatcctggcccgttctcaa
tgagctgttgggcacacctcccagacggggtggtggccgggcagagggctcctcactt
cccagtaggggcggctgggcagaggcgcccctcacctcccggacggggcggctggccgg
gcaggggggctgaccccccacctccctcccggacggggcggctggccaggcggggggg
ctgaccccccacctccctcccggacagggcggccggccgggcgggggctgaccccc
cacctcctcccggacggggcggctggccgggcagagggctcctcacttcccagtagg
ggcggccgggcagaggcgcccctcacctcccagacggggcggctggccgggcggaggc
tgaccccccacctccctcccggacggggcggccggccaggcggggggcttacccccc
acctcccttccggacggggcggctggccgggtgggggggctgaccccccatctcccgg
acgggtggctggccgggctgagggctcctcacttcccagtagggcggccgggcaga
ggcaacctcacctcccggacggggcggctggccgggcgggggctgaccccccacct
ccctcccggacggcacggctggccaggtgggggctgacccccacctccctcccgga
tggcacggctggccggtcgggggctgaccccccacctccctcccagatagggcggct
ggccgggcggggggttgaccccccccacctccctcccggacggggtggctgctgggcg
gagatgctcctcacttcccagatggggtggctgccgggcggagaggctcctcacttctc
agacggggcagctgccgggcggaggggctcctcacttctcagacggggtggttgccagg
cagagggtctcctcacttctcagacggggcggccaggcagagacgctcctcacctccca
gacggggtctcggccgggcagaggcgctcctcacatcccagatggggcggcggggcaga
ggcgctccccacatctcagacgatggggcggccgggcagagacgctcctcacttcctaga
tgtgatggcggctgggaagaggcgctcctcacttcctagatgggatggcggccgggcgg
agacgctcctcactttccagactgggcagccaggcagagggctcctcacattccagac
gatggggcggccaggcagagacactcctcacttcccagacggggtggcggccgggcagag
gctgcaatctcggcactttgggaggccaaggcaggcggctggaggtgtaggttgtagt
gagccgagatcacgccactgcactccagcctgggcaccattgagcactgagtgaacgag
actctgtctgccctgatttccttttttgaactgacttagtactgtgcataaagcaaac
tcccaagttactctttttttttttatttaaagagatgggtggcctactcttgcccaggt
tgaagtacagtggtatgatcatagctcactacagcctccagctgctgggcttaagcaat
cctcctgccttagcctcctgagtagctgggattacaggcatgcaccaccatgcctagct
aatcatcttattccttccttaaagaaagatttta agaacaaaattatatggcgtgaat
ttattgatgataattccagttgtataattagctttataaggagttttgtgagaatatt
tgaggaaatccagatagaatgggttttaattaggaattgtatttattcttatgacctt
tggaaattcatttcttttcagGGACAAGAATCCTTCAAGAAACAGGAAAAAACTCTA
AAACACCAAAAGGACCTAGTTCTGTAGAAGACATTAAAGCAAAAATGCAAGCAAGTATA
GAAAAAgtgagtaaagttatcttaaaaaaactttgtctcccccctcaaattgcacgtgt
ctggtttgcatagacttgaatgtttcttgtttttttgtttgttttggtttaatatactt
```

[Ex 9]

Exonic junction for NPM/TYK2

FIG. 12D (Cont.)

```
gcctggttcgtggtatgaattttttcaaaaatttcttataaaacatttataatcgtgtc
tgtggtgatttttgcatatgcaaaattaaatatgccttattttccattatgcaaggaac
gtagtgcactggttgcaagataacattctgaccttccatgttaaaatagatcagtgaaa
acoctttgcctattctggttgtaagatatgctagagaaccaacagagggcgtatgagac
ttcattaaaattacaaacagctggaaaagtagatgctggctgttgcttggtattatagt
taatattcatgattgaccctagtcagaagtgatttcagcagattgagacatttctctt
tgcccttacaccaagttgtcaccagttaatacatgtagtaatagctagatttcgtgaa
tgactaataggcttaaatctagtttcctttgtcttaaataatggaaatgtgggaagag
ggttaggtctctcatctgcttgactgggggatttgagtaggatatggaataaatggttt
aaatgccttggaagcacatttgagagaagctttaattctatgaataatacttttagact
ccaactattgagagcaaatgtgggtgtgaaaaattgccaactcatttccccatgttt
ttcttgtaatctatagattttcgtggcttcagtagattccttgtacagtgataagtcc
actggaaaaagaatttagaactggaacatatttctttagtcacactgtaaaccccttt
agccttctggttatcactgattttgtccttggatacaatgctaaaatgacatcttt
tagatgccctccctccatttaatatggtcctatctccttggtttaattgcaggcgc
attgaacagtcctgggcactacatgtaaattaagcccaaagatggggagaaaggaaaag
gagagacaaatatagtccatactgagtgtcatcaacaatccagactgaagtcttctatt
ttaatctcaatcccttttctgatttgccacccatgcctcttcaggctggaaacaatct
cttggttccctaaagcactttcttctgactgctgtgattcagtgaaccttgcccttgc
tttctattacttgtgcatttgcctcacctgacaatgttaaatcgcctttgtatctcc
ttagctgctcaataaatatttgaatgcatcaattaagaatgtatgtgacaataattttg
aaatggaaattgtgaggtttatttactaggttattggaggcagttaagtttcttaatg
ctatacctgattctgccaaagtcccttggacatttgaaaaccttttcaatcttttaaaa
atgcataaaagatacttagagggaaaggtattaattaaatttagtaaaaacaaatatat
tcaatgctttaaattccaaagtagtgataaatacaaacatttcaagatatttgcaatag
taatgttttgaaatttggttacaaagtcacaggtcttgccaatactgttgtagtttct
tgcctatatccgtaatttgaaggaaatggtgagagtgattagagaagtgtaattactgt
aatttttccctattgtagtttcttgcctgtatccataatttgaaggaaatggtaaga
gtgattagtgaaatgtaattactgtaattttttccccattcaactttatatatctttaa
ctgatgaccagatcattgttgttctgaaccagtttgtggtcagcaagtgttttgtgggg
ttttgtttgtttgttttaaagaacagtttgggtcacttgacatggttctccaaaggga
tgttatgggttgtatttggttctggtgataaccgacttgttagataatttagataagc
aaccgagttgccatgtttgtttgtcgaatctcaagtgtagcttatatttatgttccta
gagaggttgtcagggaagatttgacccttggcaaatctgtttgaatagagatactagc
catgctgcccaatagggctttctggccctgaaaaagatacggagtattcttggaaagtt
gaagggaaaagaataaactgatccatgtagtagcatgcagattattgaggaatttct
aaaggtatctctctcggtgtatttctctacttacctgtaataatgcttttgtcttaata
gGGTGGTTCTCTTCCCAAAGTGGAAGCCAAATTCATCAATTATGTGAAGAATTGCTTCC
GGATGACTGACCAAGAGgtaactggattttctggggacatgattaaatccaagtttttt
tgtgatttattatgattctgccttacccttttaagtgttggctcttttaaaaagtt
cctaaccacagataatatttcatttaatgaaatacctgaaaactcatgtatttaatgaa
atgcatgaagaatacagttggcagtctgagatgataactttagtatattttcccagat
ttcctatagttggtaaattatttcttggttattgaattcagttttactttttggtact
atgttggttaaggaaattgctgtggttttccttgctgttccatttgactgcttggggca
```

```
gtctggtcttggcttttttgggagttggtagagatctttttttttttttcctagatct
tatgggaaatacattatgccaaaatcatcctaacatgaaatctggaagcaagacactaa
attgtggctactaccagatacataagcttgagttagctgttagattttacagttagtac
atgtgaaagtcttagtcaacataaagattatgcatttattttgctcttatttacagtt
gactcataagtgtaaggacaatgtaaaagtggttaaatagggatgttaggtatcgtgtg
gagaacggatgctgcatttaatggtctttaggtttcctgtggtcagctttttcaaaaa
attaggaaaatttggcaattagctggtttttttctgccatagtattttgcacttcaat
tatttaattgcacttcaattttagttttcgggttcgtaaaccctgataatggttaat
tttgagtttagctttgtgaaagttgtagtgatgggctataagatgatcaggttcagtct
ttggttgctgttctgttttttctctacatttgaatcctaaagtttaaagtgtgagtttt
gggagtttatttggaatactaaacattgattaatcataaattatttgaaactccgcgt
tatgcaactgtttatttaatattgaaaatagtggaaagtcagacataaataaccagcat
gtactaacagctaagcagcataagagatgcattcttcaactactgccaaggaaagtgat
gataaatttaatgattaagttgcagtagtcttctgtactttataacaaaggcttgtagc
tacaaagtcttgtagctattaaattactgaaccagcacttctacaagaagtattttctt
tttataaaagtattttggccaggttggtcttgaactcctggcctcaagcagtcctcc
catctttcctcccaaagtgctaggattacaggcacgagccaccttgcccagcctacca
gaagtattttttgctctagaattgaaagtgttctcaagtgtcagaatgaaatttctgg
aataaatagtaaatgtttaataacttgaacttgaattgctgttacagagattatcaaaa
ctaaatgcttcctgttttgacatagagatgcatgatgcaagcaacgacaatgtatatt
tgtttgaacctgatgataagatctctggctgggcgtggtagttcatgcctataatccca
gcactttgggaggcaacatggcaaaactctgtctctactaaaaatactaaatttagctg
ggcatggtggcatgtacctgtaatcccactactcaagaggcggaggcaggaggatcgc
ttgaacctgggaggcagaggttgcagtgagcgccactgcactccagtctgggtggcaga
gtgagagtctatctcagaaagaaagatttctatgatatttaatattggcattcggtatt
cagttaccttgtacctgagaacccattggctgtgaaacagtgacagctgagagaatcct
gagtcatctcatttctagttcttggtgaacttctggacttttcttcagaaccaccttgc
catgttggccaggctggtcttgaactcctgacctctcaggtgatccaacaccttggcct
cttaaagtgctgggattacaggcatgagccaccatgcctggccagctgtttttttgtt
ggtttgttttttgttttggtacccatctgtagtgtgatcttggctcactgcaacctctg
cctcttgggctcaggcagtcctcccacctcagcctcctgagtagctgggcctcctgtag
ttgcacaccaccaagcctggctaattttttgcatttttagtagacagggtttcaccatgt
tgcccaggctggtctcaaattcctgagctgaagtgatctgcccgcctcagtctcccaaa
gtgtagggattacaggcgtgagccaccatgcctagcctcagcatatagttttttctaaa
tgtacacatgcccaggcacacatgcacaggcaattcagaataagtttctggtgtttatg
taactttatttgccaaatctggccaactctaaagctgatctcgggagatgaagttggaa
gtaacattggccatatgggtctctgttctttctgttgatttccttaagtaaataatgct
aaactattaaataattattagtatattgttcacattttatgactgattaaagtgtttg
gaattaaattacatctgagtataaattttcttggagtcatatctttatctagagttaac
tctctggtggtagaatgaaaatagatgttgaactatgcaagagacatttaatttatt
gatgtctatgaagtgttgtggttccttaaccacattctttttttttttccagGCTA
TTCAAGATCTCTGGCAGTGGAGGAAGTCTCTTAAGAAAATAGTTTAAACAATTTGTTA
AAAAATTTTCCGTCTTATTTCATTTCTGTAACAGTTGATATCTGGCTGTCCTTTTTATA
ATGCAGAGTGAGAACTTTCCCTACCGTGTTTGATAAATGTTGTCCAGGTTCTATTGCCA
```

AGAATGTGTTGTCCAAAATGCCTGTTTAGTTTTTAAAGATGGAACTCCACCCTTTGCTT
GGTTTTAAGTATGTATGGAATGTTATGATAGGACATAGTAGTAGCGGTGGTCAGACATG
GAAATGGTGGGGAGACAAAAATATACATGTGAAATAAAACTCAGTATTTTAATAAAGTA
(SEQ ID NO: 98)

FIG. 12E

Intron involved in NPM1 translocation

```
gtgagtaaagttatcttaaaaaactttgtctcccccctcaaattgcacgtgtctggtt
tgcatagacttgaatgtttcttgttttttgtttgttttggtttaatatacttgcctgg
ttcgtggtatgaattttttcaaaaatttcttataaaacatttataatcgtgtctgtggt
gattttttgcatatgcaaaattaaatatgccttattttccattatgcaaggaacgtagtg
cactggttgcaagataacattctgaccttccatgttaaaatagatcagtgaaaacccctt
tgcctattctggttgtaagatatgctagagaaccaacagagggcgtatgagacttcatt
aaaattacaaacagctggaaaagtagatgctggctgttgcttggtattatagttaatat
tcatgattgaccctagtcagaagtgattttcagcagattgagacatttctctttgccct
ttacaccaagttgtcaccagttaatacatgtagtaatagctagatttcgtgaatgacta
ataggcttaaatctagtttccttttgtcttaaataatggaaatgtgggaagagggttag
gtctctcatctgcttgactggggatttgagtaggatatggaataaatggtttaaatgc
cttggaagcacatttgagagaagctttaattctatgaataatacttttagactccaact
attgagagcaaatgtggggtggtgaaaattgccaactcatttccccatgtttttcttg
taatctatagattttttcgtggcttcagtagattccttgtacagtgataagtccactgga
aaaagaattttagaactggaacatatttcttttagtcacactgtaaacccctttagcctt
cctggttatcactgattttgtcccttggatacaatgctaaaatgacatcttttagatg
cccctcccctccattttaatatggtcctatctccttggtttaattgcaggcgcattgaa
cagtcctgggcactacatgtaaattaagcccaaagatggggagaaaggaaaaggagaga
caaatatagtccatactgagtgtcatcaacaatccagactgaagtcttctatttttaatc
tcaatccccttttctgatttgccacccatgcctcttcaggctggaaacaatctcttggt
tccctaaagcactttcttctgactgctgtgattcagtgaaccttgcccctttgctttcta
ttacttgtgcatttgcctcacctgacaatgttttaaatcgcctttgtatctccttagct
gctcaataaatatttgaatgcatcaattaagaatgtatgtgacaataattttgaaatgg
aaattgtgaggtttatttttactaggttattggaggcagttaagtttcttaatgctatac
ctgattctgccaaagtcccttggacatttgaaaaccttttcaatcttttaaaaatgcat
aaaagatacttagagggaaaggtattaattaaatttagtaaaaacaaatatattcaatg
ctttaaattccaaagtagtgataaatacaaacatttcaagatatttgcaatagtaatgt
tttgaaattttggttacaaagtcacaggtcttgccaatactgttgtagtttcttgccta
tatccgtaatttgaaggaaatggtgagagtgattagagaagtgtaattactgtaatttt
ttcccctattgtagtttcttgcctgtatccataatttgaaggaaatggtaagagtgatt
agtgaaatgtaattactgtaatttttcccattcaactttatatatctttaactgatg
accagatcattgttgttctgaaccagtttgtggtcagcaagtgttttgtggggttttgt
ttgtttgttttaaagaacagtttgggtcacttgacatggttctccaagggatgttat
gggttgtatttggttctgggtgataaccgacttgttagataatttagataagcaaccga
gttgccatgtttgtttgtcgaatctcaagtgtagcttatattttatgttcctagagagg
ttgtcagggaagatttgacccttggcaaatctgtttgaatagagatactagccatgct
gcccaatagggctttctggccctgaaaaagatacggagtattcttggaaagttgaaggg
aaaaagaataaactgatccatgtagtagcatgcagattattgaggaattttctaaaggt
atctctctcggtgtatttctctacttacctgtaataatgcttttgtcttaatag (SEQ
ID NO: 99)
```

FIG. 13A

```
NPM1/TYK2 cDNA 2711 bp

AGAAAGGAGTGGGGTTGAAAAGCGCTTGCGCAGGACGGCTACGGTACGGGGGTGGGAGGGCTTCGGAGCA
CGCGCGCGGAGGCGGGACTTGGGAAGCGCTCGCGAGATCTTCAGGGTCTATATATAAGCGCGGGGAGCCT
GCGTCCTTTCCCTGGTGTGATTCCGTCCTGCGCGGTTGTTCTCTGGAGCAGCGTTCTTTTATCTCCGTCC
GCCTTCTCTCCTACCTAAGTGCGTGCCGCCACCCGATGGAAGATTCGATGGACATGGACATGAGCCCCCT
GAGGCCCCAGAACTATCTTTTCGGTTGTGAACTAAAGGCCGACAAAGATTATCACTTTAAGGTGGATAAT
GATGAAAATGAGCACCAGTTATCTTTAAGAACGGTCAGTTTAGGGGCTGGTGCAAAGGATGAGTTGCACA
TTGTTGAAGCAGAGGCAATGAATTACGAAGGCAGTCCAATTAAAGTAACACTGGCAACTTTGAAAATGTC
TGTACAGCCAACGGTTTCCCTTGGGGGCTTTGAAATAACACCACCAGTGGTCTTAAGGTTGAAGTGTGGT
TCAGGGCCAGTGCATATTAGTGGACAGCACTTAGTAGCTGTGGAGGAAGATGCAGAGTCAGAAGATGAAG
AGGAGGAGGATGTGAAACTCTTAAGTATATCTGGAAAGCGGTCTGCCCCTGGAGGTGGTAGCAAGGTTCC
ACAGAAAAAAGTAAAACTTGCTGCTGATGAAGATGATGACGATGATGATGAAGAGGATGATGATGAAGAT
GATGATGATGATGATTTTGATGATGAGGAAGCTGAAGAAAAGCGCCAGTGAAGAAATCTATACGAGATA
CTCCAGCCAAAAATGCACAAAAGTCAAATCAGAATGGAAAAGACTCAAAACCATCATCAACACCAAGATC
AAAAGGACAAGAATCCTTCAAGAAACAGGAAAAAACTCCTAAAACACCAAAAGGACCTAGTTCTGTAGAA
GACATTAAAGCAAAAATGCAAGCAAGTATAGAAAAAGAGAACAAGAACCTGGTTCATGGTAATGTGTGTG
GCCGGAACATCCTGCTGGCCCGGCTGGGGTTGGCAGAGGGCACCAGCCCCTTCATCAAGCTGAGTGATCC
TGGCGTGGGCCTGGGCGCCCTCTCCAGGGAGGAGCGGGTGGAGAGGATCCCCTGGCTGGCCCCCGAATGC
CTACCAGGTGGGGCCAACAGCCTAAGCACCGCCATGGACAAGTGGGGGTTTGGCGCCACCCTCCTGGAGA
TCTGCTTTGACGGAGAGGCCCCTCTGCAGAGCCGCAGTCCCTCCGAGAAGGAGCATTTCTACCAGAGGCA
GCACCGGCTGCCCGAGCCCTCCTGCCCACAGCTGGCCACACTCACCAGCCAGTGTCTGACCTATGAGCCA
ACCCAGAGGCCATCATTCCGCACCATCCTGCGTGACCTCACCCGGCTGCAGCCCCACAATCTTGCTGACG
TCTTGACTGTGAACCCGGACTCACCGGCGTCGGACCCTACGGTTTTCCACAAGCGCTATTTGAAAAAGAT
CCGAGATCTGGGCGAGGGTCACTTCGGCAAGGTCAGCTTGTACTGCTACGATCCGACCAACGACGGCACT
GGCGAGATGGTGGCGGTGAAAGCCCTCAAGGCAGACTGCGGCCCCAGCACCGCTCGGGCTGGAAGCAGG
AGATTGACATTCTGCGCACGCTCTACCACGAGCACATCATCAAGTACAAGGGCTGCTGCGAGGACCAAGG
CGAGAAGTCGCTGCAGCTGGTCATGGAGTACGTGCCCCTGGGCAGCCTCCGAGACTACCTGCCCCGGCAC
AGCATCGGGCTGGCCCAGCTGCTGCTCTTCGCCCAGCAGATCTGCGAGGGCATGGCCTATCTGCACGCGC
AGCACTACATCCACCGAGACCTAGCCGCGCGCAACGTGCTGCTGGACAACGACAGGCTGGTCAAGATCGG
GGACTTTGGCCTAGCCAAGGCCGTGCCCGAAGGCCACGAGTACTACCGCGTGCGCGAGGATGGGGACAGC
CCCGTGTTCTGGTATGCCCCAGAGTGCCTGAAGGAGTATAAGTTCTACTATGCGTCAGATGTCTGGTCCT
TCGGGGTGACCCTGTATGAGCTGCTGACGCACTGTGACTCCAGCCAGAGCCCCCCCACGAAATTCCTTGA
GCTCATAGGCATTGCTCAGGGTCAGATGACAGTTCTGAGACTCACTGAGTTGCTGGAACGAGGGGAGAGG
CTGCCACGGCCCGACAAATGTCCCTGTGAGGTCTATCATCTCATGAAGAACTGCTGGGAGACAGAGGCGT
CCTTTCGCCCAACCTTCGAGAACCTCATACCCATTCTGAAGACAGTCCATGAAGTACCAAGGCCAGGC
CCCTTCAGTGTTCAGCGTGTGCTGAGGCACAATGGCAGCCCTGCCTGGGAGGACTGGACCAGGCAGTGGC
TGCAGAGGGAGCCTCCTGCTCCCTGCTCCAGGATGAAACCAAGAGGGGGATGTCAGCCTCACCCACACCG
TGTGCCTTACTCCTGTCTAGAGACCCCACCTCTGTGAACTTATTTTTCTTTCTTGGCCGTGAGCCTAACC
ATGATCTTGAGGGACCCAACATTTGTAGGGCACTAATCCAGCCCTTAAATCCCCAGCTTCCAAACTTG
AGGCCCACCATCTCCACCATCTGGTAATAAACTCATGTTTTCTCTGCTGGA (SEQ ID NO: 100)
```

FIG. 13B

```
NPM1/TYK2 coding region (2160 bp)

ATGGAAGATTCGATGGACATGGACATGAGCCCCCTGAGGCCCCAGAACTATCTTTTCGGTTGTGAACTAA
AGGCCGACAAAGATTATCACTTTAAGGTGGATAATGATGAAAATGAGCACCAGTTATCTTTAAGAACGGT
CAGTTTAGGGGCTGGTGCAAAGGATGAGTTGCACATTGTTGAAGCAGAGGCAATGAATTACGAAGGCAGT
CCAATTAAAGTAACACTGGCAACTTTGAAAATGTCTGTACAGCCAACGGTTTCCCTTGGGGGCTTTGAAA
TAACACCACCAGTGGTCTTAAGGTTGAAGTGTGGTTCAGGGCCAGTGCATATTAGTGGACAGCACTTAGT
AGCTGTGGAGGAAGATGCAGAGTCAGAAGATGAAGAGGAGGAGGATGTGAAACTCTTAAGTATATCTGGA
AAGCGGTCTGCCCCTGGAGGTGGTAGCAAGGTTCCACAGAAAAAAGTAAAACTTGCTGCTGATGAAGATG
ATGACGATGATGATGAAGAGGATGATGATGAAGATGATGATGATGATTTTGATGATGAGGAAGCTGA
AGAAAAAGCGCCAGTGAAGAAATCTATACGAGATACTCCAGCCAAAAATGCACAAAAGTCAAATCAGAAT
GGAAAAGACTCAAAACCATCATCAACACCAAGATCAAAAGGACAAGAATCCTTCAAGAAACAGGAAAAAA
CTCCTAAAACACCAAAAGGACCTAGTTCTGTAGAAGACATTAAAGCAAAAATGCAAGCAAGTATAGAAAA
AGAGAACAAGAACCTGGTTCATGGTAATGTGTGTGGCCGGAACATCCTGCTGGCCCGGCTGGGGTTGGCA
GAGGGCACCAGCCCCTTCATCAAGCTGAGTGATCCTGGCGTGGGCCTGGGCGCCCTCTCCAGGGAGGAGC
GGGTGGAGAGGATCCCCTGGCTGGCCCCGAATGCCTACCAGGTGGGGCCAACAGCCTAAGCACCGCCAT
GGACAAGTGGGGGTTTGGCGCCACCCTCCTGGAGATCTGCTTTGACGGAGAGGCCCCTCTGCAGAGCCGC
AGTCCCTCCGAGAAGGAGCATTTCTACCAGAGGCAGCACCGGCTGCCCGAGCCCTCCTGCCCACAGCTGG
CCACACTCACCAGCCAGTGTCTGACCTATGAGCCAACCCAGAGGCCATCATTCCGCACCATCCTGCGTGA
CCTCACCCGGCTGCAGCCCCACAATCTTGCTGACGTCTTGACTGTGAACCCGGACTCACCGGCGTCGGAC
CCTACGGTTTTCCACAAGCGCTATTTGAAAAAGATCCGAGATCTGGGCGAGGGTCACTTCGGCAAGGTCA
GCTTGTACTGCTACGATCCGACCAACGACGGCACTGGCGAGATGGTGGCGGTGAAAGCCCTCAAGGCAGA
CTGCGGCCCCCAGCACCGCTCGGGCTGGAAGCAGGAGATTGACATTCTGCGCACGCTCTACCACGAGCAC
ATCATCAAGTACAAGGGCTGCTGCGAGGACCAAGGCGAGAAGTCGCTGCAGCTGGTCATGGAGTACGTGC
CCCTGGGCAGCCTCCGAGACTACCTGCCCCGGCACAGCATCGGGCTGGCCCAGCTGCTGCTCTTCGCCCA
GCAGATCTGCGAGGGCATGGCCTATCTGCACGCGCAGCACTACATCCACCGAGACCTAGCCGCGCGCAAC
GTGCTGCTGGACAACGACAGGCTGGTCAAGATCGGGGACTTTGGCCTAGCCAAGGCCGTGCCCGAAGGCC
ACGAGTACTACCGCGTGCGCGAGGATGGGGACAGCCCCGTGTTCTGGTATGCCCCAGAGTGCCTGAAGGA
GTATAAGTTCTACTATGCGTCAGATGTCTGGTCCTTCGGGGTGACCCTGTATGAGCTGCTGACGCACTGT
GACTCCAGCCAGAGCCCCCCCACGAAATTCCTTGAGCTCATAGGCATTGCTCAGGGTCAGATGACAGTTC
TGAGACTCACTGAGTTGCTGGAACGAGGGGAGAGGCTGCCACGGCCCGACAAATGTCCCTGTGAGGTCTA
TCATCTCATGAAGAACTGCTGGGAGACAGAGGCGTCCTTTCGCCCAACCTTCGAGAACCTCATACCCATT
CTGAAGACAGTCCATGAGAAGTACCAAGGCCAGGCCCCTTCAGTGTTCAGCGTGTGCTGA (SEQ ID
NO: 101)
```

FIG. 13C

```
NPM-TYK2 protein (~81 kD)

MEDSMDMDMSPLRPQNYLFGCELKADKDYHFKVDNDENEHQLSLRTVSLGAGAKDELHIVEAEAMNYEGSPIKVTLA
TLKMSVQPTVSLGGFEITPPVVLRLKCGSGPVHISGQHLVAVEEDAESEDEEEEDVKLLSISGKRSAPGGGSKVPQK
KVKLAADEDDDDDEEDDDEDDDDDFDDEEAEEKAPVKKSIRDTPAKNAQKSNQNGKDSKPSSTPRSKGQESFKKQ
EKTPKTPKGPSSVEDIKAKMQASIEKENKNLVHGNVCGRNILLARLGLAEGTSPFIKLSDPGVGLGALSREERVERI
PWLAPECLPGGANSLSTAMDKWGFGATLLEICFDGEAPLQSRSPSEKEHFYQRQHRLPEPSCPQLATLTSQCLTYEP
TQRPSFRTILRDLTRLQPHNLADVLTVNPDSPASDPTVFHKRYLKKIRDLGEGHFGKVSLYCYDPTNDGTGEMVAVK
ALKADCGPQHRSGWKQEIDILRTLYHEHIIKYKGCCEDQGEKSLQLVMEYVPLGSLRDYLPRHSIGLAQLLLFAQQI
CEGMAYLHAQHYIHRDLAARNVLLDNDRLVKIGDFGLAKAVPEGHEYYRVREDGDSPVFWYAPECLKEYKFYYASDV
WSFGVTLYELLTHCDSSQSPPTKFLELIGIAQGQMTVLRLTELLERGERLPRPDKCPCEVYHLMKNCWETEASFRPT
FENLIPILKTVHEKYQGQAPSVFSVC (SEQ ID NO: 102)
```

FIG. 13D

NPM-TYK2 introns involved in translocation (3332 bp)

Gtgagtaaagttatcttaaaaaactttgtctcccccctcaaattgcacgtgtctggtt
tgcatagacttgaatgtttcttgttttttgtttgttttggtttaatata<u>cttgcctgg</u>
<u>ttcgtggtatg</u>aattttttcaaaaatttcttataaacatttataatcgtgtctgtggt
gattttgcatatgcaaaattaaatatgccttattttccattatgcaaggaacgtagtg
cactggttgcaagataacattctgaccttccatgttaaaatagatcagtgaaaacctt
tgcctattctggttgtaagatatgctagaga<u>accaacagagggcgtatga</u>gacttcatt
aaaattacaaacagctggaaaagtagatgctggctgttgcttggtattata gttaatattcatgattgaccctagtcagaagtgattttcagcagattgagacatttctc
tttgcccttt acaccaagttgtcaccagttaatacatgtagtaatagctagatttcgtg
aatgactaataggcttaaatctagtttccttttgtcttaaataatggaaatgtgggaag
agggttaggtc<u>tctcatctgcttgactgggg</u>gatttgagtaggatatggaataaatggt
ttaaatgccttggaagcacatttgagagaagctttaattctatgaataatacttttaga
ctccaactattgag<u>agcaaatgtggggtggtgaaa</u>attgccaactcatttccccatgt
ttttcttgtaatctatagattttcgtggcttcagtagattccttgtacagtgataagt
ccactggaaaagaattttagaactggaacatatttcttttagtcacactgtaaaccct
ttagccttcctggttatcactgattttgtcccttggatacaatgctaaaatgacatc<u>t</u>
<u>tttagatgcccctccctc</u>catttaatatggtcctatctccttggtttaattgcaggc
gcattgaacagtcctgggcactacatgtaaattaagcccaaagatggggagaaaggaaa
aggagagacaaatatagtccatactgagtgtcatcaacaatccagactgaagtcttcta
tttta atctcaatcccctttt<u>ctgatttgccacccatgc</u>ctcttcaggctggaaacaat
ctcttggttccctaaagcactttcttctgactgctgtgattcagtgaaccttgcccttt
gctttctattacttgtgcatttgcctcacctgacaatgttttaaatcgcctttgtatct
ccttagctgctcaataaatatttgaatgcatcaattaagaatgtatgtgacaataattt
tgaaatggaaattgtgaggtttattttactaggttattggaggcagttaagtttcttaa
tgctatacctg<u>attctgccaaagtcccttgg</u>acatttgaaaaccttttcaatcttttaa
aaatgcataaagatacttagagggaaaggtattaattaaatttagtaaaaacaaatat
attcaatgctttaaattccaaagtagtgataaatacaaacatttcaagatatttgcaat
agtaatgttttgaaattttggttacaaagtcacaggtcttgccaatactgttgtagttt
cttgcctatatccgtaatttgaaggaaatggtgagagtgattagagaagtgtaattact
gtaattttttcccctattgtagtttcttgcctgtatccataatttgaaggaaatggtaa
gagtgattagtgaaatgtaattactgtaattttttccccattcaactttatatatcttt
aactgatgaccagatcattgttgttctgaccagtttgtggtcagcaagtgttttgtgg
ggttttgtttgtttgtttttaaagaacagtttgggtcacttgacatggttctccaaagg
gatgttatgggttgtatttggttctggtgataaccgacttgttagataatttagataa
gcaaccg<u>agttgccatgtttgttt</u>gtcgaatctcaagtgtagcttatattttatgttcc
tagagaggttgtcagggaagatttgacccttggcaaatctgtttgaatagagatacta
gccatgctgcccaatagggctttctggccctgaaaagatacggagtattcttggaaag
ttgaagggaaaagaataaactgatccatgtagtagcatgcagattattgaggaattt<u>t</u>
<u>ctaaaggtatctctctcggtgt</u>atttctctacttacctgtaataatgcttttgtcttaa

FIG. 13D (Cont.)

taggtgtgtggcctgtgtgtggggcctgggtcggtcagggagggccaggagcccaggag
ttcgagaccagcctgggcaacagggcgagaccccatctttttgtttgttttgttttag
gtggagtttcgcctgtcacccaggctggagtgcaatggcatgatctcggctcactgca
accttcgcctcccgggttcaaatgattctcccgcctcagcctcccaagtagctgggatt
ataggctcctgccatcacgcccagctaattttgtatttttagtagagatggggtttca
ccatgttggtcaggctggtctcgaacttctgacctcgtgatccatccgcctcagcctcc
caaagtgctgggattccaggcgtgagccaccacgcccagctggccccatctttaaaaa
taaacaaatagccaggtgtggtggctcatacctgtaatcccagcagtttggggaggccaa
ggcgggtggatcacctgaggtcaggagtttgagaccagcctggccagtatggcaaaacc
ttgcctctactaaaaatacaaaaaaaattagccaatgtggtaacttgcacctgtaggcc
gaggtactcaggaagttgaggtgggaggatcacctgagctcaggaatttgaggccgtag
taagctatgatcacaccactgcacccagcctgggcagcagcatagctagaccccatct
ccaccaaaaatttaagaatcagctaggctgtggtgatgtgcacctgtaattctcgctac
ttggaaggcttgagcccaggagtttgaagctgcagtgagctatgttcgtgccactatac
tccaacctgagagacagagtgagaccctgtcttaaaaaaaaaaaaaaaaaaaaaaaaca
agaaaaaaataaccccccaaaaaacaaaacagaaagaaacccagtgatagtcacagttg
tccttttcacattggctgtccctatggggaccaggtttggggttggcgtctgtgcctct
cctgagtggccacaccccctctcctgcccacctcag (SEQ ID NO: 103)

SEQUENCE LISTING

```
<160> NUMBER OF SEQ ID NOS: 104

<210> SEQ ID NO 1
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<223> OTHER INFORMATION: n = A G C T (any)

<400> SEQUENCE: 1
actcaaaacc atcatcaaca cca                                           23

<210> SEQ ID NO 2
<211> LENGTH: 20
<212> TYPE: DNA
<213> ORGANISM: Artificial sequence
<220> FEATURE:
<223> OTHER INFORMATION: synthetic

<400> SEQUENCE: 2
gttccggcca cacacattac                                               20

<210> SEQ ID NO 3
<211> LENGTH: 21
<212> TYPE: DNA
<213> ORGANISM: Artificial sequence
<220> FEATURE:
```

<223> OTHER INFORMATION: synthetic

<400> SEQUENCE: 3
acagagggcg tatgagactt c                                      21

<210> SEQ ID NO 4
<211> LENGTH: 24
<212> TYPE: DNA
<213> ORGANISM: Artificial sequence
<220> FEATURE:
<223> OTHER INFORMATION: synthetic

<400> SEQUENCE: 4
ccatagggac agccaatgtg aaaa                                   24

<210> SEQ ID NO 5
<211> LENGTH: 21
<212> TYPE: DNA
<213> ORGANISM: Artificial sequence
<220> FEATURE:
<223> OTHER INFORMATION: synthetic

<400> SEQUENCE: 5
cgtgagccta accatgatct t                                      21

<210> SEQ ID NO 6
<211> LENGTH: 21
<212> TYPE: DNA
<213> ORGANISM: Artificial sequence
<220> FEATURE:
<223> OTHER INFORMATION: synthetic

<400> SEQUENCE: 6
gagtgcctga aggagtataa g                                      21

<210> SEQ ID NO 7
<211> LENGTH: 36
<212> TYPE: DNA
<213> ORGANISM: Artificial sequence
<220> FEATURE:
<223> OTHER INFORMATION: synthetic

<400> SEQUENCE: 7
aagaattcag aaaggagtgg ggttgaaaag cgcttg                      36

<210> SEQ ID NO 8
<211> LENGTH: 43
<212> TYPE: DNA
<213> ORGANISM: Artificial sequence
<220> FEATURE:
<223> OTHER INFORMATION: synthetic

<400> SEQUENCE: 8
aactcgagtc cagcagagaa aacatgagtt tattaccaga tgg              43

<210> SEQ ID NO 9
<211> LENGTH: 64
<212> TYPE: DNA
<213> ORGANISM: Artificial sequence
<220> FEATURE:
<223> OTHER INFORMATION: synthetic

<400> SEQUENCE: 9
aactcgagat ggactacaag gacgacgatg acaaggaaga ttcgatggac atggacatga   60
gccc                                                         64

<210> SEQ ID NO 10
<211> LENGTH: 35
<212> TYPE: DNA
<213> ORGANISM: Artificial sequence
<220> FEATURE:
<223> OTHER INFORMATION: synthetic

<400> SEQUENCE: 10
aatctagatc agcacacgct gaacactgaa ggggc                              35

<210> SEQ ID NO 11
<211> LENGTH: 20
<212> TYPE: DNA
<213> ORGANISM: Artificial sequence
<220> FEATURE:
<223> OTHER INFORMATION: synthetic

<400> SEQUENCE: 11
aagcgccagt gaagaaatct                                              20

<210> SEQ ID NO 12
<211> LENGTH: 20
<212> TYPE: DNA
<213> ORGANISM: Artificial sequence
<220> FEATURE:
<223> OTHER INFORMATION: synthetic

<400> SEQUENCE: 12
cctctccgtc aaagcagatc                                              20

<210> SEQ ID NO 13
<211> LENGTH: 22
<212> TYPE: DNA
<213> ORGANISM: Artificial sequence
<220> FEATURE:
<223> OTHER INFORMATION: synthetic

<400> SEQUENCE: 13
caccaaaagg acctagttct gt                                           22

<210> SEQ ID NO 14
<211> LENGTH: 20
<212> TYPE: DNA
<213> ORGANISM: Artificial sequence
<220> FEATURE:
<223> OTHER INFORMATION: synthetic

<400> SEQUENCE: 14
ctcagcttga tgaaggggct                                              20

<210> SEQ ID NO 15
<211> LENGTH: 22
<212> TYPE: DNA
<213> ORGANISM: Artificial sequence
<220> FEATURE:
<223> OTHER INFORMATION: synthetic

<400> SEQUENCE: 15
accatcatca acaccaagat ca                                           22

<210> SEQ ID NO 16
<211> LENGTH: 20
<212> TYPE: DNA
<213> ORGANISM: Artificial sequence
<220> FEATURE:

<223> OTHER INFORMATION: synthetic

<400> SEQUENCE: 16

| gccaggatca ctcagcttga | 20 |

<210> SEQ ID NO 17
<211> LENGTH: 859
<212> TYPE: DNA
<213> ORGANISM: Artificial sequence
<220> FEATURE:
<223> OTHER INFORMATION: synthetic

<400> SEQUENCE: 17

| gctggaaagt agatgctggc tgttgcttgg tattataggg agggccagga gcccaggagt | 60 |
| tcgagaccag cctgggcaac agggcgagac cccatctttt ttgtttgttt tgttttaggt | 120 |
| ggagtttcgc cctgtcaccc aggctggagt gcaatggcat gatctcggct cactgcaacc | 180 |
| ttcgcctccc gggttcaaat gattctcccg cctcagcctc caagtagct gggattatag | 240 |
| gctcctgcca tcacgcccag ctaattttg tatttttagt agagatgggg tttcaccatg | 300 |
| ttggtcaggc tggtctcgaa cttctgacct cgtgatccat ccgcctcagc ctcccaaagt | 360 |
| gctgggattc caggcgtgag ccaccacgcc cagctggccc catcttttaa aaataaacaa | 420 |
| atagccaggt gtggtggctc atacctgtaa tcccagcagt tgggaggcc aaggcgggtg | 480 |
| gatcacctga ggtcaggagt ttgagaccag cctggccagt atggcaaaac cttgcctcta | 540 |
| ctaaaaatac aaaaaaatt agccaatgtg gtaacttgca cctgtaggcc gaggtactca | 600 |
| ggaagttgag gtgggaggat cacctgagct caggaatttg aggccgtagt aagctatgat | 660 |
| cacaccactg caccccagcc tgggcagcag catagctaga ccccatctcc accaaaaatt | 720 |
| taagaatcag ctaggctgtg gtgatgtgca cctgtaattc tcgctacttg gaaggcttga | 780 |
| gcccaggagt ttgaagctgc agtgagctat gttcgtgcca ctatactcca acctgaaaga | 840 |
| cagagtgaga ccctgtctt | 859 |

<210> SEQ ID NO 18
<211> LENGTH: 1407
<212> TYPE: DNA
<213> ORGANISM: Artificial sequence
<220> FEATURE:
<223> OTHER INFORMATION: synthetic

<400> SEQUENCE: 18

| gtgagtaaag ttatcttaaa aaactttgt ctcccccctc aaattgcacg tgtctggttt | 60 |
| gcatagactt gaatgtttct tgttttttg tttgttttgg tttaatatac ttgcctggtt | 120 |
| cgtggtatga atttttttcaa aaatttctta taaaacattt ataatcgtgt ctgtggtgat | 180 |
| ttttgcatat gcaaaattaa atatgcctta ttttccatta tgcaaggaac gtagtgcact | 240 |
| ggttgcaaga taacattctg accttccatg ttaaaataga tcagtgaaaa ccctttgcct | 300 |
| attctggttg taagatatgc tagagaacca acagagggcg tatgagactt cattaaaatt | 360 |
| acaaacagct ggaaaagtag atgctggctg ttgcttggta ttatagggag ggccaggagc | 420 |
| ccaggagttc gagaccagcc tgggcaacag ggcgagaccc catcttttt gtttgttttg | 480 |
| ttttaggtgg agtttcgccc tgtcacccag gctgagtgc aatggcatga tctcggctca | 540 |
| ctgcaacctt cgcctccgg gttcaaatga ttctcccgcc tcagcctccc aagtagctgg | 600 |
| gattataggc tcctgccatc acgcccagct aattttgta tttttagtag agatggggt | 660 |
| tcaccatgtt ggtcaggctg gtctcgaact tctgacctcg tgatccatcc gcctcagcct | 720 |

```
cccaaagtgc tgggattcca ggcgtgagcc accacgccca gctggcccca tcttttaaaa     780
ataaacaaat agccaggtgt ggtggctcat acctgtaatc ccagcagttt gggaggccaa     840
ggcgggtgga tcacctgagg tcaggagttt gagaccagcc tggccagtat ggcaaaacct    900
tgcctctact aaaaatacaa aaaaaattag ccaatgtggt aacttgcacc tgtaggccga    960
ggtactcagg aagttgaggt gggaggatca cctgagctca ggaatttgag gccgtagtaa   1020
gctatgatca caccactgca ccccagcctg ggcagcagca tagctagacc ccatctccac   1080
caaaaattta agaatcagct aggctgtggt gatgtgcacc tgtaattctc gctacttgga   1140
aggcttgagc ccaggagttt gaagctgcag tgagctatgt tcgtgccact atactccaac   1200
ctgagagaca gagtgagacc ctgtcttaaa aaaaaaaaa aaaaaaaaaa acaagaaaaa   1260
aataaccccc caaaaaacaa aacagaaaga aacccagtga tagtcacagt tgtccttttc   1320
acattggctg tccctatggg gaccaggttt ggggttggcg tctgtgcctc tcctgagtgg   1380
ccacaccccc tctcctgccc acctcag                                       1407
```

<210> SEQ ID NO 19
<211> LENGTH: 20
<212> TYPE: DNA
<213> ORGANISM: Artificial sequence
<220> FEATURE:
<223> OTHER INFORMATION: synthetic

<400> SEQUENCE: 19
cttgcctggt tcgtggtatg                                                20

<210> SEQ ID NO 20
<211> LENGTH: 20
<212> TYPE: DNA
<213> ORGANISM: Artificial sequence
<220> FEATURE:
<223> OTHER INFORMATION: synthetic

<400> SEQUENCE: 20
aaccaacaga gggcgtatga                                                20

<210> SEQ ID NO 21
<211> LENGTH: 20
<212> TYPE: DNA
<213> ORGANISM: Artificial sequence
<220> FEATURE:
<223> OTHER INFORMATION: synthetic

<400> SEQUENCE: 21
tctcatctgc ttgactgggg                                                20

<210> SEQ ID NO 22
<211> LENGTH: 20
<212> TYPE: DNA
<213> ORGANISM: Artificial sequence
<220> FEATURE:
<223> OTHER INFORMATION: synthetic

<400> SEQUENCE: 22
gcaaatgtgg ggtggtgaaa                                                20

<210> SEQ ID NO 23
<211> LENGTH: 20
<212> TYPE: DNA
<213> ORGANISM: Artificial sequence
<220> FEATURE:

<223> OTHER INFORMATION: synthetic

<400> SEQUENCE: 23
ttttagatgc ccctcccctc                                                    20

<210> SEQ ID NO 24
<211> LENGTH: 20
<212> TYPE: DNA
<213> ORGANISM: Artificial sequence
<220> FEATURE:
<223> OTHER INFORMATION: synthetic

<400> SEQUENCE: 24
ttctgatttg ccacccatgc                                                    20

<210> SEQ ID NO 25
<211> LENGTH: 20
<212> TYPE: DNA
<213> ORGANISM: Artificial sequence
<220> FEATURE:
<223> OTHER INFORMATION: synthetic

<400> SEQUENCE: 25
ttctgccaaa gtcccttgga                                                    20

<210> SEQ ID NO 26
<211> LENGTH: 20
<212> TYPE: DNA
<213> ORGANISM: Artificial sequence
<220> FEATURE:
<223> OTHER INFORMATION: synthetic

<400> SEQUENCE: 26
accgagttgc catgtttgtt                                                    20

<210> SEQ ID NO 27
<211> LENGTH: 23
<212> TYPE: DNA
<213> ORGANISM: Artificial sequence
<220> FEATURE:
<223> OTHER INFORMATION: synthetic

<400> SEQUENCE: 27
tctaaaggta tctctctcgg tgt                                                23

<210> SEQ ID NO 28
<211> LENGTH: 20
<212> TYPE: DNA
<213> ORGANISM: Artificial sequence
<220> FEATURE:
<223> OTHER INFORMATION: synthetic

<400> SEQUENCE: 28
ggatggatca cgaggtcaga                                                    20

<210> SEQ ID NO 29
<211> LENGTH: 43
<212> TYPE: DNA
<213> ORGANISM: Artificial sequence
<220> FEATURE:
<223> OTHER INFORMATION: synthetic

<400> SEQUENCE: 29
gaaaaaactc ctaaacacc aaaaggacct agttctgtag aag                           43

```
<210> SEQ ID NO 30
<211> LENGTH: 34
<212> TYPE: DNA
<213> ORGANISM: Artificial sequence
<220> FEATURE:
<223> OTHER INFORMATION: synthetic

<400> SEQUENCE: 30
gtaatgtgtg tggccggaac atcctgctgg cccg                            34

<210> SEQ ID NO 31
<211> LENGTH: 45
<212> TYPE: DNA
<213> ORGANISM: Artificial sequence
<220> FEATURE:
<223> OTHER INFORMATION: synthetic

<400> SEQUENCE: 31
actggcgaga tggtggcggt gagagccctc aaggcagact gcggc                45

<210> SEQ ID NO 32
<211> LENGTH: 45
<212> TYPE: DNA
<213> ORGANISM: Artificial sequence
<220> FEATURE:
<223> OTHER INFORMATION: synthetic

<400> SEQUENCE: 32
gccgcagtct gccttgaggg ctctcaccgc caccatctcg ccagt                45

<210> SEQ ID NO 33
<211> LENGTH: 46
<212> TYPE: DNA
<213> ORGANISM: Artificial sequence
<220> FEATURE:
<223> OTHER INFORMATION: synthetic

<400> SEQUENCE: 33
gccgtgcccg aaggccacga gttctaccgc gtgcgcgagg atgggg               46

<210> SEQ ID NO 34
<211> LENGTH: 46
<212> TYPE: DNA
<213> ORGANISM: Artificial sequence
<220> FEATURE:
<223> OTHER INFORMATION: synthetic

<400> SEQUENCE: 34
ccccatcctc gcgcacgcgg tagaactcgt ggccttcggg cacggc               46

<210> SEQ ID NO 35
<211> LENGTH: 46
<212> TYPE: DNA
<213> ORGANISM: Artificial sequence
<220> FEATURE:
<223> OTHER INFORMATION: synthetic

<400> SEQUENCE: 35
gccgtgcccg aaggccacga gttcttccgc gtgcgcgagg atgggg               46

<210> SEQ ID NO 36
<211> LENGTH: 46
<212> TYPE: DNA
<213> ORGANISM: Artificial sequence
<220> FEATURE:
<223> OTHER INFORMATION: synthetic
```

```
<400> SEQUENCE: 36
ccccatcctc gcgcacgcgg aagaactcgt ggccttcggg cacggc        46

<210> SEQ ID NO 37
<211> LENGTH: 104
<212> TYPE: DNA
<213> ORGANISM: Homo sapiens

<400> SEQUENCE: 37
gaatccttca agaaacagga aaaaactcct aaaacaccaa aaggacctag ttctgtagaa    60
gacattaaag caaaatgcaa gcaagcaagt atagaaaaag agaa                    104

<210> SEQ ID NO 38
<211> LENGTH: 101
<212> TYPE: DNA
<213> ORGANISM: Homo sapiens

<400> SEQUENCE: 38
aatccttcaa gaaacaggaa aaactcctaa aacaccaaaa ggacctagtt tctgtagaag    60
acattaaagc aaaatgcaa gcaagtatag aaaagagaa c                         101

<210> SEQ ID NO 39
<211> LENGTH: 101
<212> TYPE: DNA
<213> ORGANISM: Homo sapiens

<400> SEQUENCE: 39
atccttcaag aaacagaaaa aaactcctaa aacaccaaaa ggacctagtt ctgtagaaga    60
cattaaagca aaatgcaag caagtataga aaaagagaac a                        101

<210> SEQ ID NO 40
<211> LENGTH: 101
<212> TYPE: DNA
<213> ORGANISM: Homo sapiens

<400> SEQUENCE: 40
atccttcaag aaacaggaaa aaactcctaa aacaccaaaa ggacctagtt ctgtagaaga    60
cattaaagca aaatgcaag caagtataga aaaagagaac a                        101

<210> SEQ ID NO 41
<211> LENGTH: 101
<212> TYPE: DNA
<213> ORGANISM: Homo sapiens

<400> SEQUENCE: 41
ccttcaagaa acaggaaaaa actcctaaaa caccaaaagg acctagttct gtagaagaca    60
ttaaagcaaa aatgcaagca agtatagaaa aagagaacaa g                       101

<210> SEQ ID NO 42
<211> LENGTH: 101
<212> TYPE: DNA
<213> ORGANISM: Homo sapiens

<400> SEQUENCE: 42
cttcaagaaa caggaaaaaa ctcctaaaac accaaaagga cctagttctg tagaagacat    60
taaagcaaaa atgcaagcaa gtatagaaaa agagaacaag a                       101

<210> SEQ ID NO 43
<211> LENGTH: 101
```

```
<212> TYPE: DNA
<213> ORGANISM: Homo sapiens

<400> SEQUENCE: 43
cttcaagaaa cagaaaaaaa ctcctaaaac accaaaagga cctagttctg tagaagacat      60
taaagcaaaa atgcaagcaa gtatagaaaa agagaacaag a                         101

<210> SEQ ID NO 44
<211> LENGTH: 101
<212> TYPE: DNA
<213> ORGANISM: Homo sapiens

<400> SEQUENCE: 44
ttcaagaaac aggaaaaaac tcctaaaaca ccaaaggac ctagttctgt agaagacatt       60
aaagcaaaaa tgcaagcaag tatagaaaaa gagaacaaga a                         101

<210> SEQ ID NO 45
<211> LENGTH: 106
<212> TYPE: DNA
<213> ORGANISM: Homo sapiens

<400> SEQUENCE: 45
tcaagaaaca ggaaaaaact cctaaaacac caaaggacc tagttctgtt ctgtagaaga       60
cattaaagca aaaatgcaag caagtataga aaagagaac aagaac                     106

<210> SEQ ID NO 46
<211> LENGTH: 100
<212> TYPE: DNA
<213> ORGANISM: Homo sapiens

<400> SEQUENCE: 46
caagaaacag gaaaaaactc ctaaaacacc aaaaggacct agttctgtag aagcattaa       60 agcaaaatgc aagcaagtat agaaaagag aacaagaacc                            100

<210> SEQ ID NO 47
<211> LENGTH: 101
<212> TYPE: DNA
<213> ORGANISM: Homo sapiens

<400> SEQUENCE: 47
ggaacaggaa aaactcctaa aacaccaaaa ggacctagt tctgtagaag acattaaagc        60
aaaaatgcaa gcaagtatag aaaaagagaa caagaacctg g                         101

<210> SEQ ID NO 48
<211> LENGTH: 101
<212> TYPE: DNA
<213> ORGANISM: Homo sapiens

<400> SEQUENCE: 48
gaaacaggaa aaactcctaa aacaccaaaa ggacctagt tctgtagaag acattaaagc        60
aaaaatgcaa gcaagtatag aaaaagagaa caagaacctg g                         101

<210> SEQ ID NO 49
<211> LENGTH: 101
<212> TYPE: DNA
<213> ORGANISM: Homo sapiens

<400> SEQUENCE: 49
aaacaggaaa aactcctaa aacaccaaaa ggacctagtt ctgtagaaga cattaaagca       60
```
aaaatgcaag caagtataga aaaagagaac aagaacctgg t                          101

<210> SEQ ID NO 50
<211> LENGTH: 100
<212> TYPE: DNA
<213> ORGANISM: Homo sapiens

<400> SEQUENCE: 50
aacaggaaaa aactcctaaa acaccaaaag gacctagttc tgtagaagac attaaagcaa      60
aaatgcaagc aagtatagaa aagagaaca agaacctggt                            100

<210> SEQ ID NO 51
<211> LENGTH: 100
<212> TYPE: DNA
<213> ORGANISM: Homo sapiens

<400> SEQUENCE: 51
caggaaaaaa ctcctaaaac accaaaagga cctagttctg tagaagacat taaagcaaaa     60
tgcaagcaag tatagaaaaa gagaacaaga acctggttca                           100

<210> SEQ ID NO 52
<211> LENGTH: 101
<212> TYPE: DNA
<213> ORGANISM: Homo sapiens

<400> SEQUENCE: 52
ggaaaaaact cctaaacac caaaggacc tagttctgta gaagacatta aagcaaaat        60
gcaagcaagt atagaaaaag agaacaagaa cctggttcat g                         101

<210> SEQ ID NO 53
<211> LENGTH: 109
<212> TYPE: DNA
<213> ORGANISM: Homo sapiens

<400> SEQUENCE: 53 gaaaaactc ctaaacacc aaaggacct agttctgtag aagacattaa agcattaaag        60
caaaaatgca agcaagtata gaaaagaga acaagaacct ggttcatgg                  109

<210> SEQ ID NO 54
<211> LENGTH: 101
<212> TYPE: DNA
<213> ORGANISM: Homo sapiens

<400> SEQUENCE: 54
gaaaaaactc ctaaacacc aaaggacct agttctgtag aagacattaa agcaaaaatg       60
caagcaagta agaaaaaga gaacaagaac ctggttcatg g                          101

<210> SEQ ID NO 55
<211> LENGTH: 101
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, or t

<400> SEQUENCE: 55
gaaaaaactc ctaaacacc aaaggacct agttctgtag aagacattaa agcaaaaatg       60
caagcaagta tagaaaaaga gaacaagaac ctggttcatg n                         101

```
<210> SEQ ID NO 56
<211> LENGTH: 101
<212> TYPE: DNA
<213> ORGANISM: Homo sapiens

<400> SEQUENCE: 56
gaaaaaactc ctaaaacacc aaaaggacct agttctgtag aagacattaa agcaaaaatg    60
caagcaagta tagaaaaaga gaactagaac ctggttcatg g                       101

<210> SEQ ID NO 57
<211> LENGTH: 101
<212> TYPE: DNA
<213> ORGANISM: Homo sapiens

<400> SEQUENCE: 57
gaaaaaactc ctaaaacacc aaaaggacct agttctgtag aagacattaa agcaaaaatg    60
caagcaagta tagaaaaaga gaacaagaac atggttcatg g                       101

<210> SEQ ID NO 58
<211> LENGTH: 101
<212> TYPE: DNA
<213> ORGANISM: Homo sapiens

<400> SEQUENCE: 58
gaaaaaactc ctaaaacacc aaaaggacct agttctgtag aagacattaa agcaaaaata    60
caagcaagta tagaaaaaga gaacaagaac ctggttcatg g                       101

<210> SEQ ID NO 59
<211> LENGTH: 101
<212> TYPE: DNA
<213> ORGANISM: Homo sapiens

<400> SEQUENCE: 59
aaaaaactcc taaaacacca aaggaccta gttctgtaga agacattaaa gcaaaaatgc     60
aagcaagtat agaaaaagag aacaagaacc tggttcatgg t                       101

<210> SEQ ID NO 60
<211> LENGTH: 101
<212> TYPE: DNA
<213> ORGANISM: Homo sapiens

<400> SEQUENCE: 60
aaacactcct aaaacaccaa aaggacctag ttctgtagaa gacattaaag caaaaatgca    60
agcaagtata gaaaaagaga acaagaacct ggttcacggt a                       101

<210> SEQ ID NO 61
<211> LENGTH: 101
<212> TYPE: DNA
<213> ORGANISM: Homo sapiens

<400> SEQUENCE: 61
aaaaactcct aaaagaccaa aaggacctag ttctgtagag gacattaaag caaaaatgca    60
agcaagtata gaaaaagaga acaagaacct ggttcatggt a                       101

<210> SEQ ID NO 62
<211> LENGTH: 101
<212> TYPE: DNA
<213> ORGANISM: Homo sapiens

<400> SEQUENCE: 62
```
aaaactccta aacaccaaa aggacctagt tctgtagaag acattaaagc aaaaatgcaa      60
gcaagaatag aaaaagagaa caagaacctg gttcatggta a                         101

<210> SEQ ID NO 63
<211> LENGTH: 101
<212> TYPE: DNA
<213> ORGANISM: Homo sapiens

<400> SEQUENCE: 63
ctaaaacacc aaaaggacct agttctggag aagacattaa agcaaaaatg caagcaagta      60
tagaaaaaga gaacaagaac ctggttcatg gtaatgtgtg g                         101

<210> SEQ ID NO 64
<211> LENGTH: 101
<212> TYPE: DNA
<213> ORGANISM: Homo sapiens

<400> SEQUENCE: 64
aaaacaccaa aaggacctag ttctgtagaa gacattaaag caaaaatgca agcaagtata      60
gaaaaagaga acaagaacct ggttcatggt aatgtgtgtg g                         101

<210> SEQ ID NO 65
<211> LENGTH: 101
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, or t

<400> SEQUENCE: 65
aaaacaccaa aaggacctag ttctgtagaa gacattaaag caaaaatgca agcaagtata      60
gaaaaagaga acaagaacct ggttcatggt aatgtgtgtg n                         101

<210> SEQ ID NO 66
<211> LENGTH: 101
<212> TYPE: DNA
<213> ORGANISM: Homo sapiens

<400> SEQUENCE: 66
aaaaggacct agttctgtag aagacattaa agcaaaaatg caagcaagta tagaaaaaga      60
gaacaagaac ctggttcatg gtaatgtgtg tggccggaac a                         101

<210> SEQ ID NO 67
<211> LENGTH: 101
<212> TYPE: DNA
<213> ORGANISM: Homo sapiens

<400> SEQUENCE: 67
aaaaggacct agttctgtag aagacattaa agcaaaaatg caagcaagta tagaaaaaga      60
gaacaagaac ctggttcatg gtaatgcgtg tggccggaac a                         101

<210> SEQ ID NO 68
<211> LENGTH: 101
<212> TYPE: DNA
<213> ORGANISM: Homo sapiens

<400> SEQUENCE: 68
aaaggaccta gttctgtaga agacattaaa gcaaaaatgc aagcaagtat agaaaaagag      60
aacaagaacc tggttcatgg taatgtgtgt ggccggaaca t                         101

<210> SEQ ID NO 69
<211> LENGTH: 101
<212> TYPE: DNA
<213> ORGANISM: Homo sapiens

<400> SEQUENCE: 69
aaaggaccta gttctgtaga agacattaaa gcgaaaatgc aagcaagtat agaaaaagag     60
aacaagaacc tggttcatgg taatgtgtgt ggccggaaca t                        101

<210> SEQ ID NO 70
<211> LENGTH: 99
<212> TYPE: DNA
<213> ORGANISM: Homo sapiens

<400> SEQUENCE: 70
aaaggaccta gttctgtaga agactttaaa gcaaaaatgc aagcaagtat agaaaaagag     60
aacaagaacc tggttcatgg taatgtgtgg ccggaacat                            99

<210> SEQ ID NO 71
<211> LENGTH: 101
<212> TYPE: DNA
<213> ORGANISM: Homo sapiens

<400> SEQUENCE: 71
ggacctagtt ctgtagaaga cattaaagca aaaatgcaag caagtataga aaagagaac     60 aagaaactgg ttcatggtaa tgtgtgtggc cggaacatcc t                        101

<210> SEQ ID NO 72
<211> LENGTH: 99
<212> TYPE: DNA
<213> ORGANISM: Homo sapiens

<400> SEQUENCE: 72
acctagttct gtagcagaca ttaaagcaaa aatgcaagca agtatagaaa agagaacaa     60 gaacctggtt catggtaatg tgtggccgga acatcctgc                           99

<210> SEQ ID NO 73
<211> LENGTH: 101
<212> TYPE: DNA
<213> ORGANISM: Homo sapiens

<400> SEQUENCE: 73
cctagttctg tagaagacat taaagcaaaa atgcaagcaa gtatagaaaa agagaacaag     60
aacctggttc atggtaatgt gtgtggccgg aacatcctgc t                        101

<210> SEQ ID NO 74
<211> LENGTH: 100
<212> TYPE: DNA
<213> ORGANISM: Homo sapiens

<400> SEQUENCE: 74
ctagttctgt agaagacatt aaagcaaaaa tgcaagcaag tatagaaaaa gagaacaaga     60
acctggttca tggtaatgtg tgggccggaa catgctgctg                          100

<210> SEQ ID NO 75
<211> LENGTH: 99
<212> TYPE: DNA
<213> ORGANISM: Homo sapiens

<400> SEQUENCE: 75
ctagttctgt agaagacatt aaagcaaaaa tgcaagcaag aatagaaaaa gagaacaaga    60
acctggttca tggtaatgtg tggccggaac atcctgctg                          99

<210> SEQ ID NO 76
<211> LENGTH: 101
<212> TYPE: DNA
<213> ORGANISM: Homo sapiens

<400> SEQUENCE: 76
gttctgtaga agacattaaa gcaaaaatgc aagcaagtat agaaaaagag aacaagaacc    60
tggttcatgg taatgtgtgt ggccggaaca tcctgcttgc c                      101

<210> SEQ ID NO 77
<211> LENGTH: 101
<212> TYPE: DNA
<213> ORGANISM: Homo sapiens

<400> SEQUENCE: 77
tgtagaagac attaaagcaa aaatgcacgc aagtatagaa aaagagaaca gaacctggt     60 tcatggtaat gtgtgtggcc ggaacatcct gctggcccgg c                      101

<210> SEQ ID NO 78
<211> LENGTH: 101
<212> TYPE: DNA
<213> ORGANISM: Homo sapiens

<400> SEQUENCE: 78
gtagaagaca ttaaagcaaa atgcaagca agtatagaaa aaagaacaa gaacctggtt     60 catggtaatg tgtgtggccg gaacatcctg ctggcccggc t                      101

<210> SEQ ID NO 79
<211> LENGTH: 100
<212> TYPE: DNA
<213> ORGANISM: Homo sapiens

<400> SEQUENCE: 79
aagacattaa agcaaaaatg caagcaagta tagaaaaaga gaacaagaac ctggttcatg    60
gtaatgtgtg tggccggaac atccgctggc ccggctgggg                        100

<210> SEQ ID NO 80
<211> LENGTH: 101
<212> TYPE: DNA
<213> ORGANISM: Homo sapiens

<400> SEQUENCE: 80
agacattaaa gcaaaaatgc aagcaagtat agaaaaagag aacaagaacc tggttcatgg    60
taatgtgtgt ggccggaaca tcctgctggc ccggctgggg t                      101

<210> SEQ ID NO 81
<211> LENGTH: 101
<212> TYPE: DNA
<213> ORGANISM: Homo sapiens

<400> SEQUENCE: 81
agacattaaa gcaaaaatgc aagcaagtat agaaaaagag aacaagaacc tggttcatgg    60
taatgtgtgt ggccgaaaca tcctgctggc ccggctgggg t                      101

```
<210> SEQ ID NO 82
<211> LENGTH: 101
<212> TYPE: DNA
<213> ORGANISM: Homo sapiens

<400> SEQUENCE: 82
gacattaaag caaaaatgca agcaagtata gaaaaagaga acaagaacct ggttcatggt    60
aatgtgtgtg gccggaacat cctgctggcc cggctggggt t                      101

<210> SEQ ID NO 83
<211> LENGTH: 100
<212> TYPE: DNA
<213> ORGANISM: Homo sapiens

<400> SEQUENCE: 83
attaaagcaa aaatgcaagc aagtatagaa aagagaaca agaacctggt tcatggtaat    60
gtgtgtggcc ggaacatcct gctggcccgg ctgggttggg                        100

<210> SEQ ID NO 84
<211> LENGTH: 101
<212> TYPE: DNA
<213> ORGANISM: Homo sapiens

<400> SEQUENCE: 84
aaagcaaaaa tgcaagcaag tatagaaaaa gagaacaaga acctggttca tggtaatgtg    60
tgtggccgga acatcctgct ggcccggctg gggttggcag a                      101

<210> SEQ ID NO 85
<211> LENGTH: 101
<212> TYPE: PRT
<213> ORGANISM: Homo sapiens

<400> SEQUENCE: 85

Cys Ala Ala Ala Ala Thr Gly Cys Ala Ala Gly Cys Ala Gly
1               5                  10                  15

Thr Ala Thr Ala Gly Ala Ala Ala Ala Gly Ala Gly Ala Ala Cys
                20                  25                  30

Ala Ala Gly Ala Ala Cys Cys Thr Gly Gly Thr Thr Cys Ala Thr Gly
            35                  40                  45

Gly Thr Ala Ala Thr Gly Thr Gly Thr Gly Gly Cys Cys Gly
        50                  55                  60

Gly Ala Ala Cys Ala Thr Cys Cys Thr Gly Cys Thr Gly Gly Cys Cys
65                  70                  75                  80

Cys Gly Gly Cys Thr Gly Gly Gly Gly Thr Thr Gly Gly Cys Ala Gly
                85                  90                  95

Ala Gly Gly Gly Asn
            100

<210> SEQ ID NO 86
<211> LENGTH: 101
<212> TYPE: DNA
<213> ORGANISM: Homo sapiens

<400> SEQUENCE: 86
aaaaatgcaa gcaagtatag aaaaagagaa caagaacctg gttcatggta atgtgtgtgg    60
ccggaacatc ctgctggccc ggctgggggt ggcagagggg a                      101

<210> SEQ ID NO 87
<211> LENGTH: 101
```

```
<212> TYPE: DNA
<213> ORGANISM: Homo sapiens

<400> SEQUENCE: 87
aaaaatgcaa gcaagtatag aaaaagagaa caagaacctg gttcatggta atgtgtgtgg    60
ccggaacatc ctgctggccc ggctgggggtt gggagagggc a                      101

<210> SEQ ID NO 88
<211> LENGTH: 98
<212> TYPE: DNA
<213> ORGANISM: Homo sapiens

<400> SEQUENCE: 88
tgcaagcaag tatagaaaaa gagaacaaga acctggttca tggtaatgtg tgtggccgga    60
acatcctgct ggcccggctg ggttggcag agggcacc                            98

<210> SEQ ID NO 89
<211> LENGTH: 173
<212> TYPE: DNA
<213> ORGANISM: Homo sapiens

<400> SEQUENCE: 89
gaatccttca agaaacagga aaaactccta aaacaccaaa aggacctagt tctgtagaag    60
acattaaagc aaaaatgcaa gcaagtatag aaaaagagaa caagaacctg gttcatggta   120
atgtgtgtgg ccggaacatc ctgctggccc ggctggggtt ggcagagggc acc          173

<210> SEQ ID NO 90
<211> LENGTH: 4262
<212> TYPE: DNA
<213> ORGANISM: Homo sapiens

<400> SEQUENCE: 90
aagcagtagc tacccgcggg agcggggagg ggtccgggtt cgagcttgtg ttccccggga    60
agggtgagtc tggacgcggg cgcggaagga gcgcggccgg aggtcctcag gaagaagccg   120
cggggactgg ctgcgcttga caggctgcac ttggatggga gcacctggtg cctcgggact   180
gctccgatgc ccgggtctgt gctgaatgtg taatatgcgg aactatattg aaacattaca   240
accatctttt gatggcaaca ccctgaggac ctcccttttc cagatgggga aactgaggcc   300
cagaattgct aagtggcttg cttgagttga cacaggagc tccaggactc accctcagct    360
gagccacctg ccgggagcat gcctctgcgc cactggggga tggccagggg cagtaagccc   420
gttggggatg gagcccagcc catggctgcc atggagggcc tgaaggtgct tctgcactgg   480
gctggtccag gcggcgggga gccctgggtc actttcagtg agtcatcgct gacagctgag   540
gaagtctgca tccacattgc acataaagtt ggtatcactc ctccttgctt caatctcttt   600
gccctcttcg atgctcaggc ccaagtctgg ttgcccccaa accacatcct agagatcccc   660
agagatgcaa gcctgatgct atatttccgc ataaggtttt atttccggaa ctggcatggc   720
atgaatcctc gggaaccggc tgtgtaccgt tgtgggcccc aggaaccga ggcatcctca    780
gatcagacag cacaggggat gcaactcctg gacccagcct catttgagta cctctttgag   840
cagggcaagc atgagtttgt gaatgacgtg gcatcactgt gggagctgtc gaccgaggag   900
gagatccacc actttaagaa tgagagcctg ggcatggcct ttctgcacct ctgtcacctc   960
gctctccgcc atggcatccc cctggaggag gtggccaaga agaccagctt caaggactgc  1020
atcccgcgct ccttccgccg gcatatccgg cagcacagcg ccctgacccg gctgcgcctt  1080
```

```
cggaacgtct tccgcaggtt cctgcgggac ttccagccgg gccgactctc ccagcagatg   1140
gtcatggtca ataccctagc cacactcgag cggctggcac cccgcttcgg cacagagcgt   1200
gtgcccgtgt gccacctgag gctgctggcc caggccgagg gggagccctg ctacatccgg   1260
gacagtgggg tggcccctac agaccctggc cctgagtctg ctgctggcc cccaacccac    1320 gaggtgctgg tgacaggcac tggtggcatc cagtggtggc cagtagagga ggaggtgaac   1380
aaggaggagg gttctagtgg cagcagtggc aggaaccccc aagccagcct gtttgggaag   1440
aaggccaagg ctcacaaggc agtcggccag ccggcagaca ggccgcggga ccactgtgg    1500 gcctacttct gtgacttccg ggacatcacc cacgtggtgc tgaaagagca ctgtgtcagc   1560
atccaccggc aggacaacaa gtgcctggag ctgagcttgc cttcccgggc tgcggcgctg   1620
tccttcgtgt cgctggtgga cggctatttc cgcctgacgg ccgactccag ccactacctg   1680
tgccacgagg tggctccccc acggctgtg atgagcatcc gggatgggat ccacggaccc    1740
ctgctggagc catttgtgca ggccaagctg cggcccgagg acggcctgta cctcattcac   1800
tggagcacca gccaccccta ccgcctgatc ctcacagtgg cccagcgtag ccaggcacca   1860
gacggcatgc agagcttgcg gctccgaaag ttccccattg agcagcagga cggggccttc   1920
gtgctggagg gctggggccg gtccttcccc agcgttcggg aacttggggc tgccttgcag   1980
ggctgcttgc tgagggccgg ggatgactgc ttctctctgc gtcgctgttg cctgccccaa   2040
ccaggagaaa cctccaatct catcatcatg cgggggggctc gggccagccc caggacactc   2100
aacctcagcc agctcagctt ccaccggggtt gaccagaagg agatcaccca gctgtcccac   2160
ttgggccagg gcacaaggac caacgtgtat gagggccgcc tgcgagtgga gggcagcggg   2220
gaccctgagg agggcaagat ggatgacgag gacccctcg tgcctggcag ggaccgtggg   2280
caggagctac gagtggtgct caaagtgctg gaccctagtc accatgacat cgccctggcc   2340
ttctacgaga cagccagcct catgagccag gtctcccaca cgcacctggc cttcgtgcat   2400
ggcgtctgtg tgcgcggccc tgaaaatatc atggtgacag agtacgtgga gcacggaccc   2460
ctggatgtgt ggctgcggag ggagcggggc catgtgccca tggcttggaa gatggtggtg   2520
gcccagcagc tggccagcgc cctcagctac ctggagaaca agaacctggt tcatggtaat   2580
gtgtgtggcc ggaacatcct gctggcccgg ctggggttgg cagagggcac cagccccttc   2640
atcaagctga gtgatcctgg cgtgggcctg ggcgccctct ccaggaggga gcgggtggag   2700
aggatcccct ggctggcccc cgaatgccta ccaggtgggg ccaacagcct aagcaccgcc   2760
atggacaagt gggggtttgg cgccaccctc ctggagatct gctttgacgg agaggcccct   2820
ctgcagagcc gcagtccctc cgagaaggag catttctacc agaggcagca ccggctgccc   2880
gagccctcct gcccacagct ggccacactc accagccagt gtctgaccta tgagccaacc   2940
cagaggccat cattccgcac catcctgcgt gacctcaccc ggctgcagcc ccacaatctt   3000
gctgacgtct tgactgtgaa cccggactca ccggcgtcgg accctacggt ttccacaag   3060 cgctatttga aaagatccg agatctgggc gagggtcact tcggcaaggt cagcttgtac   3120
tgctacgatc cgaccaacga cggcactggc gagatggtgg cggtgaaagc cctcaaggca   3180
gactgcggcc cccagcaccg ctcgggctgg aagcaggaga ttgacattct gcgcacgctc   3240
taccacgagc acatcatcaa gtacaagggc tgctgcgagg accaaggcga aagtcgctg    3300 cagctggtca tggagtacgt gcccctgggc agcctccgag actacctgcc ccggcacagc   3360
atcgggctgg cccagctgct gctcttcgcc cagcagatct gcgagggcat ggcctatctg   3420
cacgcgcagc actacatcca ccgagaccta gccgcgcgca acgtgctgct ggacaacgac   3480
```

```
aggctggtca agatcgggga ctttggccta gccaaggccg tgcccgaagg ccacgagtac    3540
taccgcgtgc gcgaggatgg ggacagcccc gtgttctggt atgccccaga gtgcctgaag    3600
gagtataagt tctactatgc gtcagatgtc tggtccttcg gggtgaccct gtatgagctg    3660
ctgacgcact gtgactccag ccagagcccc cccacgaaat tccttgagct cataggcatt    3720
gctcagggtc agatgacagt tctgagactc actgagttgc tggaacgagg ggagaggctg    3780
ccacggcccg acaaatgtcc ctgtgaggtc tatcatctca tgaagaactg ctgggagaca    3840
gaggcgtcct ttcgcccaac cttcgagaac ctcatacccc ttctgaagac agtccatgag    3900
aagtaccaag gccaggcccc ttcagtgttc agcgtgtgct gaggcacaat ggcagccctg    3960
cctgggagga ctggaccagg cagtggctgc agagggagcc tcctgctccc tgctccagga    4020
tgaaaccaag aggggggatgt cagcctcacc cacaccgtgt gccttactcc tgtctagaga    4080
ccccacctct gtgaacttat ttttctttct tggccgtgag cctaaccatg atcttgaggg    4140
acccaacatt tgtaggggca ctaatccagc ccttaaatcc cccagcttcc aaacttgagg    4200
cccaccatct ccaccatctg gtaataaact catgttttct ctgctggaaa aaaaaaaaa    4260 aa                                                                  4262

<210> SEQ ID NO 91
<211> LENGTH: 3564
<212> TYPE: DNA
<213> ORGANISM: Homo sapiens

<400> SEQUENCE: 91
atgcctctgc gccactgggg gatggccagg ggcagtaagc ccgttgggga tggagcccag      60
cccatggctg ccatgggagg cctgaaggtg cttctgcact gggctggtcc aggcggcggg     120
gagccctggg tcactttcag tgagtcatcg ctgacagctg aggaagtctg catccacatt     180
gcacataaag ttggtatcac tcctccttgc ttcaatctct tgccctcctt cgatgctcag     240
gcccaagtct ggttgccccc aaaccacatc ctagagatcc cagagatgc aagcctgatg     300 ctatatttcc gcataaggtt ttatttccgg aactggcatg gcatgaatcc tcgggaaccg     360
gctgtgtacc gttgtgggcc cccaggaacc gaggcatcct cagatcagac agcacagggg     420
atgcaactcc tggacccagc ctcatttgag tacctctttg agcagggcaa gcatgagttt     480
gtgaatgacg tggcatcact gtgggagctg tcgaccgagg aggagatcca ccactttaag     540
aatgagagcc tggcatggc ctttctgcac ctctgtcacc tcgctctccg ccatggcatc     600
cccctggagg aggtggccaa gaagaccagc ttcaaggact gcatcccgcg ctccttccgc     660
cggcatatcc ggcagcacag cgccctgacc cggctgcgcc ttcggaacgt cttccgcagg     720
ttcctgcggg acttccagcc gggccgactc tcccagcaga tggtcatggt caaataccta     780
gccacactcg agcggctggc acccgcttc ggcacagagc gtgtgcccgt gtgccacctg     840
aggctgctgg cccaggccga gggggagccc tgctacatcc gggacagtgg ggtggcccct     900
acagaccctg gccctgagtc tgctgctggg cccccaaccc acgaggtgct ggtgacaggc     960
actggtggca tccagtggtg gccagtagag gaggaggtga acaaggagga gggttctagt    1020
ggcagcagtg gcaggaaccc ccaagccagc ctgtttggga agaaggccaa ggctcacaag    1080
gcagtcggcc agccggcaga caggccgcgg gagccactgt gggcctactt ctgtgacttc    1140
cgggacatca cccacgtggt gctgaaagag cactgtgtca gcatccaccg gcaggacaac    1200
aagtgcctgg agctgagctt gccttcccgg gctgcggcgc tgtccttcgt gtcgctggtg    1260
```

```
gacggctatt tccgcctgac ggccgactcc agccactacc tgtgccacga ggtggctccc     1320
ccacggctgg tgatgagcat ccgggatggg atccacggac ccctgctgga gccatttgtg     1380
caggccaagc tgcggcccga ggacggcctg tacctcattc actggagcac cagccacccc     1440
taccgcctga tcctcacagt ggcccagcgt agccaggcac cagacggcat gcagagcttg     1500
cggctccgaa agttccccat tgagcagcag gacggggcct tcgtgctgga gggctggggc     1560
cggtccttcc ccagcgttcg ggaacttggg gctgccttgc agggctgctt gctgagggcc     1620
ggggatgact gcttctctct cgtcgctgt tgcctgcccc aaccaggaga aacctccaat     1680
ctcatcatca tgcgggggc tcgggccagc cccaggacac tcaacctcag ccagctcagc     1740
ttccaccggg ttgaccagaa ggagatcacc cagctgtccc acttgggcca gggcacaagg     1800
accaacgtgt atgagggccg cctgcgagtg gagggcagcg ggaccctga ggagggcaag     1860
atggatgacg aggacccct cgtgcctggc agggaccgtg ggcaggagct acgagtggtg     1920
ctcaaagtgc tggaccctag tcaccatgac atcgccctgg ccttctacga cacagccagc     1980
ctcatgagcc aggtctccca cacgcacctg gccttcgtgc atggcgtctg tgtgcgcggc     2040
cctgaaaata tcatggtgac agagtacgtg gagcacggac ccctggatgt gtggctgcgg     2100
agggagcggg gccatgtgcc catggcttgg aagatggtgg tggcccagca gctggccagc     2160
gccctcagct acctggagaa caagaacctg gttcatggta atgtgtgtgg ccggaacatc     2220
ctgctggccc ggctggggtt ggcagagggc accagcccct tcatcaagct gagtgatcct     2280
ggcgtgggcc tgggcgccct ctccagggag gagcgggtgg agaggatccc ctggctggcc     2340
cccgaatgcc taccaggtgg ggccaacagc ctaagcaccg ccatggacaa gtgggggttt     2400
ggcgccaccc tcctggagat ctgctttgac ggagaggccc ctctgcagag ccgcagtccc     2460
tccgagaagg agcatttcta ccagaggcag caccggctgc ccgagccctc ctgcccacag     2520
ctggccacac tcaccagcca gtgtctgacc tatgagccaa cccagaggcc atcattccgc     2580
accatcctgc gtgacctcac ccggctgcag ccccacaatc ttgctgacgt cttgactgtg     2640
aacccggact caccggcgtc ggaccctacg gttttccaca agcgctattt gaaaaagatc     2700
cgagatctgg gcgagggtca cttcggcaag gtcagcttgt actgctacga tccgaccaac     2760
gacggcactg gcgagatggt ggcggtgaaa gccctcaagg cagactgcgg cccccagcac     2820
cgctcgggct ggaagcagga gattgacatt ctgcgcacgc tctaccacga gcacatcatc     2880
aagtacaagg gctgctgcga ggaccaaggc gagaagtcgc tgcagctggt catggagtac     2940
gtgcccctgg gcagcctccg agactacctg ccccggcaca gcatcgggct ggcccagctg     3000
ctgctcttcg cccagcagat ctgcgagggc atggcctatc tgcacgcgca gcactacatc     3060
caccgagacc tagccgcgcg caacgtgctg ctggacaacg acaggctggt caagatcggg     3120
gactttggcc tagccaaggc cgtgcccgaa ggccacgagt actaccgcgt gcgcgaggat     3180
ggggacagcc ccgtgttctg gtatgcccca gagtgcctga aggagtataa gttctactat     3240
gcgtcagatg tctggtcctt cggggtgacc ctgtatgagc tgctgacgca ctgtgactcc     3300
agccagagcc cccccacgaa attccttgag ctcataggca ttgctcaggg tcagatgaca     3360
gttctgagac tcactgagtt gctggaacga ggggagaggc tgccacgcc cgacaaatgt     3420
ccctgtgagg tctatcatct catgaagaac tgctgggaga cagaggcgtc ctttcgccca     3480
accttcgaga acctcatacc cattctgaag acagtccatg agaagtacca aggccaggcc     3540
ccttcagtgt tcagcgtgtg ctga                                            3564
```

-continued

```
<210> SEQ ID NO 92
<211> LENGTH: 1187
<212> TYPE: PRT
<213> ORGANISM: Homo sapiens

<400> SEQUENCE: 92
```

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125

Gly Thr Glu Ala Ser Ser Asp Gln Thr Ala Gln Gly Met Gln Leu Leu
130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
    290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Val Gly Gln Pro Ala Asp Arg
        355                 360                 365

Pro Arg Glu Pro Leu Trp Ala Tyr Phe Cys Asp Phe Arg Asp Ile Thr
    370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Ala Leu Ser Phe
            405                 410                 415

Val Ser Leu Val Asp Gly Tyr Phe Arg Leu Thr Ala Asp Ser Ser His
        420                 425                 430

Tyr Leu Cys His Glu Val Ala Pro Pro Arg Leu Val Met Ser Ile Arg
    435                 440                 445

Asp Gly Ile His Gly Pro Leu Leu Glu Pro Phe Val Gln Ala Lys Leu
450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
                485                 490                 495

Met Gln Ser Leu Arg Leu Arg Lys Phe Pro Ile Glu Gln Gln Asp Gly
            500                 505                 510

Ala Phe Val Leu Glu Gly Trp Gly Arg Ser Phe Pro Ser Val Arg Glu
        515                 520                 525

Leu Gly Ala Ala Leu Gln Gly Cys Leu Leu Arg Ala Gly Asp Asp Cys
    530                 535                 540

Phe Ser Leu Arg Arg Cys Cys Leu Pro Gln Pro Gly Glu Thr Ser Asn
545                 550                 555                 560

Leu Ile Ile Met Arg Gly Ala Arg Ala Ser Pro Arg Thr Leu Asn Leu
                565                 570                 575

Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
        595                 600                 605

Arg Val Glu Gly Ser Gly Asp Pro Glu Glu Gly Lys Met Asp Asp Glu
    610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
            660                 665                 670

Val His Gly Val Cys Val Arg Gly Pro Glu Asn Ile Met Val Thr Glu
        675                 680                 685

Tyr Val Glu His Gly Pro Leu Asp Val Trp Leu Arg Arg Glu Arg Gly
    690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
            740                 745                 750

Pro Phe Ile Lys Leu Ser Asp Pro Gly Val Gly Leu Gly Ala Leu Ser
        755                 760                 765

Arg Glu Glu Arg Val Glu Arg Ile Pro Trp Leu Ala Pro Glu Cys Leu
    770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln 805                 810                 815
Ser Arg Ser Pro Ser Glu Lys Glu His Phe Tyr Gln Arg Gln His Arg
                820                 825                 830

Leu Pro Glu Pro Ser Cys Pro Gln Leu Ala Thr Leu Thr Ser Gln Cys
                835                 840                 845

Leu Thr Tyr Glu Pro Thr Gln Arg Pro Ser Phe Arg Thr Ile Leu Arg
        850                 855                 860

Asp Leu Thr Arg Leu Gln Pro His Asn Leu Ala Asp Val Leu Thr Val
865                 870                 875                 880

Asn Pro Asp Ser Pro Ala Ser Asp Pro Thr Val Phe His Lys Arg Tyr
                885                 890                 895

Leu Lys Lys Ile Arg Asp Leu Gly Glu Gly His Phe Gly Lys Val Ser
                900                 905                 910

Leu Tyr Cys Tyr Asp Pro Thr Asn Asp Gly Thr Gly Glu Met Val Ala
        915                 920                 925

Val Lys Ala Leu Lys Ala Asp Cys Gly Pro Gln His Arg Ser Gly Trp
930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
                965                 970                 975

Val Met Glu Tyr Val Pro Leu Gly Ser Leu Arg Asp Tyr Leu Pro Arg
        980                 985                 990

His Ser Ile Gly Leu Ala Gln Leu Leu Leu Phe Ala Gln Gln Ile Cys
        995                 1000                1005

Glu Gly Met Ala Tyr Leu His Ala Gln His Tyr Ile His Arg Asp
        1010                1015                1020

Leu Ala Ala Arg Asn Val Leu Leu Asp Asn Asp Arg Leu Val Lys
        1025                1030                1035

Ile Gly Asp Phe Gly Leu Ala Lys Ala Val Pro Glu Gly His Glu
        1040                1045                1050

Tyr Tyr Arg Val Arg Glu Asp Gly Asp Ser Pro Val Phe Trp Tyr
        1055                1060                1065

Ala Pro Glu Cys Leu Lys Glu Tyr Lys Phe Tyr Tyr Ala Ser Asp
        1070                1075                1080

Val Trp Ser Phe Gly Val Thr Leu Tyr Glu Leu Leu Thr His Cys
        1085                1090                1095

Asp Ser Ser Gln Ser Pro Pro Thr Lys Phe Leu Glu Leu Ile Gly
        1100                1105                1110

Ile Ala Gln Gly Gln Met Thr Val Leu Arg Leu Thr Glu Leu Leu
        1115                1120                1125

Glu Arg Gly Glu Arg Leu Pro Arg Pro Asp Lys Cys Pro Cys Glu
        1130                1135                1140

Val Tyr His Leu Met Lys Asn Cys Trp Glu Thr Glu Ala Ser Phe
        1145                1150                1155

Arg Pro Thr Phe Glu Asn Leu Ile Pro Ile Leu Lys Thr Val His
        1160                1165                1170

Glu Lys Tyr Gln Gly Gln Ala Pro Ser Val Phe Ser Val Cys
        1175                1180                1185

<210> SEQ ID NO 93
<211> LENGTH: 30045
<212> TYPE: DNA
<213> ORGANISM: Homo sapiens

<400> SEQUENCE: 93

```
aagcagtagc tacccgcggg agcggggagg ggtccgggtt cgagcttgtg ttcccccgga    60
agggtgagtc tggacgcggg cgcggaagga gcgcggccgg aggtcctcag gaagaagccg   120
cggggactgg ctgcgcttga caggctgcac ttggatggga gcacctggtg cctcgggact   180
gctccgatgc ccgtggggtg cacatcccag ttcccgccgt tgccggccgg gtttagaggt   240
tttgggggga ggacatgggg gcgtgcagcc ttcccagttg caaacttcac tccgaccctg   300
tcttcaaagc tgggtctggg tccagtgggg acgagaaagg aggaaggagg aagtaggctc   360
cgcgaaagcc ccatccccgg gatctcatct ataacatgaa taggtattaa tggcaaaggc   420
taattaagcg cttactgtat accaggcact ttctctgcct cctcgcgtta aatcctccca   480
gcagcctttt gaggtagaca ctgttacatg cccattttcc agatgaggaa accagcaaca   540
tgggtggaag tgacagcccc tccacttcca tactggcgcc ctcaggaggc tcaggccctg   600
gattgggggg atggagctgg acataaactc tcctaggctt tggggagtca acagggactg   660
aggtcactca tgggggtaaa tgtgggagag agaattgtg gcctgaaaga ggccatcacc    720
acgatgaaac taataacaat tatgttattc ttgttttggt catatttgtt cttttttgtgt  780
gtgcctgaat cagggtctgt gctgaatgtg taatatgcgg aactatattg aaacattaca   840
accatctttt gatggcaaca ccctgaggac ctcccttttc cagatgggga aactgaggcc   900
cagaattgct aagtggcttg cttgagttga cacagggagc tccaggactc accctcaggt   960
atgtttgacc acatctgcct gtctggttat tttggggagg tgtgttaaga gcagattttt  1020
atttttacttt ttatttattt atttatttat ttatttattt atttattgta ttttagtaga 1080
gatggggttt caccatgttg gtcaagatgg tctcaatctc cagacctcgt gatctgtccg  1140
ccttggcctc ccaaagtgct gggattacag tcatgagcca ccgcgcctgg cccttttttat 1200
atatttttat tacttatttta tttatttatt tatttatatt tttagagtca gggtctcact  1260
ctgtcaccca ggctggaatg cagtggtgcg atcactgctc actgcagcct ccaactcctg  1320
ggctcaggag atcctcccac ttcagcctcc cgagtagctt ggagtacaga tgtgcacccc  1380
cacgcctggc taaattttaa aaatttcttg tagaggccgg gcacagtggc tcacgcctgt  1440
aatcccagca ctttgggagg ccgaggcggg tggatcacct gaggtcagag gttcaagacc  1500
agcctggcca acatggcaaa accctgtctc tactaaaaat acaaaaatta gcccggtgtg  1560
gtggcaggcg ccagctactc aggaggctga ggcaggagaa tcacttaaac ccaggaggca  1620
gaggttgtgg tgagcaagat tgtaccattg cactccagcc tgggcaacaa gagtgaaact  1680
ctgtctcaaa ataagataa gataagataa gataagataa gataagataa gataagatat  1740
aaaataaaac gtcttgtaga aacagggtct tgctatatgg cctaggctgg tctcgagctc  1800
ctgggctcaa gcaatcctct tgcctcaaca tcccaaagtc ctgggattag aggcgtgagc  1860
cactgtacct ggccagagca gatttttata tctgtgtcaa tttgtggaaa gagaggaggg  1920
ttcagtgtta ttgttgatga gagatctagg tggggatgca taccccaacc ctgtccaata  1980
aatgtggaaa acgagactca gagagggaat cgggtctcta atgtcatgcc aagatgggag  2040
cccagaatct tcccctcagg ccttagctgg ggtgggtgga aggttgaaga gctaacaggg  2100
gtctctgggc tgagacttgg gagctgacag attgtcccct ttccagctga gccacctgcc  2160
gggagcatgc ctctgcgcca ctgggggatg gccaggggca gtaagcccgt tggggatgga  2220
gcccagccca tggctgccat gggaggcctg aaggtgcttc tgcactgggc tggtccaggc  2280
```

```
ggcggggagc cctgggtcac tttcagtgag tcatcgctga cagctgagga agtctgcatc    2340
cacattgcac ataaagttgg tgagtctggg gcgttggcac catggggact ggggtgggtg    2400
tgcaagcagc agctgggccc catccatccg tctatccacc cacccaccca tccacccacc    2460
catccaccca ctcatccatc catccatcca tccacccatc cacccaccca tccaccctcc    2520
caaccaccca tccatccacc cacccaccca tccatccacc catgcatcca tccatcctcc    2580
catccaccca tccacccacc cattcaccca cccattcacc catccaccca cccttttcacc   2640 catccaccca tccacccatt catccaccca cccacccacc catccatcca cccacgcatc    2700
catccaccca cccacccacc catccatcca cccacgcatc catccataca tccacccacc    2760
cactcatcca tccacccacc tatccaccta tccatccacc tactcacccca cccatccacc   2820 cacctatcca cccacccacc catccaccca tccatccacc cacccattca tccatctatc    2880
catccatcca cccatcgatc catccatacc cacccattca tccatccacc catccatcca    2940
cccacccatc cacccatcca tccacccatc catccattca tccatccatc catccaccca    3000
cccacccatc catccaccca cccacccatc catccatcca tccatccacc cacccactca    3060
cccactcacc cacctatcca tgcatccatc catccaccca cccatccatc ctcccaccca    3120
ttcatccatc tatccatcca tccatccatc catccatcca tccatccatc cacccaccca    3180
cccacctatt catccatcta tccatccatc catccatcca tccatccatc catccatcca    3240
tccatccacc cgttcattcg gtgaacattt tgtaagcatc tactgtgtgg cagctgcaaa    3300
tcactgcctt tgtagagctg aaattttagt agggaggaca gcaagaaata taataaatca    3360
gaaaacttgg ccaggtgcag tagctgacac ttgtaatccc agtacttgag gaggcccagg    3420
caggaggatt gcttgaggcc agtagttgga gaccagcctg gcaacatag ggagaccttg     3480 tctcaacaaa ataatttta gaaattagcc aggcatggtg gtacatgcct gtagtcccag     3540
caacttgaga gcctgaggca agaggatcgc ttgagcccag gagttcaagc ctgcaatgag    3600
gtatggtttc gtcactgcac tccagcctgg gtgacagagt gagacccagt gtcattaaaa    3660
aaagaaagtc aggccgggcg cggtggctca tgcctgtaat cccagcactt tgggaggctg    3720
aggctggtgg atcacttgag gtcagaagtt tgagagcagc ctggccaaca tggcaaaact    3780
ccagctctac taaaaataca aaaactagcc gggcgtgggg tgcgcacctg taattccagc    3840
tactcaggag gctgaggcag gagaatagct tgaacctggg acatggaggt tgcagtgagc    3900
cgagatcaca gcactgcact ccaggctggg tgacagagct agactccgtt tcaaaaataa    3960
aaaaaggcca ggtgcggtgg ctcatgcctg taatcccaac actttcagag gctgaggcgg   4020
gcagatcacc tgagatcagg agttcaagac cagcctggcc aatgtagtga aaccgcatct    4080
ctactaaaaa tacaaaatgt agccaggcat ggtggcaggt gcctgcaatc ccagctactc    4140
agaaggctga ggcaggagaa tagcttgaac ctgggacatg gaggttgcag tgagccgaga    4200
tcacagcact gcactccagg ctgggtgaca gagctagact ccgtttcaaa aataaaaaaa    4260
ggccaggtgc ggtggctcat gcctgtaatc ccaacacttt cagaggctga ggcgggcaga    4320
tcacctgaga tcaggagttc aagaccagcc tggccaatgt agtgaaaccg catctctact    4380
aaaaatacaa aatgtagcca ggcatggtgg caggtgcctg caatcctagc tactcaggag    4440
gctgaggcag gagaattgct tgaacttggg aggtggaggc tgcagtgagc tgagatcgtg    4500
ccattgtact ccagcctggg caacaagagc gaaactccat ctcaaagaaa aaaaaaaaa    4560 aaaaagaaag aaaggctttc cctcctcctg cacaggaaat tgcacttcca aatatatcta    4620
ctacagtctt tctttttttc tttttttga gatggagtct cgctctgtcc caggctgaag    4680
```

```
tgcaatggcg caatctcagc taactgcaac ctccgcctcc cgggttcaag cgattctccg   4740
gcctcagcct cccgagtagc tgggactaca ggtgtgtgcc accatgcccg gctagatttt   4800
tttttttttt ttgtatttt agtagaggtg gggtttcacc gtgttagcca ggatggtctt   4860
gatctcctga cctcgtgatc tgcccgcctc ggccctccaa agtgctggga ttacaggtgt   4920
gagccaccat gcccggccca atttctttt tttaatgaca tagggtctca ctctgtcacc   4980
caggctggag tgcagtggtg tgacctcagc tcactgcaac ctccatgtcc caggttcaag   5040
ccattctcct gcctcagccg cctgagtagc tggaattaca ggtgcacacc cacgcccgg   5100 ctagtttta tattttagt agagctggag ttttgccatg ttggccaggc tggtctcgaa   5160
cttctgacct caagtgatcc acctgcctca gcctcccaaa gtgctgggat tacaggcgtg   5220
agccaccatg cccaaccaag gaaaggcctt tctaaggcgg ctttggttac atataccttc   5280
ctccagaaac tcctcttacc tcccccattc ccagctttcc atgactggat ggggcattg   5340 taatcaattt ttataacact tcctactcc ccattgatgg ctgagtcttt ttttttttt   5400 ctttcgtaga gacagtctct ctcttgccca ggctgaaatg cagtggtgca atcatgacgc   5460
attgcagcct ctaactgccc aggctcaagt gattttcctg cctcagtctc ccaaatagct   5520
ggggctacag gcacatgtca ccacacccgg ataattttg tatttttgc atgttgcctc   5580 atgctggtct caaactcctg gctcaagcc atccacccgc cttggcttcc caaagtgttg   5640
ggaggcatga gccatcgcgc ctggccatga ctgatttttt tttttttt gaaacgaagt   5700 ctcgctcagt cctcaaagct ggagtgcaat ggcacaatct ggctcactg caacctccgc   5760 ctcccgggtt ctagcgatcc tcctgcctca gcctcctgag tagctgggat tacaggcgcc   5820
tgccaccacg cccagctaat ttttgtattt tagtagaga cggggtttca ccatgttggt   5880
caggctggtc ttgaacatgc atgctgttcc ccctgcctcg gcctctcaaa gtgctgggat   5940
gacaggtgtg agccaccgtg cccggctttt tttttttt ttttttttga cggagtct   6000 cgctctgtca cccaggctgg agtgcagtgg tgtgatctcg gctcactgca acctccgcct   6060
cccgggttca agtgattctc ctgcctcagc ctcctgagta gctgggatta caggcgccca   6120
ccaccacacc tggctaattt ttgtattc agtagagacg ggggtttcac catgttggcc   6180
aggctggtct cgaactcctg acctcaagtg atccacctgc ctcagactcc caaagtgttg   6240
ggattacaag tgtgcaccct cgagcctggc catggctgat tcttgttt gttttgttgt   6300 gttgtttgag acagagtctc gctctgtcgc ccaggctgga gtgcagtggc gcgatctcag   6360
ctcactgcaa gctccgcctt ccgggttcac gccattctcc tgcctcagcc tcccgaggag   6420
ctgggactat aggcacccac caccacgcct ggctaatttt ttgtattttt agtagagaca   6480
gggtttcact gtgctagcca ggatggtctc gatctcctga cctcgtgatc cgcccacctc   6540
agcctcccaa agtgctggga ttacaggtgt gagccactgt gcccgccccc atgactgatt   6600
attaaaggat tcagacaggt gtgcgggtga tgtgaaacac gctcagcaga gggaacagca   6660
tgcatggagg cccggagagc ttgatctgtt tgaggaagcg aaagaccttc agggtgactg   6720
gggtatcaat tttgagagtt tggaagggga agtaacaatt gaaattgggg catagcaggc   6780
aaaagccagg gtggggtac tcagaatcaa gggtcaaggg gttgggcatt ctccgggagc   6840
aatggggagc catggaaggt ttaagccaga gagtgaagca gtctgactag ttcttttatt   6900 tttattttt attttttgact ggttctttaa gaagttgtct caagccaggc acagtgggtc   6960
acgcctgtaa tcccagcact ttgggaggct gaggcgggca gatcacttga ggttaggagt   7020
```

```
ttgagaccag catggccaac atggtgaaac cccgtctcta ctaaaaatat aaaaattagc    7080
tgggcgtggt gacgcacatc ccagctactt gggaggctga ggcaggagaa tcacttaaac    7140
ctgggaggcg gagttgcagt gagccgagat cgcaccactg cactccagcc tgggtgacag    7200
agactcggtc tcaaaaaaca aaaatatgaa acattggcca ggtgccgtag ctcacacttg    7260
taatccttgc gcttagggag gccaaggcgg gtggatcact tgaggtcagg agttggagac    7320
cagtctggtc aacatgatga aaccccatct ctactgaaaa tacaaaaaat tagccgggcg    7380
tggtggcggg cgcctgtaat cccagctact caggaggctg aggcaggaga atcgcttgaa    7440
cccaggggt ggaggttaca gtgagccgag atcacgccac tgcactccag cctgggcaac    7500
aagagcaaaa actctatcca aaaaaaaaa aaatacaaaa aattagctgg gcatggtggc    7560
acatgcctgt agtcccagct actcaggagg ctgagacagg agaatgactt gaacctgaaa    7620
ggcagaagtt gcggtgaacc aagattgcaa cattgcactc cagtctgggt gactccatct    7680
aaaaaaaata tatattgttt cacagggagg tatcctccct tcacagaggg gcagtataat    7740
tccatggtgt gactttggag agtgatttga taacacagtc aaagctggat gcagtggctc    7800
acgcctgcaa tcccagcagt tttggaggct aagcgtggag gatcacttga gcccaggagt    7860
tcaagatcag cctgggcaac atcgcgaaac cccgtctcta ctaaaaatac aaaaaattag    7920
ccaggtgtgc tgtgtgctgg tgtgcacctg tagtcccagc tactcaggag gctgaggtgg    7980
gaggatcact tgagcccggg aggttgaagc tacagtgatc atgccactgc cttcagcct    8040
aggtgacaga gcaagatgct gtctcaaaaa aaaaaaaaa aaaaaaaata tatatatata    8100
tatatatata tatagctgtg tgtggtggcg tgttcctgta tttcccagct actcaggaga    8160
ctgaggcagg aggactgctt gagccaggga ggtcatggct gcactgagcc atgattgcac    8220
cactgtattc cagcctatat gtcagagcaa gatcctgctt caaaaaaaaa aaaaaaccca    8280
ggccgggcgc cgtggctcac gcctgtaatc ccagcacttt gggaggctga ggtgggcgaa    8340
tcatgaggtc aggagattgc gaccgtcctg gctaacacgg tgaaacccg tctctactaa    8400
aaaaatacaa aaaattagc tgggcatggt ggcgggcgcc tgtagtccca gctactcggg    8460
aggctgaggc aggagaatgg cgtgaaccca ggaggcagag cttgcagtga gcggagattg    8520
agccaccaca ctccagcctg ggcgacagat cgagactccg tctcaaaaaa aaaaacaaaa    8580
actcagaaac atcttccctg aggccatata gttccactcc tggacagtga cagtcactct    8640
ataaacagtc agctcatgtg ctcccaggga cacttatgag aatgtttaga gccgccttgt    8700
ttatcatatg gaaagggga gaccattgca aagtccctca ataagagact gcctaagtaa    8760
attgcaatct ggttgaatac tggactactg cgcagccggg agaaggaatt taaccagaat    8820
tactcatgtc attctgcatg aagctttata acctctcgta gcctgaaaaa gcacattgca    8880
gagggacgtc tgcagtataa taccacacat ttacagttca taactttttt ttttttgaga    8940
cagagtttcg ctcctgttgc ccaggttgga gtgcaatagc acgatctcag ctcaccgcaa    9000
cctccacctc ccaggttcaa ttctcctgcc tcagcctccc gagtagctgg gattacaggc    9060
atgcgccacc acgcccagct aattttgtat ttttagtaga cgggggtttt ctccattttg    9120
gtcaggctgg tctcgaactc ccgacctcag gtgatccgcc tccctcagcc tcccaaagtg    9180
ctgggattac aggcgtgagc cactgtgccc agccacagtt cataacattt aaggctagat    9240
tgtagaggat atgaaaatta taaacactac ttcagggcag agcacactgg cttatgcctg    9300
taatcccagc actttggagg ctgagtagct cagcctccca gctactcagg aggctgaggt    9360
gggaggatca cttgagccta ggagtttgag accagcctgg acaacatggt gagacccctt    9420
```

```
ctctacaaaa actacaaaaa tcagctgggc atggtggcgt gcgcctgtag tcccagctcc   9480
ttgggaggct gaggcaggag gattgcttta gcccagtaag tcgagggtgc agtgagccat   9540
gatcacacca ctgcactcca gccacacctg gctaatttat tttattttta gttttttag    9600
agatgagggg tctcactatg ttgcttaggc tggtcttgaa ctcctaggtt caagtgattc   9660
tcccgcctta gcctcccaaa gtgctgggat tacagatgtg agccaccata cccagcttta   9720
gataaaatta tttatttcat tttattatta tttttttaga cagagcctca ctctttcacc   9780
caggctggag cgcagtggcg tgatctcggc tcactgcaac ctctgcctcc aggttcaagc   9840
aattctcttg cctcagcctg ctgagtagct gcgattacag gtgctcaccc ccacacccag   9900
ctaattttg tattttagt agagacgagg ttttgctctg gtggccaggc tggtctcaaa     9960
ctcctgccct caagtgcttc acctgcctca gcttccgaaa gtgctgggac tataggcatg  10020
ggccactgca cccagccaga taccattttt ttttttttt tgagacagt cttgctgtgt    10080
cgccaggctg gagtgcagtg gcacaatctc ggctcactgc acctccacc tcccgggttc   10140
aagcgattgt cctgcgtcaa cctccggagt agctgggact aaaggtgcac cccaccatgg  10200
ccagccaatt ttttttttc agatctcact ctgccgccca ggctgagct cagtggcacg    10260
atcttggctc actgcaacct ccgcctcccg ggttcaagca gtcctcctgc ctcagcctcc  10320
caagtagctg gaattacagg cacatgccac caggtccagc tattttttt tttaatagag   10380
atgggatttc accatgctgg ccacgctggt ctcgaactcc tgacctcaag tgatccacct  10440
gcctcagact cccaaagtgt tgggattaca agtgtgcacc ctcgagcctg gccatggctg  10500
attctttgtt ttgttttgtt gtgttgtttg agacagagtc tcgctctgtc gcccaggctg  10560
gagtgcagtg gcgcaatctc ggctcactgc aagttccacc tcctgaattc acaccattct  10620
cttgcctcag cctcccaagt agctgggact acaggcatcc gccaccatgc ctggctaatt  10680
ttttgtattt tttagtagag acggggtttc accatgttag ccaagatggt cttgatctcc  10740
tgacctcgtg gtctgcccac ctcagcctcc caaagtgctg ggattatagg cgtgagccac  10800
tgcgcccggc cgacaggtac aattttaaa tgacatcagt agaagaaaga taccctgggt   10860
agctggtgtg ggaaattaca gcaagtctgg agactggatt ggggttgagg tttgcatttg  10920
aaggtggtgg atggagcccc aggacatgga gggtgcagga agagcaggtc ttggtgaccg  10980
atctgttttg gagcaggtgg gagaggttga agataaggac caagttcctg gtttgaagaa  11040
ctgggcagaa gccacacacc ctggctcata gccataatcc catcaactcc agagattgag  11100
gtgggaggat cgcttgagcc ctggaggttg aggctgcagt gagctaggat tgcaccactg  11160
cactgcaacc tgggtggcaa agaaagaccc tgacccttaa aaaaaaagg gcagaggaag   11220
ggaaggttgg agtttgccaa ccacagataa gatatgttgt ttggaacaag ccatatctaa  11280
ggggggcct gtgatgtcca gggggagaca gccaggaggt gactggatgt ttctttgggg   11340
ctggagttca gggagacgcc agacaattgc agcagtttgt agagttatgt gggtcaggct  11400
aggattagtt ttgctgcagg aataagcaat ccccccaaat cttaatcaag gtttacctaa  11460
aatcggccga gcacagtggc tcatgcctgt aatctcagca cttgggggg ccaaggtggg   11520
cagatcacct gaggtcagga gtttgagacc agcctggcca acatggcgaa acctcgtctc  11580
ttctaaaaat acaaaaacta gccggggttg gtggcgcaca cctgtaatcc cagcaactca  11640
ggaggctgag acaggagaat cacttgaacc caggaggcgg aagttgcagc gagccaagat  11700
cgtgtcactg ctctccagcc tgggcaacag caagactcca tctcaaaaaa aaaaaaaag   11760
```

```
ttttacttaa aatcaagtac aggttggatg gttcacctct gtcttacagc ttcaccatct   11820
gtcacaagaa gccttcatca tacctcgggt ggtgaaggtg gcaagagaat ttatttccag   11880
gcttggaaat gtacccagcc ctttggccag aaaccagcag tgcaattggc tccatcctag   11940
ctgcaaggga ggctgggaaa tgtagtcctc ctgtgaggcc acagcatggg caacatacgc   12000
actgtcctct gcccaggggc aacgtgagac tgaagctgca ggtggggag ggggcctcag   12060 agggagtgtg aaggcagaca ttgggtctgg ggggtctttg gggctgacgg tagcaaatga   12120
cgtgactcct gacctcgttt ctcacctgat ccaggtatca ctcctccttg cttcaatctc   12180
tttgccctct tcgatgctca ggcccaagtc tggttgcccc caaaccacat cctagagatc   12240
cccagagatg caagcctgat gctatatttc cgcataaggt gggtggagac ctttgcaaag   12300
ctcgtcccct cctgtgctga agctggtctg actctgtgct aagccccagc tgcgtccctc   12360
cttcctgcag gttttatttc cggaactggc atggcatgaa tcctcgggaa ccggctgtgt   12420
accgttgtgg gcccccagga accgaggcat cctcagatca gacagcacag gggatgcaac   12480
tcctggaccc agcctcattt gagtacctct ttgagcaggt atgagcaggg ctggggtggc   12540
aagactattt gtgggagact taggggcagt tgaggagccc ccatttccct ccctgattca   12600
atatagctaa taggttttcaa ctcatgctat ctggggatct ttttttttt tttgagacgg    12660 agtcttgctc tgtcgcccag gctgaagtgc agtgatgtga tctcggctca ctgcaagctc   12720
cgcctcccag gttccgtca ttttcctgcc tcagcctccc aagtagctgg gactacaggc    12780
gcccgccacc atgcccagct aattttttgt attttagtg gagacgggt ttcacagtgt    12840 tagctaggat ggtctccatc tcctgacctc gtgatctgcc cgcctcggcc tcccaaagtg   12900
ctgggattac aggcgtgagc caccgctccc agccgatctt tttttttga aatggagtct   12960 tgctctgtgg cccaggctgg agtgcagtgg cgtgatctca gctcactgca acttccacct   13020
cccaggttga agcgattctt ccacctcagc ctcccaagta actgagatta cagaagcccg   13080
ccaccacccc aggctaattt ttctattttt agtaaagacg gggtttcacc atgttggcca   13140
ggctggtctc aaactcctga cctcaagtga ttcacctgcc tcagcctcct aaattgtggg   13200
attataggtg tgagccacca tgcccagcca agagttcagg ttgaagggga tagagtgctg   13260
tgattgatta gtaatgtctg ccacaggcac aagattgaca agaggagggg tgtatgctgt   13320
gtatttggcc tttccagtaa atggtggtct ctcccctcct caaggtggta agacgcagga   13380
aattagagtt ctctggctag agtaagcttg tccaacccct ggcctgcgga ctgcatgctg   13440
cccaggacag ctttgaatga agcccaacac aaattcataa actatcttaa atattctga    13500 gattttgctg tgatttttt tttttttga acagagttt cattcttgtt gctcaggctg     13560
gagtgcaatg tcatgatctc agctcactgc aacctctgcc tcccaggttc aagtgattct   13620
cctgcctcag cctccggagt agctgggatt acagacatgc gccaccacac ctggctaatt   13680 ttgtatttt agtataggcg agttttctcc atgttggtca ggctggtctc aaactcctga   13740
cctcaggtga cccgcccgcc ttggcctccc aaagtgctgg gattataggc gtgagccacc   13800
atgcccggct tgcgatattc ttttttttt ttttttttta gctcatcagc tatcattagt    13860
gttagtgtat tttatgtagg gcccaagaca cttcttccag tgtggtccag ggtagccaga   13920
agattggata cctctgggct agagaggaac gcattctcac acctcccttt ctgctcaatt   13980
tcctgttccc agggcaagca tgagtttgtg aatgacgtgg catcactgtg ggagctgtcg   14040
accgaggagg agatccacca cttaagaat gagagcctgg gcatggcctt tctgcacctc     14100
tgtcacctcg ctctccgcca tggcatcccc ctggaggagg tggccaagaa gaccaggtgt   14160
```

```
ctgggaatgg ggtggggacg ctgtgtaggc aggggggaaat gtcctgagca tctgggagcc   14220
agggtagact ttgcatattg ccgtgcctct actttttttt ttttctgagc cggagtctct   14280
ctctgtcacc taggctggag tacagtggcg caatcttggc tcactgcaac ctctgcgtcc   14340
caggttcaag agattctcct tcctcagcct cctgagtagc tgggattaca ggtgcccacc   14400
atcaagccca gctaattttt gtattttag tagagacaga ctgagtttca tcatgttggc   14460
caggctggtc tcgaactcct gacctcaagc gatccttccg ccttggcttc caagtagctg   14520
gagactacag gctcaagtca ccacacctgg ctagtgtgcc tgttttccag atgaggcagc   14580
tgaggctcaa agaggttaag ccacttgccc tgtgtcaccc agctgggcct gcaacccagg   14640
tccctgacca gcccctcact gtgtttcccc ccagcttcaa ggactgcatc ccgcgctcct   14700
tccgccggca tatccggcag cacagcgccc tgacccggct gcgccttcgg aacgtcttcc   14760
gcaggttcct gcgggacttc cagccgggcc gactctccca gcagatggtc atggtcaaat   14820
acctagccac actcgagcgg ctggcacccc gcttcggcac agagcgtgtg cccgtgtgcc   14880
acctgaggct gctggcccag gccgaggggg agccctgcta catccgggac agtggggtgg   14940
cccctacaga ccctggccct gagtctgctg ctgggccccc aacccacgag gtgctggtga   15000
caggcactgg tggcatccag tggtggccag tagaggagga ggtgaacaag gaggaggtga   15060
gcaaggcgcc cctccgcccc tgggggttca ggttgggctg gggtgggttt ctgtgttcat   15120
ccttgaccct agcctctgag ggtggctgac ctgagccctc tccccacatg gctctggggc   15180
acctgtccgc tagggccagt ttcttggaga aggtcctcca tctgcttacc ccctggggac   15240
cttatttctg gggtctgcac ctccagggaa ccccttcatc tggggactgg cacctgggtg   15300 tgaggggggtc aggattcttc tctctgcctt ccctaagggt ccggcttcca gcatgtgtat   15360
gattttgggg tgggtcccca tcccacctgt gacactggga cttgggaggt caacctaggt   15420
tggtgcctgg cccttctggc tccagtctct ccccagggga aagtgcagga ggtataaacg   15480
ggcattgccc tctccatcct ctgccccact tgctgggtgt tcagggttct agtggcagca   15540
gtggcaggaa ccccccaagcc agcctgtttg ggaagaaggc caaggctcac aaggcagtcg   15600
gccagccggc agacaggccg cgggagccac tgtgggccta cttctgtgac ttccgggaca   15660
tcacccacgt ggtgctgaaa gagcactgtg tcagcatcca ccggcaggac aacaagtgcc   15720
tggtgaggcc cagggtaggg gctggctag ggcccatcat ggcctgggag gacacccacc   15780
tgatgcgccc ctggctggca ggagctgagc ttgccttccc gggctgcggc gctgtccttc   15840
gtgtcgctgt tggacggcta tttccgcctg acggccgact ccagccacta cctgtgccac   15900
gaggtggctc ccccacggct ggtgatgagc atccgggatg ggatccacgg accccctgctg   15960 tgagtgctgg gtgggggggcg ctgggggcca ccgccaaggg tgccaactag actgtgagcc   16020
ctaggggctg tgcagggtgt gtgtgtaggt gcacgtctta tttttttttt attttttgtc   16080
gcccaaactg gagtgcagtg gcatgatctc agctcactgc agcctccgcc tcccgggttc   16140
aagcgattct cctgcctcag cctcccaact gactacctgg gactacaggc actcgccacc   16200
atgccaggct aattttttgta ttttttgtaga gatggggttt catcagattg gccaacctag   16260
tcttgaactc ctgacctcag gtgatccacc cgcctcggcc tcccaaagtg ctggtattac   16320
aggcatgagc caccacgccc ggccatgact gtcattgtgt gttgaggttg tcattgcaca   16380
gaactggtga ttttcatggg actgtgtgtt accctgacgc tggtgaccat tcaggcgtat   16440
gttggatgct tccacctctg caggcggctg cctgtgctgg taacttgtga gtcaccatct   16500
```

```
cagcggggtc ctgtgtgtga cttgtgggcc tgagggcgtg aagttgtcgg tacttatgtc   16560
atcatcaggt gcaggggagt gtgtggctgt cctgtgtgct gccaagtcgt gatttgtgac   16620
tgtctctttg tctggtcact ggccctgtga ctctctgtcc cttgtcctac ctgtgatgcc   16680
aggggagggg gaagtggcca tttcaccttg tgaggcctgt ggccgtgcct gctgtcaagg   16740
ctatatgtgt gctgccccccg tacagacagg tgtttgggga ccacgtgtgt cagccactgc   16800
acatgtaggt gtctggacct atgtgaccat gacactttat agtgcatgtt tgtgtcacct   16860
ctgtgtctgg gatgccctgg cccctatgtt gccctgtcat attgggtgat tagttgtgtc   16920
tgggatcgtt gtcctttgct tgtgtgattg ccatccacc gtgtgtcacc cttgtgagtg   16980
gcgatggtca tggctgggtg tgtgcccatc cggctcctga tggctgtttc caatcttgga   17040
gtgtgtgtca ccttgtcagg gcccgtctgg cgtcaagtac aagagtagga gtaggctggg   17100
tgtggtggct cacacctgta atcccagcgc tttaggaggc cgaggtggga gaatcacttg   17160
agcccaggag ttcaagagca gcctgggcaa tgtagcaagg tcttttaact acagaaaaca   17220
caaaaattag ctgggcacac ctgtaatcct ggctcctcag gaggctgagg tgggagaatc   17280
tcttgagcct gggaggtcca ggctgaagtg agccaagatt gcaccgctgc actccagcct   17340
gggcaacaga gcaagaccct gtctcaaaaa aaaaaaaaaa aaaagagag atcaggtagc   17400 cgggcacagt ggctcatgcc tgtaatccca gcactttggg aggctgaggc tggcagatca   17460
gctgaggtca ggaatttgag accaggctgg ctaacatggt gaaacccccct ctgtactaaa   17520 aatataaaaa ttagctgggc atggtggcag ggacctgtaa tcccagctac tcgggaggtt   17580
gaggtgttga ggcaagagaa ttgcttgaac ccaggtgggc agaggttgca ataagctgag   17640
atcacgccat tgcattccag cctgggtgac gagggaaaat ccgtctaaaa aatacaaaca   17700
aataaacaaa aaagcaggtg tgtgcctgct gctgcattgt gtctccatgt aagtggctgt   17760
gtgtccagag ttagtgtccc cacaagagtg gctgtgtctg acacttgtcc tagctgtgtg   17820
tgtgccctct aagtaggtaa tgagtgtcat tgttcccggg tatgggtcca gagtggcccc   17880
aggtggcctg atagtccccc tggaccacct tccagggagc catttgtgca ggccaagctg   17940
cggcccgagc acggcctgta cctcattcac tggagcacca gccacccccta ccgcctgatc   18000 ctcacagtgg cccagcgtag ccaggtgagc ccagggctgg gggctggggc tggggctgga   18060
cacgttccct gcctggtccc ctgcttactg ctcccacctc tgccacctcc tgccaggcac   18120
cagacggcat gcagagcttg cggctccgaa agttccccat tgagcagcag gacggggcct   18180
tcgtgctgga gggctgggc cggtccttcc ccagcgttcg ggaacttggg gctgccttgc   18240
agggctgctt gctgagggcc ggggatgact gcttctctct gcgtcgctgt tgcctgcccc   18300
aaccaggagg tacgatgata gggggacctc tgggtgggat gtggcatctc tcccccaggc   18360 ccgcccctcca tgacttgatg cctgcccccca gaaacctcca atctcatcat catgcggggg   18420
gctcgggcca gccccaggac actcaacctc agccagctca gcttccaccg ggttgaccag   18480
aaggagatca cccaggtggg tgcagggaag gggcccgggg caagggcagg gcccctgggg   18540
atgtgggtgc tgggggccct gggagatcag ctgctaactt tcaccatggc ggtattctgt   18600
gccacatgat cccgcagctg tcccacttgg gccaggcac aaggaccaac gtgtatgagg   18660
gccgcctgcg agtggagggc agcggggacc ctgaggaggg caagatggat gacgaggacc   18720
ccctcgtgcc tggcagggac cgtgggcagg agctacgagt ggtgctcaaa gtgctggacc   18780
ctagtcacca tgacatcgcc ctggtgagtg gcagggcca ggcctggggg tgtgtctgtg   18840
gaggaggtgg ccggaggagg tgggatggga ggggtgtgtc tgtggaggag gtgggatggg   18900
```

```
agggggtgtgt ccgtggagga ggtgggatgg gaggggtcgg ctttgcagcc acctgacctg    18960
cccggtcccc acaggccttc tacgagacag ccagcctcat gagccaggtc tcccacacgc    19020
acctggcctt cgtgcatggc gtctgtgtgc gcggccctga aagtgagtgg gtcccgccat    19080
acccatcccc ctttggcagg ccaccccctga cttataccca ctccctgatc tgtacccaa    19140 ccctcgacct acaccccaac ctatgcctat ttctcaactc tcacctgtac tctgatcccg    19200
ggctacacct tgaccttcaa cctagacccc aaccctaac gatattccag cccataactt    19260
acatcccaac acgtcgaccc tcacctgccc tcagtctcaa cccccaccct gattcccaac    19320
tacatcccca cttccatcaa cctcccaaac aacctctaca gtccagcccc catctgctcc    19380
tggccccatc agcactatgg cctcaggcag actccagtgc tgatgtgtgc tgattctcct    19440
aggcctcagc cctgcacat ccaaccctgc ctaaccccac ctcttccttt cctctgcagg    19500
tagctcaaaa ctccttgtat aggctaggtg tggtggctca cacctatccc agcactttgg    19560
gaggcagagg tgggaggatc gcttaaaccc aggagttcaa gaccagcctg ggtaacatgt    19620 ccagaccta tctttacaaa aaatttaaaa atcagggcca ggcatggtga cctatgcctg    19680
tagtcctagc tacttgtgag gctggaatgg aaggatcact tgagcccagg agttcaaggc    19740
tgcagtgagc catgattgta ccactgcact ccagcctggg cgacagggcg agactctgtc    19800
tcaaaaaata taataaataa ataaaaaata aagccccttgt acagaacaac cctagaccca    19860
cccatccctc aacccccctg tgtgtgtgtg tgtgtgcatc tcccccactt tcccctggac    19920
cctggccgac accctgaccc acatccctct gactactctg gtaccaaac atctcctaca    19980 ccccaacctc aagccctag cctctgctta tccatgccca tcccccccat ccctagttgc    20040
ttactttgta ggctcaccttt tatctctttt tttgtgagac tagggtctcc ctctgttgcc    20100
ccggctgcaa tgcagtggtg ccatcatggc tcactgaagc ctcgacctcc cgggctcaag    20160
cgatccttcc gcctcagcct cttgagcacc tgggatgaca ggcgtgtgct atcacacccg    20220
gctgattttt aaaattttt tgtagagatg gggtctcact atgttgctta ggctgatctc    20280
aaactcctgg gctcaaggga tcttcctgcc tcagcctccc aaagtgacag gattgcaggc    20340
atgagccact gtaccctgcc acctttatct cttttttttt ttaattttt tgagacggag    20400 tctcactgtg tcacccaggc tggaatacag tggcgtgatc tcggctcact gcaacctccg    20460
cctcccgggt tcaagcaatt ctcctgcctc agcctcccga atagctggga ttacaggcat    20520
gtgccaccat gcccagctaa tttttttttt tttcttcttt ttgagatgga gtcttgctct    20580
atcgcccagg ctggagtgca atgacgtgat ctcggctcac tgcaagctcc gtctcccacc    20640
attcttctgc ctcagcctcc caagtagctg ggactaccgg cgcccaccac catgcctggc    20700 taatttttt gtcttttag tagagatggg gtttcactgt aattttttttg tattttagt    20760 agagttgggg tttcaccata ttgaccaggc tggtctcgaa ctcctgaact tgtgatccgc    20820
ccgcctcagc ctcccaaagt gctgggatta caggcgtgag ccaccgcgcc cggctgtatt    20880 tttttttta gtagtgatgg agtttcatca tgttgggcag gctgcccttg aactcctgac    20940
ctcaggtgat ccacctgcct cagcctccca aagtgctggg attacaggcg tgagccacta    21000
cgcccagccc acctttctct cttgaacttc aacttcttcc gtgccccatc ccacttggac    21060
cccaatgccc tcatccaccg ctgcctctgc tgcattccgc atttcttctc tccccaaact    21120
cactttcaac ccagaccaaa ctccacccac acctctgccc tgacacctcc ccagccacat    21180
gccaagtccc tccctggcgt ctccccaat tccccgccat ccagagggca gaagcaggca    21240
```

```
ggttgcccca gagcagctgt gtctttacag atatcatggt gacagagtac gtggagcacg   21300
gacccctgga tgtgtggctg cggagggagc ggggccatgt gcccatggct tggaagatgg   21360
tggtggccca gcagctggcc agcgccctca gctacctggt gtgtggcctg tgtgtggggc   21420
ctgggtcggt cagggagggc caggagccca ggagttcgag accagcctgg gcaacagggc   21480 gagacccat cttttttgtt tgttttgttt taggtggagt ttcgccctgt cacccaggct    21540
ggagtgcaat ggcatgatct cggctcactg caaccttcgc ctcccgggtt caaatgattc   21600
tcccgcctca gcctcccaag tagctgggat tataggctcc tgccatcacg cccagctaat   21660
ttttgtattt ttagtagaga tggggtttca ccatgttggt caggctggtc tcgaacttct   21720
gacctcgtga tccatccgcc tcagcctccc aaagtgctgg gattccaggc gtgagccacc   21780
acgcccagct ggccccatct tttaaaaata aacaaatagc caggtgtggt ggctcatacc   21840
tgtaatccca gcagtttggg aggccaaggc gggtggatca cctgaggtca ggagtttgag   21900
accagcctgg ccagtatggc aaaccttgc ctctactaaa aatacaaaaa aaattagcca    21960
atgtggtaac ttgcacctgt aggccgaggt actcaggaag ttgaggtggg aggatcacct   22020
gagctcagga atttgaggcc gtagtaagct atgatcacac cactgcaccc cagcctgggc   22080
agcagcatag ctagacccca tctccaccaa aaatttaaga atcagctagg ctgtggtgat   22140
gtgcacctgt aattctcgct acttggaagg cttgagccca ggagtttgaa gctgcagtga   22200
gctatgttcg tgccactata ctccaacctg agagacagag tgagaccctg tcttaaaaaa   22260
aaaaaaaaaa aaaaaaaaca agaaaaaaat aaccccccaa aaaacaaaac agaaagaaac   22320
ccagtgatag tcacagttgt cctttcaca ttggctgtcc ctatgggac caggtttggg      22380 gttggcgtct gtgcctctcc tgagtggcca cacccctct cctgcccacc tcaggagaac     22440 aagaacctg ttcatggtaa tgtgtgtggc cggaacatcc tgctgcccg gctgggttg      22500 gcagagggca ccagccccct catcaagctg agtgatcctg gcgtgggcct gggcgccctc   22560
tccagggagg gtgagtacct gaggggacct gggcacagtg gggggcttcc cctgctcctt   22620
tcacccttgg tgacctctga ccttggcctc ccagagcggg tggagaggat ccctggctg    22680 gcccccgaat gcctaccagg tggggccaac agcctaagca ccgccatgga caagtggggg   22740
tttggcgcca ccctcctgga gatctgcttt gacggagagg cccctctgca gagccgcagt   22800
ccctccgagg tatgtctagg agaccctggg gcctccccg cagtgggggc cctccaaga      22860 aatccagagg acagaatcag agctcaaagc tgcatccctt ctggcctcgt gacttcaagt   22920
ctctctgggc taccagcagg tgggccactc gctggggctc aatgtagtcc cagccttttt   22980
aggtccttgt ggaagtcact tgtgcctggc acacagaagg caagtaagag acttgatttc   23040
agttttaggc agagtgacca gggcagcgat gggagacgcc caggctgcag agtggggaag   23100
aagggctgag gatgcgcctc acccagcagt ggggtcagac aaggcttccc aaaggaggtt   23160
catgagtgtg gtgggttttat tttgagacga agttccactc taattgccca ggctggaatg   23220
caatggcgtg atctcagctc actgcaacct ctgcctcctg ggttcaagcg attctcctgt    23280
ctcagcctcc cgagtagggg ggattacagg cacatgccac cacacccggc taatttttgt   23340
attttttgta gagatgggt ttcattatat tggtcaggct ggtctcaaac tcctgacctc     23400
aggtgatccg cccacctcgg cctcccaaag tgctgggatt acaggcatga gccacagtgc   23460
ccggccccag aagaggtttt atctaagtgt agaattatgc caacaagcct ggctaggaag   23520
ggcagcctag gcagagtgca tggcctgtgc aaaggctgag gcttcagtgt attaaggagc   23580
tgtggtctac aggaggggca ggagggaagc ttggggcagg aggctgactg tgacactcca   23640
```

```
gctctgcata atcactggac ctgggtccca gtcctggttc tacggctgtg agcacgtcct   23700
cccactttgt ggagcctcag ttgcctcatc tgtataatgg aactgataag agcgggcacc   23760
tggcggtcca ctctggggac ttgactctgc ctcttgggga acgggttggg ggcgagggga   23820
ggatgttgac tcctctgggt ccctttccca acagaaggag catttctacc agaggcagca   23880
ccggctgccc gagccctcct gcccacagct ggccacactc accagccagt gtctgaccta   23940
tgagccaacc cagaggccat cattccgcac catcctgcgt gacctcaccc ggctgcagcc   24000
ccacagtgag ctccatccca gtgctgggac cctggggaag tgggacgggg ctgggatccc   24060
tgctgtatgc ctatagcgca cgagaggtct ctgcacagtg gttcagggtg tgtgccaatt   24120
tcttgcagtg gcattcataa gcatgccctg cctggctgcc ctgagctctc attaatgtat   24180
ttatttattt atttgcaatg gaatcttgct ctgtcaccca gcctggagcg cagtgacgtg   24240
atcttggctc actgcaacct ccacctccca ggttcaagca atcctcccac ctcagcctcc   24300
caagtagctg ggattacaag cgtgtgccac catgcccggc taattttgt attttagta   24360 gaggtggggt tttgccatgt tggccaggct ggtctcaaac tctagacctc aaatgatcta   24420
tctgcttcag cctcccaaat tgctgggatt acaggcgtga ccactgcgc ctggcctcct   24480 taatgttttg tctggggaga acacaactt ctttggatta gagaattaga ccactgcagt   24540 ttttttttc tttttaaaaa agttttgtat tgttctcttt aaaaaattaa tatgctcttt   24600 tttcttttt ttgagacgga gtctcactct gttgccaggc tggagtgcag tggtgcaatc   24660
ttggctcact gcaacctccg tctcccaggt tcaagtaatt gtcctgcctc agcctcctgg   24720
gtagctggga ctacaggcgc ccaccaccac gccgggctaa ttttgtatt tttagtagag   24780 acggaattc accatgttgg ccaggatggt ctcagtctct tgacctcgtg atccaccgc   24840 ctcggcctcc caaagtgctg ggattacagg catgagccac tgcgcctgac ctattttctt   24900 ttttttttc tttctttctt tttttttttt ttgagatgga gttttgctct tgttgcacag   24960
gctggagtgc aatggcacga tctcggccca ctgcaacctc cgcctcctgg gttcgagcaa   25020
ttctcctgcc tcagcctccc gagtagctgg gattacaggc gtccaccacc acacccagct   25080 aattttgta tttttagtag agacgggggtt tcactgtgtt ggctaggctg gtctcaaact   25140
cctgacctca ggtgatccac cctcctcagc ctcccaaagt gttgggatta caggcgtgag   25200
ccaccacgcc cggcctaata tgccatttc aactggtcat atcacatttt tctttctctt   25260
ttttgtttta aagactaggt cttgctgtgt tgcccaggca ggagtgtggt ggttattcag   25320
aggcacgatc atgctcact gcagcctgag actcctgggc tctagggatc ctcctgcctc   25380
ggcctcccaa agtgctggga ttacaggtgt gagccaccac gcctggccag ttttctctt   25440 ttctctatga aatatctgtg ccctctaccc aatctcggaa cttccagatg tcaggttttt   25500
ctgttttttc ttttttctttc tttctttctt ttttttttttt ttaaagacag tgtctctctg   25560
tggcccagac tcactgcagc ctcaaaactc ctgggctcaa acgatcctcc tacctcagcc   25620
tcctgagtag ctgggaccac aggcatgcac caccacacct ggctaatttt tttttttaac   25680
ttttttgtag agagggggtt tcaccatgtt gtccaggctg gtcttgaact cccgggctca   25740
agtgatcttc ccgcctcggc ctcccaaaca ggtgtcagtt ttgatgcagc caactctgca   25800
tcattttgta caataagtgg actctttcag ctgttgcagg aaaaagtttt cttacctcta   25860
gaatcggatc ctggggtagc tgtggctggc tttgtgactc ccaagtgtgg gcctgctggg   25920
gaaaggatcg gggtcaggcc tttacccacc gcaactcttc cagatcttgc tgacgtcttg   25980
```

```
actgtgaacc cggactcacc ggcgtcggac cctacggttt tccacaagcg ctatttgaaa   26040
aagatccgag atctgggcga ggtgagggac gggcctgagc tgctaaaagg cccgcctggt   26100
cgggaaggag tttgggggtt gaggataaat tcctacctaa ggtgattctc aggagatgtg   26160
ggtgggaccc tctgctttga gggaggccta ggtgccaagg agtcttaata gagcggagta   26220
ggcggggcct ggggtattcc gaaaggatct gcctggagga gtggcccggg aaatcggggg   26280
ttggggagtg gtgcagggat tggggaggtg gagctgaccc tcgtgcgctc ccgaccaggg   26340
tcacttcggc aaggtcagct tgtactgcta cgatccgacc aacgacggca ctggcgagat   26400
ggtggcggtg aaagccctca aggcagactg cggcccccag caccgctcgg gctggaagca   26460
ggagattgac attctgcgca cgctctacca cgagcacatc atcaagtaca agggctgctg   26520
cgaggaccaa ggtgggcggg acccggcgag tcctagagac ttgaggggc gtggttagag   26580 cgtgggtgtg gccttgtggg cggggccagt ctggcctagc caattagaga ctctcaaccc   26640
caggctgcag tacgcggttc ttggcatctg ggtgagcgtg gctgggctgc ctccttccca   26700 tctgggggt gctacctgct ggggccagga tggacgggag ccaccagcag ctccctcaag   26760
tgagaatggg gttctggatg ggtccatccc acctgagaac tgggtctagt gtgcgcgggt   26820
cttggccttc cctcccgacc ttggaggggc tctgctgggc tcaaggtagg cggtccccgg   26880
cccgccctct atcgtccccc accggggccg cccctctccg cggcaggcga gaagtcgctg   26940
cagctggtca tggagtacgt gcccctgggc agcctccgag actacctgcc ccggcacagc   27000
atcgggctgg cccagctgct gctcttcgcc cagcagatct gcgaggttgg tcggccccgc   27060
ccctgcttct ggagcttgcc ccttcctctt cagcttgggc tggcctgagc gatccggtgc   27120
agtctgctct cacgctccgc ccctgctcgt ttgcccaggc tgtcttgtcc ttgcactgac   27180
ctccgaactg tttggcttgc ttggccacac cccctcctcc caagggacca cgcacagccg   27240
gctcggcccc tcccaactcg ccctcctgcc cagctttgct cgtctagccc cgtccctgct   27300
ttctggctca gcctccttt gcttggtgcc acgtgccatc cggccctctc cagcggccgg   27360
gtagccaccg gcctgacctg actgtccccc agccctcctg gctgctcagg tcctgccgcc   27420
gcccccggcc gaaccccgcc ccactgaaac tcacgagccc tgccccgtcc cagggcatg   27480 gcctatctgc acgcgcagca ctacatccac cgagacctag ccgcgcgcaa cgtgctgctg   27540
gacaacgaca ggctggtcaa gatcgggcac tttggcctag ccaaggccgt gcccgaaggc   27600
cacgagtact accgcgtgcg cgaggatggg gacagccccg tgttctggtg accaggcggg   27660
gtgcagtctg aggggtgct ggggtcactt ggaacaggca gggtggagta gacggatgct   27720
gggtatcatg ataggggcatg atcccagtga agcgcggcgg ggcctagcgg tgcggggtg   27780 gggcctatgg aggcaagggg cggtgtatag agtgcggctt ggcctggtgg gcggggttaa   27840
cccggcctag ccaatgagcg gcctagccaa tgagcatatc accccgctca ggctgcgctc   27900
ttaagggtgg gtcccaactg agcccagagg gtccttcagt ctcaggtgag ggcttcagcc   27960
tggtctgatc cccaagccct cagtgcagcc ccccgtggcc tgagtgcccc cctcccccta   28020
ggtatgcccc agagtgcctg aaggagtata agttctacta tgcgtcagat gtctggtcct   28080
tcggggtgac cctgtatgag ctgctgacgc actgtgactc cagccagagc ccccccacgg   28140
tgagagccag gcccgcagcc ccaccgggag tttgctagag caattagaaa ggcataggct   28200
gggccaggcg cggtggctca agcctgtaat cccagcactt tgggaggccg aggcgggcgg   28260
atcacgaggt caggagatcg agaccaacct ggctaacacg gtgaaacccg tctctactaa   28320
aaatacaaaa aaaattagcc aggcgtggtg gcgggcgcct gtagtcccag ctactcagga   28380
```

```
gactgaggca ggagaatggc atgaacccgg gaggcggagc ttgcagtgag ccgagatctc    28440
ccgactgcac tccagctggg tgacagagcg agactccgtc taagacagga caggacggag    28500
agagagagaa agaaaagaaa ggaaagaaag gcataggccg ggcgcggtgg ctgacacctg    28560
taatcgcagc actttgggag gccgaggcgg gcagatcacg aggtcaggag atcgagacca    28620
gcctggccaa catggtgaaa ccccgtctct actaaaaata caaaaattag ccgggcgtgg    28680
tggcaggtgc ctgtaatccc agctactcag gcggctgagg cagggagaat tgcttgaacc    28740
cggtaggcga aggttgcagt gagccgagat catgccactg cactccagcc tgggtgaaag    28800
agcgagagac tgtctcaaaa aaaaaattct ggacggtaag aacaatctgc tgtgaggctt    28860
aataataacg gcaaacacct gactcacgct tactctatga atattagttt aacgttcaca    28920
gtaatcccag gtggcagatg ttattaccct atttacgga tgagaaaaca ggcccagaga    28980
agtgaactca aattcaaagt cacacagctg agaagtgtaa gaggtgggat tggaacccat    29040
gcagtcgatt tcatgaagtt gcagagtgat ttcttttct ttttgagat ggagtttcac    29100 acttgtatcc caggctggag tgcaatggca caatctcggc tcactgcaac ctccgcctcc    29160
caggttcaga cgatcctcct gcctcagcct cccaagtagc tgggattacg ggcgcctgcc    29220
attatgccca gctaattttt gtatttttag tagagatggg gtttcaccat gttggccagg    29280
ctggtctcga actcctgacc tcaggtgatc cacccacctc agccttccaa agtgctggga    29340
ttacaggcat gagccaccgt gcctgccttt cattgcctct tgaaaagagc ttgtcttgtt    29400
tatactgtag aaattccttg agctcatagg cattgctcag ggtcagatga cagttctgag    29460
actcactgag ttgctggaac gagggagag gctgccacgg cccgacaaat gtccctgtga    29520
ggtgagactt cctttgtctt tccctgaccc cactatcctg ctgtggagag ggcagccccc    29580
accagccctg gttttccctt ctaggtctat catctcatga agaactgctg ggagacagag    29640
gcgtcctttc gcccaaccttt cgagaacctc atacccattc tgaagacagt ccatgagaag    29700
taccaaggcc aggccccttc agtgttcagc gtgtgctgag gcacaatggc agccctgcct    29760
gggaggactg gaccaggcag tggctgcaga gggagcctcc tgctccctgc tccaggatga    29820
aaccaagagg gggatgtcag cctcacccac accgtgtgcc ttactcctgt ctagagaccc    29880
cacctctgtg aacttatttt tctttcttgg ccgtgagcct aaccatgatc ttgagggacc    29940
caacatttgt agggggcacta atccagccct taaatcccc agcttccaaa cttgaggccc    30000
accatctcca ccatctggta ataaactcat gttttctctg ctgga                    30045
```

<210> SEQ ID NO 94
<211> LENGTH: 1036
<212> TYPE: DNA
<213> ORGANISM: Homo sapiens

<400> SEQUENCE: 94

```
gtgtgtggcc tgtgtgtggg gcctgggtcg gtcagggagg gccaggagcc caggagttcg      60
agaccagcct gggcaacagg gcgagacccc atcttttttg tttgttttgt tttaggtgga     120
gtttcgccct gtcacccagg ctggagtgca atggcatgat ctcggctcac tgcaaccttc     180
gcctcccggg ttcaaatgat tctcccgcct cagcctccca gtagctggg attataggct     240 cctgccatca cgcccagcta atttttgtat ttttagtaga gatggggttt caccatgttg     300
gtcaggctgg tctcgaactt ctgacctcgt gatccatccg cctcagcctc ccaaagtgct     360
gggattccag gcgtgagcca ccacgcccag ctggccccat cttttaaaaa taaacaaata     420
```

```
gccaggtgtg gtggctcata cctgtaatcc cagcagtttg ggaggccaag gcgggtggat      480
cacctgaggt caggagtttg agaccagcct ggccagtatg gcaaaacctt gcctctacta      540
aaaatacaaa aaaaattagc caatgtggta acttgcacct gtaggccgag gtactcagga      600
agttgaggtg ggaggatcac ctgagctcag gaatttgagg ccgtagtaag ctatgatcac      660
accactgcac cccagcctgg gcagcagcat agctagaccc catctccacc aaaaatttaa      720
gaatcagcta ggctgtggtg atgtgcacct gtaattctcg ctacttggaa ggcttgagcc      780
caggagtttg aagctgcagt gagctatgtt cgtgccacta tactccaacc tgagagacag      840
agtgagaccc tgtcttaaaa aaaaaaaaaa aaaaaaaaaa caagaaaaaa ataacccccc      900
aaaaaacaaa acagaaagaa acccagtgat agtcacagtt gtccttttca cattggctgt      960
ccctatgggg accaggtttg gggttggcgt ctgtgcctct cctgagtggc cacacccccct     1020 ctcctgccca cctcag                                                     1036

<210> SEQ ID NO 95
<211> LENGTH: 1448
<212> TYPE: DNA
<213> ORGANISM: Homo sapiens

<400> SEQUENCE: 95
agaaaggagt ggggttgaaa agcgcttgcg caggacggct acggtacggg ggtgggaggg       60
cttcggagca cgcgcgcgga ggcgggactt gggaagcgct cgcgagatct tcagggtcta      120
tatataagcg cggggagcct gcgtcctttc cctggtgtga ttccgtcctg cgcggttgtt      180
ctctggagca gcgttctttt atctccgtcc gccttctctc ctacctaagt gcgtgccgcc      240
acccgatgga agattcgatg gacatggaca tgagcccct gaggccccag aactatcttt       300
tcggttgtga actaaaggcc gacaaagatt atcactttaa ggtggataat gatgaaaatg      360
agcaccagtt atctttaaga acggtcagtt taggggctgg tgcaaaggat gagttgcaca      420
ttgttgaagc agaggcaatg aattacgaag gcagtccaat taaagtaaca ctggcaactt      480
tgaaaatgtc tgtacagcca acggtttccc ttgggggctt tgaaataaca ccaccagtgg      540
tcttaaggtt gaagtgtggt tcagggccag tgcatattag tggacagcac ttagtagctg      600
tggaggaaga tgcagagtca gaagatgaag aggaggagga tgtgaaactc ttaagtatat      660
ctggaaagcg gtctgcccct ggaggtggta gcaaggttcc acagaaaaaa gtaaaacttg      720
ctgctgatga agatgatgac gatgatgatg aagaggatga tgatgaagat gatgatgatg      780
atgattttga tgatgaggaa gctgaagaaa aagcgccagt gaagaaatct atacgagata      840
ctccagccaa aaatgcacaa aagtcaaatc agaatggaaa agactcaaaa ccatcatcaa      900
caccaagatc aaaaggacaa gaatccttca agaaacagga aaaaactcct aaaacaccaa      960
aaggacctag ttctgtagaa gacattaaag caaaaatgca agcaagtata gaaaaaggtg     1020
gttctcttcc caagtggaa gccaaattca tcaattatgt gaagaattgc ttccggatga     1080
ctgaccaaga ggctattcaa gatctctggc agtggaggaa gtctctttaa gaaaatagtt     1140
taaacaattt gttaaaaaat tttccgtctt atttcatttc tgtaacagtt gatatctggc     1200
tgtccttttt ataatgcaga gtgagaactt tccctaccgt gtttgataaa tgttgtccag     1260
gttctattgc caagaatgtg ttgtccaaaa tgcctgttta gttttaaag atggaactcc     1320 acccttgct tggttttaag tatgtatgga atgttatgat aggacatagt agtagcggtg     1380
gtcagacatg gaaatggtgg ggagacaaaa atatacatgt gaaataaaac tcagtatttt     1440
aataaagt                                                             1448
```

<210> SEQ ID NO 96
<211> LENGTH: 885
<212> TYPE: DNA
<213> ORGANISM: Homo sapiens

<400> SEQUENCE: 96

```
atggaagatt cgatggacat ggacatgagc ccctgaggc cccagaacta tcttttcggt        60
tgtgaactaa aggccgacaa agattatcac tttaaggtgg ataatgatga aaatgagcac       120
cagttatctt aagaacggt cagtttaggg gctggtgcaa aggatgagtt gcacattgtt       180
gaagcagagg caatgaatta cgaaggcagt ccaattaaag taacactggc aactttgaaa       240
atgtctgtac agccaacggt ttcccttggg ggctttgaaa taacaccacc agtggtctta       300
aggttgaagt gtggttcagg gccagtgcat attagtggac agcacttagt agctgtggag       360
gaagatgcag agtcagaaga tgaagaggag gaggatgtga aactcttaag tatatctgga       420
aagcggtctg cccctggagg tggtagcaag gttccacaga aaaagtaaa acttgctgct       480
gatgaagatg atgacgatga tgatgaagag gatgatgatg aagatgatga tgatgatgat       540
tttgatgatg aggaagctga agaaaaagcg ccagtgaaga aatctatacg agatactcca       600
gccaaaatg cacaaaagtc aaatcagaat ggaaaagact caaaaccatc atcaacacca       660
agatcaaaag acaagaatc cttcaagaaa caggaaaaaa ctcctaaaac accaaaagga       720
cctagttctg tagaagacat taagcaaaa atgcaagcaa gtatagaaaa aggtggttct       780
cttcccaaag tggaagccaa attcatcaat tatgtgaaga attgcttccg gatgactgac       840
caagaggcta ttcaagatct ctggcagtgg aggaagtctc tttaa                      885
```

<210> SEQ ID NO 97
<211> LENGTH: 294
<212> TYPE: PRT
<213> ORGANISM: Homo sapiens

<400> SEQUENCE: 97

```
Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
    130                 135                 140

Pro Gly Gly Gly Ser Lys Val Pro Gln Lys Lys Val Lys Leu Ala Ala
145                 150                 155                 160

Asp Glu Asp Asp Asp Asp Asp Asp Glu Glu Asp Asp Glu Asp Asp
                165                 170                 175
```

```
Asp Asp Asp Asp Phe Asp Asp Glu Glu Ala Glu Lys Ala Pro Val
            180                 185                 190

Lys Lys Ser Ile Arg Asp Thr Pro Ala Lys Asn Ala Gln Lys Ser Asn
        195                 200                 205

Gln Asn Gly Lys Asp Ser Lys Pro Ser Thr Pro Arg Ser Lys Gly
    210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Gly Gly Ser Leu Pro Lys Val Glu Ala Lys Phe Ile Asn Tyr Val
            260                 265                 270

Lys Asn Cys Phe Arg Met Thr Asp Gln Glu Ala Ile Gln Asp Leu Trp
        275                 280                 285

Gln Trp Arg Lys Ser Leu
    290

<210> SEQ ID NO 98
<211> LENGTH: 23181
<212> TYPE: DNA
<213> ORGANISM: Homo sapiens

<400> SEQUENCE: 98
agaaaggagt gggggttgaaa agcgcttgcg caggacggct acggtacggg ggtgggaggg    60
cttcggagca cgcgcgcgga ggcgggactt gggaagcgct cgcgagatct tcagggtcta   120
tatataagcg cggggagcct gcgtcctttc cctggtgtga ttccgtcctg cgcggttgtt   180
ctctggagca gcgttctttt atctccgtcc gccttctctc ctacctaagt gcgtgccgcc   240
acccgatgga agattcgatg gacatggaca tgagccccct gaggccccag aactatcttt   300
tcggtaactg ctgggggggag ctggagcgag gccgagcggg gcctggtggc ggtgagggtg   360
ggggtgaggg gcgggaatcc ggctgcaacc gggtctggtg gagaccgcca gaccgacggg   420
aggcctgagc gggtgggaag agctgcctga gccctggacc tggagggatt ggagccgcgg   480
ggggagccgg tggcgtgaag ggggaggaga cgagcggcct gaagcgtctg ggcgtgagc    540 ggtccgaggc ccggggcctg aggtaaagtg gaaccggccg cctggaagtt cggcctttgc   600
cggggatacg tggcggagct ccaggcgtgg tttatttct aacggcggtg gttcataggc    660
ttctgatgcc aggccccggg ttggtggtcc tggaggctgg gttcaccggg aagcatgggc   720
ctgcttgttg gagcgggtag atgcacagcc tggcgttatt ctggcctcag agcctggagc   780
tgccggacgt agacttacct cgcgtgcttc ggccagttac tgggggtggg gaggcgcggc   840
gcggcgtgag gaggccgcaa ccgctgggag cacgtggttg ccacgtggtt ggggaggga    900 gggggggtgtg ggcgctacat ccgggactca ccggcgtgtt gccactcgtg agccagggat   960
gctgtggctc tgttgaagtg gaaatgtta agaggctggt agcactaggg ttctggaggt  1020
ctttgttcag tgcttacagc atgtactgtg atggcagctc tcattttttt gagccccttt  1080
tctgtctcac tgcggtaggt ggagctagcc ccactttgca gatgaggata ctggtgccca  1140
gagataaact cacttaacga aggttgtact tagtaaaggc aataagagac taaatctaaa  1200
ccaagacgct tgactccgta gctgctgctt cgtgaatatt aatgaggctt cgttttaggg  1260
ggacgtcctc gcatgccgcc atttgtgcgg cattgaccaa actgcttttc taaatacaag  1320
aaacacgtag agtgttcggt ttgagtcaga tcaagaccta agactattcg cagaattttg  1380
```

```
ggagcaccac ccccctcgac ttgcggtagt cctgccccaa aaaggagagt cccacttggg    1440
tttttgatct cagtaggatt aattgcagaa gcctaatctt tgtactattc agactttgaa    1500
gtaaatgcaa atcctaccgt gaattttatc ttgttcatta tccgtgctga gatttgttaa    1560
ttaaacgtct gttcacattt aagcatgtat atgtattggt aacggttaga tgatagttaa    1620
atggaatcat ttaaaatttt tattctgaca gtgttttgaa gaattttgcc cattcatgga    1680
gtgagagtag acatatgtat tcaaaacatt aaggctttaa ttcctagtta tttttggatag   1740 ctgagaattc tggtaaattt atatcagtac tttttgataa ctatcggaaa gaaccctcct    1800
tgtcttaaac ataatttctg aatatagttt gaggcgtatg tcactttctg ttgctttaaa    1860
gagtggagtg ttgatccctg tagcaaactt cggttctttt acttttgtca ttttctttt     1920 gtaatagtaa gctattcatg tttgtaaccg ttctcatttc gaaattgcca tttgggaatt    1980
taggtaggta aatcagctgt tttaaatagt gggaaactta acattggaca ttacatttgg    2040
tttcagataa ttgcttcagg ttgagattta ctaaaccatt gagcttgttt atgcagaata    2100
acagtaccta tcagcgtagt tagagatgaa atatggtatg atgagagaat ggaattatag    2160
tcttttatgg gtgtctgtag aggtttctgt tcaagaaatc taggaattga tcattctgct    2220
ttgccctctg gtagctaaaa tagtgaaaaa ctagttcaaa agttagacct gacctttttg    2280
gttacccaca cttaagtttc agtgttattt ttctccttgt tagagttgct ttttcttca    2340 tttacaggtt gtgaactaaa ggccgacaaa gattatcact ttaaggtgga taatgatgaa    2400
aatgagcacc agttatcttt aagaacggta cttaaacttt caaaataaac tacttaaccc    2460
tacttgattt cagcctttta gtttctattc atgtggcttg agactttttt tcctttgctg    2520
actgcttata aaatactatt tcttacacct gggtattgtg tgtacctcac tgtctgtaca    2580
tctttgaaga acttggcatc tataccactc atttggtaac catgtaaatt ccagtcacac    2640
tgttcaactt gccttatttt cttcagttga attacaaagc ccttgtaaaa ggcatcgata    2700
atctttcatg tctaccagag actagccttc tgctcaactt agaagttgct caataaatat    2760
gttaggtggt ctatattgtg tgtatgcata tttatgcatt tcttaaattt tctgaatatg    2820
agaaactgat ttgccaagat cacaaaacct gaggacaaca ttgcacaaat ttgttttcca    2880
gggtaatagt gagaggttta tacttgtttt ttaaaaaaat cacagtcatg tgcctcattg    2940
caactgctgg gtcaacagat ggatcgcata taatggtg gtcccataag attattatac       3000
cttattttta atataccttt cctgtttttt tttttctttg gaggcagtct cgctctgtca    3060
cccaggctgg agtgcagtgg tgtaatctcg gctcactgca acctctgatt ccgagttca    3120 agtaattccc tgcctcaccc tcccgagtag ctgggattac aggcatgtgc caccacacct    3180
ggctaatttt tgtgttttta gtagagacga ggttgttacc atgttgtcca ggctggtctc    3240
aaactcctga cctcatgatc tgcccgcctc agcctcccta gtgttggga ttacaggcat     3300 gagccaccaa gcccggccct ttcctatgct tagatgcaca aatactgtgt ttcggttgct    3360
tacagtattc agtacagtaa cactgtacag gtttgtagcc taggtgtgtg tagtaggcta    3420
taccatctag gtttgtataa gcacattctt atgattgtac aaagatgaaa ttgtctaaca    3480
acacatttct cagaacctag ccctgtggtt aagtgacgca tggctgcata taacatttag    3540
tgggggggtg taaataggt ggaactcaaa agttgaagta gtattttttt tttgttcaca     3600
ggtcagttta ggggctggtg caaaggatga gttgcacatt gttgaagcag aggcaatgaa    3660
ttacgaaggc agtccaatta aagtaacact ggcaactttg aaaatgtctg tacagccaac    3720
ggtaagggca cttacatact ttggatgttg tgtcaaggtt taattctgtt ttaaggtagg    3780
```

```
tttggtgtca tttagttgtg ccaaggagat agaaagtggt tctttatctt ctgtcactgg   3840
agttcgatgg tcaactcttg aacatggggg cttctgctgc tacttttatc agaggtggaa   3900
aaacaggttc actggtttgt tgatttggct tatgtgtttg cctgtaatgt ttattgttca   3960
ttttcttcac atgtttagtg atgaaaaatt tctcccttct aggtttccct tgggggcttt   4020
gaaataacac caccagtggt cttaaggttg aagtgtggtt cagggccagt gcatattagt   4080
ggacagcact tagtaggtat gttattttta tatattatac tacttagttt gtcctcttta   4140
gtgcagttgc ttggttccca gtttggactt aaagcatggg tatagtacta ctgtcttttt   4200
aataggttcc aatgtgagtc tagaaattgg agaggacaaa taaattttg gggcggggg   4260 gagaggaaat cttgctgtca cccaggctag agtacagtgg cacgatcttg gctcactgga   4320
acctctccgg gattcaagcg atcctcctgt ctcagcctcc ccagtagctg ggccacaga   4380 cgtgcaccac caagtccagt tgcgtttcat agttatagta gagaaggggt tcgtgatgt   4440 tggccaggcc gatcttgaac tcctggcctt aacgtgatct gcacgccctg gcctctcaaa   4500
gtgctagtat tacacgtgtc agccactgtg cctggcctaa aaattatttt ttaataaaga   4560
cagtctcatt ataacggctg gagtgcagtg atgtgatcat agcttgctat atcctcgaac   4620
tgctactggg ttcacctcag cctctggaat agctagaact acaggcacac tccacgcctg   4680
gctaattttt tttgtatatg tgcagatggg gtctcagtat gttgcccaga ttggactctt   4740
ggcctcaagt ggtccgcctt ggcctcccca aagtgagatt acaggcatga gccaccctcc   4800
ccaggcttct tgcatttaaa acctggcagt gaacattagg cctcaaaata cttttgttaa   4860
aaagttcctt ttcccatgtg ctcttttttt tttttttttt aaatagaata gaagtctcag   4920 ttttagagt atttactatc agtgttcttt tttttctga cttcttgctg cttgagtttt   4980
ataatgtcta ataaattgta ttttagctgt ggaggaagat gcagagtcag aagatgaaga   5040
ggaggaggat gtgaaactct taagtatatc tggaaagcgg tctgcccctg gaggtggtag   5100
caaggttcca caggtagaga tggcaatttt attataggtt ttgtattata gcttttagtt   5160
tggtgataga acagctcttg ttcatgagta cgtatctttt cttttaaaag aaaaaagtaa   5220
aacttgctgc tgatgaagat gatgacgatg atgatgaaga ggatgatgat gaagagtaag   5280
tatgatttta gaaacttgat atacttccgg aatcttgaca aaaaaaggaa tttgacatag   5340
ttatatgcat gagggtttta taaaagtcat ttacaaaaag ccatcctatg taatagttta   5400
taataaaagg gcaggtggtc atctgttgtc agtttaagtt aaatgagctg agttgaaagg   5460
atattgggtc tgtgagcctt tacaatgctg tgacttgtga ctcttcagaa gggtagacta   5520
tagtgtttgt gaagtttgat tatgtcccct tgttctgaag atttagtgga tgtgttatac   5580
ccatcaagcc tggtatgttt tatggtgagc agttaatgag attgggttga agaaaaatat   5640
gattaaatag ctctatattc attttacaag ttgttactca aggtttgtta ttccctaaaa   5700
ggattttgtc ttatgttttt atgtagatat ttattgacaa aaataagatt ctaaagggga   5760
tattaagatt ttcttgggat ttaaaatatg gttggaaaca atatttgatg actttatatt   5820
aaactagatc aaactattgt tacaaacagt taatacgcac actggtataa agtactgttt   5880
ataattggtc ttatgtgtgc cagtaccagt aatgcattga atactttgat ttggctctca   5940
gctttgtcct tcagttctga ggttggtcca tatgcattta ttgaaaacaa atataagaac   6000 atgcactttta aaagagaacc tgcatgaaag atcaaattgg gagtttaggt tttaagctgg   6060
tggttcttca aaatctttga gcatgacgat gaaggcagaa aacaggaaaa aggccgaaag   6120
```

```
agccgaaagc ttaaaaattc aaagtatgac caggcgcagt ggttcacacc cgtaatccta      6180
acacccagcc aagatgagag gatctcttga ggccagcccg gtcaaaatag caagacccaa      6240
tctcaaaaga aaaataaaaa ttcaaagtac ttgcatgtca aacttataaa tgaacgcaaa      6300
cttaaaggta gtatttgact gttgctgttt ttgttttctt tttttttttt tttttttttg      6360
agatggagtc tccagttgct caggctggag tgcggtggcg ccatctcggc tcaccacaac      6420
ctctgcctcc tgggttcaag cgattgtcct gcctcagcct cccgggtagc tgggactgca      6480 ggctcgggc accatgccct gctaattttt gtatttagta gagacagggt ttcagtatgt       6540
tggtccggct ggtcttgaac tcctaacctc gtgatctacc tgcctcggtc tcccaaagtg      6600
ctgggattgc agatgtgaac cactgcgccc agccaaattt ttgtattttt aatagacatg      6660
gggtttcacc acgttggcta ggctattctc aaactcctaa cctcgggcga tctggtcacc      6720
tcatcctccc aaagtgctgg gattacaggc atgagccacc gtgcccggcc acttttttc       6780 ttgagatggt gttttaccat gctactcaga ctggacttga atctctgggc acaagctatc      6840
ctcccctctc agactatgaa gcaggtgggg ttacaggagc ataaccaagc ccagcttgtt      6900
tggttatcac ttttaagaat atttctcgtt agtaagaatt gaaatacatt ccaagagaag      6960
aatgggaaac aggctaaaaa cacaaattag aaatagggat ggtatggttc ggattggttt      7020
agtctgattt tgagttacct ttgtacaagt ttataaaata agtgtttaat agcattcacc      7080
gaggctcggg gacaagcaat cccttccaga aaggctttgg agtaggacct gattgtagta      7140
ttgaccctgt tggggctttg gaagatttcc ttttttaaaa attgatataa ttaggccagg      7200
catggtggct cacgcctgta atcccagcac tttgggaggc tgaggtgggt ggatcacttg      7260
aggtcaggag ttcaagacca gcctggccaa catggtgaaa cccggtatct actaaaaata      7320
caaaaattag ctgggtatcg tggtgcctgc ctattggtcc cagttactta ggaggttgag      7380
tcaggagaat tgcttgaacc tgggaggtgg aggttgcagc aagccaagaa tgcgccaccg      7440
tgttccatcc tgggcaacag agggagactc ccatctcaga aaaatgggta taaattcatg      7500
atgtaaccac aatgtaattt tgtttgtctt taagttgggc attgatagga atgaaaagtg      7560
tagatatcaa ggtccaaatc agtacctggt ttttttgtg ggattttttt ttttcggca       7620 agtctcgctc ttgtgcccca ggctggtgtg caatggtatg atctctgctc gctgcaacct      7680
ctgccttcca ggttcaagtg attctcctgc ctcggcctcc agagtagctt ggattacagg      7740
cacttgccac cacgcctggc taagttttgt attttttagta gagacggggt ttcaccatgt     7800
tggccaagct ggtctcgaac tccaaagtgc tgggattaca ggcgtgagcc accatgcacc      7860
gccgcaagtt ttcatataag ttgaagaaag tgtactaagg tctgcatagt agtaaaggat      7920
gccttgaggg aaacaaatat taatagaaac ttcagtggtg agatggcaag ggcccagcat      7980
agatagatgg caatgaaaat gcaaagaggt gcatgaaggt tcgttatagt tacttagaaa      8040
tctaaccttt tgaacacaga tcaaagggga atttggttcc ttttgagga tggaatgggt       8100 atatggtgtg ggctcagatg actcttgatt taagcaagaa aggctatgta atgtgcatag      8160
tgctgatgta tactatacat agatgtatgt aatacgttga tagtatgtgg cccttaaatg      8220
tcttttttaa ttttttggga atttcttaag taaagctgaa ttttttttttt tttttttgga    8280 gacagtctct gttgccccgg ctgaagtgca ttgttggcta ggctggagtg cagtggtgca      8340
atcatggctc actgtaactt ctgcctcccg ggttcaagtg attctcctgc ctcagcctcc      8400
caagtagctg ggattacagg catgtgccag catgccaggc taatttttg tatttttaat       8460 agagatgggg tttcgccatg ttggtcaggc tagtcttgaa ctcctgacct caggtgatct      8520
```

```
gcccacccca gcctcccaga gtgctgagat tacaggtgtg agccaccaca ccctgccagt   8580
aaagctgttt tgatagtagt tttgatagct attttgatag tagtttaata gacttgtttt   8640
aacaaataag aaaaaatgtt taaaaaaagc attctcatct tgtttctagc acaggggagg   8700
cacctgcagg gattgggttc taatgccaga aacttgtact gacaaaatca ctgttaaaaa   8760
gccacttgaa gggctatttg tgacagcttt ttaagttatg atacttttc taaatacagc    8820 aaatatttct tcggtattgg aaagataggt gtttcttaca tgaagttgct gtattgggat   8880
ttagagacca gtacgttcag ttgttgaatt aaacgtgaac cccttggtat tgctaatag    8940 agacttctgc ctgacttgcc ctccagtgac tcgatttgat tactcccctc cattgtttac   9000
ctattaacag ttcacacctg taatcccagc actttgggtg gtcgatgcgg gcagatcacc   9060
tgaggtcagg agttgaagac cagcctggcc aatatggtga aacccgtct ctgctaacat    9120 acagctgggt gtgatggtgg gcgcttgcaa tcccagctgc tggggaggct gaggcaggag   9180
aattgcttga acccgggagg cggaggttgc agtgagccga gatcgcacca ttgcattcca   9240
gattgggcaa caagagtaaa actcaaaaaa aaatagtgtg cagttcagtg gttttagtat   9300
gcatagttgt gtagccatca ccataatcaa ttttagaaca tttcatcacc tcaatgagaa   9360
atcgtactct ataggtatta cccctcatgc tcttcagctc tagtcaacca cgaatgaact   9420
ttgtctatag gttcctgtc cctcatattt tgcacgaatg gacttctgtg actgttttct    9480
tagcacagtg ttttcaagtt tcatccatgt tatagcatta tcagtactcc atttatttat   9540
atggttgaat acattgtatg ggtatgtttg gttattcatc agttggtgag catttgagtt   9600
gcttctactt gttgactgct atgaacgctt gtagacatgt cattttactt ggatgtacac   9660
ctaaagcaga gtggctcacc cattgtattc ccactagcag tgtatggggc ttctgatttc   9720
actccaacct actgatttca ctacaccctc acttgccatt atctgactct aatcctggtg   9780
gtatgaagtg ctgattgtgg gtttgattgc gtctccctgt ggactaataa tgagcatctt   9840
ttcatgtatt cattggccat atatctttgg agaaatgttt tgcccactt aaatccattt     9900 acttctcttt gtctttacta agttgtaaga attctttttt cttttttctt tttgatatga   9960
tttttgtatt tttagtagag aagggggtttt gccatgttgg ccaggctgtt cttaaactcc  10020
tgtcttcagt gatccacctc cctctgcctc ccaaactgct gagattacag ctgtgagcca  10080
ctgtgcctgg caagaattct tttttttttt ttttgacaa gtctctgttg cccaggcttg    10140
agtgcagtga tgtgatcttg gctcactgca acctcctcct cccttgttca agcaattctt  10200
ctgcctctcc caagtagttg ggattacagg caccccccc accacgcccg ctaatttttc   10260
tgtattttaa atagagaccg ggtttcgcca tgttggccag ctggtcttg aactcctgag    10320 gtcaggcccg cctcggcctc ccacaagtgc tgggattaca ggcgtgagcc actgcactgg  10380
gcccaagaat tctttatgta ttctgcaaac aagtccctta tcagacacaa gatttacaga  10440
ttatcttcca ccattccgtg aattgttact taactttcat gatggtggcc tttgaacaag  10500 ttttttaattt ttatgacgtc cgatttcttt tgttgcttgt gcctttggtg tcaatcctaa  10560
gaaatcattg ctaaattcaa agttgtgaaa atttgccccc ttaattctga gttttgtcct  10620
ttatatttag ggctttgttc cattttgagt aaacttatgt gtatggtgtg aatggagggg  10680
tctaaatata gactttggat gtagattagc agttgcccca acatgatttg ttcaaaaact  10740
attttttccc cattgaatga tcttggcaac ctttaaaaga gtcacttatg gctgggtgtg  10800
gtggctcaca cctgtaatcc cggcactttg agaggctgag gcaggcggat catgaccagg  10860
```

```
agattgagac tatcctggcc aatttggtga aaccctgtct ctactaaaaa tacaaatttt   10920
agctgggcat ggtagcgtgt gcctgtagtc ccagctactc aggaggctga ggctggagaa   10980
ttcgcttgaa cctgggaggc agaggttgca gtgatctgag attgcaccac tgcactccag   11040
cctggcgaca gagcgagact ccgcctcaaa aacaaaaaa atcactgttt ctggactgtt   11100
ctgttgatgt gtctatcctt aacatgtaag aacagtacaa cactgttcct ctgtggtttt   11160
tatttattta ttttttgaa atgagtctca ctgtcaccca ggctgtagca cagtggcgtg   11220
atcttggctc actgcaacct ccgcctcctg gttcctcctg cttcagcttc ctgagtagct   11280
gggattacag gcgcccgcca ccatgcccgg ctaattttg tattttagt agagactggg    11340
tttccccatt agccaggctg gtctcaaact cctgacctca ggtgatctgg ccgtctcggc   11400
ctcctaaaaa gtgccgggat tacaagcgtg agccacggtg ccttggcccc tttgtaggtc   11460
ttatagctga ttttttgaaa tcaagtgtga gttttctagc tttcttcctt tccagattgc   11520
atttggcctc tttgggtccc ttaagtgtct ttttgtttt tgtttttga gatagggtct    11580
tgctctgtca cccaggctgg agtgcagtgg cagaattaca cagttacagt tcactgtctc   11640
aagcagatcc tcctgcctta gcttttcaaa tagctaggac tacaggcgca caccaccacg   11700
cctgctaatt aaaattttt tttgtagaga gggttctcat tatgttgcct aggctggtct   11760
tgaactaaaa cgatcctccc acctcagcct cccaaagtgt taggattata ggtgtgagac   11820
actgtgccag ttcttgggtt tgtttataaa ttttaggatc tgtttctaca gagaaaccag   11880
cttggggagt cttctaacga ttgtatttaa cctgtatatt cggggagtgt ttccatcttg   11940
gcaatatctg aacatggaat gtttctattt aggtctttaa tttttttttt taacacaaat   12000
tcactctgag tgtacagttt aatagaacta tacattactt aaatatacat acattataca   12060
gtggtatagt gtgtatttat gcaaaactac tcattgagca acttcatttc ccagccccta   12120
gcgatcacaa ttataccttc tatttctttg agtttgacta cttttagata cttaatgaat   12180
agaatcatac agtgtttgtt cttttgtggc tggcttattt cactttgttc aaggttcagt   12240
catgtagcat gcaagaggat tttcattgtg tgtacatata catttcatt tagtcattta    12300
acacttgggt tgcttttcacc tcttggctgt tgtgaacaat gcttcgataa acatgggtgc   12360
acaaataatc acttcaaggt cctgctttca attcttgtgt ctactcccaa attttgaaag   12420
tgcttaatgt cttgacattt catttgtagt gatgatgatg atgattttga tgatgaggaa   12480
gctgaagaaa aagcgccagt gaagaaagtg agtagataca atgctacaag gttgttaaac   12540
taacaataga aatggtgatt ttttagtgct atttgcttgt tttgtagtta agggaagctg   12600
gtgtgggaga tcatctcata ctgaaaatta gtcctgagga ggattacaga aaacttaaga   12660
gtggggaatg gtctgttttc tttatccatg tggccctcca cccagtttgt tagtcttgtg   12720
taaccttttg tccaagtggt tgctgctttt tccttccttt tttttttt tttgagacgg     12780
agtctcaatg tcacccgggc tggagtacag tggcgcgatc tcagctcact gcaacttctg   12840
cctcccgggt tgaagcgatt ctcctgcctc agcctcctga gtagctggaa ttacagactc   12900
atgccaccac acccagctaa ttttgcatt tttagtagac caccatgtcg gccaggctgg    12960
tctcgaactc ctgacctcgt gatccacctg cctcggcctc ccaaagtcct gggattacag   13020
gcatgagcca ccacgccaag cctgtggttg ctgcttgtct tacatggctt ggacagcttt   13080
gtttgcactg ttgttggggt cagggacagt gattaagata aatttctaat tgcagtctat   13140
acgagatact ccagccaaaa atgcacaaaa gtcaaatcag aatggaaaag actcaaaacc   13200
atcatcaaca ccaagatcaa aagtaagtgg ctacatttac acgtgggtct cattgatcta   13260
```

```
gttggggaaa aagattctac tgtggaagaa tctagtgtgt ctgaaatttg ataggccttt    13320
atagaacccc tgtaattgct gtttaaaagt taaaatcagc ttgctgcagc caggctcagt    13380
ggctcactcc tgtaatccca gcactttggg agggaggcca aggtgggtgg gatcacctga    13440
ggtcaggagt ttgagactag cccggccaac atcgtgaaac cctgtcttta ctaaaaacac    13500
aaaaattagc caggcatggt ggtatgtgcc tgtaattcca cctactcagg aggtggagac    13560
aggagaattg cttgaacctg ggaggtggag tgcagtgaga ttgcaccact gcactccagc    13620
ttgggcaaaa gagcgagact ccgcctccaa aaaaaaaaat cagcttgttg tgtgttgtag    13680
gtacacacac acacacaaac atactaaatg taaggtggtg gggcggggg agccaataga    13740 cttttttgaa agagatggac cctcactttg tcactcagtc tgggttagag ttgcgtgatc    13800
tcggcttact gcaaccttca cttcccgggt tcaagcgatt ctcctgcctc agcttcccaa    13860
gtagctggga ctacatgcgc gtgccaccag gcccagcgta ttttgtatt tttgagtaga    13920 gatgggttt cactctatat gttggccagg ctggtctcaa acccctgact gcaggtgatc    13980
cgccctcctg ggcctctcaa agtgtgtgag ccaccacgcc tggcctgaat tttttgtgat    14040
tgtgaagtca atagttgttt cctgtaagga atctttgttg aaaggtatgt ctgcatagag    14100
tagaagttct caaccttggc tgcatgttag cttgaagtag aacatttggg cctagacagg    14160
gtgtattgat ctcattcctg accctaccca cttccctgca gaaaatggaa tttaaaggaa    14220 aaaaagtta aaggaaccc agtacttgtg ctctacttat ggagattgtc ataaaatgg    14280 tctggggtgg gcgccaggca tcagactaca gtgactttct tgctttattc ttagggattt    14340
tctgatttcc ttttttttt tttttaacc tgatgaaata gtttatttac aatttaaacg    14400
aataaatttc atattctaca acacatataa tctattgact aaatgtaact aatgatgaac    14460
ctccatacaa acaaccccac taaaaagtgg gcaaaggaca taaacagaca cttttcaaaa    14520
gacatacaag tggccaaaaa gcatatgaaa aacagctcaa tatcactgat tagagaaatg    14580
caaatcgaaa ccacaatgag ataccatctc acaccagtca gaatagctat tattaaaaac    14640
tcaaaaaaca acagctgctg gcaaggttgc agaaaaaagg gaatgcttac acactcttgg    14700
tgggagtgta aattagttca accattgtgg aaagcagagt ggcgattcct caagagcta    14760 aaaacagaac taccatttga cccagcaatc ccattacatt cccaaaggaa tataaatcat    14820
tctaccataa agatacatgc acacaaatat tcactgcagc actattcaca atagcaaaga    14880
catggaatca acctaatacc tgatatggtc tggctttgtg tccccaccca catctcatct    14940
caaattgtaa tccccacgtg ttggaagagg ggcctggtgg gaggtaattg gatcatgggg    15000
tagatttccc tcttgctgtt ctgttgatag tgaattctca tgagatctgg ttgtttgaaa    15060
gtgtgtagca cctcccctt tgtgctctct ctcttctgct gccatgtaag atgtgccttg    15120 cttcccottt gccttctgcc atgattgtaa atttcctgtg gcctcctagc catgcttcct    15180
atacagccta cagcactgta agtcaattaa acctctttc ttcataaatt acccaatctc    15240
aggtagttct ttttttttt tttcatttta tttatttatt tatttatttt ttattttat    15300 ttttttta atttatttt ttattgataa ttcttgggtg tttctcacag agggggattt    15360
ggcagggtca tgggacaata gtggagggaa ggtcagcaga taaacaagtg aacaaaggtc    15420
tctggttttc ctaggcagag gaccctgcgg ccttccgcag tgtttgtgta cctgattact    15480
tgagattagg gattggtgat gactcttaac gagcatgctg ccttcaagca tctgtttaac    15540
aaagcacatc ttgcaccgcc cttaatccat ttaaccctga gtggacacag cacatgtttc    15600
```

```
agagagcaca gggttggggg taaggtcaca gatcaacagg atcccaaggc agaggaattt   15660
ttcttagtgc agaacaaaat gaaaagtctc ccatgtctac ttctttctac acagacacgg   15720
caaccatccg atttctcaat cttttcccca cctttcctgc ctttctattc cacaaagctg   15780
ccatcgtcat cctggcccgt tctcaatgag ctgttgggca cacctcccag acggggtggt   15840
ggccgggcag aggggctcct cacttcccag taggggcggc tgggcagagg cgcccctcac   15900 ctcccgacg gggcggctgg ccgggcaggg gggctgaccc cccccacctc cctcccggac    15960
ggggcggctg gccaggcggg gggctgaccc cccacctcc ctcccggaca gggcggccgg     16020
ccgggcgggg ggctgacccc cccacctccc tcccggacgg ggcggctggc cgggcagagg   16080
ggctcctcac ttcccagtag gggcggccgg gcagaggcgc ccctcacctc ccagacgggg   16140
cggctggccg ggcggagggc tgacccccc acctccctcc ggacggggc ggccggccag     16200 gcgggggct acccccccca cctccctccc ggacggggcg gctggccggg tgggggggct    16260 gacccccca tctcccggac ggggtggctg gccgggctga ggggctcctc acttcccagt   16320
aggggcggcc gggcagaggc aaccctcacc tcccggacgg ggcggctggc cgggcggggg   16380 gctgacccccc ccacctccct cccggacggc acggctggcc aggtgggggg ctgacccccc   16440
cacctccctc ccggatggca cggctggccg gtcggggggg ctgacccccc acctccctcc   16500
cagatagggc ggctggccgg gcgggggggtt gacccccccc cacctccctc ccggacgggg   16560
tggctgctgg gcggagatgc tcctcacttc ccagatgggg tggctgccgg gcggagaggc   16620
tcctcacttc tcagacgggg cagctgccgg gcggagggc tcctcacttc tcagacgggg    16680
tggttgccag gcagagggtc tcctcacttc tcagacgggg cggccaggca gagacgctcc   16740
tcacctccca gacgggtct cggccgggca gaggcgctcc tcacatccca gatgggcgg     16800 cggggcagag gcgctcccca catctcagac gatgggcggc cgggcagaga cgctcctcac   16860
ttcctagatg tgatggcggc tgggaagagg cgctcctcac ttcctagatg ggatggcggc   16920
cgggcggaga cgctcctcac tttccagact gggcagccag gcagagggc tcctcacatt    16980 ccagacgatg ggcggccagg cagagacact cctcacttcc cagacggggt ggcggccggg   17040
cagaggctgc aatctcggca ctttgggagg ccaaggcagg cggctgggag gtgtaggttg   17100
tagtgagccg agatcacgcc actgcactcc agcctgggca ccattgagca ctgagtgaac   17160
gagactctgt ctgccctgat ttcctttttt gaactgactt agtactgtgc ataaaagcaa   17220
actcccaagt tactcttttt tttttattt aaagagatgg gtggcctact cttgcccagg     17280
ttgaagtaca gtggtatgat catagctcac tacagcctcc agctgctggg cttaagcaat   17340
cctcctgcct tagcctcctg agtagctggg attacaggca tgcaccacca tgcctagcta   17400
atcatcttat tccttcctta aaggaaagat tttaagaaca aaattatatg gcgtgaattt   17460
attgatgata attccagttg tataaattag tttataaggg agttttgtga gaatatttga   17520
ggaaatccag atagaatggg ttttaattag gaattgtatt tattcttatg accttttgga   17580
aattcatttc tttttcaggg acaagaatcc ttcaagaaac aggaaaaaac tcctaaaaca   17640
ccaaaaggac ctagttctgt agaagacatt aaagcaaaaa tgcaagcaag tatagaaaaa   17700
gtgagtaaag ttatcttaaa aaactttgt ctccccctc aaattgcacg tgtctggttt      17760
gcatagactt gaatgtttct tgtttttttg tttgttttgg tttaatatac ttgcctggtt   17820
cgtggtatga attttttcaa aaatttctta taaaacattt ataatcgtgt ctgtggtgat   17880
ttttgcatat gcaaaattaa atatgcctta ttttccatta tgcaaggaac gtagtgcact   17940
ggttgcaaga taacattctg accttccatg ttaaaataga tcagtgaaaa ccctttgcct   18000
```

```
attctggttg taagatatgc tagagaacca acagagggcg tatgagactt cattaaaatt    18060
acaaacagct ggaaaagtag atgctggctg ttgcttggta ttatagttaa tattcatgat    18120
tgaccctagt cagaagtgat tttcagcaga ttgagacatt tctctttgcc ctttacacca    18180
agttgtcacc agttaataca tgtagtaata gctagatttc gtgaatgact aataggctta    18240
aatctagttt ccttttgtct taaataatgg aaatgtggga agagggttag gtctctcatc    18300
tgcttgactg ggggatttga gtaggatatg gaataaatgg tttaaatgcc ttggaagcac    18360
atttgagaga agctttaatt ctatgaataa tacttttaga ctccaactat tgagagcaaa    18420 tgtgggggtgg tgaaaaattg ccaactcatt tccccatgtt tttcttgtaa tctatagatt    18480
tttcgtggct tcagtagatt ccttgtacag tgataagtcc actggaaaaa gaattttaga    18540 actgaacat atttcttta gtcacactgt aaaccctta gccttcctgg ttatcactga    18600
tttttgtccc ttggatacaa tgctaaaatg acatctttta gatgcccctc ccctccattt    18660
taatatggtc ctatctcctt ggtttaattg caggcgcatt gaacagtcct gggcactaca    18720
tgtaaattaa gcccaaagat ggggagaaag gaaaaggaga gacaaatata gtccatactg    18780
agtgtcatca acaatccaga ctgaagtctt ctattttaat ctcaatcccc ttttctgatt    18840
tgccacccat gcctcttcag gctggaaaca atctcttggt tccctaaagc actttcttct    18900
gactgctgtg attcagtgaa ccttgcccctt tgctttctat tacttgtgca tttgcctcac    18960
ctgacaatgt tttaaatcgc cttttgtatct ccttagctgc tcaataaata tttgaatgca    19020
tcaattaaga atgtatgtga caataatttt gaaatggaaa ttgtgaggtt tattttacta    19080
ggttattgga ggcagttaag tttcttaatg ctatacctga ttctgccaaa gtcccttgga    19140
catttgaaaa cctttttcaat cttttaaaaa tgcataaaag atacttagag ggaaaggtat    19200
taattaaatt tagtaaaaac aaatatattc aatgctttaa attccaaagt agtgataaat    19260
acaaacattt caagatattt gcaatagtaa tgttttgaaa ttttggttac aaagtcacag    19320
gtcttgccaa tactgttgta gtttcttgcc tatatccgta atttgaagga aatggtgaga    19380
gtgattagag aagtgtaatt actgtaatttt ttccccctat tgtagtttct tgcctgtatc    19440
cataatttga aggaaatggt aagagtgatt agtgaaatgt aattactgta attttttccc    19500
cattcaactt tatatatctt taactgatga ccagatcatt gttgttctga accagtttgt    19560
ggtcagcaag tgttttgtgg ggttttgttt gtttgttttt aaagaacagt ttgggtcact    19620
tgacatggtt ctccaaaggg atgttatggg ttgtatttgg ttctgggtga taaccgactt    19680
gttagataat ttagataagc aaccgagttg ccatgtttgt ttgtcgaatc tcaagtgtag    19740
cttatatttt atgttcctag agaggttgtc agggaagatt tgacccttg gcaaatctgt    19800 ttgaatagag atactagcca tgctgcccaa tagggctttc tggccctgaa aaagatacgg    19860
agtattcttg gaaagttgaa gggaaaaaga ataaactgat ccatgtagta gcatgcagat    19920
tattgaggaa ttttctaaag gtatctctct cggtgtattt ctctacttac ctgtaataat    19980
gcttttgtct taatagggtg gttctcttcc caaagtggaa gccaaattca tcaattatgt    20040
gaagaattgc ttccggatga ctgaccaaga ggtaactgga ttttctgggg acatgattaa    20100
atccaagttt ttttgtgatt tattatgatt ctgcctttac cctttttaag tgttggctct    20160
ttttaaaaag ttcctaacca cagataaatat ttcatttaat gaaatacctg aaaactcatg    20220
tatttaatga aatgcatgaa gaatacagtt ggcagtctga gatgataact ttagtatatt    20280
tttcccagat ttcctatagt tggtaaatta tttcttggtt attgaattca gttttacttt    20340
```

```
tttggtacta tgttggttaa ggaaattgct gtggttttcc ttgctgttcc atttgactgc    20400
ttggggcagt ctggtcttgg cttttttggg agttggtaga gatcttttt tttttttttcc    20460
tagatcttat gggaaataca ttatgccaaa atcatcctaa catgaaatct ggaagcaaga    20520
cactaaattg tggctactac cagatacata agcttgagtt agctgttaga ttttacagtt    20580
agtacatgtg aaagtcttag tcaacataaa gattatgcat ttattttttgc tcttatttac    20640
agttgactca taagtgtaag gacaatgtaa aagtggttaa atagggatgt taggtatcgt    20700
gtggagaacg gatgctgcat ttaatggtct ttaggtttcc tgtggtcagc ttttttcaaa    20760
aaattaggaa aatttggcaa ttagctggtt tttttctgc catagtattt tgcacttcaa    20820
ttatttaatt gcacttcaat ttttagtttt cgggttcgta aaaccctgat aatggttaat    20880
tttgagttta gctttgtgaa agttgtagtg atgggctata agatgatcag gttcagtctt    20940
tggttgctgt tctgttttttt ctctacattt gaatcctaaa gtttaaagtg tgagttttgg    21000
gagtttattt ggaatactaa acattgatta atcataaatt attttgaaac tccgcgttat    21060
gcaactgttt atttaatatt gaaaatagtg gaaagtcaga cataaataac cagcatgtac    21120
taacagctaa gcagcataag agatgcattc ttcaactact gccaaggaaa gtgatgataa    21180
atttaatgat taagttgcag tagtcttctg tactttataa caaaggcttg tagctacaaa    21240
gtcttgtagc tattaaatta ctgaaccagc acttctacaa gaagtatttt cttttttataa    21300
aaagtatttt tggccaggtt ggtcttgaac tcctggcctc aagcagtcct cccatcttttt    21360
cctcccaaag tgctaggatt acaggcacga gccaccttgc ccagcctacc agaagtattt    21420
ttttgctcta gaattgaaag tgttctcaag tgtcagaatg aaatttctgg aataaaatagt    21480
aaatgtttaa taacttgaac ttgaattgct gttacagaga ttatcaaaac taaatgcttc    21540
ctgttttttga catagagatg catgatgcaa gcaacgacaa tgtatatttg tttgaacctg    21600
atgataagat ctctggctgg gcgtggtagt tcatgcctat aatcccagca ctttgggagg    21660
caacatggca aaactctgtc tctactaaaa atactaaatt tagctgggca tggtggcatg    21720
tacctgtaat cccacctact caagaggcgg aggcaggagg atcgcttgaa cctgggaggc    21780
agaggttgca gtgagcgcca ctgcactcca gtctgggtgg cagagtgaga gtctatctca    21840
gaaagaaaga tttctatgat atttaatatt ggcattcggt attcagttac cttgtacctg    21900
agaacccatt ggctgtgaaa cagtgacagc tgagagaatc ctgagtcatc tcatttctag    21960
ttcttggtga acttctggac ttttcttcag aaccaccttg ccatgttggc caggctggtc    22020
ttgaactcct gacctctcag gtgatccaac accttggcct cttaaagtgc tgggattaca    22080
ggcatgagcc accatgcctg gccagctgtt ttttttgttg gtttgttttt tgttttggta    22140
cccatcgtca gtgtgatctt ggctcactgc aacctctgcc tcttgggctc aggcagtcct    22200
cccacctcag cctcctgagt agctgggcct cctgtagttg cacaccacca agcctggcta    22260
atttttgcat ttttagtaga cagggtttca ccatgttgcc caggctggtc tcaaattcct    22320
gagctgaagt gatctgcccg cctcagtctc ccaaagtgta gggattacag gcgtgagcca    22380
ccatgcctag cctcagcata tagttttttc taaatgtaca catgcccagg cacacatgca    22440
caggcaattc agaataagtt tctggtgttt atgtaactttt atttgccaaa tctggccaac    22500
tctaaagctg atctcgggag atgaagttgg aagtaacatt ggccatatgg gtctctgttc    22560
tttctgttga tttccttaag taaataatgc taaactatta ataattatt agtatattgt    22620
tcacattttt atgactgatt aaagtgtttg gaattaaatt acatctgagt ataaattttc    22680
ttggagtcat atctttatct agagttaact ctctggtggt agaatgaaaa atagatgttg    22740
```

| | | | | |
|---|---|---|---|---|
| aactatgcaa | agagacattt | aatttattga | tgtctatgaa gtgttgtggt | tccttaacca 22800 |
| catttctttt | tttttttttc | caggctattc | aagatctctg gcagtggagg | aagtctcttt 22860 |
| aagaaaatag | tttaaacaat | ttgttaaaaa | attttccgtc ttatttcatt | tctgtaacag 22920 |
| ttgatatctg | gctgtccttt | ttataatgca | gagtgagaac tttccctacc | gtgtttgata 22980 |
| aatgttgtcc | aggttctatt | gccaagaatg | tgttgtccaa aatgcctgtt | tagtttttaa 23040 |
| agatggaact | ccacccttg  | cttggtttta | agtatgtatg gaatgttatg | ataggacata 23100 |
| gtagtagcgg | tggtcagaca | tggaaatggt | ggggagacaa aaatatacat | gtgaaataaa 23160 |
| actcagtatt | ttaataaagt | a | | 23181 |

<210> SEQ ID NO 99
<211> LENGTH: 2296
<212> TYPE: DNA
<213> ORGANISM: Homo sapiens

<400> SEQUENCE: 99

| | | | | |
|---|---|---|---|---|
| gtgagtaaag | ttatcttaaa | aaaactttgt | ctcccccctc aaattgcacg | tgtctggttt 60 |
| gcatagactt | gaatgtttct | tgttttttg  | tttgttttgg tttaatatac | ttgcctggtt 120 |
| cgtggtatga | atttttcaa  | aaatttctta | taaaacattt ataatcgtgt | ctgtggtgat 180 |
| ttttgcatat | gcaaaattaa | atatgcctta | ttttccatta tgcaaggaac | gtagtgcact 240 |
| ggttgcaaga | taacattctg | accttccatg | ttaaaataga tcagtgaaaa | cccttttgcct 300 |
| attctggttg | taagatatgc | tagagaacca | acagagggcg tatgagactt | cattaaaatt 360 |
| acaaacagct | ggaaaagtag | atgctggctg | ttgcttggta ttatagttaa | tattcatgat 420 |
| tgaccctagt | cagaagtgat | tttcagcaga | ttgagacatt tctctttgcc | ctttacacca 480 |
| agttgtcacc | agttaataca | tgtagtaata | gctagatttc gtgaatgact | aataggctta 540 |
| aatctagttt | cctttttgtct | taaataatgg | aaatgtggga agagggttag | gtctctcatc 600 |
| tgcttgactg | ggggatttga | gtaggatatg | gaataaatgg tttaaatgcc | ttggaagcac 660 |
| atttgagaga | agctttaatt | ctatgaataa | tactttaga  ctccaactat | tgagagcaaa 720 |
| tgtggggtgg | tgaaaaattg | ccaactcatt | tccccatgtt tttcttgtaa | tctatagatt 780 |
| tttcgtggct | tcagtagatt | ccttgtacag | tgataagtcc actggaaaaa | gaattttaga 840 |
| actgaacat  | atttcttta  | gtcacactgt | aaaccctta  gccttcctgg | ttatcactga 900 |
| tttttgtccc | ttggatacaa | tgctaaaatg | acatcttta  gatgcccctc | ccctccattt 960 |
| taatatggtc | ctatctcctt | ggtttaattg | caggcgcatt gaacagtcct | gggcactaca 1020 |
| tgtaaattaa | gcccaaagat | ggggagaaag | gaaaggaga  gacaaatata | gtccatactg 1080 |
| agtgtcatca | acaatccaga | ctgaagtctt | ctattttaat ctcaatcccc | ttttctgatt 1140 |
| tgccacccat | gcctcttcag | gctggaaaca | atctcttggt tccctaaagc | actttcttct 1200 |
| gactgctgtg | attcagtgaa | ccttgcccctt | tgctttctat tacttgtgca | tttgcctcac 1260 |
| ctgacaatgt | tttaaatcgc | ctttgtatct | ccttagctgc tcaataaata | tttgaatgca 1320 |
| tcaattaaga | atgtatgtga | caataatttt | gaaatggaaa ttgtgaggtt | tattttacta 1380 |
| ggttattgga | ggcagttaag | tttcttaatg | ctatacctga ttctgccaaa | gtcccttgga 1440 |
| catttgaaaa | ccttttcaat | cttttaaaaa | tgcataaaag atacttagag | ggaaaggtat 1500 |
| taattaaatt | tagtaaaaac | aaatatattc | aatgctttaa attccaaagt | agtgataaat 1560 |
| acaaacattt | caagatattt | gcaatagtaa | tgttttgaaa ttttggttac | aaagtcacag 1620 |

| | |
|---|---|
| gtcttgccaa tactgttgta gtttcttgcc tatatccgta atttgaagga aatggtgaga | 1680 |
| gtgattagag aagtgtaatt actgtaattt ttccccctat tgtagtttct tgcctgtatc | 1740 |
| cataatttga aggaaatggt aagagtgatt agtgaaatgt aattactgta attttttccc | 1800 |
| cattcaactt tatatatctt taactgatga ccagatcatt gttgttctga accagtttgt | 1860 |
| ggtcagcaag tgttttgtgg ggttttgttt gtttgttttt aaagaacagt ttgggtcact | 1920 |
| tgacatggtt ctccaaaggg atgttatggg ttgtatttgg ttctgggtga taaccgactt | 1980 |
| gttagataat ttagataagc aaccgagttg ccatgtttgt ttgtcgaatc tcaagtgtag | 2040 |
| cttatatttt atgttcctag agaggttgtc agggaagatt tgacccttg gcaaatctgt | 2100 |
| ttgaatagag atactagcca tgctgcccaa tagggctttc tggccctgaa aaagatacgg | 2160 |
| agtattcttg gaaagttgaa gggaaaaaga ataaactgat ccatgtagta gcatgcagat | 2220 |
| tattgaggaa ttttctaaag gtatctctct cggtgtattt ctctacttac ctgtaataat | 2280 |
| gcttttgtct taatag | 2296 |

<210> SEQ ID NO 100
<211> LENGTH: 2711
<212> TYPE: DNA
<213> ORGANISM: Homo sapiens

<400> SEQUENCE: 100

| | |
|---|---|
| agaaaggagt ggggttgaaa agcgcttgcg caggacggct acggtacggg ggtgggaggg | 60 |
| cttcggagca cgcgcgcgga ggcgggactt gggaagcgct cgcgagatct tcagggtcta | 120 |
| tatataagcg cggggagcct gcgtcctttc cctggtgtga ttccgtcctg cgcggttgtt | 180 |
| ctctggagca gcgttctttt atctccgtcc gccttctctc ctacctaagt gcgtgccgcc | 240 |
| acccgatgga agattcgatg gacatggaca tgagccccct gaggcccag aactatcttt | 300 |
| tcggttgtga actaaaggcc gacaaagatt atcactttaa ggtggataat gatgaaaatg | 360 |
| agcaccagtt atctttaaga acggtcagtt taggggctgg tgcaaaggat gagttgcaca | 420 |
| tgttgaagc agaggcaatg aattacgaag gcagtccaat taaagtaaca ctggcaactt | 480 |
| tgaaaatgtc tgtacagcca acggtttccc ttggggggctt tgaaataaca ccaccagtgg | 540 |
| tcttaaggtt gaagtgtggt tcagggccag tgcatattag tggacagcac ttagtagctg | 600 |
| tggaggaaga tgcagagtca gaagatgaag aggaggagga tgtgaaactc ttaagtatat | 660 |
| ctggaaagcg gtctgcccct ggaggtggta gcaaggttcc acagaaaaaa gtaaaacttg | 720 |
| ctgctgatga agatgatgac gatgatgatg aagaggatga tgatgaagat gatgatgatg | 780 |
| atgattttga tgatgaggaa gctgaagaaa aagcgccagt gaagaaatct atacgagata | 840 |
| ctccagccaa aaatgcacaa aagtcaaatc agaatggaaa agactcaaaa ccatcatcaa | 900 |
| caccaagatc aaaaggacaa gaatccttca gaaacagga aaaaactcct aaaacaccaa | 960 |
| aaggacctag ttctgtagaa gacattaaag caaaatgca agcaagtata gaaaagagaa | 1020 |
| acaagaacct ggttcatggt aatgtgtgtg gccggaacat cctgctggcc cggctggggt | 1080 |
| tggcagaggg caccagcccc ttcatcaagc tgagtgatcc tggcgtgggc ctgggcgccc | 1140 |
| tctccaggga ggagcgggtg agaggatccc ctggctggc ccccgaatgc ctaccaggtg | 1200 |
| gggccaacag cctaagcacc gccatggaca gtgggggtt tggcgccacc ctcctggaga | 1260 |
| tctgctttga cggagaggcc cctctgcaga gccgcagtcc ctccgagaag gagcatttct | 1320 |
| accagaggca gcaccggctg cccgagccct cctgcccaca gctggccaca ctcaccagcc | 1380 |
| agtgtctgac ctatgagcca acccagaggc catcattccg caccatcctg cgtgacctca | 1440 |

```
cccggctgca gccccacaat cttgctgacg tcttgactgt gaacccggac tcaccggcgt    1500
cggaccctac ggttttccac aagcgctatt tgaaaaagat ccgagatctg ggcgagggtc    1560
acttcggcaa ggtcagcttg tactgctacg atccgaccaa cgacggcact ggcgagatgg    1620
tggcggtgaa agccctcaag gcagactgcg gcccccagca ccgctcgggc tggaagcagg    1680
agattgacat tctgcgcacg ctctaccacg agcacatcat caagtacaag ggctgctgcg    1740
aggaccaagg cgagaagtcg ctgcagctgg tcatggagta cgtgcccctg ggcagcctcc    1800
gagactacct gccccggcac agcatcgggc tggcccagct gctgctcttc gcccagcaga    1860
tctgcgaggg catggcctat ctgcacgcgc agcactacat ccaccgagac ctagccgcgc    1920
gcaacgtgct gctggacaac gacaggctgg tcaagatcgg ggactttggc ctagccaagg    1980
ccgtgcccga aggccacgag tactaccgcg tgcgcgagga tggggacagc cccgtgttct    2040
ggtatgcccc agagtgcctg aaggagtata agttctacta tgcgtcagat gtctggtcct    2100
tcggggtgac cctgtatgag ctgctgacgc actgtgactc cagccagagc cccccacga    2160 aattccttga gctcataggc attgctcagg gtcagatgac agttctgaga ctcactgagt    2220
tgctggaacg aggggagagg ctgccacggc ccgacaaatg tccctgtgag gtctatcatc    2280
tcatgaagaa ctgctgggag acagaggcgt cctttcgccc aaccttcgag aacctcatac    2340
ccattctgaa gacagtccat gagaagtacc aaggccaggc cccttcagtg ttcagcgtgt    2400
gctgaggcac aatggcagcc ctgcctggga ggactggacc aggcagtggc tgcagaggga    2460
gcctcctgct ccctgctcca ggatgaaacc aagagggga tgtcagcctc acccacaccg    2520
tgtgccttac tcctgtctag agaccccacc tctgtgaact tatttttctt tcttggccgt    2580
gagcctaacc atgatcttga gggacccaac atttgtaggg gcactaatcc agcccttaaa    2640
tcccccagct tccaaacttg aggcccacca tctccaccat ctggtaataa actcatgttt    2700
tctctgctgg a                                                         2711
```

<210> SEQ ID NO 101
<211> LENGTH: 2160
<212> TYPE: DNA
<213> ORGANISM: Homo sapiens

<400> SEQUENCE: 101

```
atggaagatt cgatggacat ggacatgagc cccctgaggc cccagaacta tcttttcggt      60
tgtgaactaa aggccgacaa agattatcac tttaaggtgg ataatgatga aaatgagcac     120
cagttatctt taagaacggt cagtttaggg gctggtgcaa aggatgagtt gcacattgtt     180
gaagcagagg caatgaatta cgaaggcagt ccaattaaag taacactggc aactttgaaa     240
atgtctgtac agccaacggt ttcccttggg ggctttgaaa taacaccacc agtggtctta     300
aggttgaagt gtggttcagg gccagtgcat attagtggac agcacttagt agctgtggag     360
gaagatgcag agtcagaaga tgaagaggag gaggatgtga aactcttaag tatatctgga     420
aagcggtctg cccctggagg tggtagcaag gttccacaga aaaaagtaaa acttgctgct     480
gatgaagatg atgacgatga tgatgaagag gatgatgatg aagatgatga tgatgatgat     540
tttgatgatg aggaagctga agaaaaagcg ccagtgaaga atctatacg agatactcca     600 gccaaaaatg cacaaaagtc aaatcagaat ggaaaagact caaaccatc atcaacacca     660 agatcaaaag acaagaatc cttcaagaaa caggaaaaaa ctcctaaaac accaaaagga     720
cctagttctg tagaagacat taaagcaaaa atgcaagcaa gtatagaaaa agagaacaag     780
```

```
aacctggttc atggtaatgt gtgtggccgg aacatcctgc tggcccggct ggggttggca    840
gagggcacca gccccttcat caagctgagt gatcctggcg tgggcctggg cgccctctcc    900
agggaggagc gggtggagag gatcccctgg ctggcccccg aatgcctacc aggtggggcc    960
aacagcctaa gcaccgccat ggacaagtgg gggtttggcg ccaccctcct ggagatctgc   1020
tttgacggag aggcccctct gcagagccgc agtccctccg agaaggagca tttctaccag   1080
aggcagcacc ggctgcccga gccctcctgc ccacagctgg ccacactcac cagccagtgt   1140
ctgacctatg agccaaccca gaggccatca ttccgcacca tcctgcgtga cctcacccgg   1200
ctgcagcccc acaatcttgc tgacgtcttg actgtgaacc cggactcacc ggcgtcggac   1260
cctacggttt tccacaagcg ctatttgaaa aagatccgag atctgggcga gggtcacttc   1320
ggcaaggtca gcttgtactg ctacgatccg accaacgacg gcactggcga gatggtggcg   1380
gtgaaagccc tcaaggcaga ctgcggcccc cagcaccgct cgggctggaa gcaggagatt   1440
gacattctgc gcacgctcta ccacgagcac atcatcaagt acaagggctg ctgcgaggac   1500
caaggcgaga agtcgctgca gctggtcatg gagtacgtgc ccctgggcag cctccgagac   1560
tacctgcccc ggcacagcat cgggctggcc cagctgctgc tcttcgccca gcagatctgc   1620
gagggcatgg cctatctgca cgcgcagcac tacatccacc gagacctagc cgcgcgcaac   1680
gtgctgctgg acaacgacag gctggtcaag atcggggact tggcctagc  caaggccgtg   1740 cccgaaggcc acgagtacta ccgcgtgcgc gaggatgggg acagcccgt  gttctggtat   1800 gccccagagt gcctgaagga gtataagttc tactatgcgt cagatgtctg gtccttcggg   1860
gtgaccctgt atgagctgct gacgcactgt gactccagcc agagccccc  cacgaaattc   1920 cttgagctca taggcattgc tcagggtcag atgacagttc tgagactcac tgagttgctg   1980
gaacgagggg agaggctgcc acggcccgac aaatgtccct gtgaggtcta tcatctcatg   2040
aagaactgct gggagacaga ggcgtccttt cgcccaacct tcgagaacct catacccatt   2100
ctgaagacag tccatgagaa gtaccaaggc caggcccctt cagtgttcag cgtgtgctga   2160
```

<210> SEQ ID NO 102
<211> LENGTH: 719
<212> TYPE: PRT
<213> ORGANISM: Homo sapiens

<400> SEQUENCE: 102

```
Met Glu Asp Ser Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
```

```
            130                 135                 140
Pro Gly Gly Ser Lys Val Pro Gln Lys Val Lys Leu Ala Ala
145                 150                 155                 160

Asp Glu Asp Asp Asp Asp Asp Glu Glu Asp Asp Glu Asp Asp
                    165                 170                 175

Asp Asp Asp Asp Phe Asp Glu Glu Ala Glu Lys Ala Pro Val
            180                 185                 190

Lys Lys Ser Ile Arg Asp Thr Pro Ala Lys Asn Ala Gln Lys Ser Asn
                195                 200                 205

Gln Asn Gly Lys Asp Ser Lys Pro Ser Thr Pro Arg Ser Lys Gly
210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Glu Asn Lys Asn Leu Val His Gly Asn Val Cys Gly Arg Asn Ile
                260                 265                 270

Leu Leu Ala Arg Leu Gly Leu Ala Glu Gly Thr Ser Pro Phe Ile Lys
                275                 280                 285

Leu Ser Asp Pro Gly Val Gly Leu Gly Ala Leu Ser Arg Glu Glu Arg
290                 295                 300

Val Glu Arg Ile Pro Trp Leu Ala Pro Glu Cys Leu Pro Gly Gly Ala
305                 310                 315                 320

Asn Ser Leu Ser Thr Ala Met Asp Lys Trp Gly Phe Gly Ala Thr Leu
                325                 330                 335

Leu Glu Ile Cys Phe Asp Gly Glu Ala Pro Leu Gln Ser Arg Ser Pro
                340                 345                 350

Ser Glu Lys Glu His Phe Tyr Gln Arg Gln His Arg Leu Pro Glu Pro
                355                 360                 365

Ser Cys Pro Gln Leu Ala Thr Leu Thr Ser Gln Cys Leu Thr Tyr Glu
                370                 375                 380

Pro Thr Gln Arg Pro Ser Phe Arg Thr Ile Leu Arg Asp Leu Thr Arg
385                 390                 395                 400

Leu Gln Pro His Asn Leu Ala Asp Val Leu Thr Val Asn Pro Asp Ser
                405                 410                 415

Pro Ala Ser Asp Pro Thr Val Phe His Lys Arg Tyr Leu Lys Lys Ile
                420                 425                 430

Arg Asp Leu Gly Glu Gly His Phe Gly Lys Val Ser Leu Tyr Cys Tyr
                435                 440                 445

Asp Pro Thr Asn Asp Gly Thr Gly Glu Met Val Ala Val Lys Ala Leu
                450                 455                 460

Lys Ala Asp Cys Gly Pro Gln His Arg Ser Gly Trp Lys Gln Glu Ile
465                 470                 475                 480

Asp Ile Leu Arg Thr Leu Tyr His Glu His Ile Ile Lys Tyr Lys Gly
                485                 490                 495

Cys Cys Glu Asp Gln Gly Glu Lys Ser Leu Gln Leu Val Met Glu Tyr
                500                 505                 510

Val Pro Leu Gly Ser Leu Arg Asp Tyr Leu Pro Arg His Ser Ile Gly
                515                 520                 525

Leu Ala Gln Leu Leu Leu Phe Ala Gln Gln Ile Cys Glu Gly Met Ala
                530                 535                 540

Tyr Leu His Ala Gln His Tyr Ile His Arg Asp Leu Ala Ala Arg Asn
545                 550                 555                 560
```

Val Leu Leu Asp Asn Asp Arg Leu Val Lys Ile Gly Asp Phe Gly Leu
            565                 570                 575

Ala Lys Ala Val Pro Glu Gly His Glu Tyr Tyr Arg Val Arg Glu Asp
        580                 585                 590

Gly Asp Ser Pro Val Phe Trp Tyr Ala Pro Glu Cys Leu Lys Glu Tyr
    595                 600                 605

Lys Phe Tyr Tyr Ala Ser Asp Val Trp Ser Phe Gly Val Thr Leu Tyr
610                 615                 620

Glu Leu Leu Thr His Cys Asp Ser Ser Gln Ser Pro Pro Thr Lys Phe
625                 630                 635                 640

Leu Glu Leu Ile Gly Ile Ala Gln Gly Gln Met Thr Val Leu Arg Leu
            645                 650                 655

Thr Glu Leu Leu Glu Arg Gly Glu Arg Leu Pro Arg Pro Asp Lys Cys
        660                 665                 670

Pro Cys Glu Val Tyr His Leu Met Lys Asn Cys Trp Glu Thr Glu Ala
    675                 680                 685

Ser Phe Arg Pro Thr Phe Glu Asn Leu Ile Pro Ile Leu Lys Thr Val
690                 695                 700

His Glu Lys Tyr Gln Gly Gln Ala Pro Ser Val Phe Ser Val Cys
705                 710                 715

<210> SEQ ID NO 103
<211> LENGTH: 3332
<212> TYPE: DNA
<213> ORGANISM: Homo sapiens

<400> SEQUENCE: 103
gtgagtaaag ttatcttaaa aaaactttgt ctcccccctc aaattgcacg tgtctggttt      60
gcatagactt gaatgtttct tgtttttttg tttgttttgg tttaatatac ttgcctggtt     120
cgtggtatga attttttcaa aaatttctta taaaacattt ataatcgtgt ctgtggtgat     180
ttttgcatat gcaaaattaa atatgcctta ttttccatta tgcaaggaac gtagtgcact     240
ggttgcaaga taacattctg accttccatg ttaaaataga tcagtgaaaa cccttttgcct    300 attctggttg taagatatgc tagagaacca acagagggcg tatgagactt cattaaaatt     360
acaaacagct ggaaaagtag atgctggctg ttgcttggta ttatagttaa tattcatgat     420
tgaccctagt cagaagtgat tttcagcaga ttgagacatt tctctttgcc ctttacacca     480
agttgtcacc agttaataca tgtagtaata gctagatttc gtgaatgact aataggctta     540
aatctagttt ccttttgtct taaataatgg aaatgtggga agagggttag gtctctcatc     600
tgcttgactg ggggatttga gtaggatatg gaataaatgg tttaaatgcc ttggaagcac     660
atttgagaga agctttaatt ctatgaataa tactttagta ctccaactat tgagagcaaa     720
tgtggggtgg tgaaaaattg ccaactcatt tccccatgtt tttcttgtaa tctatagatt     780
tttcgtggct tcagtagatt ccttgtacag tgataagtcc actggaaaaa gaattttaga     840
actggaacat atttctttta gtcacactgt aaacccttta gccttcctgg ttatcactga     900
tttttgtccc ttggatacaa tgctaaaatg acatctttta gatgcccctc ccctccattt     960
taatatggtc ctatctcctt ggtttaattg caggcgcatt gaacagtcct gggcactaca    1020
tgtaaattaa gcccaaagat ggggagaaag gaaaaggaga gacaaatata gtccatactg    1080
agtgtcatca acaatccaga ctgaagtctt ctattttaat ctcaatcccc ttttctgatt    1140
tgccacccat gcctcttcag gctggaaaca atctcttggt tccctaaagc actttcttct    1200

```
gactgctgtg attcagtgaa ccttgcccctt tgctttctat tacttgtgca tttgcctcac      1260
ctgacaatgt tttaaatcgc ctttgtatct ccttagctgc tcaataaata tttgaatgca      1320
tcaattaaga atgtatgtga caataatttt gaaatggaaa ttgtgaggtt tattttacta      1380
ggttattgga ggcagttaag tttcttaatg ctatacctga ttctgccaaa gtcccttgga      1440
catttgaaaa ccttttcaat cttttaaaaa tgcataaaag atacttagag ggaaaggtat      1500
taattaaatt tagtaaaaac aaatatattc aatgctttaa attccaaagt agtgataaat      1560
acaaacattt caagatattt gcaatagtaa tgttttgaaa ttttggttac aaagtcacag      1620
gtcttgccaa tactgttgta gtttcttgcc tatatccgta atttgaagga atggtgaga      1680
gtgattagag aagtgtaatt actgtaattt ttccccctat tgtagtttct tgcctgtatc      1740
cataatttga aggaaatggt aagagtgatt agtgaaatgt aattactgta attttttccc      1800
cattcaactt tatatatctt taactgatga ccagatcatt gttgttctga accagtttgt      1860
ggtcagcaag tgttttgtgg ggttttgttt gtttgttttt aaagaacagt ttgggtcact      1920
tgacatggtt ctccaaaggg atgttatggg ttgtatttgg ttctgggtga taaccgactt      1980
gttagataat ttagataagc aaccgagttg ccatgtttgt ttgtcgaatc tcaagtgtag      2040
cttatatttt atgttcctag agaggttgtc agggaagatt tgaccctttg gcaaatctgt      2100
ttgaatagag atactagcca tgctgcccaa tagggctttc tggccctgaa aaagatacgg      2160
agtattcttg gaaagttgaa gggaaaaaga ataaactgat ccatgtagta gcatgcagat      2220
tattgaggaa ttttctaaag gtatctctct cggtgtattt ctctacttac ctgtaataat      2280
gcttttgtct taataggtgt gtggcctgtg tgtgggcct gggtcggtca gggagggcca      2340
ggagcccagg agttcgagac cagcctgggc aacaggcga gaccccatct ttttgtttg      2400
ttttgttta ggtggagttt cgccctgtca cccaggctgg agtgcaatgg catgatctcg      2460
gctcactgca accttcgcct cccgggttca atgattctc ccgcctcagc ctcccaagta      2520
gctgggatta taggctcctg ccatcacgcc cagctaattt ttgtattttt agtagagatg      2580
gggtttcacc atgttggtca ggctggtctc gaacttctga cctcgtgatc catccgcctc      2640
agcctcccaa agtgctggga ttccaggcgt gagccaccac gcccagctgg ccccatcttt      2700
taaaaataaa caaatagcca ggtgtggtgg ctcatacctg taatcccagc agtttgggag      2760
gccaaggcgg gtggatcacc tgaggtcagg agtttgagac cagcctggcc agtatggcaa      2820
aaccttgcct ctactaaaaa tacaaaaaaa attagccaat gtggtaactt gcacctgtag      2880
gccgaggtac tcaggaagtt gaggtgggag gatcacctga gctcaggaat tgaggccgt      2940
agtaagctat gatcacacca ctgcacccca gcctgggcag cagcatagct agaccccatc      3000
tccaccaaaa atttaagaat cagctaggct gtggtgatgt gcacctgtaa ttctcgctac      3060
ttggaaggct tgagcccagg agtttgaagc tgcagtgagc tatgttcgtg ccactatact      3120
ccaacctgag agacagagtg agaccctgtc ttaaaaaaa aaaaaaaaa aaaaaacaag      3180
aaaaaaataa ccccccaaaa aacaaaacag aaagaaaccc agtgatagtc acagttgtcc      3240
ttttcacatt ggctgtccct atggggacca ggtttgggt tggcgtctgt gcctctcctg      3300
agtggccaca cccccctctcc tgcccaccte ag                                   3332
```

```
<210> SEQ ID NO 104
<211> LENGTH: 45
<212> TYPE: DNA
<213> ORGANISM: Homo sapiens

<400> SEQUENCE: 104
tggctgttgc ttggtattat agggagggcc aggagcccag gagtt            45
```

RECURRENT GENE FUSIONS IN CUTANEOUS CD30-POSITIVE LYMPHOPROLIFERATIVE DISORDERS

CROSS-REFERENCE TO RELATED APPLICATIONS

The present application claims the priority benefit of U.S. Provisional Patent Application 62/110,034, filed Jan. 30, 2015, which is incorporated by reference in its entirety.

FIELD OF THE INVENTION

Provided herein are kits, compositions and methods for cancer diagnosis, research and therapy, including but not limited to, cancer markers. In particular, the present invention relates to recurrent gene fusions (e.g., recurrent translocations involving TYK2) as diagnostic markers and clinical targets for cutaneous CD30-positive lymphoproliferative disorders (e.g., lymphomatoid papulosis; primary cutaneous anaplastic large cell lymphoma).

BACKGROUND OF THE INVENTION

Lymphoproliferative disorders (LPDs) refer to several conditions in which lymphocytes are produced in excessive quantities. They typically occur in patients who have compromised immune systems. Examples of LPDs include, but are not limited to, follicular lymphoma, chronic lymphocytic leukemia, acute lymphoblastic leukemia, hairy cell leukemia, lymphomas, multiple myeloma, Waldenstrom's macroglobulinemia, Wiskott-Aldrich syndrome, post-transplant lymphoproliferative disorder, autoimmune lymphoproliferatieve syndrome (ALPS), lymphoid interstitial pneumonia, and CD30-positive lymphoproliferative disorders. Examples of CD30-positive lymphoproliferative disorders include lymphomatoid papulosis and primary cutaneous anaplastic large cell lymphoma.

Lymphomatoid papulosis (LYP) is characterized by multiple papules and nodules, which regress spontaneously. Three histologic subtypes have been described, which represent a spectrum with overlapping features and do not carry prognostic significance. Type A lesions have a few tumor cells in a background of inflammatory cells including neutrophils, eosinophils, and histiocytes. Type B lesions are characterized by epidermotropic lymphocytes with cerebriform nuclei mimicking mycosis fungoides. Type C lesions have sheets of large atypical lymphoid cells with only a few admixed inflammatory cells. The large atypical lymphoid cells are thought to be of T cell origin. Various histologic types may be present in individual patients at the same time. In LYP types A and C the large atypical cells express CD30, CD3, and CD4. CD2 and CD5 are usually expressed. These cells also express the cytotoxic markers TIA-1 and granzyme. The large atypical cells do not express CD8, CD7, or CD56. The cells may lose expression of CD3. In LYP type B the atypical cells are usually CD30 negative. Five year survival rates for LYP are 100%; however up to 20% of patients develop LYP-associated malignant lymphomas (e.g., mycosis fungoides, Hodgkin lymphoma, systemic or cutaneous CD30+ large T-cell lymphoma), which result in a fatal outcome of 2% of patients.

Primary cutaneous anaplastic large cell lymphoma (ALCL) is composed of large atypical to anaplastic appearing lymphoid cells. This disease mainly affects adults with a peak in the sixth decade, but cases have been reported in children. It usually presents as a solitary rapidly growing nodule. The skin overlying the lesion may ulcerate. Histologically the cells grow in sheets. Mitotic figures are frequent. Clusters of small reactive lymphocytes are found within and around the tumor cells. The malignant cells express CD2, CD3, CD4, CD30, and cytotoxic markers including TIA-1, granzyme, and perforin. Loss of T-cell antigen expression is not infrequent. The malignant cells do not express EMA or ALK. Five year survival rates approach 90%. Interestingly, up to 40% of C-ALCL show spontaneous regression similarly to LYP.

Improved methods for detecting, investigating, and treating CD30-positive lymphoproliferative disorders (e.g., lymphomatoid papulosis; primary cutaneous anaplastic large cell lymphoma) are needed.

SUMMARY OF THE INVENTION

The cutaneous CD30-positive lymphoproliferative spectrum of disorders (LPD) includes lymphomatoid papulosis (LYP) and primary cutaneous anaplastic large cell lymphoma (ALCL). Chromosomal translocations targeting tyrosine kinases in CD30-positive LPD have not been described. Using whole transcriptome sequencing, experiments conducted during the course of developing embodiments for the present invention identified a chimeric fusion involving NPM1 (5q35) and TYK2 (19p13) which encodes an NPM1-TYK2 protein containing the oligomerization domain of NPM1 and an intact catalytic domain in TYK2. Fluorescence in situ hybridization revealed NPM1-TYK2 fusions in 2 of 47 (4%) primary cases of CD30-positive LPDs and was absent in other mature T-cell neoplasms (n=151). Functionally, NPM1-TYK2 induced constitutive TYK2, STAT1, STAT3 and STAT5 activation. Conversely, a kinase-defective NPM1-TYK2 mutant abrogated STAT1/3/5 signaling. In addition, shRNA-mediated silencing of TYK2 abrogated lymphoma cell growth. Moroever, it was demonstrated that TYK2 is targeted by multiple different translocation partners in CD30-positive LPD. Such experiments indicate recurrent translocations involving TYK2 and highlights therapeutic opportunities in the treatment of CD30-positive LPDs with TYK2 translocations.

Accordingly, provided herein are kits, compositions and methods for cancer diagnosis, research and therapy, including but not limited to, cancer markers. In particular, the present invention relates to recurrent gene fusions (e.g., recurrent translocations involving TYK2) as diagnostic markers and clinical targets for cutaneous CD30-positive lymphoproliferative disorders (e.g., lymphomatoid papulosis; primary cutaneous anaplastic large cell lymphoma).

In certain embodiments, the present invention provides, but is not limited to, methods, compositions, and kits involving gene fusions having a 3' portion from a TYK2 gene and a 5' portion from a TYK2-gene-fusion-partner.

Such embodiments (e.g., composition, methods, kits) are not limited to a particular portion of a TYK2 gene.

In some embodiments, the portion of the TYK2 gene comprises any portion of TYK2 enabling tyrosine kinase activity upon expression as a polypeptide. In some embodiments, the portion of the TYK2 gene comprises at least a portion (e.g., 1%, 10%, 25%, 50%, 75%, 80%, 95%, 99%, 100%) of the C-terminal kinase domain of TYK2. In some embodiments, the portion of the TYK2 gene comprises the entire C-terminal kinase domain of TYK2. In some embodiments, the portion of the TYK2 gene comprises at least a portion of the TYK2 pseudokinase domain. In some embodiments, the portion of the TYK2 gene comprises at least a portion (e.g., 1%, 10%, 25%, 50%, 75%, 80%, 95%, 99%, 100%) of the C-terminal kinase domain of TYK2 and/or at least a portion (e.g., 1%, 10%, 25%, 50%, 75%, 80%, 95%, 99%, 100%) of the TYK2 pseudokinase domain.

Such embodiments (e.g., composition, methods, kits) are not limited to a particular TYK2-gene-fusion-partner.

In some embodiments, the TYK2-gene-fusion-partner is any gene such that upon fusion with TYK2 the resulting gene fusion encodes a polypeptide capable of having constitutively activated tyrosine kinase activity when expressed in a cell.

In some embodiments, the TYK2-gene-fusion-partner is any gene such that upon fusion with TYK2 the resulting gene fusion encodes a polypeptide that when expressed in a cell is capable of constitutively activating downstream targets of TYK2 (e.g., STAT1, STAT3, STAT5) within the cell.

In some embodiments, the TYK2-gene-fusion-partner is any gene such that upon fusion with TYK2 the resulting gene fusion encodes a polypeptide that when expressed in a cell results in increased cellular proliferation of that cell.

In some embodiments, the TYK2-gene-fusion-partner is any gene such that upon fusion with TYK2 the resulting gene fusion encodes a polypeptide, wherein 1) the polypeptide is capable of having constitutively activated tyrosine kinase activity when expressed in a cell, 2) expression of the polypeptide in a cell results in constitutive activation of downstream targets of TYK2 (e.g., STAT1, STAT3, STAT5), and 3) expression of the polypeptide in a cell results in increased cellular proliferation of the cell.

In some embodiments, the TYK2-gene-fusion-partner is any portion of NPM1.

In some embodiments, the TYK2-gene-fusion-partner comprises at least a portion (e.g., 1%, 10%, 25%, 50%, 75%, 80%, 95%, 99%, 100%) of the NPM1 oligomerization domain. In some embodiments, the TYK2-gene-fusion-partner comprises the entire NPM1 oligomerization domain.

In some embodiments, the TYK2-gene-fusion-partner comprises at least a portion (e.g., 1%, 10%, 25%, 50%, 75%, 80%, 95%, 99%, 100%) of the NPM1 histone binding domains. In some embodiments, the TYK2-gene-fusion-partner comprises the entire NPM1 histone binding domains.

In some embodiments, the TYK2-gene-fusion-partner comprises at least a portion (e.g., 1%, 10%, 25%, 50%, 75%, 80%, 95%, 99%, 100%) of the distal portion of the NPM1 DNA/RNA binding domains. In some embodiments, the TYK2-gene-fusion-partner comprises the entire distal portion of the NPM1 DNA/RNA binding domains.

In some embodiments, the TYK2-gene-fusion-partner comprises the entire NPM1 oligomerization domain, the entire NPM1 histone binding domain, and the entire distal portion of the NPM1 DNA/RNA binding domain.

In certain embodiments, the present invention provides methods for detecting cutaneous CD30-positive lymphoproliferative disorders (e.g., lymphomatoid papulosis; primary cutaneous anaplastic large cell lymphoma) in a subject (e.g., a human patient) comprising, consisting essentially of, or consisting of: providing a sample from the patient; and, detecting the presence or absence in the sample of a gene fusion having a 3' portion from a TYK2 gene and a 5' portion from a TYK2-gene-fusion-partner, wherein the presence in the sample of the gene fusion is indicative of a cutaneous CD30-positive lymphoproliferative disorder (e.g., lymphomatoid papulosis; primary cutaneous anaplastic large cell lymphoma) in the subject.

In some embodiments, the sample includes biopsy tissue, tissue, blood, plasma, serum, urine, stool, and/or cells.

Detecting the presence or absence in the sample of such a gene fusion may comprise detecting chromosomal rearrangements of genomic DNA having a 5' portion from a TYK2-gene-fusion-partner (e.g., NPM1) and a 3' portion from a TYK2 gene. A variety of techniques may be used for detecting the chromosomal rearrangements of genomic DNA, including nucleic acid sequencing, nucleic acid hybridization, and nucleic acid amplification. Nucleic acid hybridization techniques include in situ hybridization (ISH), microarray, and Southern blot. Nucleic acid amplification techniques include polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA).

Detecting the presence or absence in the sample of such a gene fusion may alternatively comprise detecting chimeric mRNA transcripts having a 5' portion from a TYK2-gene-fusion-partner (e.g., NPM1) and a 3' portion from a TYK2 gene. A variety of techniques may be used for detecting the chimeric mRNA, including nucleic acid sequencing, nucleic acid hybridization, and, nucleic acid amplification. Nucleic acid hybridization techniques include in situ hybridization (ISH) (e.g., Fluorescence in situ hybridization (FISH)), microarray, and Northern blot). Nucleic acid amplification techniques include, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA).

Detecting the presence or absence in the sample of a gene fusion may also alternatively comprise detecting an amino-terminally truncated TYK2 protein resulting from a fusion of a TYK2-gene-fusion-partner (e.g., NPM1) to a TYK2 gene, or detecting a chimeric protein having an amino-terminal portion from a a TYK2-gene-fusion-partner (e.g., NPM1) and a carboxy-terminal portion from an TYK2 gene. A variety of techniques may be used for detecting the truncated TYK2 protein or chimeric protein: protein sequencing; and, immunoassay. Immunoassay techniques include immunoprecipitation, Western blot, ELISA, immunohistochemistry, immunocytochemistry, flow cytometry, and immuno-PCR.

The present invention further provides, but is not limited to, compositions and kits for detecting/diagnosing cutaneous CD30-positive lymphoproliferative disorders (e.g., lymphomatoid papulosis; primary cutaneous anaplastic large cell lymphoma) in a subject (e.g., human patient). The compositions and kits may comprise:

a single labeled probe comprising a sequence that hybridizes to the junction at which a 5' portion from a TYK2-gene-fusion-partner (e.g., NPM1) fuses to a 3' portion from a TYK2 gene;

a pair of labeled probes wherein the first labeled probe comprises a sequence that hybridizes to a TYK2-gene-fusion-partner (e.g., NPM1) and the second labeled probe comprises a sequence that hybridizes to a TYK2 gene;

a pair of amplification oligonucleotides wherein the first amplification oligonucleotide comprises a sequence that hybridizes to a TYK2-gene-fusion-partner (e.g., NPM1) and the second amplification oligonucleotide comprises a sequence that hybridizes to a TYK2 gene;

an antibody to an amino-terminally truncated TYK2 protein resulting from a fusion of a TYK2-gene-fusion-partner (e.g., NPM1) to a TYK2 gene; and/or, an antibody to a chimeric protein having an amino-terminal portion from a TYK2-gene-fusion-partner (e.g., NPM1) and a carboxy-terminal portion from a TYK2 gene.

In certain embodiments, the present invention provides methods for treating cutaneous CD30-positive lymphoproliferative disorders (e.g., lymphomatoid papulosis; primary cutaneous anaplastic large cell lymphoma) in a subject (e.g., a human patient) comprising: administering to the patient an agent that inhibits at least one biological activity of such a gene fusion having a 5' portion from a TYK2-gene-fusion-partner (e.g., NPM1) and a 3' portion from a TYK2 gene. In some embodiments, the agent inhibits tyrosine kinase activity resulting from the gene fusion. In some embodiments, the agent inhibits STAT1, STAT3, and/or STAT5 activity resulting from the gene fusion. In some embodiments, the agent inhibits increased cellular proliferation resulting from the gene fusion. In some embodiments, the agent inhibits one or more of tyrosine kinase activity resulting from the gene fusion, STAT1, STAT3, and/or STAT5 activity resulting from the gene fusion, and increased cellular proliferation resulting from the gene fusion. In some embodiments, the agent inhibits expression of the gene fusion. In some embodiments, the agent inhibits any expression and/or activity resulting from the gene fusion. The agent may be a small molecule, an siRNA, an antisense nucleic acid, or an antibody. In some embodiments, the agent is co-administered with an additional agent known to treat cancer (e.g., an agent for treating cutaneous CD30-positive lymphoproliferative disorders (e.g., lymphomatoid papulosis; primary cutaneous anaplastic large cell lymphoma)).

In certain embodiments, the present invention provides kits for detecting gene fusions associated with CD30-positive lymphoproliferative disorders (e.g., lymphomatoid papulosis; primary cutaneous anaplastic large cell lymphoma) in a subject, comprising or consisting essentially of or consisting of detecting the presence of one or more gene fusions involving TYK2. In some embodiments, such kits comprise, consist essentially of, or consist of informative reagents for detecting a gene fusion having or resulting from the fusion of, rearrangement of, or genomic deletion between, a 3' portion from a TYK family member gene and a 5' portion from a TYK2-gene-fusion-partner (e.g., NPM1), wherein detecting the presence in a sample (e.g., a sample from a human subject) (e.g., biopsy tissue, tissue, blood, plasma, serum, urine, stool, and/or cells) of the gene fusion between a TYK2 gene and a TYK2-gene-fusion-partner (e.g., NPM1) identifies or characterizes cutaneous CD30-positive lymphoproliferative disorders (e.g., lymphomatoid papulosis; primary cutaneous anaplastic large cell lymphoma).

Such embodiments are not limited to a particular reagent(s). Examples include but are not limited to, a probe that specifically hybridizes to the fusion junction of a TYK2 gene and a TYK2-gene-fusion-partner (e.g., NPM1), a pair of primers that amplify a fusion junction of a gene fusion between a TYK2 gene and a TYK2-gene-fusion-partner (e.g., NPM1) (e.g., a first primer that hybridizes to a TYK2 nucleic acid and second primer that hybridizes to nucleic acid from a TYK2-gene-fusion-partner (e.g., NPM1)), an antibody that binds to the fusion junction of a fusion polypeptide of TYK2 and a TYK2-gene-fusion-partner (e.g., NPM1) (e.g., a NPM1-TYK2 fusion polypeptide), a sequencing primer that binds to a fusion between TYK2 and a TYK2-gene-fusion-partner (e.g., NPM1) (e.g., a NPM1-TYK2 fusion polypeptide) and generates an extension product that spans the fusion junction of said gene fusion between TYK2 and a TYK2-gene-fusion-partner (e.g., NPM1) (e.g., a NPM1-TYK2 fusion polypeptide), or a pair of probes wherein the first probe hybridizes to TYK2 gene and the second probe hybridizes to a TYK2-gene-fusion-partner (e.g., NPM1).

Further embodiments of the present invention provide uses and methods for characterizing/detecting/identifying cutaneous CD30-positive lymphoproliferative disorders (e.g., lymphomatoid papulosis; primary cutaneous anaplastic large cell lymphoma) in a subject (e.g., human subject) using the aforementioned kits or other components.

For example, in some embodiments, the present invention provides a method for characterizing/detecting/identifying cutaneous CD30-positive lymphoproliferative disorders (e.g., lymphomatoid papulosis; primary cutaneous anaplastic large cell lymphoma) in a subject (e.g., human subject), comprising: (a) contacting a biological sample from a subject (e.g., biopsy tissue, tissue, blood, plasma, serum, urine, stool, and/or cells) with a nucleic acid or polypeptide detection assay comprising at least a first gene fusion informative reagent for identification of a NPM1-TYK2 gene fusion under conditions that the presence of such a gene fusion is detected; and (b) characterizing/detecting/identifying cutaneous CD30-positive lymphoproliferative disorders (e.g., lymphomatoid papulosis; primary cutaneous anaplastic large cell lymphoma) in the subject when the NPM1-TYK2 gene fusion is present in the sample.

In some embodiments, step (a) comprises detecting chromosomal rearrangements of genomic DNA having a 5' portion from NPM1 and a 3' portion from TYK2. In some embodiments, step (a) comprises detecting chromosomal rearrangements of genomic DNA using a nucleic acid sequencing technique. In some embodiments, step (a) comprises detecting chromosomal rearrangements of genomic DNA using a nucleic acid hybridization technique. In some embodiments, step (a) comprises detecting chromosomal rearrangements of genomic DNA using a nucleic acid hybridization technique (e.g., including but not limited to, in situ hybridization (ISH), microarray or Southern blot). In some embodiments, step (a) comprises detecting chromosomal rearrangements of genomic DNA using a nucleic acid amplification method (e.g., including but not limited to, polymerase chain reaction (PCR), reverse transcription polymerase chain reaction (RT-PCR), transcription-mediated amplification (TMA), ligase chain reaction (LCR), strand displacement amplification (SDA), or nucleic acid sequence based amplification (NASBA)). In some embodiments, step (a) comprises detecting chimeric mRNA transcripts having 5' portion from NPM1 and a 3' portion from TYK2.

In some embodiments, step (a) comprises detecting chimeric mRNA transcripts using a nucleic acid sequencing technique. In some embodiments, step (a) comprises detecting chimeric mRNA transcripts using a nucleic acid hybridization technique. In some embodiments, step (a) comprises detecting chimeric mRNA transcripts using a nucleic acid hybridization technique (e.g., including but not limited to, in situ hybridization (ISH), microarray or Northern blot). In some embodiments, step (a) comprises detecting chimeric mRNA transcripts using a nucleic acid amplification method (e.g., including but not limited to, polymerase chain reaction (PCR), reverse transcription polymerase chain reaction (RT-PCR), transcription-mediated amplification (TMA), ligase chain reaction (LCR), strand displacement amplification (SDA), or nucleic acid sequence based amplification (NASBA)).

In some embodiments, the method further comprises the step of collecting the sample from the subject. In some embodiments, the sample is, for example, biopsy tissue, tissue, blood, plasma, serum, urine, stool, and/or cells.

In some embodiments, the described methods further comprise the step of detecting the level of expression of the gene fusion in the sample, wherein detecting an enhanced level of expression of the gene fusion in the patient sample relative to the level of expression of the gene fusion in a normal sample (e.g., relative to the level in normal cells, increase or decrease in level relative to a prior time point, increase or decrease relative to a pre-established threshold level, etc.) indicates the presence of neoplastic cells or cells predisposed to the onset of a neoplastic state in the sample.

Further embodiments provide the step of determining a treatment course of action based on the presence or absence of the gene fusion. For example, in some embodiments, the treatment course of action comprises administration of an inhibitor of activity resulting from such a gene fusion (e.g., NPM1-TYK2) (e.g., tyrosine kinase activity resulting from the gene fusion, STAT1, STAT3, and/or STAT5 activity resulting from the gene fusion, and increased cellular proliferation resulting from the gene fusion) when the gene fusion is present in the sample. In some embodiments, the agent inhibits expression of the gene fusion. In some embodiments, the agent inhibits any expression and/or activity resulting from the gene fusion. The agent may be a small molecule, an siRNA, an antisense nucleic acid, or an antibody.

In certain embodiments, the present invention provides a method for diagnosing a neoplastic disorder or susceptibility to a neoplastic disorder comprising detecting the presence of a NPM1-TYK2 gene fusion in a sample from a subject (e.g., a human patient), wherein the NPM1-TYK2 gene fusion is a fusion between chromosome 5, exon 9 of NPM1 and chromosome 19, exon 15 of TYK2 (e.g., N5; T19), and diagnosing the subject as having or being susceptible to a neoplastic disorder when the gene fusion is present. In some embodiments, the neoplastic disorder is a cutaneous CD30-positive lymphoproliferative disorder (e.g., lymphomatoid papulosis; primary cutaneous anaplastic large cell lymphoma).

In certain embodiments, the present invention provides a method of determining the NPM1-TYK2 gene fusion status of a human by: (a) determining the presence or absence of the the N5; T19 gene fusion in both alleles of the of the NPM1-TYK2 fusion gene of the human in a nucleic acid sample obtained from the human, and (b) identifying the human (i) as being homozygous for N5; T19 gene fusion in the NPM1-TYK2 fusion gene when one of the gene fusions is present in both alleles of the NPM1-TYK2 fusion gene, or (ii) as being heterozygous for the N5; T19 gene fusion in the NPM1-TYK2 fusion gene when one of the gene fusions is present in one of the alleles of the NPM1-TYK2 fusion gene, or (iii) as having no alteration in the NPM1-TYK2 fusion gene caused by the N5; T19 gene fusion when each of the gene fusions is absent from both alleles of the NPM1-TYK2 fusion gene.

In some embodiments, the NPM1-TYK2 gene fusion is N5; T19. An NPM1-TYK2 gene fusion may be detected by amplifying any of SEQ ID NOs: 1, 2, 3, or 4, or diagnostic fragments thereof. In one embodiment, the method includes detecting one or more additional NPM1-TYK2 gene fusions in a sample from the subject.

The NPM1-TYK2 fusion may be detected by assessing sample nucleic acid by PCR, RT-PCR, and/or nucleic acid hybridization. In one embodiment, the sample is amplified by reverse transcriptase polymerase chain reaction (RT-PCR). In one embodiment, the amplifying employs a detectably labeled primer. In one embodiment, the detecting is accomplished with electrophoresis. In one embodiment, the detecting is accomplished using a real-time PCR-based detection system, such as TaqMan®.

The present invention also provides a method for diagnosing a neoplastic disorder or susceptibility to a neoplastic disorder by detecting the presence or absence of an NPM1-TYK2 fusion protein in a sample from a subject, wherein the NPM1-TYK2 fusion protein is a fusion between exon 9 of NPM1 and exon 15 of ALK, and diagnosing the subject has having or being susceptible to a neoplastic disorder when the fusion protein is present.

The invention also provides kits for detecting a NPM1-TYK2 fusion mutations which include one or more oligonucleotides (e.g., a primer) for amplifying a fragment of a nucleic acid sample which contains the N5; T19 mutation, if present. Optionally, the kit further contains one or more mutation-specific oligonucleotide probes.

Additional embodiments of the present invention are provided in the description and examples below.

DESCRIPTION OF THE FIGURES

FIG. 1: FISH Results and Clinical Data for Cutaneous CD30-Positive Lymphoproliferative Disorders.

Figure 2A:
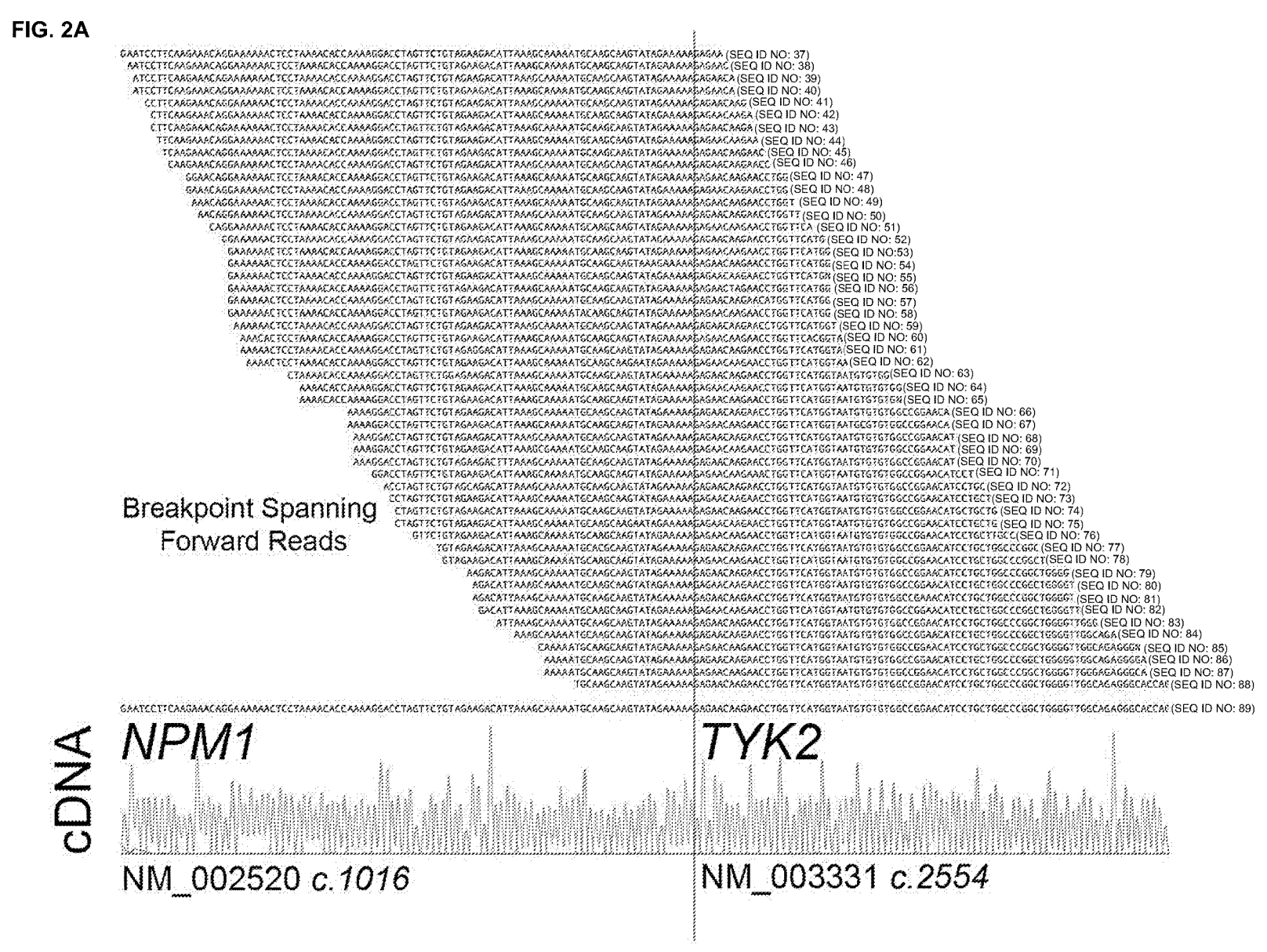

FIG. 2A-F: Identification of TYK2 translocations in cutaneous T cell lymphoma-derived cell line and primary CD30 positive LPD patient samples. (A) Read support from RNA sequencing illustrating the forward fragment reads spanning the breakpoint between 5' NPM1 (NM_002520 c.1016) component and 3' TYK2 (NM_003331 c.2554) component and confirmation by Sanger sequencing. (B) Protein domain and exon diagram illustrating the preservation of N-terminal oligomerization and histone and DNA/RNA binding domains of NPM1 and the C-terminal kinase domain of TYK2 in the NPM1-TYK2 fusion protein. (C) Cloning of the genomic breakpoint of the t(5; 19) fusion event at chr5:170,832,813 and chr19:10,469,815 and confirmation by Sanger sequencing. (D) The NPM1-TYK2 fusion joins the positive strand of the NPM1 locus up to and including exon 9, with the inverted negative strand of the TYK2 locus between exons 15 and 16. (E) FISH studies. A TYK2 break-apart assay shows a TYK2 rearrangement in the MyLa cell line and in a primary cutaneous CD30-positive LPD (upper panel). NPM1-TYK2 fusion FISH reveals that NPM1 is the partner gene in both. A case that is negative for TYK2 translocation is also illustrated (lower panel). (F) NPM1-TYK2 fusion probe FISH assay shows the occurrence of t(5; 19) translocation in a cutaneous ALCL primary sample.

FIG. 3: Summary of RNAseq data for MyLa.

FIG. 10: Immunohistochemical staining for pSTAT5 in primary patient samples. In the absence of NPM1-TYK2, there is weak expression of pSTAT5, predominantly limited to the cytoplasm (left panel). In a patient with NPM1-TYK2 fusion, expression of pSTAT5 is stronger and increased nuclear expression is present (right panel). (Anti-pSTAT5, 400× magnification).

FIG. 11A-E: A) wild type cDNA sequence for TYK2; B) wild type ORF nucleic acid sequence for TYK2; C) wild type amino acid sequence for TYK2; D) wild type nucleic acid sequence for TYK2; and E) TYK2 nucleic acid intron involved in TYK2 translocation.

FIG. 12A-E: A) wild type cDNA sequence for NPM1; B) wild type ORF nucleic acid sequence for NPM1; C) wild type amino acid sequence for NPM1; D) wild type nucleic acid sequence for NPM1; and E) NPM1 nucleic acid intron involved in NPM1 translocation.

FIG. 13A-D: A) cDNA sequence for NPM1-TYK2 gene fusion; B) coding region for NPM1-TYK2 gene fusion; C) amino acid sequence for NPM1-TYK2 gene fusion product; and D) NPM1-TYK2 introns involved in translocation.

DEFINITIONS

Figure 2B:
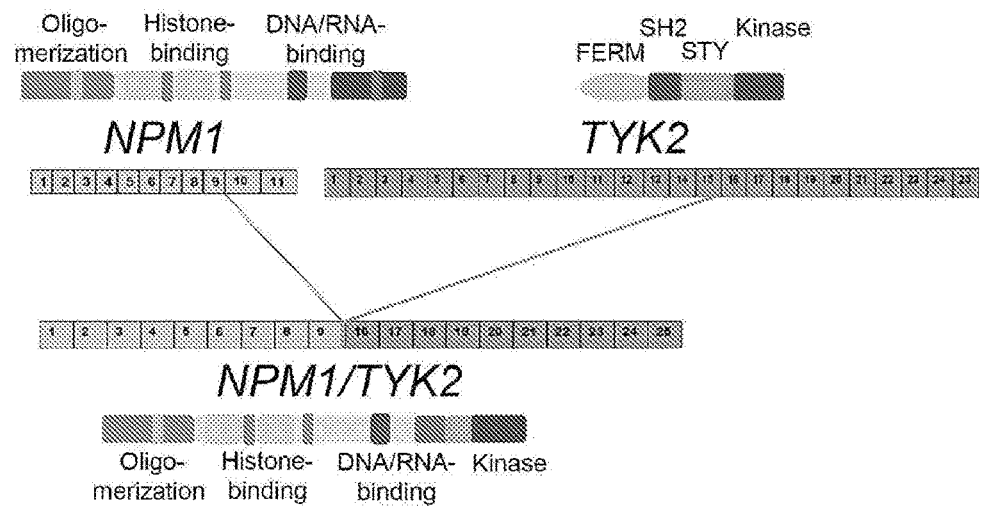
Figure 2C:
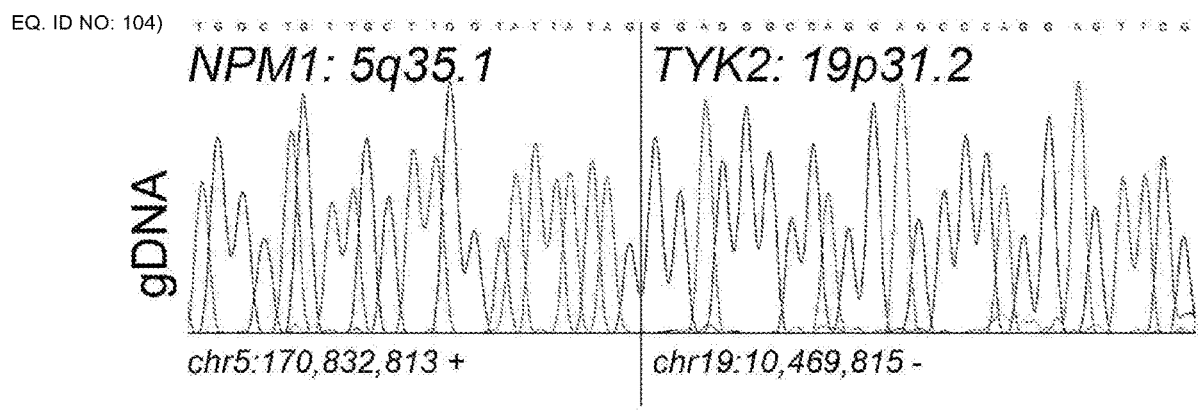
Figure 2D:
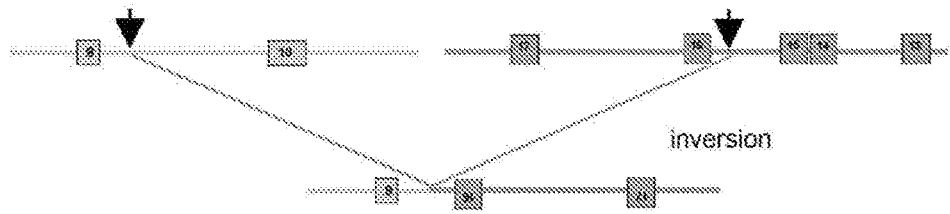

To facilitate an understanding of the present invention, a number of terms and phrases are defined below:

As used herein, the term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of the true negatives and false positives.

As used herein, the term "informative" or "informativeness" refers to a quality of a marker or panel of markers, and specifically to the likelihood of finding a marker (or panel of markers) in a positive sample.

Figure 11D:
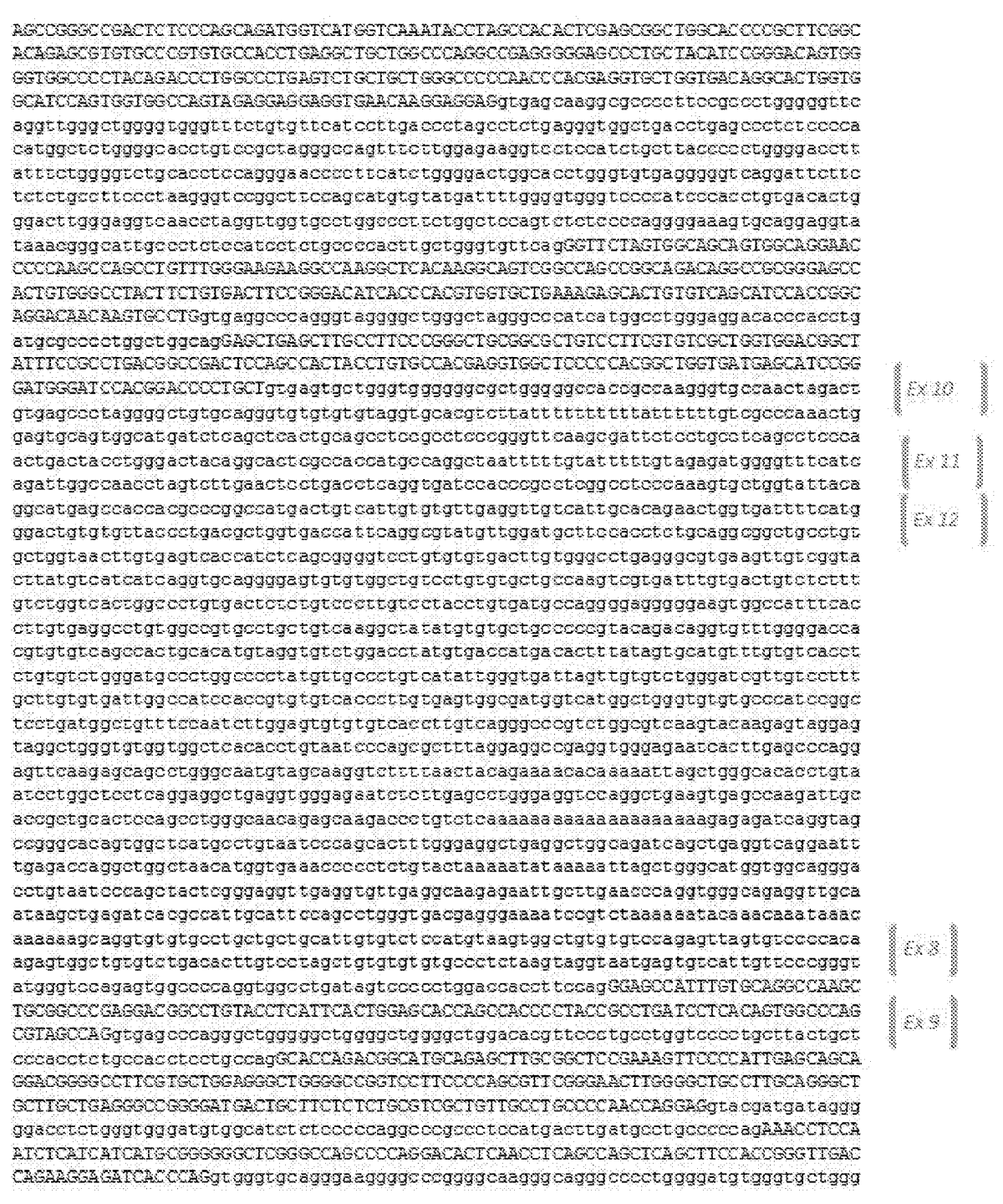
Figure 11D:
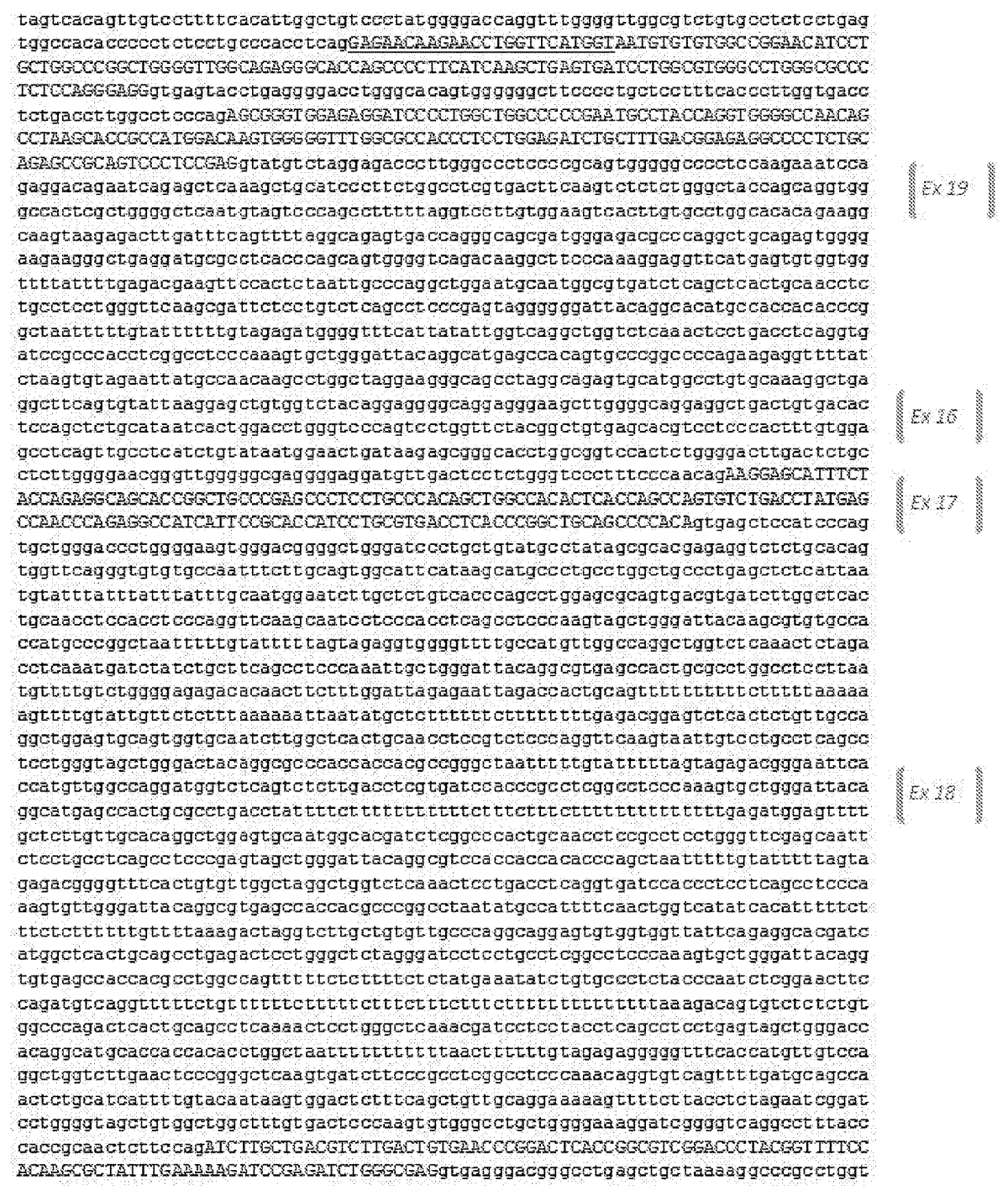

As used herein, "TYK2" refers to a member of the Janus Kinase (JAK) family of tyrosine kinases. An example of TYK2 polypeptide is the human polypeptide sequence described in Genbank accession number P29597.3. An exemplary TYK2 coding sequence is the human sequence described in Genbank accession number X54637. TYK2 also includes species homologs, splice variants, polymorphic variants, and conservatively modified variants of TYK2 that retain TYK2 tyrosine kinase activity. FIG. 11 provides: A) human wild type cDNA sequence for TYK2; B) human wild type ORF nucleic acid sequence for TYK2; C) human wild type amino acid sequence for TYK2; D) human wild type nucleic acid sequence for TYK2; and E) human TYK2 nucleic acid intron involved in TYK2 translocation.

As used herein, "NPM1" refers to a gene which encodes a phosphoprotein which moves between the nucleus and the cytoplasm. The gene product is thought to be involved in several processes including regulation of the ARF/p53 pathway. An exemplary NPM1 coding sequence is the human sequence described in Genbank accession number P06748. NPM1 also includes species homologs, splice variants, polymorphic variants, and conservatively modified variants of NPM1 that retain its wild type activity. FIG. 12 provides: A) human wild type cDNA sequence for NPM1; B) human wild type ORF nucleic acid sequence for NPM1; C) human wild type amino acid sequence for NPM1; D) human wild type nucleic acid sequence for NPM1; and E) human NPM1 nucleic acid intron involved in NPM1 translocation.

As used herein, "NPM1-TYK2" refers to a chimeric genomic DNA, a chimeric messenger RNA, a truncated protein or a chimeric protein resulting from the fusion of at least a portion of an NPM1 gene to at least a portion of a TYK2 gene. The gene fusion need not include entire genes or exons of genes. FIG. 13 provides: A) cDNA sequence for NPM1-TYK2 gene fusion; B) coding region for NPM1-TYK2 gene fusion; C) amino acid sequence for NPM1-TYK2 gene fusion product; and D) NPM1-TYK2 introns involved in translocation.

As used herein, the terms "NPM1/TYK2 informative reagent" refers to a reagent or reagents that are informative for identification of gene fusions described herein. In some embodiments, reagents are primers, probes or antibodies for detection of NPM1-TYKE2 gene fusions described herein.

As used herein, the term "transcriptional regulatory region" refers to the non-coding upstream regulatory sequence of a gene, also called the 5' untranslated region (5'UTR).

As used herein, the terms "detect", "detecting", or "detection" may describe either the general act of discovering or discerning or the specific observation of a detectably labeled composition.

As used herein, the term "inhibits at least one biological activity of a gene fusion" refers to any agent that decreases any activity of a gene fusion of the present invention (e.g., including, but not limited to, the activities described herein), via directly contacting gene fusion protein, contacting gene fusion mRNA or genomic DNA, causing conformational changes of gene fusion polypeptides, decreasing gene fusion protein levels, or interfering with gene fusion interactions with signaling partners, and affecting the expression of gene fusion target genes. Inhibitors also include molecules that indirectly regulate gene fusion biological activity by intercepting upstream signaling molecules.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

Numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the conditions that promote hybridization under conditions of high stringency (e.g., increasing the temperature of the hybridization and/or wash steps, the use of formamide in the hybridization solution, etc.) (see definition above for "stringency") can be utilized.

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

Recurrent chromosomal translocations frequently underlie the pathogenesis of several hematopoietic malignancies and often define molecular subtypes with distinct biological behavior (see, e.g., Rowley J D, Nature reviews Cancer 2001; 1:245-50; Mitelman F, et al., Nature reviews Cancer 2007; 7:233-45). Frequently, these translocations target tyrosine kinases resulting in constitutive activation and promotion of oncogenesis (see, e.g., Greuber E K, et al., Nature reviews Cancer 2013; 13:559-71). Cutaneous CD30-positive LPD represents a clinicopathologic spectrum including lymphomatoid papulosis (LYP) and primary cutaneous anaplastic large cell lymphoma (ALCL) (see, e.g., Swerdlow S H, Campo, E., Harris, N. L., Jaffe, E. S., Pileri, S. A., Stein, H., Thiele, J., Vardiman, J. W, ed. WHO Classification of Tumours of Haematopoietic and Lymphoid Tissues. Lyon: IARC; 2008). Gene fusions targeting tyrosine kinases underlying the pathogenesis of CD30-positive LPD have not been described.

Experiments conducted during the course of developing embodiments for the present invention identified a novel recurrent NPM1-TYK2 gene fusion in CD30-positive LPD. Functional support for NPM1-TYK2 in mediating activation of STAT1/3/5 signaling to promote cell proliferation was provided. Functional inactivation of TYK2 was shown to significantly diminish proliferation indicating TYK2 as an oncogenic driver kinase. Additionally, FISH studies provided evidence that TYK2 is targeted by translocation partners other than NPM1. Taken together, such results indicate TYK2 as a therapeutic target in the treatment of CD30-positive LPDs.

Accordingly, provided herein are kits, compositions and methods for cancer diagnosis, research and therapy, including but not limited to, cancer markers. In particular, the present invention relates to recurrent gene fusions (e.g., recurrent translocations involving TYK2) as diagnostic markers and clinical targets for cutaneous CD30-positive lymphoproliferative disorders (e.g., lymphomatoid papulosis; primary cutaneous anaplastic large cell lymphoma).

I. Gene Fusions

Embodiments of the present invention provide diagnostic, screening, research, and therapeutic methods for detecting, diagnosing and characterizing cancer (e.g., cutaneous CD30-positive lymphoproliferative disorders (e.g., lymphomatoid papulosis; primary cutaneous anaplastic large cell lymphoma)) based on the presence of gene fusions including TYK2 and a TYK2-gene-fusion-partner in a sample. In some embodiments, the gene fusion comprises an intact catalytic domain in TYK2, although other regions are specifically encopossed by embodiments of the present invention.

Such embodiments are not limited to a particular portion of a TYK2 gene.

In some embodiments, the portion of the TYK2 gene comprises any portion of TYK2 enables tyrosine kinase activity upon expression as a polypeptide. In some embodiments, the portion of the TYK2 gene comprises at least a portion (e.g., 1%, 10%, 25%, 50%, 75%, 80%, 95%, 99%, 100%) of the C-terminal kinase domain of TYK2. In some embodiments, the portion of the TYK2 gene comprises the entire C-terminal kinase domain of TYK2. In some embodiments, the portion of the TYK2 gene comprises at least a portion of the TYK2 pseudokinase domain. In some embodiments, the portion of the TYK2 gene comprises at least a portion (e.g., 1%, 10%, 25%, 50%, 75%, 80%, 95%, 99%, 100%) of the C-terminal kinase domain of TYK2 and/or at least a portion (e.g., 1%, 10%, 25%, 50%, 75%, 80%, 95%, 99%, 100%) of the TYK2 pseudokinase domain.

In some embodiments, the gene fusion is a NPM1-TYK2 gene fusion. In some embodiments, gene fusions comprise the oligomerization domain of NPM1 and an intact catalytic domain in TYK2, although other regions are specifically encopossed by embodiments of the present invention.

Such embodiments are not limited to a particular TYK2-gene-fusion-partner.

In some embodiments, the TYK2-gene-fusion-partner is any gene such that upon fusion with TYK2 the resulting gene fusion encodes a polypeptide capable of having constitutively activated tyrosine kinase activity when expressed in a cell.

In some embodiments, the TYK2-gene-fusion-partner is any gene such that upon fusion with TYK2 the resulting gene fusion encodes a polypeptide that when expressed in a cell is capable of constitutively activating downstream targets of TYK2 (e.g., STAT1, STAT3, STAT5) within the cell.

In some embodiments, the TYK2-gene-fusion-partner is any gene such that upon fusion with TYK2 the resulting gene fusion encodes a polypeptide that when expressed in a cell results in increased cellular proliferation of that cell.

In some embodiments, the TYK2-gene-fusion-partner is any gene such that upon fusion with TYK2 the resulting gene fusion encodes a polypeptide, wherein 1) the polypeptide is capable of having constitutively activated tyrosine kinase activity when expressed in a cell, 2) expression of the polypeptide in a cell results in constitutive activation of downstream targets of TYK2 (e.g., STAT1, STAT3, STAT5), and 3) expression of the polypeptide in a cell results in increased cellular proliferation of the cell.

In some embodiments, the TYK2-gene-fusion-partner is any portion of NPM1.

In some embodiments, the TYK2-gene-fusion-partner comprises at least a portion (e.g., 1%, 10%, 25%, 50%, 75%, 80%, 95%, 99%, 100%) of the NPM1 oligomerization domain. In some embodiments, the TYK2-gene-fusion-partner comprises the entire NPM1 oligomerization domain.

In some embodiments, the TYK2-gene-fusion-partner comprises at least a portion (e.g., 1%, 10%, 25%, 50%, 75%, 80%, 95%, 99%, 100%) of the NPM1 histone binding domains. In some embodiments, the TYK2-gene-fusion-partner comprises the entire NPM1 histone binding domains.

In some embodiments, the TYK2-gene-fusion-partner comprises at least a portion (e.g., 1%, 10%, 25%, 50%, 75%, 80%, 95%, 99%, 100%) of the distal portion of the NPM1 DNA/RNA binding domains. In some embodiments, the TYK2-gene-fusion-partner comprises the entire distal portion of the NPM1 DNA/RNA binding domains.

In some embodiments, the TYK2-gene-fusion-partner comprises the entire NPM1 oligomerization domain, the entire NPM1 histone binding domain, and the entire distal portion of the NPM1 DNA/RNA binding domain.

In some embodiments, the NPM1-TYK2 gene fusion is a fusion between chromosome 5, exon 9 of NPM1 and chromosome 19, exon 15 of TYK2 (e.g., N5; T19).

II. Antibodies

The gene fusion proteins of the present invention, including fragments, derivatives and analogs thereof, may be used as immunogens to produce antibodies having use in the diagnostic, research, and therapeutic methods described below. The antibodies may be polyclonal or monoclonal, chimeric, humanized, single chain or Fab fragments. Various procedures may be used for the production and labeling of such antibodies and fragments. See, e.g., Burns, ed., Immunochemical Protocols, 3$^{rd}$ ed., Humana Press (2005); Harlow and Lane, Antibodies: A Laboratory Manual, Cold Spring Harbor Laboratory (1988); Kozbor et al., Immunology Today 4: 72 (1983); Köhler and Milstein, Nature 256: 495 (1975).

III. Diagnostic Applications

The present invention provides DNA, RNA and protein based diagnostic methods that either directly or indirectly detect the gene fusions. The present invention also provides compositions and kits for diagnostic purposes.

The diagnostic methods of the present invention may be qualitative or quantitative. Quantitative diagnostic methods may be used, for example, to discriminate between indolent and aggressive cancers via a cutoff or threshold level. Where applicable, qualitative or quantitative diagnostic methods may also include amplification of target, signal or intermediary (e.g., a universal primer).

An initial assay may confirm the presence of a gene fusion but not identify the specific fusion. A secondary assay is then performed to determine the identity of the particular fusion, if desired. The second assay may use a different detection technology than the initial assay.

The gene fusions of embodiments of the present invention may be detected along with other markers in a multiplex or panel format. Markers are selected for their predictive value alone or in combination with the gene fusions. Markers for other cancers, diseases, infections, and metabolic conditions are also contemplated for incluidsion in a multiplex of panel format.

The diagnostic methods of embodiments of the present invention may also be modified with reference to data correlating particular gene fusions with the stage, aggressiveness or progression of the disease or the presence or risk of metastasis. Ultimately, the information provided by the methods of the present invention will assist a physician in choosing the best course of treatment for a particular patient.

A. Sample

Any patient sample suspected of containing the gene fusions may be tested according to the methods of the present invention. By way of non-limiting examples, the sample may be tissue (e.g., a biopsy sample), blood, or a fraction thereof (e.g., plasma, serum, or cells).

In some embodiments, the patient sample typically requires preliminary processing designed to isolate or enrich the sample for the gene fusions or cells that contain the gene fusions. A variety of techniques may be used for this purpose, including but not limited: centrifugation; immunocapture; cell lysis; and, nucleic acid target capture.

B. DNA and RNA Detection

The gene fusions of the present invention may be detected as chromosomal rearrangements of genomic DNA or chimeric mRNA using a variety of nucleic acid techniques, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, fluorescent or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

Some embodiments of the present invention utilize next generation or high-throughput sequencing. A variety of nucleic acid sequencing methods are contemplated for use in the methods of the present disclosure including, for example, chain terminator (Sanger) sequencing, dye terminator sequencing, and high-throughput sequencing methods. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299: 682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques can be used including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485, 944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, capillary electrophoresis (CE) is utilized to analyze amplification fragments. During capillary electrophoresis, nucleic acids (e.g., the products of a PCR reaction) are injected electrokinetically into capillaries filled with polymer. High voltage is applied so that the fluorescent DNA fragments are separated by size and are detected by a laser/camera system. In some embodiments, CE systems from Life Technogies (Grand Island, N.Y.) are utilized for fragment sizing (See e.g., U.S. Pat. Nos. 6,706,162, 8,043, 493, each of which is herein incorporated by reference in its entirety).

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 FISH

In some embodiments, fusion sequences are detected using fluorescence in situ hybridization (FISH). The preferred FISH assays for the present invention utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor. In some embodiments, the detection assay is a FISH assay utilizing a probe for TYK2 and/or a TYK2-gene-fusion-partner (e.g., NPM1).

2.2 Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Chromosomal rearrangements of genomic DNA and chimeric mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

4. Detection Methods

Non-amplified or amplified gene fusion nucleic acids can be detected by any means. For example, the gene fusions can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification including methods disclosed in U.S. Pat. Nos. 6,303,305 and 6,541,205, each of which is herein incorporated by reference in its entirety can be used. Another method for determining the quantity of target sequence initially present in a sample, but which is not based on a real-time amplification, is disclosed in U.S. Pat. No. 5,710, 029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing are, for example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Protein Detection

The gene fusions of the present invention may be detected as truncated or chimeric proteins using a variety of protein techniques, including but not limited to: protein sequencing; and, immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

D. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. In Vivo Imaging

The gene fusions of the present invention may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention. In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. Agents with paramagnetic ions as labels for magnetic resonance imaging can be utilized (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

F. Compositions & Kits

Compositions for use in the diagnostic methods of the present invention include, but are not limited to, probes, amplification oligonucleotides, and antibodies. Particularly preferred compositions detect a product only when a gene fusion of TYK2 and a TYK2-gene-fusion-partner (e.g., NPM1) is present in a sample (e.g., NPM1-TYK2). In some embodiments, the compositions include a single labeled probe comprising a sequence that hybridizes to the junction at which a 5' portion from a TYK2-gene-fusion-partner (e.g., NPM1) fuses to a 3' portion from a TYK2 gene (i.e., spans the gene fusion junction). In some embodiments, the compositions include a pair of amplification oligonucleotides wherein the first amplification oligonucleotide comprises a sequence that hybridizes to a TYK2-gene-fusion-partner (e.g., NPM1) and the second amplification oligonucleotide comprises a sequence that hybridizes to TYK2 gene. In some embodiments, the compositions include an antibody to a gene fusion between TYK2 and a TYK2-gene-fusion-partner (e.g., NPM1).

Other useful compositions, however, include: a pair of labeled probes wherein the first labeled probe comprises a sequence that hybridizes to a TYK2-gene-fusion-partner (e.g., NPM1) and a second labeled probe comprises a sequence that hybridizes to an TYK2 gene.

Any of these compositions, alone or in combination with other compositions of the present invention, may be provided in the form of a kit. For example, the single labeled probe and pair of amplification oligonucleotides may be provided in a kit for the amplification and detection of gene fusions of the present invention. Kits may further comprise appropriate controls and/or detection reagents.

The probe and antibody compositions of the present invention may also be provided in the form of an array.

IV. Drug Screening Applications

In some embodiments, the present invention provides drug screening assays (e.g., to screen for anticancer drugs). The screening methods of the present invention utilize cancer markers identified using the methods of the present invention (e.g., including but not limited to gene fusions between TYK2 and a TYK2-gene-fusion-partner (e.g., NPM1)). For example, in some embodiments, the present invention provides methods of screening for compounds that alter (e.g., decrease) the expression of cancer marker genes. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly cutaneous CD30-positive lymphoproliferative disorders (e.g., lymphomatoid papulosis; primary cutaneous anaplastic large cell lymphoma).

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

VI. Therapeutic Applications

In some embodiments, the present invention provides therapies for cancer (e.g., cutaneous CD30-positive lymphoproliferative disorders (e.g., lymphomatoid papulosis; primary cutaneous anaplastic large cell lymphoma)). In some embodiments, therapies directly or indirectly target cancer markers (e.g., including but not limited to, gene fusions between TYK2 and a TYK2-gene-fusion-partner (e.g., NPM1).

A. RNA Interference and Antisense Therapies

In some embodiments, the present invention targets the expression of cancer markers. For example, in some embodiments, the present invention employs compositions comprising oligomeric antisense or RNAi compounds, particularly oligonucleotides (e.g., those identified in the drug screening methods described above), for use in modulating the function of nucleic acid molecules encoding cancer markers of the present invention, ultimately modulating the amount of cancer marker expressed.

1. RNA Interference (RNAi)

In some embodiments, RNAi is utilized to inhibit fusion protein function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of fusion proteins.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference). An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually Comers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

2. Antisense

In other embodiments, fusion protein expression is modulated using antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result.

Chimeric antisense compounds of the present invention may be formed as composite structures of two or more oligonucleotides, modified oligonucleotides, oligonucleosides and/or oligonucleotide mimetics as described above. The present invention also includes pharmaceutical compositions and formulations that include the antisense compounds of the present invention as described below.

B. Gene Therapy

The present invention contemplates the use of any genetic manipulation for use in modulating the expression of cancer markers of the present invention. Examples of genetic manipulation include, but are not limited to, gene knockout (e.g., removing the fusion gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target cells that express a cancer marker of the present invention (e.g., a gene fusion between TYK2 and a TYK2-gene-fusion-partner (e.g., NPM1)). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies can be utilized (See e.g., U.S. Pat. Nos. 6,180, 370, 5,585,089, 6,054,297, and 5,565,332; each of which is herein incorporated by reference).

In some embodiments, the therapeutic antibodies comprise an antibody generated against a cancer marker of the present invention (e.g., a gene fusion between TYK2 and a TYK2-gene-fusion-partner (e.g., NPM1)), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and anti-tumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using conjugation technology (See, e.g., Ghose et al., Methods Enzymol., 93:280 [1983]).

For example, in some embodiments the present invention provides immunotoxins targeted to a cancer marker of the present invention (e.g., a gene fusion between TYK2 and a TYK2-gene-fusion-partner (e.g., NPM1)). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising pharmaceutical agents that modulate the expression or activity of gene fusions of the present invention (e.g., a gene fusion between TYK2 and a TYK2-gene-fusion-partner (e.g., NPM1)). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to techniques such as, for example, bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

EXPERIMENTAL

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example 1

This example describes the methods for Examples 2 and 3.

RNAseq

RNA was isolated from the MyLa cell lines using RNeasy kit from Qiagen (Valencia, Calif., USA) and quantitated using the Agilent 2100 bio-analyzer (Agilent Biotechnologies, Santa Clara, Calif., USA). Samples with RNA integrity score (RIN)>6 were used for preparing cDNA libraries for transcriptome sequencing. Paired-end libraries for sequencing with Illumina Genome Analyzer II were prepared according to the protocol provided by Illumina, with minor modifications, with the mRNA-seq sample prep kit (Illumina). Sequence analysis was carried out using a combination of custom designed bioinformatics tools and Chimerascan (see, e.g., Iyer M K, Bioinformatics 2011; 27:2903-4).

Clinical Samples

Clinical samples of primary cutaneous CD30-positive T-cell lymphoproliferative disorders (n=47); mycosis fungoides (n=44); systemic ALK-negative anaplastic large cell lymphoma (n=44); ALK-positive anaplastic large cell lymphoma (n=22); peripheral T-cell lymphoma, not otherwise specified (n=24); angioimmunoblastic T-cell lymphoma (n=7); extranodal NK/T-cell lymphoma (n=5); enteropathy-associated T-cell lymphoma (n=3); hepatosplenic T-cell lymphoma (n=1); cutaneous gamma/delta T-cell lymphoma (n=1) were obtained with IRB approval from the pathology archives of the University of Michigan, the University of Texas MD Anderson Cancer Center, Henry Ford Health System, and Seoul National University Hospital. Diagnoses were established by using 2008 World Health Organization criteria (see, e.g., Swerdlow S H, et al., WHO Classification of Tumours of Haematopoietic and Lymphoid Tissues. Lyon: IARC; 2008). Patients with CD30-positive T-cell lymphoproliferative disorders were further subclassified as having either lymphomatoid papulosis or primary cutaneous anaplastic large cell lymphoma based on the combination of histologic and clinical features (see, e.g., Bekkenk M W, et al., Blood 2000; 95:3653-61). 1 mm diameter cores were taken in triplicate from tumor-rich areas of each formalin-fixed, paraffin-embedded specimen for tissue microarray construction and subsequent immunohistochemical and fluorescence in situ hybridization analysis.

Clinical Information

Clinical information was available for four of the seven patients demonstrating TYK2 translocations, including 1 patient with NPM1-TYK2 fusion (FIG. 1). The patient with NPM1-TYK2 fusion presented at the age of 71 with localized disease diagnosed as LYP. Phototherapy resulted in 6 years of remission. The patient's disease recurred and was controlled with methotrexate. Another patient presented at the age of 40 with localized disease diagnosed as LYP. After initial treatment with radiation therapy, he developed more widespread involvement that was currently controlled with methotrexate and topical steroids. A third patient presented at the age of 49 with disease diagnosed as LYP. Her disease was currently controlled with methotrexate. The fourth patient was diagnosed with LYP at the age of 31 which progressed to cutaneous ALCL. The patient received radiation and methotrexate with stable disease. Of note, no difference in clinical behavior or presentation was discernable between cases with and without a TYK2 rearrangement.

Fluorescence In Situ Hybridization (FISH)

Interphase FISH was performed to assess for TYK2 rearrangements and for specific NPM1-TYK2 fusions. Fluorescently labeled BAC clones were purchased from Empire Genomics, Buffalo, N.Y., USA. Tissue microarrays containing clinical samples were sectioned at 4 μm and deparaffinized. The deparaffinized tissue microarray and cytospin slides of MyLa cells were hybridized with the probes overnight and assessed by fluorescent microscopy. BAC clones used for FISH included TYK2 probes: RP11-177J4 labeled with ROX (5' of TYK2), RP11-347E20, labeled with fluorescein (3' of TYK2) and NPM1 probe RP11-1072120, labeled with ROX (5' of NPM1).

Quantitative Real Time Polymerase Chain Reaction (qRT-PCR) Validation Reverse Transcription.

1 μg of total RNA was used for preparation of cDNA using SuperScript II reverse transcription kit (Life Technologies, Grand Island, N.Y., USA). The final product was diluted to 100 μl in nuclease free water. 1 μl of this diluted cDNA was used for quantitative real-time polymerase chain reaction (qRT-PCR) analyses.

SYBR Green Assay.

qRT-PCR was performed using Power SYBR Green Mastermix (Applied Biosystems, Carlsbad, Calif., USA) on an Applied Biosystems StepOne Plus Real-Time PCR System. All oligonucleotide primers were obtained from Integrated DNA Technologies (Coralville, Iowa). Control primers were used to amplify the GAPDH housekeeping gene. All assays were performed and repeated twice and results were plotted as average fold change relative to GAPDH.

Primers used for validation of NPM1-TYK2 fusion transcripts in cell lines by SYBR green assay:

```
NPM-TYK2 Q F1
                                          (SEQ ID NO: 1)
5'ACTCAAAACCATCATCAACACCA3'

NPM-TYK2 Q R1
                                          (SEQ ID NO: 2)
5'GTTCCGGCCACACACATTAC3'
```

Sanger Sequencing of NPM1-TYK2 Fusion Chimera

NPM1-TYK2 fusion chimera was amplified from MyLa T-cell line using two different primer sets for NPM1 and TYK2. The primers were designed to amplify across the fusion chimera generating two different amplicons (175 bp and 468 bp) using Phusion DNA polymerase (New England Biolabs, Ipswich, Mass., USA) followed by conventional Sanger sequencing technology using BigDye version 3.1 chemistry run on an Applied Biosystems 3730xl DNA Sequencer. The PCR products were separated on a 1% agarose gel, bands excised and purified for Sanger sequencing.

Genomic PCR for Genomic Breakpoint Mapping

To identify the genomic break point in the index NPM1-TYK2 fusion event, a series of forward primers were designed that spanned from last exon of NPM1 present in NPM1-TYK2 fusion to the end of the following intron. Similarly, reverse primers were designed to span the region between the first exon of TYK2 in NPM1-TYK2 through the entire intron proximal to the exon. Genomic DNA was isolated from MyLa and HH cells using QIAamp DNA extraction kit (Valencia, Calif., USA). 40 ng of genomic DNA was used as template for performing genomic PCR using High Fidelity Phusion DNA Polymerase.

Primers used for amplifying across the juxtaposed NPM1 and TYK2 introns:

```
NPMg F
                                          (SEQ ID NO: 3)
5'ACAGAGGGCGTATGAGACTTC3'

TYK2g R
                                          (SEQ ID NO: 4)
5'CCATAGGGACAGCCAATGTGAAAA3'
```

Molecular Cloning of NPM1-TYK2 Full Length Fusion Gene and Transient Expression in HEK293FT Cells The full length wild-type NPM1-TYK2 fusion gene was amplified from MyLa cell line using high fidelity Phusion DNA polymerase. The amplified gene product was then cloned into pLentilox IRES GFP mammalian expression Lenti virus vector (University of Michigan Vector Core, MI, USA) between Xho1 and Xba1restriction sites. FLAG sequences were artificially introduced at the N-terminal end of the gene by PCR. NPM1-TYK2 K462R kinase dead mutant (see, e.g., Gauzzi M C, et al., The Journal of biological chemistry 1996; 271:20494-500 was generated by performing site directed mutagenesis PCR using mutant primers and wild type NPM1-TYK2 gene as template. Sequence verified clones were transfected into HEK293FT cells and checked for expression of fusion protein after 48 hrs post transfection using PolyJet (SignaGen, Rockville, Md., USA).

Cell Culture

The hematological cell lines used for such experiments were stocked and HEK293FT cells were obtained from American Type Culture Collection (ATCC, Manassas, Va., USA). T-cell derived cell lines were maintained in RPMI-1640 medium supplemented with 20% FBS, L-glutamine and penicillin/streptomycin (Thermo Scientific, Waltham, Mass., USA). HEK293FT cells were maintained in Dulbecco's modified Eagle's medium (DMEM) supplemented with 10% FBS, glutamine and penicillin/streptomycin. Stable TYK2 knockdown MyLa cell lines were generated by transducing the lentivirus supernatant containing shRNAs for TYK2 and selecting them with puromycin (1 μg/mL) for 48 hrs post transduction.

Immunoblotting

The levels of pSTAT1, pSTAT3, pSTAT5 and pTYK2 were analysed in cell lines after treating them with 1 mM activated Na3VO4 for 1 hr prior harvesting. The lysates used in the immunoblotting experiments were prepared from the cell lines using RIPA buffer containing 50 mM Tris HCl, pH 7.4; 1% NP-40; 0.25% Na-deoxycholate; 150 mM NaCl; 1 mM PMSF; 1 mM EDTA; 1 mM $Na_3VO_4$; 1 mM NaF; and 0.1% SDS. The samples were incubated on ice for 30 min followed by centrifugation at 10,000× for 15 min. The protein content of the supernatants was estimated using a protein BCA assay kit (Pierce protein research products, Rockford, Ill., USA). 20 μg of protein extract was separated on a high resolution SDS PAGE using MES SDS running buffer, and analyzed for expression of proteins by immunoblotting using antibodies specific for monoclonal ANTI-FLAG M2 (clone M2) antibody (Sigma, St. Louis, Mo., USA). pSTAT1 (Y701), STAT1, pSTAT3 (Y705), STAT3, pSTAT5 (Y694), STAT5, pTYK2 (Y1054/55) and TYK2 antibodies were purchased from Cell Signaling Technologies (Beverly, Mass., USA) and used in our study.

Transcriptional Activation Assay

DNA constructs containing vector and NPM1-TYK2 wild type and K462R mutant were co-transfected along with luciferase reporter system plasmids sensitive to appropriate STAT proteins (pGL4.52 luc2P/STAT5RE; pGL4.45 luc2P/ISRE; Promega; Madison, Wis., Cignal STAT3 reporter, SA Biosciences, Valencia, Calif.) to HEK293FT cells. After 48 hrs post transfection, the cells were lysed and transcriptional activity of STAT proteins were measured by using the Dual Luciferase kit (Promega) and a specially configured luminometer (Berthold Technologies; Germany). Western blotting was performed using the extracts to ensure equal expression of different constructs (data not shown).

Stable knockdown of TYK2 expression in MyLa Lentiviral mediated gene transduction was performed as described earlier (see, e.g., Sahasrabuddhe A A, et al., Oncogene 2014). Briefly, 293FT cells were co-transfected with lentiviral construct and packaging vectors (Invitrogen). Virus-producing supernatant was harvested 48 h after transfection and supplemented with polybrene and used to infect MyLa cells. Lentiviral mission shRNA constructs targeting different region of TYK2 (TRCN0000003123-5'CGTGAGCCTAACCATGATCTT3' (SEQ ID NO: 5) and TRCN0000320620-5'GAGTGCCTGAAGGAGTATAAG3' (SEQ ID NO: 6)) and Vector control (SHC201) were purchased from Sigma (St. Louis, Mo., USA).

Cell Proliferation Assay

Cell proliferation assay was performed using water soluble tetrazolium-1 (WST-1) procured from Roche Applied Sciences, Indianapolis, Ind., USA, based on manufacturer's protocol (see, e.g., McDonnell S R, et al., Oncogene 2011). Briefly, equal numbers of cells were plated in 96-well plates with growth media and 10 μl of WST-1 reagent was added at different time intervals (0, 12, 36, 48 hours). After addition of WST-1 reagent, the plates were incubated at 3TC in an incubator with 5% $CO_2$ for 2 hours. Based on the cleavage of the tetrazolium salt WST-1 by mitochondrial dehydrogenases in viable cells, the intensities of the color developed in each well was determined by measuring the absorbance at 440 nm. The assay was performed in triplicate for all the samples at each time point.

Screening for somatic mutations in TYK2 by Sanger resequencing PCR fragments targeting exon 14 to 16 and 20 to 23, were amplified from genomic DNA of CD30 positive LPD samples (n=25). Genomic DNA was extracted using both the QIAGEN BioRobot EZ1 and QIAamp FFPE DNA extraction kits (QIAGEN). For all Sanger sequencing reactions, PCR amplification was performed using Phusion DNA polymerase (New England Biolabs) followed by conventional Sanger sequencing technology using BigDye version 3.1 chemistry run on an Applied Biosystems 3730xl DNA Sequencer at the University of Michigan DNA sequencing Core. All sequencing reactions were performed using nested sequencing primers. Sequencing trace analysis was performed using Mutation Surveyor software. All mutations were verified in at least two independent PCR amplification and sequencing reactions.

Immunostaining for NPM1 and pSTAT5 Immunohistochemical staining was performed on formalin-fixed, paraffin-embedded tissue microarrays containing patient samples using an automated immunostainer (Autostainer Link, Dako, Carpinteria, Calif.). Following deparafinization and heat-induced epitope retrieval, the slides were incubated with either anti-NPM1 (1:800 dilution, clone EP1848Y, Abcam, Cambridge, Mass.) or anti-pSTAT5 (1:400 dilution, clone AX1, Advantex BioReagents LLC, Houston, Tex.) for 60 min. Staining was visualized with Dako Envision detection system and diaminobenzadine chromagen.

Immunofluorescence analysis Cultured suspension cells from HH and MyLa cell lines were deposited onto glass slides by cytocentrifugation. Cells were fixed and permeabilized with methanol/glacial acetic acid (3:1). After fixation, cells were first incubated with the following primary antibodies (Cell Signaling Technology): Y701 phospho-STAT1 (clone 58D6, rabbit monoclonal IgG), Y705 phospho-SATA3 (mouse monoclonal IgG1, clone M9C6) or Y694/Y699 phospho-STAT5 monoclonal antibody (rabbit monoclonal IgG, clone D47E7). The secondary antibodies were Alexa-conjugated donkey anti-rabbit IgG or Alexa-conjugated goat anti-mouse IgG (Alexa594, Life Technologies). Coverslips were mounted on standard slides with mounting media supplemented with 4', 6'-diamidino-2-phenylindole (DAPI). The images were captured and recorded using an Olympus BX-51 upright light microscope equipped with an Olympus DP-70 camera.

Example 2

Patient biopsy samples were obtained with institutional review board approval. RNA was subjected to chimera analysis by producing paired end libraries sequenced on the Illumina Genome Analyzer II. Sequencing data was analyzed using custom bioinformatics tools and Chimerascan software (see, e.g., Iyer M K, et al., Bioinformatics 2011; 27:2903-4). Sequencing confirmation of NPM1-TYK2 fusion transcripts was achieved using SYBR Green-based quantitative real-time polymerase chain reaction (qRT-PCR) assays and Sanger sequencing of amplicons by reverse transcription (RT)-PCR. Fluorescence In Situ Hybridization (FISH) was performed on tissue microarrays of primary patient samples using standard methods. TYK2 break-apart FISH and NPM1-TYK2 fusion FISH assays were designed to detect TYK2 rearrangements and NPM1-TYK2 fusions, respectively. Immunohistochemistry for pSTAT5 (AX1, Advantex BioReagents LLC, Houston, Tex.) and NPM1 (EP1848Y, Abcam, Cambridge, Mass.) was performed on primary patient samples. Mutations in TYK2 were assessed by targeted Sanger sequencing of the genomic DNA. The NPM1-TYK2 fusion gene was amplified from MyLa cells and cloned into a mammalian expression vector for functional studies. Stable MyLa cell lines depleted of TYK2 were generated using lenti-viral mediated gene transduction (see, e.g., Sahasrabuddhe A A, et al., Oncogene 2014) of shRNAs and used in cell proliferation assays.

Example 3

Figure 3:
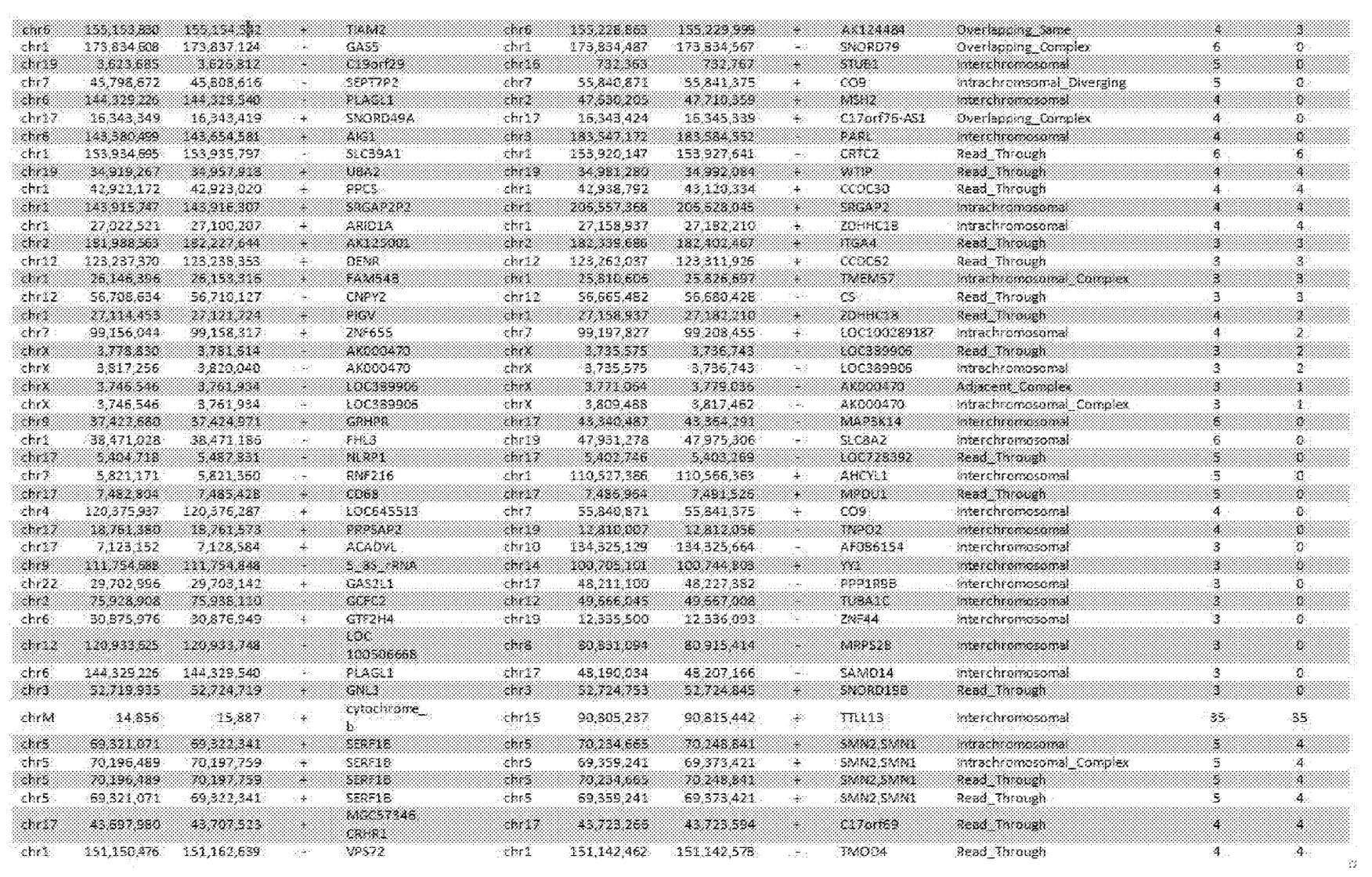
Figure 3:
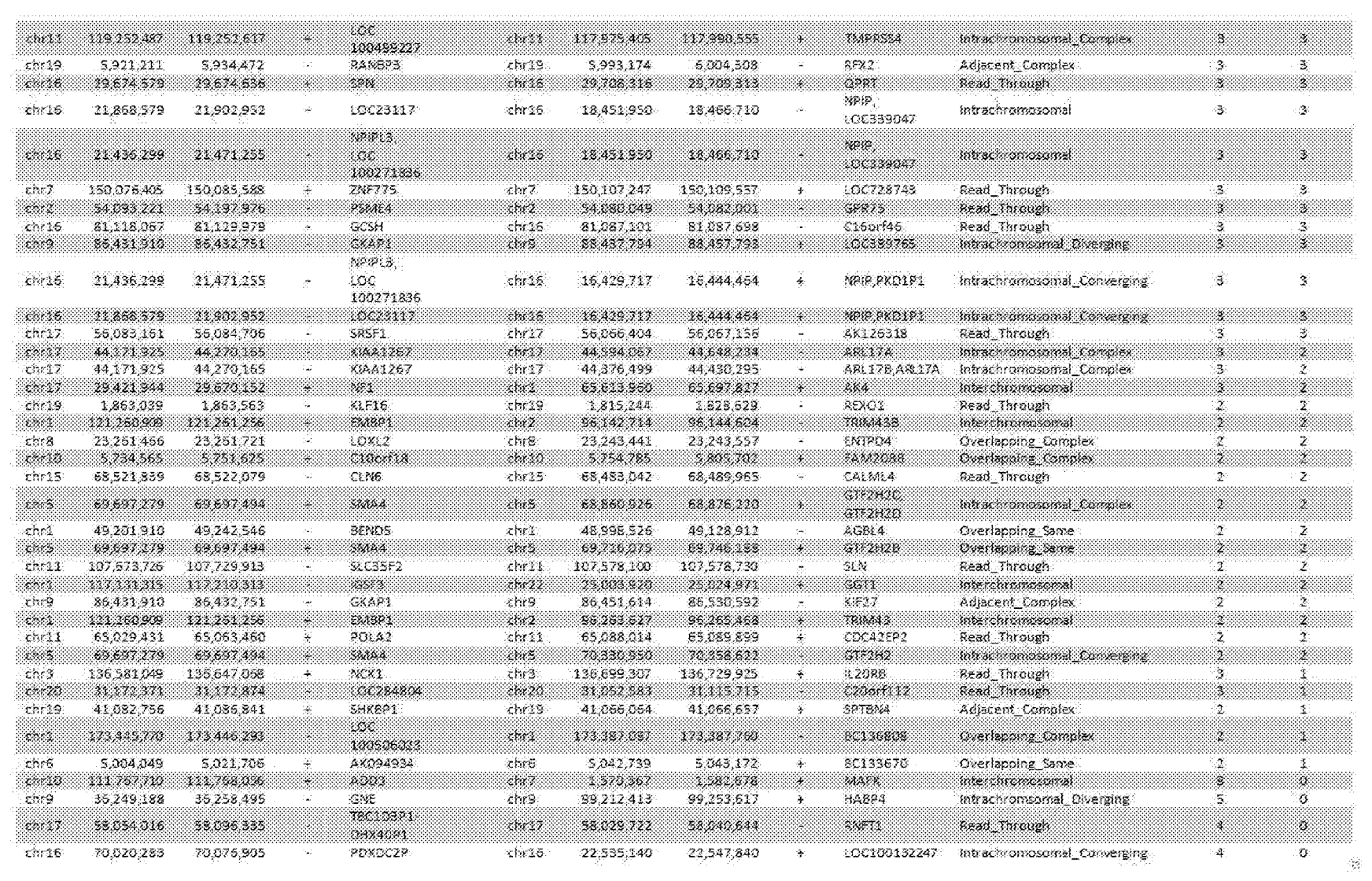
Figure 4:
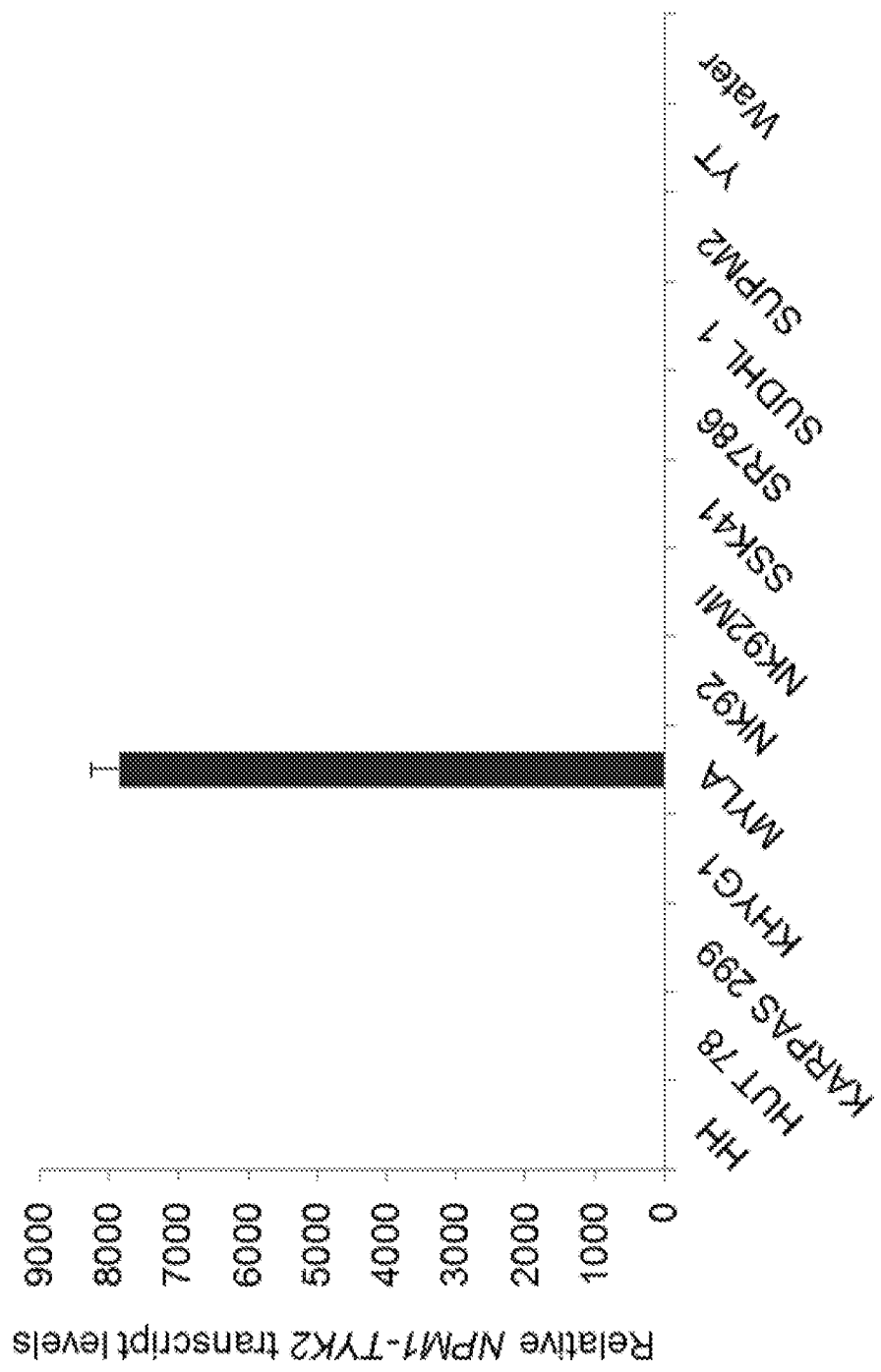
FIG. 4: SYBR Green-based qRT-PCR validation of NPM1-TYK2 fusion transcript expression in MyLa and other hematological cell lines.
Figure 5:
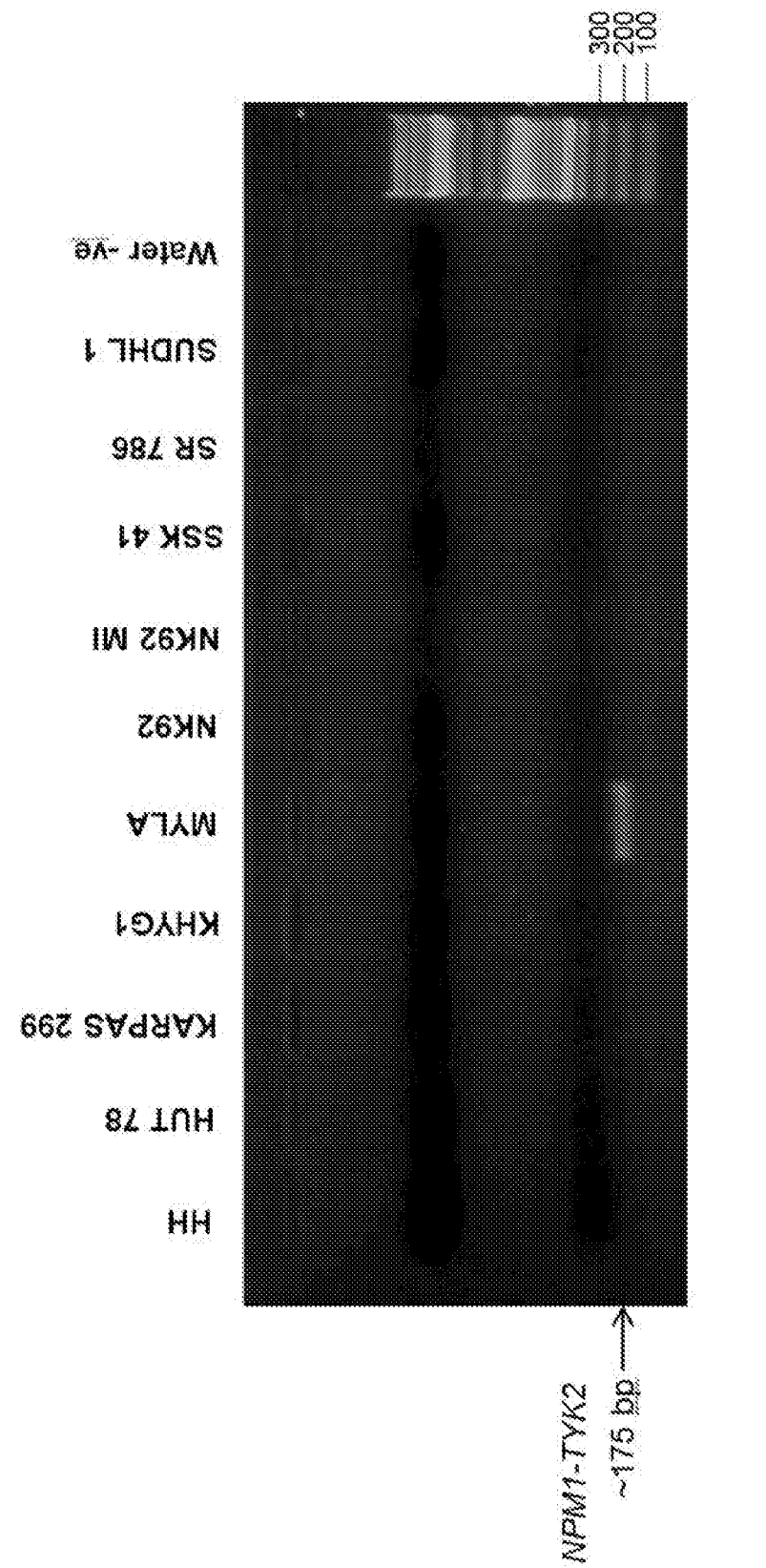
FIG. 5: Conventional gel based RT-PCR validation of NPM1-TYK2 fusion transcript expression in MyLa and other hematological cell lines.

To discover novel gene fusions that may be involved in the pathogenesis of cutaneous T-cell lymphoproliferative disorders, RNAseq was performed on the cutaneous T-cell lymphoma-derived cell line MyLa. Interestingly, RNA sequencing analysis of MyLa revealed 803 total fragments representing a chimeric fusion between the N-terminal region of NPM1 and the C-terminal region of TYK2 (FIG. 2A, upper panel; FIG. 3). RT-PCR analysis confirmed high levels and exclusive expression of the NPM1-TYK2 RNA chimera in MyLa, but not in 11 other hematological cell lines (FIG. 4; FIG. 5). The fusion occurred at NPM1 NM_002520 c.1016 (exon 9) and TYK2 NM_003331 c.2554 (exon 16) and was confirmed by Sanger sequencing (FIG. 2A, lower panel). The fusion gene was predicted to yield a product comprising the entire oligomerization, histone binding domains and the distal portion of the DNA/RNA binding domains of NPM1 and a small portion of the TYK2 pseudokinase domain and the entire C-terminal kinase domain (FIG. 2B).

Figure 2E:
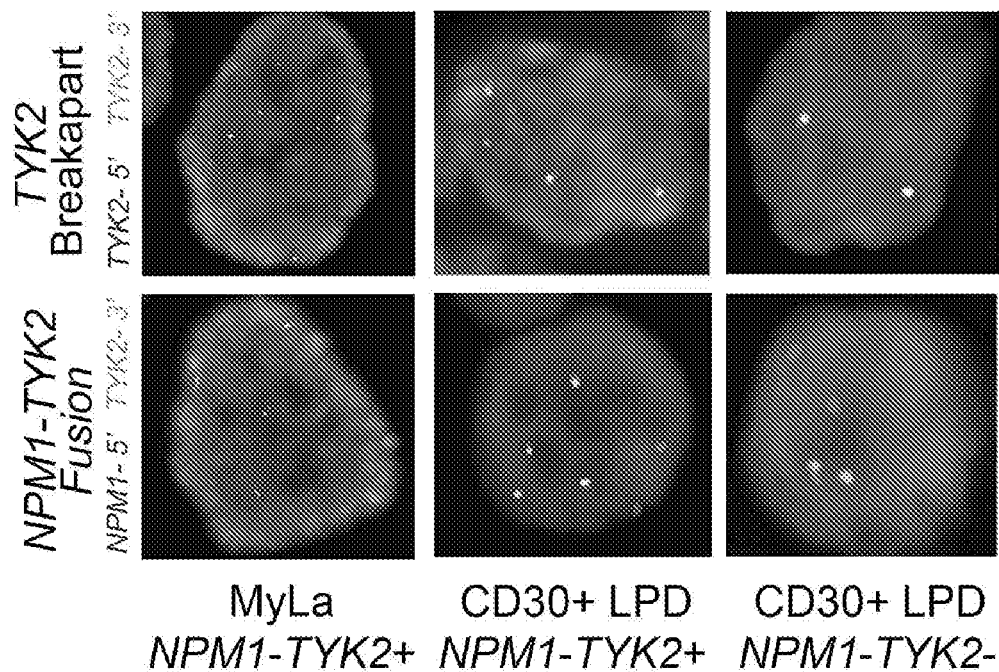
Figure 6:
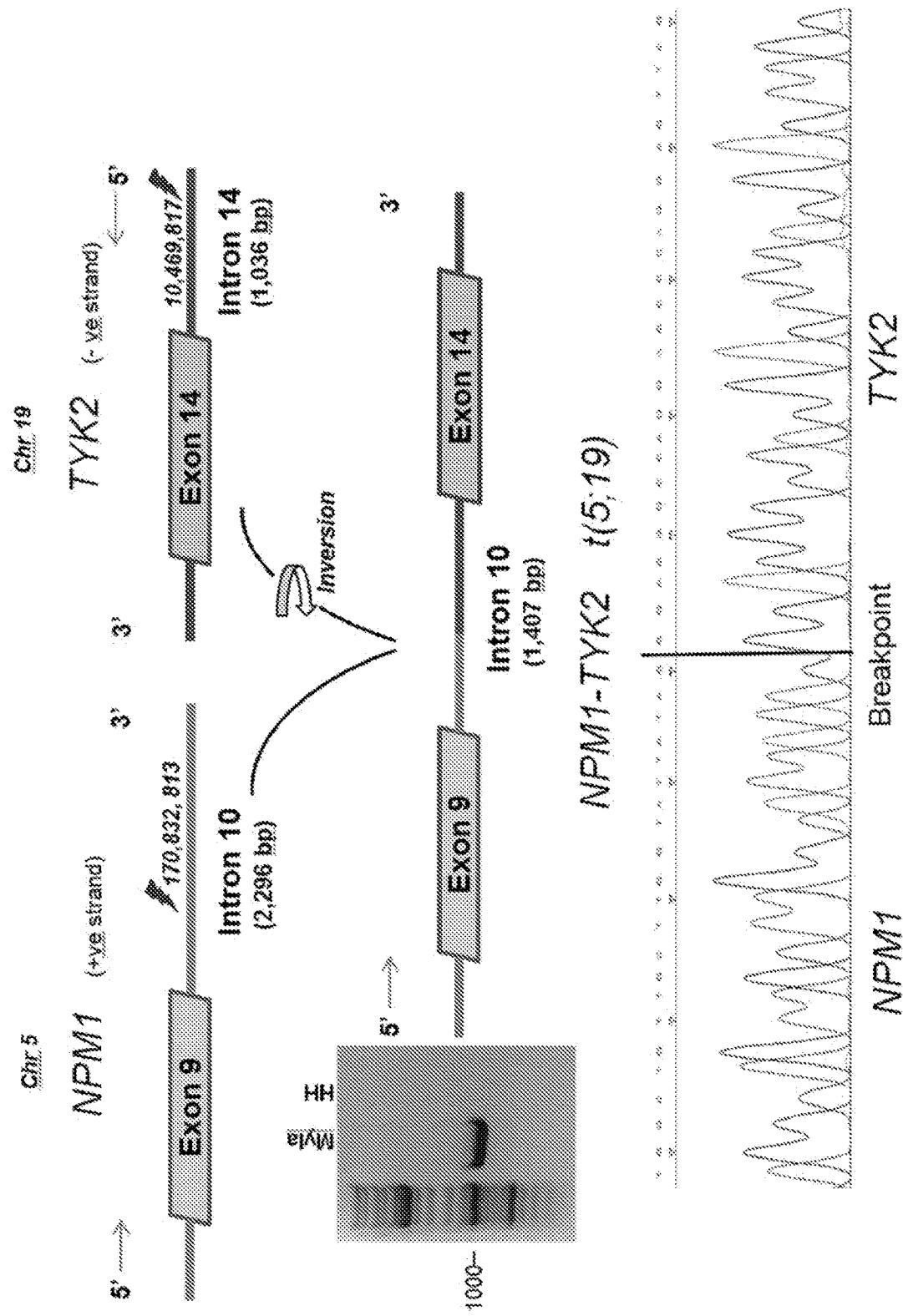
FIG. 6: Agarose gel electrophoresis of PCR products for genomic breakpoint mapping from NPM1-TYK2 positive MyLa and the negative control HH. The cartoon depicts the location of genomic breakpoint in NPM1 and TYK2 genes and their juxtaposition. The bottom panel shows the Sanger sequencing of the PCR product which shows the exact genomic fusion point.

To precisely map the genomic breakpoints, a conventional PCR-based assay using a series of forward primers starting from the C-terminal part of exon 9 through intron 10 of NPM1 (positive strand) and reverse primers located from exon 16 through intron 16 of TYK2 (negative strand) was designed. Bi-directional Sanger sequencing of the PCR product revealed break points at position chr5:170,832,813 within the NPM1 gene and chr19:10,469,817 in the TYK2 gene (FIG. 1C; FIG. 1D; FIG. 6). TYK2 break-apart and NPM1-TYK2 fusion FISH assays confirmed the presence of the NPM1-TYK2 rearrangement in MyLa (FIG. 2E).

Figure 2F:
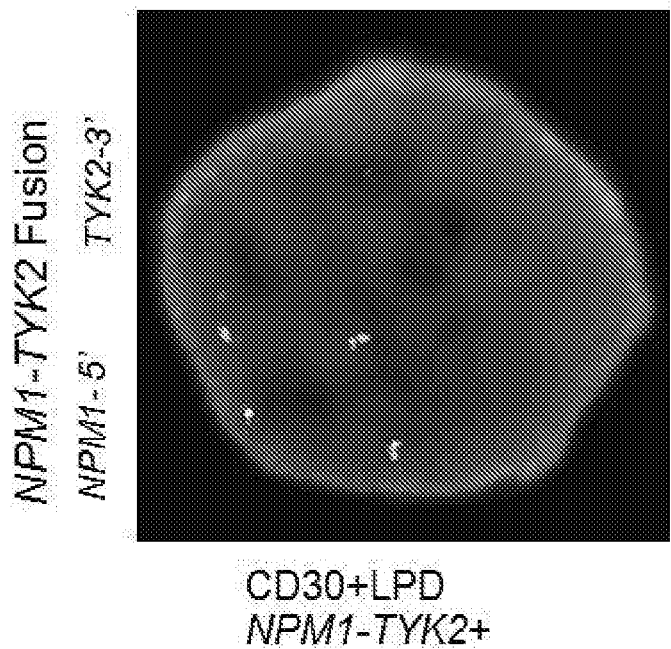

Next the TYK2 break-apart FISH assay was employed to screen for TYK2 gene rearrangements in a large cohort of primary mature T-cell LPD/lymphomas (n=198). TYK2 rearrangements were identified in 7/47 (15%) primary CD30-positive LPD including 3/15 (20.0%) cases of LYP and 4/32 (12.5%) cases of primary cutaneous ALCL. Each of the 7 cases that were identified by TYK2 break-apart FISH was also evaluated with the NPM1-TYK2 fusion FISH assay. Two cases (1 LYP, 1 cutaneous ALCL) harbored the NPM1-TYK2 rearrangement (FIG. 2E; FIG. 2F). These results indicate that TYK2 is targeted by multiple different translocation partners in CD30-positive LPD. This is not unexpected since other prominent oncogenes are known to utilize multiple translocation partners (see, e.g., Mitelman F, et al., Nature reviews Cancer 2007; 7:233-45; Chen Y W, et al., Blood 2003; 102:1931-2; author reply 2; Harper D P, et al., Cancer research 2008; 68:10024-7; Chiarle R, et al., Nature reviews Cancer 2008; 8:11-23). Of note, TYK2 translocations were absent in all (n=151) cases of other mature T-cell lymphomas including mycosis fungoides (n=44); systemic ALK-negative ALCL (n=44) systemic ALK-positive ALCL (n=22); peripheral T-cell lymphoma, not otherwise specified (n=24); angioimmunoblastic T-cell lymphoma (n=7); extranodal NK/T-cell lymphoma (n=5); enteropathy-associated T-cell lymphoma (n=3); hepatosplenic T-cell lymphoma (n=1) and cutaneous gamma/delta T-cell lymphoma (n=1). To investigate whether point mutations may represent a mechanism for activation of TYK2, targeted sequencing of TYK2 pseudokinase and kinase domains including previously reported mutations in T-lymphoblastic lymphoma cell lines was performed (see, e.g., Sanda T, et al., Cancer discovery 2013; 3:564-77). No mutations were identified in TYK2 in 25 cases of CD30-positive LPD.

Figure 7A:
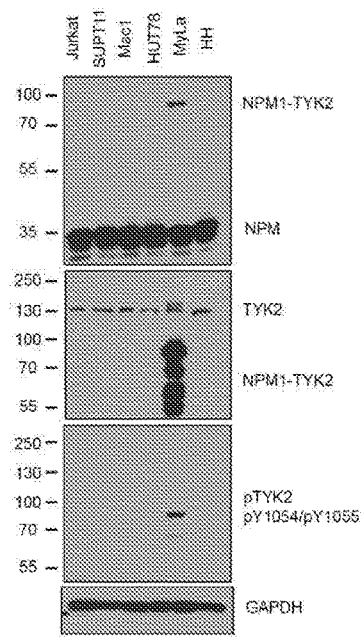
FIG. 7A-F: Oncogenic potential of NPM1-TYK2 fusion gene product. (A) Presence of the NPM1-TYK2 fusion protein in MyLa and not in other T-cell lines. Individual NPM1 and TYK2 western blot assays show shift in the size of the protein in MyLa as a result of the fusion. (B) Hyperactivation of TYK2 and elevated STAT pathway activation in MyLa cells endogenously expressing NPM1-TYK2 fusion protein as compared with other T-cell lines. The Mac1 cell line that has a JAK2 rearrangement is used as a positive control. HUT78 cell line exhibits constitutive STAT5 activation. (C) Ectopic expression of NPM1-TYK2 fusion protein in HEK293T cells reveals activation of STAT proteins in Western blot assays. Note the significantly reduced levels of STAT activation in cells expressing NPM1-TYK2 kinase-defective mutant K462R. (D) Exogenously expressed NPM1-TYK2 fusion protein in HEK293FT cells leads to transcriptional activation of STAT1/3/5. Cells expressing kinase-defective mutant K462R NPM1-TYK2 fusion protein show reduced levels of STAT activation indicating a specific effect of TYK2 kinase activity on downstream STAT activation. (E) Diminished STAT pathway activation following knockdown of TYK2 protein in MyLa cell line by shRNA knockdown. (F) ShRNA-mediated silencing of TYK2 reduces proliferation of MyLa cells demonstrating oncogenic potential of NPM1-TYK2.
Figure 7B:
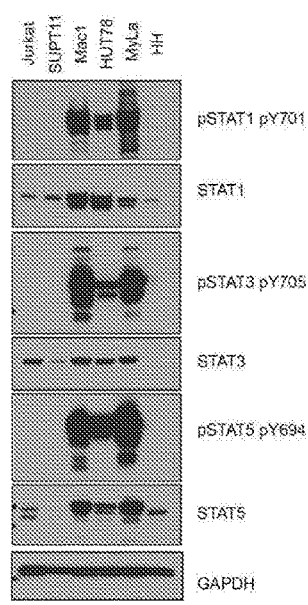
Figure 8:
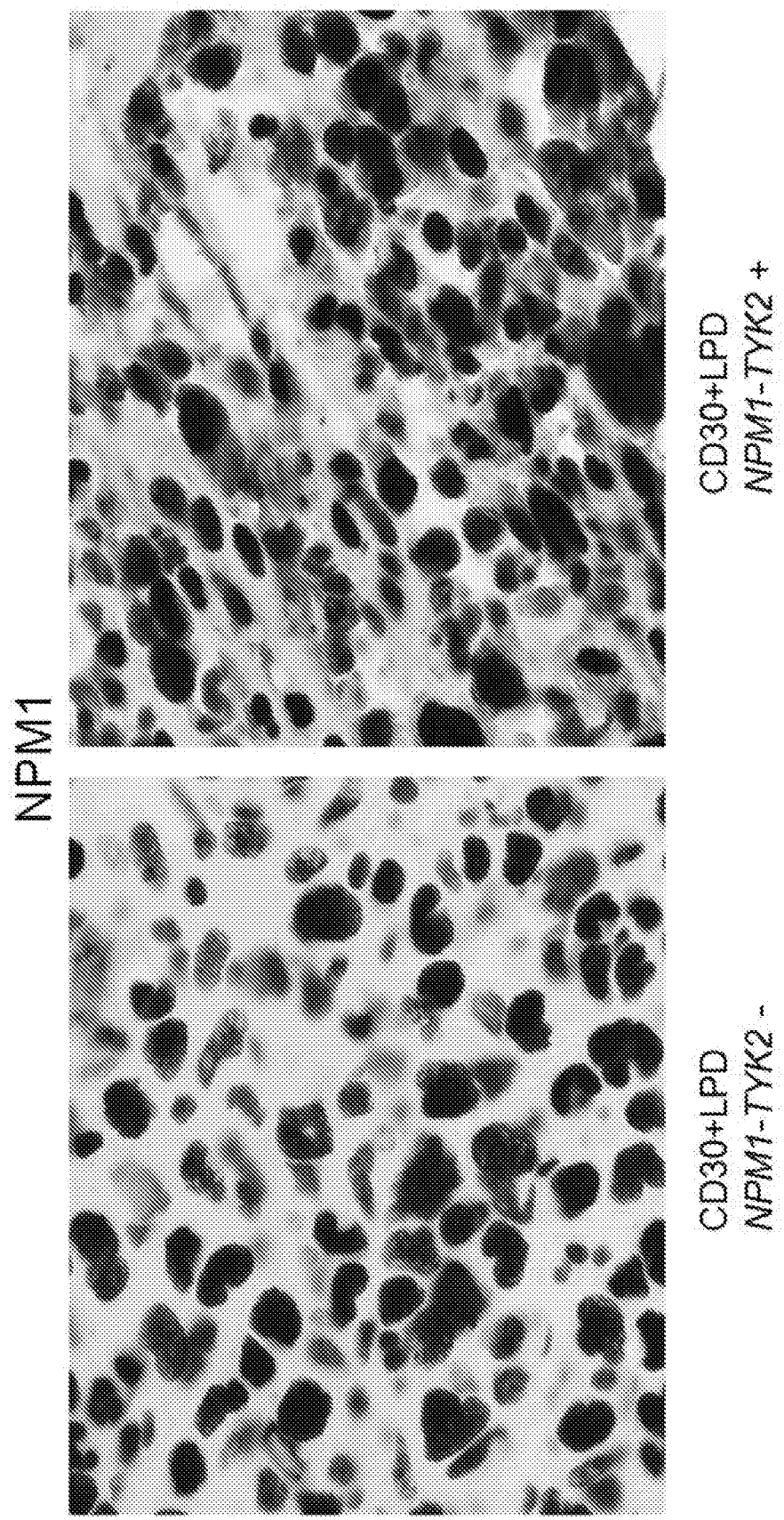
FIG. 8: Immunohistochemical staining for NPM1 in primary patient samples. In the absence of NPM1-TYK2, NPM1 expression is restricted to the nucleus (left panel). In a patient with NPM1-TYK2 fusion, there is atypical cytoplasmic localization of NPM1 (right panel). (Anti-NPM1, 500× magnification).
Figure 9:
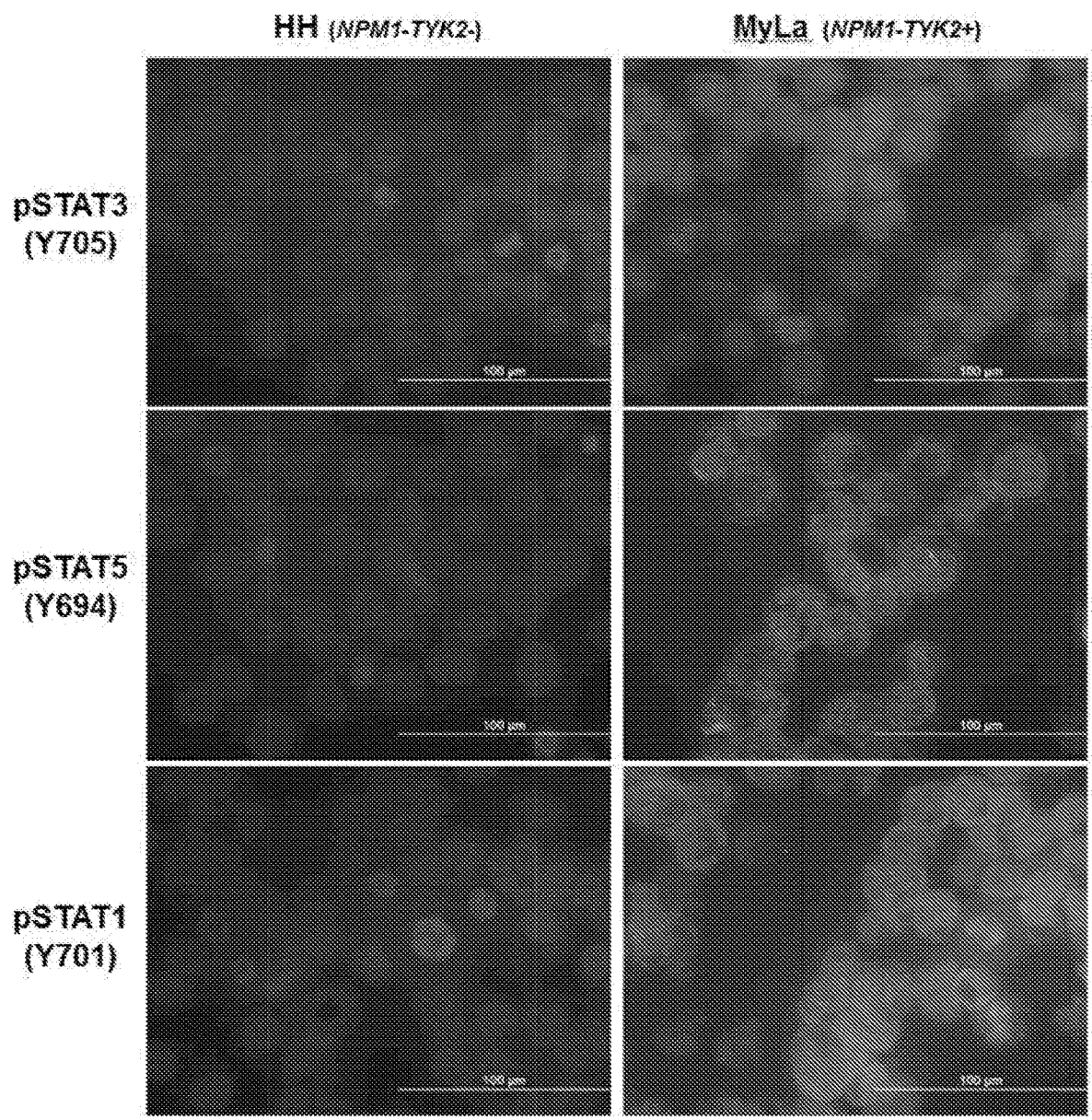
FIG. 9: Immunofluorescence staining demonstrates a marked expression of cytoplasmic and nuclear phosphorylated STAT 1/3/5 in NPM-TYK2 positive MyLa cell line as compared to fusion negative HH cell line.

In the NPM1-TYK2 fusion reported herein, the 5' partner of the fusion protein NPM1 retained the oligomerization domain (FIG. 2B) which was hypothesized to lead to constitutive activation of TYK2 through a mechanism similar to that observed with NPM1-ALK (see, e.g., Pearson J D, et al., Journal of signal transduction 2012; 2012:123253; Bischof D, et al., Molecular and cellular biology 1997; 17:2312-25). The pTYK2 (Y1054/1055) levels in the NPM1-TYK2-positive MyLa cell line and in other T-cell lines were evaluated, and confirmed high levels of pTYK2 in only MyLa indicating constitutive activation of TYK2 kinase (FIG. 7A). Notably, western blot analysis for NPM1 and total TYK2 demonstrates the presence of a fusion protein (81 kD) supporting the expression of the NPM1-TYK2 fusion protein. Further, immunostaining for NPM1 in NPM1-TYK2 fusion positive cases revealed cytoplasmic reactivity and mislocalization of NPM1, a predominantly nuclear protein, indicating abnormal subcellular localization (FIG. 8). To investigate whether the NPM1-TYK2 fusion conferred constitutive activation of STAT signaling, western blot analysis and immunofluorescence microscopy was performed which revealed that STAT-family members (pSTAT1, pSTAT3 and pSTAT5) downstream of TYK2 are constitutively activated in the MyLa cell line (FIG. 7B; FIG. 9). Importantly, constitutively activated STAT signaling was confirmed in primary NPM1-TYK2 fusion positive CD30 positive LPD tissue samples (n=2), where nuclear expression of pSTAT5 was observed compared to TYK2 negative cases (FIG. 10).

Figure 7C:
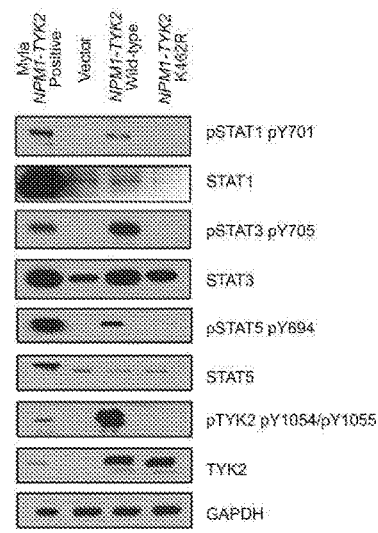
Figure 7D:
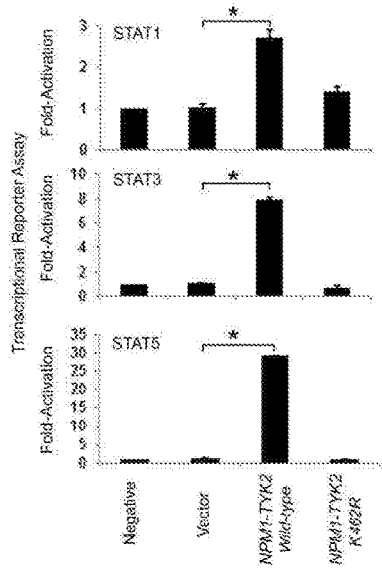

FLAG-tagged NPM1-TYK2 and NPM1-TYK2 (K462R) kinase-defective mutant proteins were ectopically expressed in HEK293FT cells. Expression of NPM1-TYK2 protein demonstrated constitutive TYK2 autophosphorylation whereas the kinase-defective NPM1-TYK2 (K462R) mutant completely abolished its phosphorylation (FIG. 7C). Similarly, pSTAT1, pSTAT3 and pSTAT5 were induced by the kinase-active NPM1-TYK2 while the kinase-defective NPM1-TYK2 (K462R) mutant completely abrogated their phosphorylation. Activation of STAT1/3/5 specifically by NPM1-TYK2 was further corroborated by transcriptional activation (reporter) assays (FIG. 7D). Altogether, these results indicate that expression of the NPM1-TYK2 fusion protein results in constitutive activation of the STAT signaling pathway.

Figure 7E:
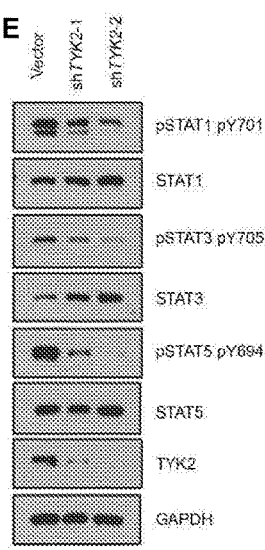
Figure 7F:
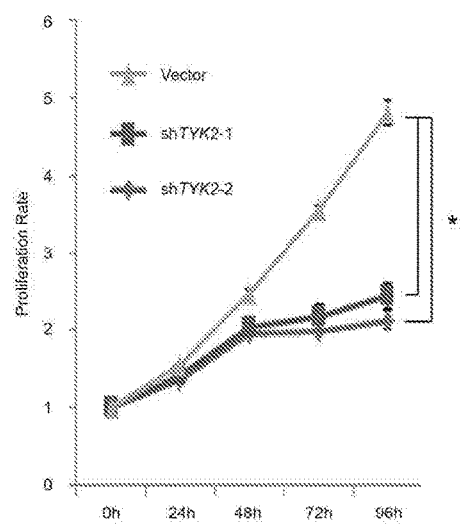

The oncogenic potential of NPM1-TYK2 was further assessed by examining the effect of TYK2 knockdown on STAT1/3/5 activation and cell proliferation. Lentivirus-based shRNA-mediated knockdown of TYK2 in MyLa resulted in decreased pSTAT1, pSTAT3 and pSTAT5 without affecting their total protein levels (FIG. 7E). Importantly, a significant decrease (2.2 fold) in cell proliferation was observed compared to vector control (P<0.01) (FIG. 7F).

Example 4

In some embodiments, the following primers are used for cloning in pCAGGS:

```
NPM 1 exon 1 ecorl F
                                          (SEQ ID NO: 7)
AAgaattcAGAAAGGAGTGGGGTTGAAAAGCGCTTG TYK2 exon 23 xhol R
                                          (SEQ ID NO: 8)
AActcgagTCCAGCAGAGAAAACATGAGTTTATTACCAGATGG.
```

In some embodiments, the following primers are used for cloning in plentilox IRES GFP:

```
NPM1 xhol flag F
                                          (SEQ ID NO: 9)
AActcgagATGGACTACAAGGACGACGATGACAAGGAAGATTCGATGGA
CATGGACATGAGCCC TYK2 xba1 stop R
                                          (SEQ ID NO: 10)
AAtctagaTCAGCACACGCTGAACACTGAAGGGGC.
```

In some embodiments, the following PCR primers are used for PCR amplification for sequencing a NPM1-TYK2 gene fusion:

NPM1 PCR

AAGCGCCAGTGAAGAAATCT (SEQ ID NO: 11)

TYK2 PCR

CCTCTCCGTCAAAGCAGATC. (SEQ ID NO: 12)

In some embodiments, the following primers are used for NPM1-TYK2 Q-PCR:

NPM-TYK2 Q F1

ACTCAAAACCATCATCAACACCA (SEQ ID NO: 1)

NPM-TYK2 Q R1

GTTCCGGCCACACACATTAC (SEQ ID NO: 2)

NPM-TYK2 Q F2

CACCAAAAGGACCTAGTTCTGT (SEQ ID NO: 13)

NPM-TYK2 Q R2

CTCAGCTTGATGAAGGGGCT (SEQ ID NO: 14)

NPM-TYK2 Q F3

ACCATCATCAACACCAAGATCA (SEQ ID NO: 15)

NPM-TYK2 Q R3

GCCAGGATCACTCAGCTTGA. (SEQ ID NO: 16)

In some embodiments, NPM1-TYK2 Q-PCR yields the following sequencing result:

(SEQ ID NO: 17)
GCTGGAAAGTAGATGCTGGCTGTTGCTTGGTATTATAGGGAGGGCCAGG
AGCCCAGGAGTTCGAGACCAGCCTGGGCAACAGGGCGAGACCCCATCTT
TTTTGTTTGTTTTGTTTTAGGTGGAGTTTCGCCCTGTCACCCAGGCTGG
AGTGCAATGGCATGATCTCGGCTCACTGCAACCTTCGCCTCCCGGGTTC
AAATGATTCTCCCGCCTCAGCCTCCCAAGTAGCTGGGATTATAGGCTCC
TGCCATCACGCCCAGCTAATTTTTGTATTTTTAGTAGAGATGGGGTTTC
ACCATGTTGGTCAGGCTGGTCTCGAACTTCTGACCTCGTGATCCATCCG
CCTCAGCCTCCCAAAGTGCTGGGATTCCAGGCGTGAGCCACCACGCCCA
GCTGGCCCCATCTTTTAAAAATAAACAAATAGCCAGGTGTGGTGGCTCA
TACCTGTAATCCCAGCAGTTTGGGAGGCCAAGGCGGGTGGATCACCTGA
GGTCAGGAGTTTGAGACCAGCCTGGCCAGTATGGCAAAACCTTGCCTCT
ACTAAAAATACAAAAAAATTAGCCAATGTGGTAACTTGCACCTGTAGG
CCGAGGTACTCAGGAAGTTGAGGTGGGAGGATCACCTGAGCTCAGGAAT
TTGAGGCCGTAGTAAGCTATGATCACACCACTGCACCCCAGCCTGGGCA
GCAGCATAGCTAGACCCCATCTCCACCAAAAATTTAAGAATCAGCTAGG
CTGTGGTGATGTGCACCTGTAATTCTCGCTACTTGGAAGGCTTGAGCCC
AGGAGTTTGAAGCTGCAGTGAGCTATGTTCGTGCCACTATACTCCAACC
TGAAAGACAGAGTGAGACCCTGTCTT.

In some embodiments, the NPM1-TYK2 gene fusion break point on sequencing is provided:

(SEQ ID NO: 18)
Gtgagtaaagttatcttaaaaaaactttgtctccccctcaaattgcacg
tgtctggtttgcatagacttgaatgtttcttgtattagtttgattggttt
aatatacttgcctggttcgtggtatgaattattcaaaaatttcttataaa
acatttataatcgtgtctgtggtgatttagcatatgcaaaattaaatatg
ccttattttccattatgcaaggaacgtagtgcactggttgcaagataaca
ttctgaccttccatgttaaaatagatcagtgaaaacccttgcctattct
ggttgtaagatatgctagagaaccaacagagggcgtatgagacttcatta
aaattacaaacagctggaaaagtagatgctggctgttgcttggtattata
gggagggccaggagcccaggagttcgagaccagcctgggcaacagggcga
gaccccatctttttgtttgttttgttttaggtggagtttcgccctgtca
cccaggctggagtgcaatggcatgatctcggctcactgcaaccttcgcct
cccgggttcaaatgattctcccgcctcagcctcccaagtagctgggatta
taggctcctgccatcacgcccagctaattttttgtatttttagtagagatg
gggtttcaccatgttggtcaggctggtctcgaacttctgacctcgtgatc
catccgcctcagcctcccaaagtgctgggattccaggcgtgagccaccac
gcccagctggccccatcttttaaaaataaacaaatagccaggtgtggtgg
ctcatacctgtaatcccagcagtttgggaggccaaggcgggtggatcacc
tgaggtcaggagtttgagaccagcctggccagtatggcaaaaccttgcct
ctactaaaaatacaaaaaaattagccaatgtggtaacttgcacctgtag
gccgaggtactcaggaagttgaggtgggaggatcacctgagctcaggaat
ttgaggccgtagtaagctatgatcacaccactgcacccccagcctgggcag
cagcatagctagaccccatctccaccaaaaatttaagaatcagctaggct
gtggtgatgtgcacctgtaattctcgctacttggaaggcttgagcccagg
agtttgaagctgcagtgagctatgttcgtgccactatactccaacctgag
agacagagtgagaccctgtcttaaaaaaaaaaaaaaaaaaaaaaaaaacaag
aaaaaaataaccccccaaaaaacaaaacagaaagaaacccagtgatagtc
acagttgtccttttcacattggctgtccctatgggaccaggtttgggt
tggcgtctgtgcctctcctgagtggccacaccccctctcctgcccacctc
ag.

In some embodiments, the following primers are provided:

NPMg F1 exonic primer

CACCAAAAGGACCTAGTTCTGT (SEQ ID NO: 13)

NPMg F2 cttgcctggttcgtggtatg (SEQ ID NO: 19)

NPMg F3 aaccaacagagggcgtatga (SEQ ID NO: 20)

NPMg F4 tctcatctgcttgactgggg (SEQ ID NO: 21)

NPMg F5

(SEQ ID NO: 22)

gcaaatgtggggtggtgaaa

NPMg F6

(SEQ ID NO: 23)

ttttagatgcccctccctc

NPMg F7

(SEQ ID NO: 24)

ttctgatttgccacccatgc

NPMg F8

(SEQ ID NO: 25)

ttctgccaaagtcccttgga

NPMg F9

(SEQ ID NO: 26)

accgagttgccatgtttgtt

NPMg F10

(SEQ ID NO: 27)

tctaaaggtatctctctcggtgt

TYK2g R1

(SEQ ID NO: 28)

ggatggatcacgaggtcaga

TYK2g exonic R2

(SEQ ID NO: 2)

GTTCCGGCCACACACATTAC

NPMg F1 exonic primer long (SEQ ID NO: 29)

GAAAAAACTCCTAAAACACCAA
AAGGACCTAGTTCTGTAGAA

TYK2g exonic R2 long (SEQ ID NO: 30)

GTAATGTGTGTGGCCGGAAC
ATCCTGCTGGCCCG

TYK2 K930R F (SEQ ID NO: 31)

ACTGGCGAGATGGTGGCGGTGAGAGCCCTCAAGGCAGACTGCGGC

TYK2 K930R R (SEQ ID NO: 32)

GCCGCAGTCTGCCTTGAGGGCTCTCACCGCCACCATCTCGCCAGT

TYK2 Y1054Fe F (SEQ ID NO: 33)

GCCGTGCCCGAAGGCCACGAGTTCTACCGCGTGCGCGAGGATGGGG

TYK2 Y1054Fe R (SEQ ID NO: 34)

CCCCATCCTCGCGCACGCGGTAGAACTCGTGGCCTTCGGGCACGGC

TYK2 Y1054/55Fe F (SEQ ID NO: 35)

GCCGTGCCCGAAGGCCACGAGTTCTTCCGCGTGCGCGAGGATGGGG

TYK2 Y1054/55Fe R (SEQ ID NO: 36)

CCCCATCCTCGCGCACGCGGAAGAACTCGTGGCCTTCGGGCACGGC.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method, comprising
   a) obtaining a nucleic acid sample from a subject suspected of having or having a neoplastic disorder, wherein the neoplastic disorder is a cutaneous CD30-positive lymphoproliferative disorder, wherein the cutaneous CD30-positive lymphoproliferative disorder is lymphomatoid papulosis and/or primary cutaneous anaplastic large cell lymphoma;
   b) amplifying the obtained nucleic acid sample with a pair of primers that amplify a fusion junction of a NPM1-TYK2 gene fusion having the sequence of SEQ ID NO: 89; and
   c) measuring amplification of SEQ ID NO: 89 by Q-PCR.

* * * * *